US009376418B2

(12) United States Patent
Haidle et al.

(10) Patent No.: US 9,376,418 B2
(45) Date of Patent: Jun. 28, 2016

(54) SUBSTITUTED PYRIDINE SPLEEN TYROSINE KINASE (SYK) INHIBITORS

(71) Applicants: Merck Sharp & Dohme Corp., Rahway, NJ (US); Merck Canada Inc., Kirkland, Quebec (CA)

(72) Inventors: Andrew M. Haidle, Cambridge, MA (US); Sandra Lee Knowles, Princeton, NJ (US); Solomon D. Kattar, Arlington, MA (US); Denis Deschenes, Lachine (CA); Jason Burch, Redwood City, CA (US); Joel Robichaud, Dollard-des-Ormeaux (CA); Matthew Christopher, Brookline, MA (US); Michael D. Altman, Needham, MA (US); James P. Jewell, Newtown, MA (US); Alan B. Northrup, Reading, VA (US); Marc Blouin, Saint-Lazare (CA); John Michael Ellis, Needham, MA (US); Hua Zhou, Acton, MA (US); Christian Fischer, Natick, MA (US); Adam J. Schell, Decatur, GA (US); Michael H. Reutershan, Brookline, MA (US); Brandon M. Taoka, Hoboken, NJ (US); Anthony Donofrio, Cambridge, MA (US)

(73) Assignees: Merck Sharp & Dohme Corp., Rahway, NJ (US); Merck Canada Inc., Kirkland, Quebec (CA)

( * ) Notice: Subject to any disclaimer, the term of this patent is extended or adjusted under 35 U.S.C. 154(b) by 13 days.

(21) Appl. No.: 14/409,151

(22) PCT Filed: Jun. 17, 2013

(86) PCT No.: PCT/US2013/046151
§ 371 (c)(1),
(2) Date: Dec. 18, 2014

(87) PCT Pub. No.: WO2013/192098
PCT Pub. Date: Dec. 27, 2013

(65) Prior Publication Data
US 2015/0148327 A1      May 28, 2015

Related U.S. Application Data

(60) Provisional application No. 61/663,290, filed on Jun. 22, 2012.

(51) Int. Cl.
*C07D 401/12* (2006.01)
*C07D 401/14* (2006.01)
(Continued)

(52) U.S. Cl.
CPC ............ *C07D 401/12* (2013.01); *A61K 31/505* (2013.01); *A61K 31/506* (2013.01); *A61K 31/5377* (2013.01); *A61K 31/5383* (2013.01); *A61K 31/551* (2013.01); *A61K 45/06* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01);
(Continued)

(58) Field of Classification Search
CPC ............... C07D 401/12; C07D 401/14; A61K 31/5377; A61K 31/506
USPC ................ 544/122, 331; 514/235.8, 275
See application file for complete search history.

(56) References Cited

U.S. PATENT DOCUMENTS 5,710,129 A    1/1998  Lynch et al.
6,248,790 B1   6/2001  Uckun et al.
(Continued)

FOREIGN PATENT DOCUMENTS

EP    877020 A1    11/1998
EP    2441755 A1    4/2012
(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
(Continued)

*Primary Examiner* — Deepak Rao
(74) *Attorney, Agent, or Firm* — Eric A. Meade; Anna L. Cocuzzo

(57) ABSTRACT

The invention provides certain substituted pyridines of the Formula (I) or pharmaceutically acceptable salts thereof, wherein $R^1$, $R^2$, $R^3$, $R^4$, $R^{Cy}$, $C^y$, and t are as defined herein. The invention also provides pharmaceutical compositions comprising such compounds, and methods of using the compounds for treating diseases or conditions mediated by Spleen Tyrosine Kinase (Syk) kinase.

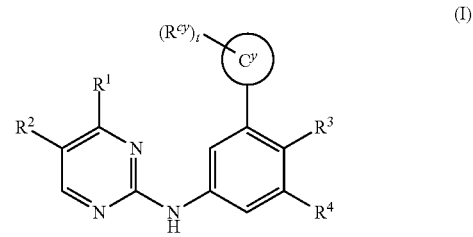

18 Claims, No Drawings

(51) Int. Cl.
*A61K 31/506* (2006.01)
*A61K 31/505* (2006.01)
*A61K 45/06* (2006.01)
*A61K 31/5377* (2006.01)
*A61K 31/5383* (2006.01)
*A61K 31/551* (2006.01)
*C07D 405/14* (2006.01)
*C07D 413/14* (2006.01)
*C07D 417/14* (2006.01)
*C07D 471/04* (2006.01)
*C07D 471/10* (2006.01)
*C07D 487/04* (2006.01)
*C07D 491/107* (2006.01)
*C07D 491/113* (2006.01)
*C07D 498/04* (2006.01)
*C07D 491/08* (2006.01)
*C07D 409/14* (2006.01)
*C07D 487/10* (2006.01)

(52) U.S. Cl.
CPC ......... *C07D 471/10* (2013.01); *C07D 487/04* (2013.01); *C07D 487/10* (2013.01); *C07D 491/08* (2013.01); *C07D 491/107* (2013.01); *C07D 491/113* (2013.01); *C07D 498/04* (2013.01)

(56) References Cited

U.S. PATENT DOCUMENTS

| | | | |
|---|---|---|---|
| 6,432,963 | B1 | 8/2002 | Hisamichi et al. |
| 6,552,029 | B1 | 4/2003 | Davis et al. |
| 6,589,950 | B1 | 7/2003 | Hayler et al. |
| 6,770,643 | B2 | 8/2004 | Cox et al. |
| 6,797,706 | B1 | 9/2004 | Hisamichi et al. |
| 6,897,207 | B2 | 5/2005 | Cox et al. |
| 6,897,208 | B2 | 5/2005 | Edwards et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,259,154 | B2 | 8/2007 | Cox et al. |
| 7,276,502 | B2 | 10/2007 | Brenchley et al. |
| 7,803,801 | B2 | 9/2010 | Kodama et al. |
| 8,551,984 | B2 | 10/2013 | Altman et al. |
| 8,735,417 | B2 | 5/2014 | Altman et al. |
| 8,759,366 | B2 | 6/2014 | Childers et al. |
| 8,796,310 | B2 | 8/2014 | Romeo et al. |
| 8,987,456 | B2 | 3/2015 | Altman et al. |
| 9,006,444 | B2 | 4/2015 | Altman et al. |
| 9,120,785 | B2 | 9/2015 | Altman et al. |
| 2004/0029902 | A1 | 2/2004 | Singh et al. |
| 2004/0054179 | A1 | 3/2004 | Yura et al. |
| 2006/0135543 | A1 | 6/2006 | Singh et al. |
| 2006/0178407 | A1 | 8/2006 | Argade et al. |
| 2006/0211657 | A1 | 9/2006 | Singh et al. |
| 2006/0234483 | A1 | 10/2006 | Arak et al. |
| 2006/0247262 | A1 | 11/2006 | Baenteli et al. |
| 2007/0004626 | A1 | 1/2007 | Masuda et al. |
| 2007/0129362 | A1 | 6/2007 | Bhamidipati et al. |
| 2007/0197782 | A1 | 8/2007 | Clough et al. |
| 2008/0221171 | A1* | 9/2008 | Eberle et al. ............... 514/352 |
| 2011/0245205 | A1 | 10/2011 | Altman et al. |
| 2011/0301175 | A1 | 12/2011 | Molteni et al. |
| 2014/0148474 | A1 | 5/2014 | Altman et al. |
| 2014/0243336 | A1 | 8/2014 | Altman et al. |
| 2014/0249130 | A1 | 9/2014 | Deschenes et al. |
| 2015/0166486 | A1 | 6/2015 | Haidle et al. |
| 2015/0175575 | A1 | 6/2015 | Lim et al. |
| 2015/0191461 | A1 | 7/2015 | Machacek et al. |
| 2015/0239866 | A1 | 8/2015 | Machacek et al. |

FOREIGN PATENT DOCUMENTS

| | | |
|---|---|---|
| JP | 2004203748 | 12/2002 |
| WO | WO03078404 A1 | 9/2003 |
| WO | WO2004080463 A1 | 9/2004 |
| WO | WO2005013996 A2 | 2/2005 |
| WO | WO2006093247 A1 | 2/2005 |
| WO | WO2005026158 A1 | 3/2005 |
| WO | WO2005033103 A1 | 4/2005 |
| WO | WO2006004865 A1 | 1/2006 |
| WO | 2006/027348 A1 | 3/2006 |
| WO | WO2006028833 A1 | 3/2006 |
| WO | WO2006050480 A2 | 5/2006 |
| WO | WO2006068770 A1 | 6/2006 |
| WO | WO2006078846 A1 | 7/2006 |
| WO | WO2006129100 A1 | 12/2006 |
| WO | WO2006133426 A2 | 12/2006 |
| WO | WO2006135915 A2 | 12/2006 |
| WO | WO2007009681 A1 | 1/2007 |
| WO | WO2007009773 A1 | 1/2007 |
| WO | WO2007028445 A1 | 3/2007 |
| WO | WO2007042298 A1 | 4/2007 |
| WO | WO2007042299 A1 | 4/2007 |
| WO | WO2007070872 A1 | 6/2007 |
| WO | WO2007085540 A1 | 8/2007 |
| WO | WO2007120980 A2 | 10/2007 |
| WO | WO2009084695 A1 | 12/2007 |
| WO | WO2009031011 A2 | 3/2009 |
| WO | WO2009097287 A1 | 8/2009 |
| WO | WO2009102468 A1 | 8/2009 |
| WO | WO2009131687 A2 | 10/2009 |
| WO | WO2009136995 A2 | 11/2009 |
| WO | WO2009145856 A1 | 12/2009 |
| WO | WO2010068257 A1 | 6/2010 |
| WO | WO2010068258 A1 | 6/2010 |
| WO | 2011/075515 A1 | 6/2011 |
| WO | WO2014031438 A2 | 2/2014 |

OTHER PUBLICATIONS

Gura, Systems for identifying New Drugs Are Often Faulty, Cancer Models, Science, vol. 278, No. 5340, pp. 1041-1042, Nov. 1997.*
Pamuk et al., Spleen tyrosine kinase inhibition in the treatment of autoimmune, allergic and autoinflammatory diseases, Arthritis Research & Therapy, (2010), 12:222, pp. 1-11.*
International Search Report and Written Opinion for PCT/US13/46151 mailed on Nov. 1, 2013.
Villasenor et al., Structural Insights for Design of Potent Spleen Tyrosine Kinase Inhibitors from Crystallographic Analysis of Three Inhibitor Complexes, Chem Biol Drug Des., 2009, 466-470, 73.
Yamamoto et al, "The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents", The Journal of Pharmacology and Experimental Therapeutics, 2003, pp. 1174-1181, vol. 306(3).
European Search Report for PCT/US2013/046151 mailed Nov. 18, 2015.

* cited by examiner

SUBSTITUTED PYRIDINE SPLEEN TYROSINE KINASE (SYK) INHIBITORS

CROSS REFERENCE TO RELATED APPLICATIONS

This application is a U.S. National Phase application under 35 U.S.C. §371 of PCT Application No. PCT/US2013/046151, filed Jun. 17, 2013, which claims priority under 35 U.S.C. §119(e) from U.S. Provisional Application No. 61/663,290, filed Jun. 22, 2012.

FIELD OF THE INVENTION

The present invention relates to certain substituted pyridine compounds of the Formula (I) (also referred to herein as the "compounds of the Formula (I)" or "compounds of Formula (I)") which are inhibitors of Spleen Tyrosine Kinase (Syk) kinase activity, or are prodrugs thereof. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signalling cascade. In mast cells, for example, the early sequence of $Fc_{epsilon}RI$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, *Journal of Allergy and Clinical Immunology* (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterized by a block in B cell development (M. Turner et al. 1995 *Nature* 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

SUMMARY OF THE INVENTION

The present invention provides novel compounds that are potent inhibitors of Syk, or are prodrugs thereof, as well as pharmaceutical compositions containing them. As Syk inhibitors compounds of Formula (I) are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or condition mediated by Syk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of cancer pain or an inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 F atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocyclyl as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl," as used herein, refers to a non-aromatic saturated or partially saturated monocyclic or multicyclic ring system containing 3 to 11 ring atoms, wherein from 1 to 4 of the ring atoms are independently O, S, or N, and the remainder of the ring atoms are carbon atoms. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. A heterocyclyl group can be joined to the rest of the molecule via a ring carbon or ring nitrogen atom. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms.

The term "spiroheterocyclic ring," as used herein, refers to a bicyclic heterocyclic ring as defined above wherein the two rings are joined through a common ring carbon atom. In one embodiment, a spiroheterocyclic ring is a 8- to 11-membered ring system containing one to three heteroatoms, e.g., one to two heteroatoms, selected from the group consisting of N and O. Non-limiting examples of heterocyclic rings include 1,9-diazaspiro[5.5]undecane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa- 7-azaspiro[4.5]decane; 1,4-dioxa-7-azaspiro[4.5]decane; 1,4-dioxa-8-azaspiro[4.5]decane, and 1,4-dioxaspiro[4.5]decane.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

When a structural formula specifies a methylene or substituted methylene group in parentheses which bridges two adjacent moieties, and a variable to indicate the number of such methylenes, when such variable is 0, it is meant that such methylene group is replaced by a bond. By way of example, in the group of the formula

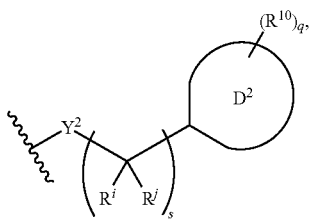

when s is 0, it is meant that $Y^2$ is bonded to D2 as shown in the following structural formula:

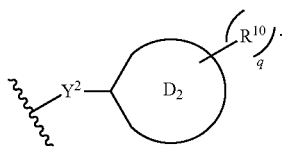

In the structural formula for the group

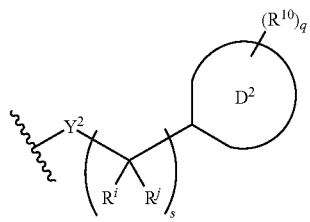

for $R^{cy}$, it will be understood that the moiety $R^{10}$ may be substituted on the ring carbon atom which joins D2 to the remaining structure of group (and may be substituted on other ring atoms), where the valency of such ring carbon atom permits substitution. By way of example in some embodiments, the group $R^{cy}$ has the formula

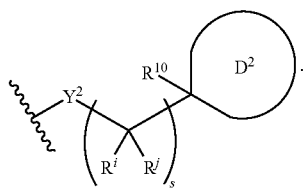

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $R^1$, $R^2$, $R^3$, $R^4$, $R^{cy}$, $C^y$, and t are as defined below. Described below are embodiments of the compound of Formula (I). The compounds of the Formulas (IA) and (IB), shown below, are embodiments of the compound of Formula (I).

In embodiment no. 1, the invention provides a compound of Formula (I),

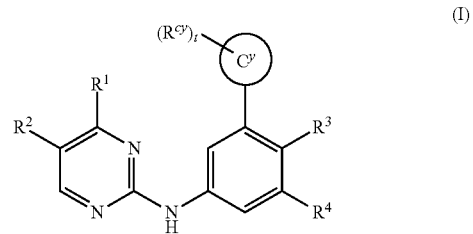

or a pharmaceutically acceptable salt thereof, wherein
$R^1$ is selected from the group consisting of H, $C_1$-$C_3$ alkyl, $C_1$-$C_3$ fluoroalkyl, $C_1$-$C_3$ alkoxy, $C_3$-$C_6$ cycloalkyl, and 4-piperidinyloxy;
$R^2$ is selected from the group consisting of H, methyl, methoxy, —CHF$_2$, —CF$_3$, halo, and cyano;
$R^3$ is selected from the group consisting of H, $C_1$-$C_3$ alkyl and halo;

$R^4$ is selected from the group consisting of H, $C_1$-$C_3$ alkyl, $C_1$-$C_3$ fluoroalkyl, $C_3$-$C_6$ cycloalkyl, halo, —$N(R^{4a})_2$, —$N(R^{4a})C(O)R^{4b}$, —$N(R^{4a})C(O)N(R^{4a})_2$, —$CO_2H$,

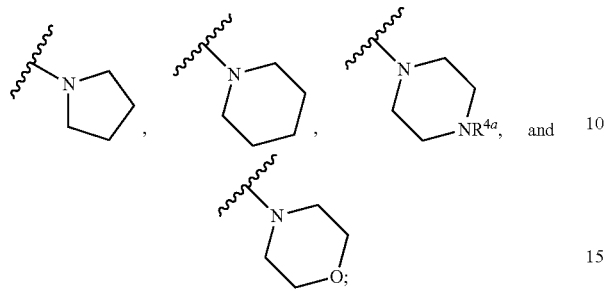
and each $R^{4a}$ is independently selected from the group consisting of H and $C_1$-$C_3$ alkyl;
$R^{4b}$ is $C_1$-$C_3$ alkyl;
$C^y$ is a 6-membered heteroaryl selected from the group consisting of:

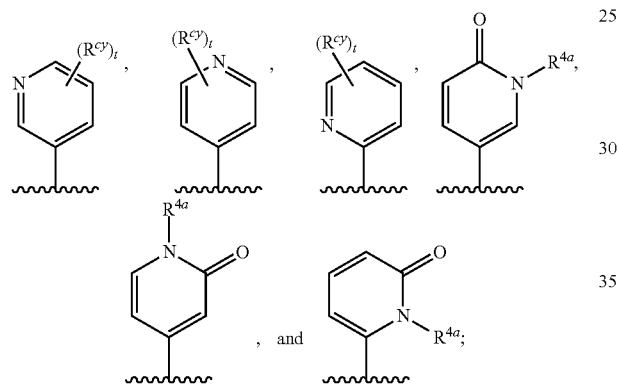
, and t is 0, 1, 2, or 3;
each $R^{cy}$ is independently selected from the group consisting of:
A. a group of the formula

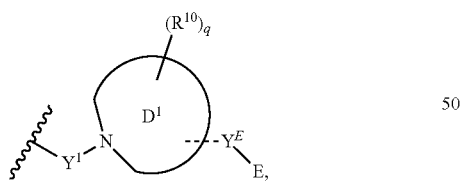

wherein
$Y^1$ is a bond, —$CH_2$—, or —C(O)—;
$D^1$ is
(i) a 4- to 9-membered mono- or bicyclic heterocyclic ring optionally containing one to two additional heteroatoms selected from the group consisting of N, O, S, S(O), and $S(O)_2$;
(ii) a 9- to 11-membered spiroheterocyclic ring containing one to two additional heteroatoms selected from the group consisting of N and O;
each $R^{10}$ is independently selected from the group consisting of $C_1$-$C_3$ alkyl, $C_1$-$C_3$ alkoxy, halo, hydroxyl, $C_1$-$C_3$ fluoroalkyl, —$(CH_2)_{n5}CO_2R$, hydroxyl($C_1$-$C_3$)alkyl, —$(CH_2)_{n5}OCH_3$, —C(O)—($C_1$-$C_3$)alkyl, —$(CH_2)_{n5}C(O)N(R^h)_2$, —$S(O)_2$—($C_1$-$C_3$)alkyl, —$C(O)CH_2CN$, and —$C(O)CH_2OH$, or wherein when two $R^{10}$ moieties are geminally substituted on a common ring carbon atom of $D^1$, the two geminally substituted $R^{10}$ moieties together with the carbon atom on which they are attached form —C(O)—;
n5 is 0, 1, 2, or 3;
each $R^g$ is independently selected from the group consisting of:
(i) H;
(ii) $C_1$-$C_8$ alkyl;
(iii) a group of the formula -M-$R^{CH}$, wherein
M is a bond or —$(CH_2)_{n6}$—, wherein n6 is 1 or 2;
$R^{CH}$ is (a) aryl or $C_3$-$C_6$ cycloalkyl optionally substituted with 1-3 groups independently selected from halo, $C_1$-$C_4$ alkyl, or $C_1$-$C_4$ alkoxy; or (b) a 5- to 6-membered monocyclic heterocycle containing 1 or 2 heteroatoms independently selected from the group consisting of N and O, wherein said heterocycle of $R^{CH}$ is optionally substituted with 1 or 2 groups independently selected from the group consisting of oxo and $C_{1-3}$ alkyl;
(iv) a group of the formula —$(CH_2)_{n6}$—$R^m$ or —$(CH_2)_2$—O—$(CH_2)_2$—$R^m$ wherein
$R^m$ is —$CO_2R^{m1}$, —$C(O)N(R^{m2})_2$, or —$O(CO)R^{m1}$;
$R^{m1}$ is $C_1$-$C_4$ alkyl; and
$R^{m2}$ is H or $C_1$-$C_4$ alkyl;
n6 is 1 or 2;
(v) a group of the formula —$(CH_2)_2$—$R^n$,
$R^n$ is OH, —O—($C_1$-$C_4$ alkyl), —O—$(CH_2)_2$—O—($C_1$-$C_4$ alkyl), $NH_2$, —N(H)($C_1$-$C_4$ alkyl) or —$N(C_1$-$C_4$ alkyl)$_2$;
(vi) a group of the formula

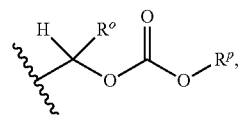

wherein
$R^o$ is H or $C_1$-$C_4$ alkyl; and
$R^p$ is $C_1$-$C_4$ alkyl, $C_3$-$C_6$ cycloalkyl, or phenyl; and,
(vii) a group of the formula

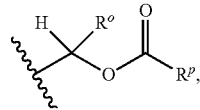

wherein $R^o$ and $R^p$ are as set forth above;
each $R^h$ is independently H, $C_1$-$C_3$ alkyl, $C_3$-$C_6$ cycloalkyl, —$CH_2CO_2H$, —$CH_2C(O)NH_2$, —$S(O)_2$—$C_1$-$C_3$ alkyl, or —$S(O)_2$—$NH_2$;
q is 0, 1, 2, 3, 4, or 5;
the group —$Y^E$-E is absent or present, and if present, —$Y^E$ is a bond or —C(O)—;

E is
  (i) a $C_3$-$C_6$ cycloalkyl ring;
  (ii) a 5- or 6-membered heterocyclic ring containing one N atom; or
  (iii) an indolyl,
  wherein E is unsubstituted or substituted by one to three $R^{YE}$ moieties, wherein said $R^{YE}$ moieties are selected from the group consisting of $C_1$-$C_3$ alkyl, —$CO_2H$, or wherein when two $R^{YE}$ moieties are geminally substituted on a common ring carbon atom of E, the two geminally substituted $R^{YE}$ moieties together with the carbon atom on which they are attached form —C(O)—;

B. a group of the formula

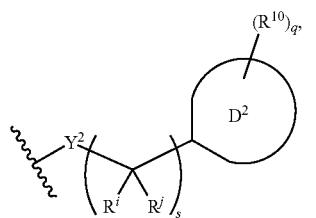

wherein
  $Y^2$ is a bond, —$CH_2$—, —C(O)—, —N($R^k$)—, —O—, —C(O)—N($R^k$)—, —$S(O)_2$—N($R^k$)—, or —N($R^k$)—$S(O)_2$—;
  $R^k$ is H or $C_1$-$C_3$ alkyl;
  $D^2$ is selected from the group consisting of:
    (i) a $C_3$-$C_6$ cycloalkyl,
    (ii) a 5- to 9-membered mono- or bicyclic heterocyclyl containing 1 or 4 heteroatoms selected from the group consisting of N, O, S, S(O), and $S(O)_2$;
    (iii) a 5- to 6-membered heteroaryl containing 1 to 2 heteroatoms selected from the group consisting of N, O, and S, wherein said heteroaryl of D2 is other than indolyl; and
    (iv) phenyl;
  each $R^i$ is independently H, $C_1$-$C_3$ alkyl, hydroxyl, —$CO_2H$, or —N(H)C(O)$NH_2$;
  each $R^j$ is independently H, $C_1$-$C_4$ alkyl, or cyclopropyl;
  s is 0, 1, 2, or 3; and
  $R^{10}$ and q are as described above;

C. a group of the formula

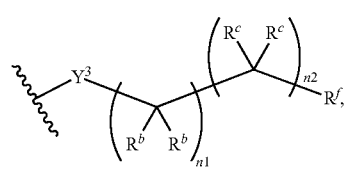

wherein
$Y^3$ is (i) a bond,

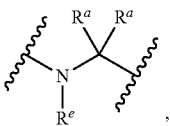  (ii)

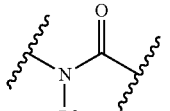  (iii)

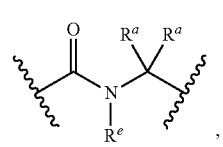  (iv)

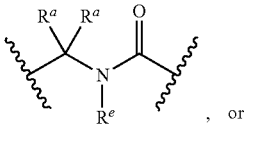  (v)

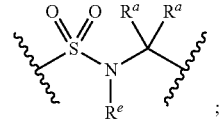  , or (vi) shown above;

$R^e$ is H, $C_1$-$C_3$ alkyl; hydroxyl($C_2$-$C_3$)alkyl, or —($CH_2$)$_{n3}$CN;
    wherein n3 is 2 or 3
  each $R^a$ is independently selected from the group consisting of H, $C_1$-$C_6$ alkyl, $C_1$-$C_3$ fluoroalkyl, hydroxy($C_1$-$C_3$)alkyl, —($CH_2$)$_{n4}$—O—($C_1$-$C_3$)alkyl, —($CH_2$)$_{n4}$C(O)$NH_2$, —($CH_2$)$_{n4}$S—($C_1$-$C_3$)alkyl, and —($CH_2$)$_{n4}$$S(O)_2$—($C_1$-$C_3$)alkyl;
    wherein each n4 is independently 1, 2 or 3;
  each $R^b$ is independently selected from the group consisting of H, hydroxyl, fluoro, $C_1$-$C_6$ alkyl, $C_1$-$C_3$ fluoroalkyl, hydroxy($C_1$-$C_3$)alkyl, —($CH_2$)$_{n4}$—O—($C_1$-$C_3$)alkyl, —($CH_2$)$_{n4}$C(O)$NH_2$, —($CH_2$)$_{n4}$S—($C_1$-$C_3$)alkyl, and —($CH_2$)$_{n4}$$S(O)_2$—($C_1$-$C_3$)alkyl;
  each $R^c$ is independently selected from the group consisting of H and $C_1$-$C_3$ alkyl;
  $R^f$ is H, $CHF_2$, $CF_3$, —$CO_2R^g$, —C(O)N($R^h$)$_2$, —CN, hydroxyl, —N($R^h$)$_2$, or ($C_1$-$C_3$)alkoxy,
  n1 is 0, 1, 2, or 3;
  n2 is 0 or 1;
  $R^g$ and $R^h$ are as defined above;
D. amino;
E. halo;
F. —C(O)$NH_2$;
G. —$S(O)_2NH_2$;
H. a group of the formula

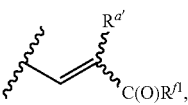

wherein
R$^{a'}$ is H or F; and
R$^{f1}$ is hydroxyl, C$_1$-C$_3$ alkoxy, or —NH$_2$;

I. —C(O)—R$^q$, wherein R$^q$ is C$_1$-C$_3$ alkyl, or —(CH$_2$)$_{n4}$CN, wherein n4 is as defined above;

J. —C(O)N(H)—S(O)$_2$—R$^s$, wherein R$^s$ is C$_1$-C$_3$ alkyl, —NH$_2$, —N(H)(C$_1$-C$_3$ alkyl), or —N(C$_1$-C$_3$ alkyl)$_2$;

K. a group of the —N(H)C(O)—CH$_2$—C(O)OR$^g$ or —N(H)S(O)$_2$—CH$_2$—C(O)OR$^g$; and L. —N(H)S(O)$_2$—(C$_1$-C$_3$ alkyl);

or two R$^{cy}$ moieties when substituted on adjacent carbon atoms of Cy optionally form a 5- or 6-membered ring selected from the group consisting of pyrroline, imidazolidone, or dihydrooxazine, wherein said 5- or 6-membered ring is unsubstituted or substituted by C$_1$-C$_3$ alkyl.

In embodiment no. 2, the invention provides a compound of Formula (I) wherein In embodiment no. 2, the invention provides a compound of Formula (I) wherein C$^y$ is a 6-membered heteroaryl selected from the group consisting of:

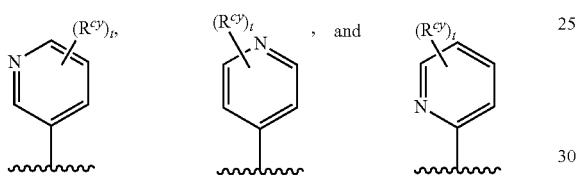

and the remaining variables are as described in embodiment no. 1.

In embodiment no. 3, the invention provides a compound of Formula (I), wherein t is 1; and R$^{cy}$ is a group of the formula

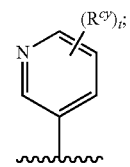

wherein Y$^1$, D$^1$, R$^{10}$, q, Y$^E$, and E are as set forth in embodiment no. 1.

In embodiment no. 4, the invention provides a compound of Formula (I), wherein t is 1 and R$^{cy}$ is a group of the formula

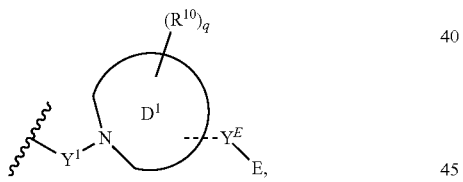

wherein Y$^2$, D$^2$, R$^{10}$, R$^i$, R$^j$, s, q, and E are as set forth in embodiment no. 1.

In embodiment no. 5, the invention provides a compound of Formula (I), wherein t is 1 and R$^{cy}$ is a group of the formula

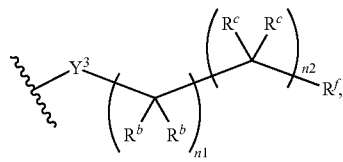

wherein Y$^3$, R$^b$, R$^c$, R$^f$, n1 and n2 are as set forth in embodiment no. 1.

In embodiment no. 6, the invention provides a compound of Formula (I), wherein
R$^1$ is selected from the group consisting of C$_1$-C$_3$ fluoroalkyl;
R$^2$ is H;
R$^3$ is H;
R$^4$ is selected from the group consisting of C$_1$-C$_3$ alkyl and —N(H)C(O)R$^{4b}$;
R$^{4b}$ is C$_{1-3}$ alkyl;
C$^y$ is

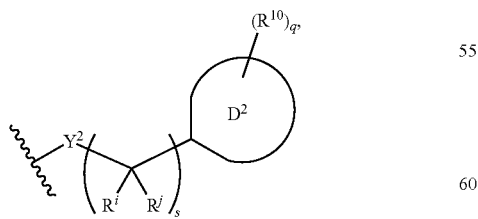

t is 1;
R$^{cy}$ is a group of the formula

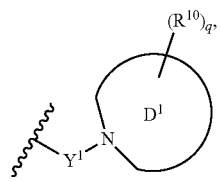

wherein
Y1 is a bond;
D$^1$ is a 4- to 8-membered mono- or bicyclic heterocyclic ring optionally containing one additional heteroatom selected from the group consisting of N and S;
each R$^{10}$ is independently selected from the group consisting of C$_1$-C$_3$ alkyl, hydroxyl, —CO$_2$H, —CH$_2$CO$_2$R$^g$, —C(O)N(H)—(CH$_2$CO$_2$H), or wherein when two R$^{10}$ moieties are geminally substituted on a common ring carbon atom of D$^1$, the two geminally substituted R$^{10}$ moieties together with the carbon atom on which they are attached form —C(O)—;
R$^g$ is as set forth in embodiment no. 1; and
q is 1.

In embodiment no. 7, the invention provides a compound of Formula (I), wherein
R$^1$ is selected from the group consisting of C$_1$-C$_3$ alkyl, C$_1$-C$_3$ fluoroalkyl, C$_1$-C$_3$ alkoxy, and cyclopropyl;
R$^2$ is H or halo;
R$^3$ is H;
R$^4$ is selected from the group consisting of H, C$_1$-C$_3$ alkyl, and halo;
C$^y$ is a 6-membered heteroaryl selected from the group consisting of:

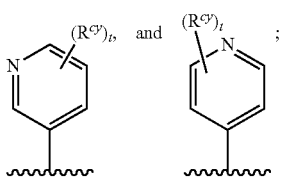

t is 1;
$R^{cy}$ is a group of the formula

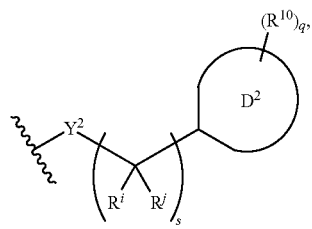

wherein
$Y^2$ is a bond or —N(H)—;
s is 0, 1 or 2;
$R^i$ is H, methyl, hydroxyl, or —$CO_2H$;
$R^j$ is H or methyl;
$D^2$ is selected from the group consisting of:
  (i) cyclohexyl;
  (ii) a 5- to 6-membered heterocyclyl containing one to two N atoms;
  (iii) a 5-membered heteroaryl containing two to three N atoms; and
  (iv) phenyl;
each $R^{10}$ is independently selected from the group consisting of $C_1$-$C_3$ alkyl, hydroxyl, —$CO_2R^g$, —C(O)NH_2, —$C(O)CH_2CN$, and —$C(O)CH_2OH$;
$R^g$ is as set forth in embodiment no. 1; and
q is 0, 1, 2, 3, or 4.

In embodiment no. 8, the invention provides a compound of Formula (I), wherein
$R^1$ is selected from the group consisting of $C_1$-$C_3$ fluoroalkyl and cyclopropyl;
$R^2$ is H or halo;
$R^3$ is H;
$R^4$ is selected from the group consisting of H, $C_1$-$C_3$ alkyl, and —$N(H)C(O)R^{4b}$;
$R^{4b}$ is $C_1$-$C_3$ alkyl;
$C^y$ is a 6-membered heteroaryl selected from the group consisting of:

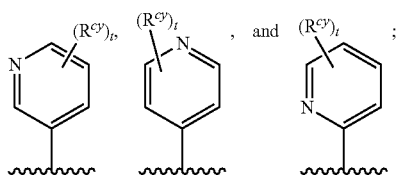

t is 1;
$R^{cy}$ is a group of the formula

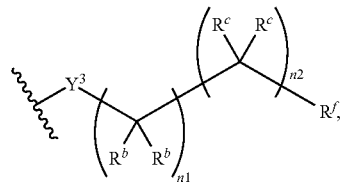

wherein
$Y^3$ is a bond,

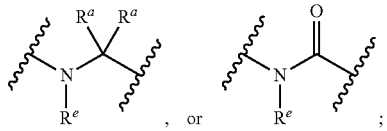

$R^e$ is H, $C_1$-$C_3$ alkyl, or —$(CH_2)_{n3}CN$;
  wherein n3 is 2 or 3;
each $R^a$ is independently selected from the group consisting of H, $C_1$-$C_6$ alkyl, hydroxy($C_1$-$C_3$)alkyl, —$(CH_2)_{n4}$—O—$(C_1$-$C_3)$alkyl, —$(CH_2)_{n4}C(O)NH_2$, —$(CH_2)_{n4}S$—$(C_1$-$C_3)$alkyl, and —$(CH_2)_{n4}S(O)_2$—$(C_1$-$C_3)$alkyl; wherein each n4 is independently 1, 2, or 3;
each $R^b$ is independently selected from the group consisting of H, hydroxyl, $C_1$-$C_6$ alkyl, fluoro, $C_1$-$C_3$ fluoralkyl, hydroxy($C_1$-$C_3$)alkyl, —$(CH_2)_{n4}$—O—$(C_1$-$C_3)$alkyl, —$(CH_2)_{n4}C(O)NH_2$, —$(CH_2)_{n4}S$—$(C_1$-$C_3)$alkyl, and —$(CH_2)_{n4}S(O)_2$—$(C_1$-$C_3)$alkyl;
each $R^c$ is independently selected from the group consisting of H and $C_1$-$C_3$ alkyl;
$R^f$ is —$CO_2R^g$, hydroxyl, or —$C(O)N(R^h)_2$;
$R^g$ is as set forth in embodiment no. 1;
  wherein each $R^h$ is independently H, $C_1$-$C_3$ alkyl, or —$CH_2CO_2H$;
n1 is 0, 1 or 2; and
n2 is 0 or 1.

In embodiment no. 9, the invention provides a compound having the Formula (IA),

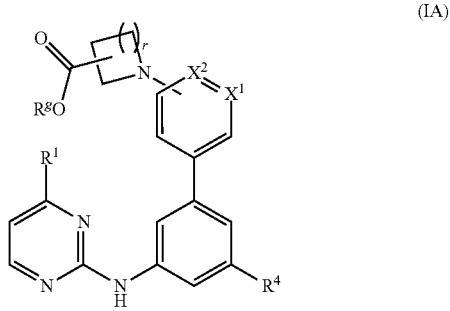

(IA)

wherein
$R^1$ is selected from the group consisting of $C_1$-$C_3$ alkyl, $C_1$-$C_3$ fluoroalkyl, and $C_3$-$C_6$ cycloalkyl;
$R^4$ is selected from the group consisting of H, $C_1$-$C_3$ alkyl and $C_1$-$C_3$ fluoroalkyl;

one of $X^1$ and $X^2$ is N and the other is C;
r is 1, 2, or 3; and
$R^g$ is as set forth in embodiment no. 1.

In embodiment no. 10, the invention provides a compound having the Formula (IA), wherein the group

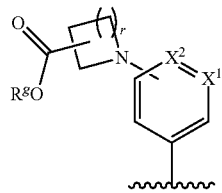

has the formula

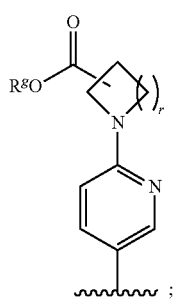

$R^1$ is selected from the group consisting of methyl, —$CF_3$, and cyclopropyl;

$R^4$ is selected from the group consisting of H, methyl, and —$CF_3$; and r is 1 or 2.

In embodiment no. 11, the invention provides a compound having the Formula (IA), wherein the group

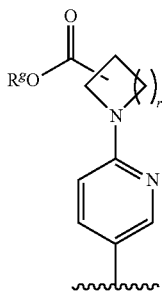

has the formula

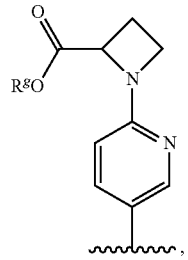

and the remaining variables are as set forth in embodiment no. 10.

In embodiment no. 12, the invention provides a compound having the Formula (IB),

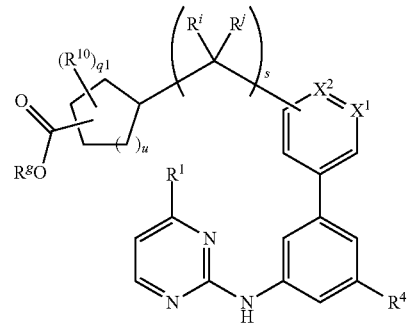

(IB)

wherein $R^1$ is selected from the group consisting of $C_1$-$C_3$ alkyl, $C_1$-$C_3$ fluoroalkyl, and $C_3$-$C_6$ cycloalkyl;

$R^4$ is selected from the group consisting of H, $C_1$-$C_3$ alkyl and $C_1$-$C_3$ fluoroalkyl;

one of $X^1$ and $X^2$ is N and the other is C;

$R^i$ is H or hydroxyl;

$R^j$ is H or $C_1$-$C_3$ alkyl;

s is 0, 1, 2, or 3;

$R^{10}$ is $C_1$-$C_3$ alkyl or hydroxyl;

q1 is 0, 1, 2, or 3;

u is 1 or 2; and $R^g$ is as set forth in embodiment no. 1.

In embodiment no. 13, the invention provides a compound having the Formula (IB), wherein.

$R^1$ is selected from the group consisting of methyl, —$CF_3$, and cyclopropyl;

$R^4$ is selected from the group consisting of H, methyl, and —$CF_3$; and $R^i$ is H or hydroxyl;

$R^j$ is H or methyl;

s is 0 or 1; and $R^{10}$ is methyl or hydroxyl; and $X^1$ and $X^2$ are as set forth in embodiment no. 12;

$R^g$ is as set forth in embodiment no. 1.

In embodiment no. 14, the invention provides a compound having the Formula (IB), wherein the group

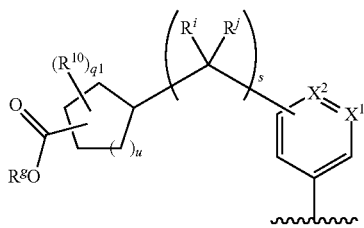

is a group of the formula

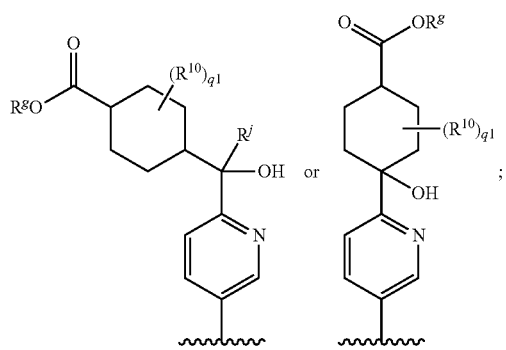

q1 is 0, 1, or 2;
$R^1$, $R^4$, $R^i$, $R^j$, s, and $R^{10}$ are as set forth in embodiment no. 10; and
$R^g$ is as set forth in embodiment no. 1.

In embodiment no. 15, the invention provides a compound having the Formula (I), (IA), or (IB), wherein $R^g$ is H or $C_1$-$C_3$ alkyl; and wherein the remaining variables are as described in any one of embodiment nos. 1-14.

In embodiment no. 16, the invention provides a compound having the Formula (I), (IA), or (IB), wherein $R^g$ is H; and wherein the remaining variables are as described in any one of embodiment nos. 1-14.

In embodiment no. 17, the compound is selected from any one of the compounds described in Examples 1-29.

In embodiment no. 18, the compound is selected from any one of the compounds described in Examples 1-26.

In embodiment no. 19, the compound is selected from any one of the following compounds:

trans-4-[1-hydroxy-1-(5-{3-[(4-methoxypyrimidin-2-yl)amino]-5-methylphenyl}pyridin-2-yl)ethyl]cyclohexanecarboxylic acid;
trans-4-{1-[5-(3-{[4-(difluoromethyl)pyrimidin-2-yl]amino}-5-methylphenyl)pyridin-2-yl]-1-hydroxyethyl}cyclohexanecarboxylic acid;
trans-4-{1-hydroxy-1-[5-(3-methyl-5-{[4-(trifluoromethyl)pyrimidin-2-yl]amino}phenyl)pyridin-2-yl]ethyl}cyclohexanecarboxylic acid;
trans-4-[1-hydroxy-1-(5-{3-methyl-5-[(4-methylpyrimidin-2-yl)amino]phenyl}pyridin-2-yl)ethyl]cyclohexanecarboxylic acid;
2-methyl-N-[5-(3-methyl-5-{[4-(trifluoromethyl)pyrimidin-2-yl]amino}phenyl)pyridin-2-yl]alanine;
trans-4-[1-(5-{3-[(4-cyclopropylpyrimidin-2-yl)amino]-5-methylphenyl}pyridin-2-yl)-1-hydroxyethyl]cyclohexanecarboxylic acid;
cis-4-hydroxy-4-[5-(3-methyl-5-{[4-(trifluoromethyl)pyrimidin-2-yl]amino}phenyl)pyridin-2-yl]cyclohexanecarboxylic acid;
trans-4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid;
1-{[5-(3-methyl-5-{[4-(trifluoromethyl)pyrimidin-2-yl]amino}phenyl)pyridin-2-yl]amino}cyclobutanecarboxylic acid;
3-[5-(3-Methyl-5-{[4-(trifluoromethyl)pyrimidin-2-yl]amino}phenyl)pyridin-2-yl]propanoic acid;
1-[5-(3-methyl-5-{[4-(trifluoromethyl)pyrimidin-2-yl]amino}phenyl)pyridin-2-yl]-L-proline;
N-[5-(3-methyl-5-{[4-(trifluoromethyl)pyrimidin-2-yl]amino}phenyl)pyridin-2-yl]serine;
N-[5-(3-methyl-5-{[4-(trifluoromethyl)pyrimidin-2-yl]amino}phenyl)pyridin-2-yl]-L-homoserine;
4-{[5-(3-methyl-5-{[4-(trifluoromethyl)pyrimidin-2-yl]amino}phenyl)pyridin-2-yl]amino}piperidine-4-carboxylic acid;
1-[5-(3-methyl-5-{[4-(trifluoromethyl)pyrimidin-2-yl]amino}phenyl)pyridin-2-yl]azetidine-2-carboxylic acid;
O-methyl-N-[5-(3-methyl-5-{[4-(trifluoromethyl)pyrimidin-2-yl]amino}phenyl)pyridin-2-yl]serine;
1-{[5-(3-methyl-5-{[4-(trifluoromethyl)pyrimidin-2-yl]amino}phenyl)pyridin-2-yl]amino}cyclopentanecarboxylic acid;
1-{[5-(3-methyl-5-{[4-(trifluoromethyl)pyrimidin-2-yl]amino}phenyl)pyridin-2-yl]amino}cyclopropanecarboxylic acid;
2-methyl-1-[5-(3-methyl-5-{[4-(trifluoromethyl)pyrimidin-2-yl]amino}phenyl)pyridin-2-yl]-L-proline;
N-[5-(3-methyl-5-{[4-(trifluoromethyl)pyrimidin-2-yl]amino}phenyl)pyridin-2-yl]-L-alanine;
N-[5-(3-methyl-5-{[4-(trifluoromethyl)pyrimidin-2-yl]amino}phenyl)pyridin-2-yl]glycine;
N-[5-(3-methyl-5-{[4-(trifluoromethyl)pyrimidin-2-yl]amino}phenyl)pyridin-2-yl]-D-alanine;
N-[5-(3-methyl-5-{[4-(trifluoromethyl)pyrimidin-2-yl]amino}phenyl)pyridin-2-yl]-D-valine;
N-[5-(3-methyl-5-{[4-(trifluoromethyl)pyrimidin-2-yl]amino}phenyl)pyridin-2-yl]-L-threonine;
N-2-[5-(3-methyl-5-{[4-(trifluoromethyl)pyrimidin-2-yl]amino}phenyl)pyridin-2-yl]-D-asparagine;
N-2-[5-(3-methyl-5-{[4-(trifluoromethyl)pyrimidin-2-yl]amino}phenyl)pyridin-2-yl]-L-asparagine;
N-[5-(3-methyl-5-{[4-(trifluoromethyl)pyrimidin-2-yl]amino}phenyl)pyridin-2-yl]-L-methionine;
2-{[5-(3-methyl-5-{[4-(trifluoromethyl)pyrimidin-2-yl]amino}phenyl)pyridin-2-yl]amino}butanoic acid;
N-[5-(3-methyl-5-{[4-(trifluoromethyl)pyrimidin-2-yl]amino}phenyl)pyridin-2-yl]-L-leucine;
N-[5-(3-methyl-5-{[4-(trifluoromethyl)pyrimidin-2-yl]amino}phenyl)pyridin-2-yl]-L-histidine;
4-[5-(3-Methyl-5-{[4-(trifluoromethyl)pyrimidin-2-yl]amino}phenyl)pyridin-3-yl]piperidin-4-ol;
3-hydroxy-3-[5-(3-methyl-5-{[4-(trifluoromethyl)pyrimidin-2-yl]amino}phenyl)pyridin-2-yl]cyclohexanecarboxylic acid;
(2S)-1-[5-(3-methyl-5-{[4-(trifluoromethyl)pyrimidin-2-yl]amino}phenyl)pyridin-2-yl]azetidine-2-carboxylic acid;
1-[5-(3-methyl-5-{[4-(trifluoromethyl)pyrimidin-2-yl]amino}phenyl)pyridin-2-yl]azetidine-2-carboxylic acid;
1-[5-(3-methyl-5-{[4-(trifluoromethyl)pyrimidin-2-yl]amino}phenyl)pyridin-2-yl]piperidine-2-carboxylic acid;
2,2-dimethyl-3-[5-(3-methyl-5-{[4-(trifluoromethyl)pyrimidin-2-yl]amino}phenyl)pyridin-2-yl]propanoic acid;

trans-4-[(5-{3-methyl-5-[(4-methylpyrimidin-2-yl)amino]
phenyl}pyridin-2-yl)amino]cyclohexanecarboxylic acid;
trans-4-[(5-{3-[(4-methoxypyrimidin-2-yl)amino]-5-
methylphenyl}pyridin-2-yl)amino]cyclohexanecarboxylic acid;
4-{1-hydroxy-1-[5-(3-methyl-5-{[4-(trifluoromethyl)pyrimidin-2-yl]amino}phenyl)pyridin-2-yl]ethyl}benzoic acid;
3-methyl-N-[5-(3-methyl-5-{[4-(trifluoromethyl)pyrimidin-2-yl]amino}phenyl)pyridin-2-yl]-L-valine;
cis-4-{[5-(3-methyl-5-{[4-(trifluoromethyl)pyrimidin-2-yl]amino}phenyl)pyridin-2-yl]amino}cyclohexanecarboxylic acid;
trans-4-{[5-(3-methyl-5-{[4-(trifluoromethyl)pyrimidin-2-yl]amino}phenyl)pyridin-2-yl]amino}cyclohexanecarboxylic acid;
2-methyl-N-[5-(3-{[4-(trifluoromethyl)pyrimidin-2-yl]amino}phenyl)pyridin-2-yl]alanine;
N-[5-(3-methyl-5-{[4-(trifluoromethyl)pyrimidin-2-yl]amino}phenyl)pyridin-2-yl]-beta-alanine;
N-[5-(3-methyl-5-{[4-(trifluoromethyl)pyrimidin-2-yl]amino}phenyl)pyridin-2-yl]-L-phenylalanine;
3-{[5-(3-methyl-5-{[4-(trifluoromethyl)pyrimidin-2-yl]amino}phenyl)pyridin-2-yl]amino}-3-oxopropanoic acid;
1-{5-[3-(acetylamino)-5-{[4-(trifluoromethyl)pyrimidin-2-yl]amino}phenyl]pyridin-2-yl}azetidine-2-carboxylic acid;
N-{5-[3-(acetylamino)-5-{[4-(trifluoromethyl)pyrimidin-2-yl]amino}phenyl]pyridin-2-yl}-2-methylalanine;
2-methyl-2-{[4-(3-methyl-5-{[4-(trifluoromethyl)pyrimidin-2-yl]amino}phenyl)pyridin-2-yl]amino}propane-1,3-diol;
2-methyl-2-{[4-(3-methyl-5-{[4-(trifluoromethyl)pyrimidin-2-yl]amino}phenyl)pyridin-2-yl]amino}propan-1-ol;
2-{[4-(3-methyl-5-{[4-(trifluoromethyl)pyrimidin-2-yl]amino}phenyl)pyridin-2-yl]amino}propan-1-ol;
5-hydroxy-5-[5-(3-methyl-5-{[4-(trifluoromethyl)pyrimidin-2-yl]amino}phenyl)pyridin-2-yl]azepan-2-one;
N-[5-(3-methyl-5-{[4-(trifluoromethyl)pyrimidin-2-yl]amino}phenyl)pyridin-2-yl]-D-histidine;
4-{[5-(3-methyl-5-{[4-(trifluoromethyl)pyrimidin-2-yl]amino}phenyl)pyridin-2-yl]amino}pyrrolidin-2-one;
3-{[5-(3-methyl-5-{[4-(trifluoromethyl)pyrimidin-2-yl]amino}phenyl)pyridin-2-yl]amino}pyrrolidin-2-one;
4-hydroxy-4-[5-(3-methyl-5-{[4-(trifluoromethyl)pyrimidin-2-yl]amino}phenyl)pyridin-3-yl]piperidine-1-carboxamide;
4-[5-(3-methyl-5-{[4-(trifluoromethyl)pyrimidin-2-yl]amino}phenyl)pyridin-3-yl]piperazin-2-one;
N-(3-[6-(3-oxopiperazin-1-yl)pyridin-3-yl]-5-{[4-(trifluoromethyl)pyrimidin-2-yl]amino}phenyl)acetamide;
N,N-dimethyl-N-2-[5-(3-methyl-5-{[4-(trifluoromethyl)pyrimidin-2-yl]amino}phenyl)pyridin-2-yl]glycinamide;
3-(4-{3-[(4-cyclopropylpyrimidin-2-yl)amino]-5-methylphenyl}pyridin-2-yl)propanoic acid;
trans-4-[(5-{3-[(5-chloro-4-methylpyrimidin-2-yl)amino]-5-methylphenyl}pyridin-2-yl)amino]cyclohexanecarboxylic acid;
N-methyl-N-[5-(3-methyl-5-{[4-(trifluoromethyl)pyrimidin-2-yl]amino}phenyl)pyridin-2-yl]-L-alanine;
trans-4-[(5-{3-[(5-fluoro-4-methoxypyrimidin-2-yl)amino]-5-methylphenyl}pyridin-2-yl)amino]cyclohexanecarboxylic acid;
1-[5-(3-methyl-5-{[4-(trifluoromethyl)pyrimidin-2-yl]amino}phenyl)pyridin-2-yl]piperidine-3-carboxylic acid;
N-[5-(3-methyl-5-{[4-(trifluoromethyl)pyrimidin-2-yl]amino}phenyl)pyridin-2-yl]-D-leucine;
4-(methylsulfonyl)-2-{[5-(3-methyl-5-{[4-(trifluoromethyl)pyrimidin-2-yl]amino}phenyl)pyridin-2-yl]amino}butanoic acid;
N-(2-cyanoethyl)-N-[5-(3-methyl-5-{[4-(trifluoromethyl)pyrimidin-2-yl]amino}phenyl)pyridin-2-yl]glycine;
1-[5-(3-methyl-5-{[4-(trifluoromethyl)pyrimidin-2-yl]amino}phenyl)pyridin-2-yl]-L-prolylglycine;
1-[5-(3-methyl-5-{[4-(trifluoromethyl)pyrimidin-2-yl]amino}phenyl)pyridin-2-yl]-L-proline;
2,2-difluoro-3-hydroxy-3-[5-(3-methyl-5-{[4-(trifluoromethyl)pyrimidin-2-yl]amino}phenyl)pyridin-2-yl]propanoic acid;
2,2-difluoro-3-[5-(3-methyl-5-{[4-(trifluoromethyl)pyrimidin-2-yl]amino}phenyl)pyridin-2-yl]propanoic acid;
3-hydroxy-2,2-dimethyl-3-[5-(3-methyl-5-{[4-(trifluoromethyl)pyrimidin-2-yl]amino}phenyl)pyridin-2-yl]propanoic acid;
3-hydroxy-3-[5-(3-methyl-5-{[4-(trifluoromethyl)pyrimidin-2-yl]amino}phenyl)pyridin-3-yl]pyrrolidine-1-carboxamide;
{1-[5-(3-methyl-5-{[4-(trifluoromethyl)pyrimidin-2-yl]amino}phenyl)pyridin-2-yl]piperidin-2-yl}acetic acid;
1-[5-(3-methyl-5-{[4-(trifluoromethyl)pyrimidin-2-yl]amino}phenyl)pyridin-2-yl]azetidine-3-carboxylic acid;
3-hydroxy-1-[5-(3-methyl-5-{[4-(trifluoromethyl)pyrimidin-2-yl]amino}phenyl)pyridin-2-yl]-L-proline;
1-[5-(3-methyl-5-{[4-(trifluoromethyl)pyrimidin-2-yl]amino}phenyl)pyridin-2-yl]piperidine-4-carboxylic acid;
3-[5-(3-methyl-5-{[4-(trifluoromethyl)pyrimidin-2-yl]amino}phenyl)pyridin-2-yl]-1,3-thiazolidine-4-carboxylic acid;
N-[5-(3-methyl-5-{[4-(trifluoromethyl)pyrimidin-2-yl]amino}phenyl)pyridin-2-yl]glycylglycine;
{4-[5-(3-methyl-5-{[4-(trifluoromethyl)pyrimidin-2-yl]amino}phenyl)pyridin-2-yl]piperazin-1-yl}acetic acid;
N-[5-(3-{[5-bromo-4-(trifluoromethyl)pyrimidin-2-yl]amino}-5-methylphenyl)pyridin-2-yl]-2-methylalanine;
3-(5-{3-[(4-cyclopropylpyrimidin-2-yl)amino]-5-methylphenyl}pyridin-3-yl)propanoic acid; and
4-({[5-(3-methyl-5-{[4-(trifluoromethyl)pyrimidin-2-yl]amino}phenyl)pyridin-2-yl]amino}methyl)cyclohexanecarboxylic acid.

In embodiment no. 20, the compound is selected from any one of the following compounds:
trans-4-[(1R)-1-hydroxy-1-(5-{3-[(4-methoxypyrimidin-2-yl)amino]-5-methylphenyl}pyridin-2-yl)ethyl]cyclohexanecarboxylic acid;
trans-4-[(1S)-1-hydroxy-1-(5-{3-[(4-methoxypyrimidin-2-yl)amino]-5-methylphenyl}pyridin-2-yl)ethyl]cyclohexanecarboxylic acid;
trans-4-{(1R)-1-[5-(3-{[4-(difluoromethyl)pyrimidin-2-yl]amino}-5-methylphenyl)pyridin-2-yl]-1-hydroxyethyl}cyclohexanecarboxylic acid;
trans-4-{((1S))-1-[5-(3-{[4-(difluoromethyl)pyrimidin-2-yl]amino}-5-methylphenyl)pyridin-2-yl]-1-hydroxyethyl}cyclohexanecarboxylic acid;
trans-4-{(1R)-1-hydroxy-1-[5-(3-methyl-5-{[4-(trifluoromethyl)pyrimidin-2-yl]amino}phenyl)pyridin-2-yl]ethyl}cyclohexanecarboxylic acid;
trans-4-{((1S))-1-hydroxy-1-[5-(3-methyl-5-{[4-(trifluoromethyl)pyrimidin-2-yl]amino}phenyl)pyridin-2-yl]ethyl}cyclohexanecarboxylic acid;
trans-4-[(1R)-1-hydroxy-1-(5-{3-methyl-5-[(4-methylpyrimidin-2-yl)amino]phenyl}pyridin-2-yl)ethyl]cyclohexanecarboxylic acid;

trans-4-[(1S)-1-hydroxy-1-(5-{3-methyl-5-[(4-methylpyrimidin-2-yl)amino]phenyl}pyridin-2-yl)ethyl]cyclohexanecarboxylic acid;
2-methyl-N-[5-(3-methyl-5-{[4-(trifluoromethyl)pyrimidin-2-yl]amino}phenyl)pyridin-2-yl]alanine;
trans-4-[(1R)-1-(5-{3-[(4-cyclopropylpyrimidin-2-yl)amino]-5-methylphenyl}pyridin-2-yl)-1-hydroxyethyl]cyclohexanecarboxylic acid;
trans-4-[(1S)-1-(5-{3-[(4-cyclopropylpyrimidin-2-yl)amino]-5-methylphenyl}pyridin-2-yl)-1-hydroxyethyl]cyclohexanecarboxylic acid;
trans-4-[1-hydroxy-1-(5-{3-[(4-methoxypyrimidin-2-yl)amino]-5-methylphenyl}pyridin-2-yl)ethyl]cyclohexanecarboxylic acid;
cis-4-hydroxy-4-[5-(3-methyl-5-{[4-(trifluoromethyl)pyrimidin-2-yl]amino}phenyl)pyridin-2-yl]cyclohexanecarboxylic acid;
trans-4-[(1R)-1-(5-{3-[(4-cyclopropylpyrimidin-2-yl)amino]-5-methylphenyl}pyridin-2-yl)-1-hydroxyethyl]cyclohexanecarboxylic acid;
trans-4-[(1S)-1-(5-{3-[(4-cyclopropylpyrimidin-2-yl)amino]-5-methylphenyl}pyridin-2-yl)-1-hydroxyethyl]cyclohexanecarboxylic acid;
trans-4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid;
trans-4-[1-hydroxy-1-(5-{3-methyl-5-[(4-methylpyrimidin-2-yl)amino]phenyl}pyridin-2-yl)ethyl]cyclohexanecarboxylic acid;
1-{[5-(3-methyl-5-{[4-(trifluoromethyl)pyrimidin-2-yl]amino}phenyl)pyridin-2-yl]amino}cyclobutanecarboxylic acid;
3-[5-(3-methyl-5-{[4-(trifluoromethyl)pyrimidin-2-yl]amino}phenyl)pyridin-2-yl]propanoic acid;
1-[5-(3-methyl-5-{[4-(trifluoromethyl)pyrimidin-2-yl]amino}phenyl)pyridin-2-yl]-L-proline;
N-[5-(3-methyl-5-{[4-(trifluoromethyl)pyrimidin-2-yl]amino}phenyl)pyridin-2-yl]serine;
N-[5-(3-methyl-5-{[4-(trifluoromethyl)pyrimidin-2-yl]amino}phenyl)pyridin-2-yl]-L-homoserine;
4-{[5-(3-methyl-5-{[4-(trifluoromethyl)pyrimidin-2-yl]amino}phenyl)pyridin-2-yl]amino}piperidine-4-carboxylic acid;
1-[5-(3-methyl-5-{[4-(trifluoromethyl)pyrimidin-2-yl]amino}phenyl)pyridin-2-yl]azetidine-2-carboxylic acid;
O-methyl-N-[5-(3-methyl-5-{[4-(trifluoromethyl)pyrimidin-2-yl]amino}phenyl)pyridin-2-yl]serine;
1-{[5-(3-methyl-5-{[4-(trifluoromethyl)pyrimidin-2-yl]amino}phenyl)pyridin-2-yl]amino}cyclopentanecarboxylic acid;
1-{[5-(3-methyl-5-{[4-(trifluoromethyl)pyrimidin-2-yl]amino}phenyl)pyridin-2-yl]amino}cyclopropanecarboxylic acid;
2-methyl-1-[5-(3-methyl-5-{[4-(trifluoromethyl)pyrimidin-2-yl]amino}phenyl)pyridin-2-yl]-L-proline;
N-[5-(3-methyl-5-{[4-(trifluoromethyl)pyrimidin-2-yl]amino}phenyl)pyridin-2-yl]-L-alanine;
N-[5-(3-methyl-5-{[4-(trifluoromethyl)pyrimidin-2-yl]amino}phenyl)pyridin-2-yl]glycine;
N-[5-(3-methyl-5-{[4-(trifluoromethyl)pyrimidin-2-yl]amino}phenyl)pyridin-2-yl]-D-alanine;
N-[5-(3-methyl-5-{[4-(trifluoromethyl)pyrimidin-2-yl]amino}phenyl)pyridin-2-yl]-D-valine;
N-[5-(3-methyl-5-{[4-(trifluoromethyl)pyrimidin-2-yl]amino}phenyl)pyridin-2-yl]-L-threonine;
N-2-[5-(3-methyl-5-{[4-(trifluoromethyl)pyrimidin-2-yl]amino}phenyl)pyridin-2-yl]-D-asparagine;
N-2-[5-(3-methyl-5-{[4-(trifluoromethyl)pyrimidin-2-yl]amino}phenyl)pyridin-2-yl]-L-asparagine;
N-[5-(3-methyl-5-{[4-(trifluoromethyl)pyrimidin-2-yl]amino}phenyl)pyridin-2-yl]-L-methionine;
(2 S)-2-{[5-(3-methyl-5-{[4-(trifluoromethyl)pyrimidin-2-yl]amino}phenyl)pyridin-2-yl]amino}butanoic acid;
N-[5-(3-methyl-5-{[4-(trifluoromethyl)pyrimidin-2-yl]amino}phenyl)pyridin-2-yl]-L-leucine;
N-[5-(3-methyl-5-{[4-(trifluoromethyl)pyrimidin-2-yl]amino}phenyl)pyridin-2-yl]-L-histidine;
4-[5-(3-methyl-5-{[4-(trifluoromethyl)pyrimidin-2-yl]amino}phenyl)pyridin-3-yl]piperidin-4-ol;
3-hydroxy-3-[5-(3-methyl-5-{[4-(trifluoromethyl)pyrimidin-2-yl]amino}phenyl)pyridin-2-yl]cyclohexanecarboxylic acid;
(2 S)-1-[5-(3-methyl-5-{[4-(trifluoromethyl)pyrimidin-2-yl]amino}phenyl)pyridin-2-yl]azetidine-2-carboxylic acid;
trans-4-[(1R)-1-hydroxy-1-(5-{3-[(4-methoxypyrimidin-2-yl)amino]-5-methylphenyl}pyridin-2-yl)ethyl]cyclohexanecarboxylic acid;
trans-4-[(1S)-1-hydroxy-1-(5-{3-[(4-methoxypyrimidin-2-yl)amino]-5-methylphenyl}pyridin-2-yl)ethyl]cyclohexanecarboxylic acid;
1-[5-(3-methyl-5-{[4-(trifluoromethyl)pyrimidin-2-yl]amino}phenyl)pyridin-2-yl]azetidine-2-carboxylic acid;
(2R)-1-[5-(3-methyl-5-{[4-(trifluoromethyl)pyrimidin-2-yl]amino}phenyl)pyridin-2-yl]piperidine-2-carboxylic acid;
2,2-dimethyl-3-[5-(3-methyl-5-{[4-(trifluoromethyl)pyrimidin-2-yl]amino}phenyl)pyridin-2-yl]propanoic acid;
trans-4-[(5-{3-methyl-5-[(4-methylpyrimidin-2-yl)amino]phenyl}pyridin-2-yl)amino]cyclohexanecarboxylic acid;
trans-4-[(5-{3-[(4-methoxypyrimidin-2-yl)amino]-5-methylphenyl}pyridin-2-yl)amino]cyclohexanecarboxylic acid;
4-{1-hydroxy-1-[5-(3-methyl-5-{[4-(trifluoromethyl)pyrimidin-2-yl]amino}phenyl)pyridin-2-yl]ethyl}benzoic acid;
3-methyl-N-[5-(3-methyl-5-{[4-(trifluoromethyl)pyrimidin-2-yl]amino}phenyl)pyridin-2-yl]-L-valine;
cis-4-{[5-(3-methyl-5-{[4-(trifluoromethyl)pyrimidin-2-yl]amino}phenyl)pyridin-2-yl]amino}cyclohexanecarboxylic acid;
trans-4-{[5-(3-methyl-5-{[4-(trifluoromethyl)pyrimidin-2-yl]amino}phenyl)pyridin-2-yl]amino}cyclohexanecarboxylic acid;
2-methyl-N-[5-(3-{[4-(trifluoromethyl)pyrimidin-2-yl]amino}phenyl)pyridin-2-yl]alanine;
N-[5-(3-methyl-5-{[4-(trifluoromethyl)pyrimidin-2-yl]amino}phenyl)pyridin-2-yl]-beta-alanine;
N-[5-(3-methyl-5-{[4-(trifluoromethyl)pyrimidin-2-yl]amino}phenyl)pyridin-2-yl]-L-phenylalanine;
3-{[5-(3-methyl-5-{[4-(trifluoromethyl)pyrimidin-2-yl]amino}phenyl)pyridin-2-yl]amino}-3-oxopropanoic acid;
(2 S)-1-{5-[3-(acetylamino)-5-{[4-(trifluoromethyl)pyrimidin-2-yl]amino}phenyl]pyridin-2-yl}azetidine-2-carboxylic acid;
N-{5-[3-(acetylamino)-5-{[4-(trifluoromethyl)pyrimidin-2-yl]amino}phenyl]pyridin-2-yl}-2-methylalanine;
2-methyl-2-{[4-(3-methyl-5-{[4-(trifluoromethyl)pyrimidin-2-yl]amino}phenyl)pyridin-2-yl]amino}propane-1,3-diol;
2-methyl-2-{[4-(3-methyl-5-{[4-(trifluoromethyl)pyrimidin-2-yl]amino}phenyl)pyridin-2-yl]amino}propan-1-ol;
(2 S)-2-{[4-(3-methyl-5-{[4-(trifluoromethyl)pyrimidin-2-yl]amino}phenyl)pyridin-2-yl]amino}propan-1-ol;
5-hydroxy-5-[5-(3-methyl-5-{[4-(trifluoromethyl)pyrimidin-2-yl]amino}phenyl)pyridin-2-yl]azepan-2-one;

N-[5-(3-methyl-5-{[4-(trifluoromethyl)pyrimidin-2-yl]
amino}phenyl)pyridin-2-yl]-D-histidine
4-{[5-(3-methyl-5-{[4-(trifluoromethyl)pyrimidin-2-yl]
amino}phenyl)pyridin-2-yl]amino}pyrrolidin-2-one;
3-{[5-(3-methyl-5-{[4-(trifluoromethyl)pyrimidin-2-yl]
amino}phenyl)pyridin-2-yl]amino}pyrrolidin-2-one;
4-hydroxy-4-[5-(3-methyl-5-{[4-(trifluoromethyl)pyrimidin-2-yl]amino}phenyl)pyridin-3-yl]piperidine-1-carboxamide;
4-[5-(3-methyl-5-{[4-(trifluoromethyl)pyrimidin-2-yl]
amino}phenyl)pyridin-3-yl]piperazin-2-one;
N-(3-[6-(3-oxopiperazin-1-yl)pyridin-3-yl]-5-{[4-(trifluoromethyl)pyrimidin-2-yl]amino}phenyl)acetamide;
N,N-dimethyl-N-2-[5-(3-methyl-5-{[4-(trifluoromethyl)pyrimidin-2-yl]amino}phenyl)pyridin-2-yl]glycinamide;
3-(4-{3-[(4-cyclopropylpyrimidin-2-yl)amino]-5-methylphenyl}pyridin-2-yl)propanoic acid;
trans-4-[(5-{3-[(5-chloro-4-methylpyrimidin-2-yl)amino]-5-methylphenyl}pyridin-2-yl)amino]cyclohexanecarboxylic acid;
N-methyl-N-[5-(3-methyl-5-{[4-(trifluoromethyl)pyrimidin-2-yl]amino}phenyl)pyridin-2-yl]-L-alanine;
trans-4-[(5-{3-[(5-fluoro-4-methoxypyrimidin-2-yl)amino]-5-methylphenyl}pyridin-2-yl)amino]cyclohexanecarboxylic acid;
1-[5-(3-methyl-5-{[4-(trifluoromethyl)pyrimidin-2-yl]
amino}phenyl)pyridin-2-yl]piperidine-3-carboxylic acid;
N-[5-(3-methyl-5-{[4-(trifluoromethyl)pyrimidin-2-yl]
amino}phenyl)pyridin-2-yl]-D-leucine;
(2S)-4-(methylsulfonyl)-2-{[5-(3-methyl-5-{[4-(trifluoromethyl)pyrimidin-2-yl]amino}phenyl)pyridin-2-yl]
amino}butanoic acid;
N-(2-cyanoethyl)-N-[5-(3-methyl-5-{[4-(trifluoromethyl)pyrimidin-2-yl]amino}phenyl)pyridin-2-yl]glycine;
1-[5-(3-methyl-5-{[4-(trifluoromethyl)pyrimidin-2-yl]
amino}phenyl)pyridin-2-yl]-L-prolylglycine;
1-[5-(3-methyl-5-{[4-(trifluoromethyl)pyrimidin-2-yl]
amino}phenyl)pyridin-2-yl]-L-proline;
2,2-difluoro-3-hydroxy-3-[5-(3-methyl-5-{[4-(trifluoromethyl)pyrimidin-2-yl]amino}phenyl)pyridin-2-yl]propanoic acid;
2,2-difluoro-3-[5-(3-methyl-5-{[4-(trifluoromethyl)pyrimidin-2-yl]amino}phenyl)pyridin-2-yl]propanoic acid;
3-hydroxy-2,2-dimethyl-3-[5-(3-methyl-5-{[4-(trifluoromethyl)pyrimidin-2-yl]amino}phenyl)pyridin-2-yl]propanoic acid;
3-hydroxy-3-[5-(3-methyl-5-{[4-(trifluoromethyl)pyrimidin-2-yl]amino}phenyl)pyridin-3-yl]pyrrolidine-1-carboxamide;
{1-[5-(3-methyl-5-{[4-(trifluoromethyl)pyrimidin-2-yl]
amino}phenyl)pyridin-2-yl]piperidin-2-yl}acetic acid;
1-[5-(3-methyl-5-{[4-(trifluoromethyl)pyrimidin-2-yl]
amino}phenyl)pyridin-2-yl]azetidine-3-carboxylic acid;
(3 S)-3-hydroxy-1-[5-(3-methyl-5-{[4-(trifluoromethyl)pyrimidin-2-yl]amino}phenyl)pyridin-2-yl]-L-proline;
1-[5-(3-methyl-5-{[4-(trifluoromethyl)pyrimidin-2-yl]
amino}phenyl)pyridin-2-yl]piperidine-4-carboxylic acid;
3-[5-(3-methyl-5-{[4-(trifluoromethyl)pyrimidin-2-yl]
amino}phenyl)pyridin-2-yl]-1,3-thiazolidine-4-carboxylic acid;
N-[5-(3-methyl-5-{[4-(trifluoromethyl)pyrimidin-2-yl]
amino}phenyl)pyridin-2-yl]glycylglycine;
{4-[5-(3-methyl-5-{[4-(trifluoromethyl)pyrimidin-2-yl]
amino}phenyl)pyridin-2-yl]piperazin-1-yl}acetic acid;
N-[5-(3-{[5-bromo-4-(trifluoromethyl)pyrimidin-2-yl]
amino}-5-methylphenyl)pyridin-2-yl]-2-methylalanine;
3-(5-{3-[(4-cyclopropylpyrimidin-2-yl)amino]-5-methylphenyl}pyridin-3-yl)propanoic acid; and
4-({[5-(3-methyl-5-{[4-(trifluoromethyl)pyrimidin-2-yl]
amino}phenyl)pyridin-2-yl]amino}methyl)cyclohexanecarboxylic acid.

The invention also provides a compound of Formula (I) or a pharmaceutically acceptable salt thereof in purified form.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, severe asthma, asthma exacerbations, airway hyperresponsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi- Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, cystic fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 µg to 1 µg, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering Corporation), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
| --- | --- |
| Compound of Formula (I) | 10 |
| Methylcellulose | 5.0 |
| Tween 80 | 0.5 |
| Benzyl alcohol | 9.0 |

| Tablet | mg/tablet |
|---|---|
| Benzalkonium chloride | 1.0 |
| Water for injection to a total volume of 1 mL | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity will generally be in the range of 5 μg to 100 mg/kg body weight of recipient (patient) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. For the treatment of the inflammatory diseases, rheumatoid arthritis, psoriasis, inflammatory bowel disease, COPD, asthma and allergic rhinitis, these additional therapeutic agents include, but are not limited to: (1) TNF-α inhibitors such as infliximab (Remicade®), etanercept (Enbrel®), adalimumab (Humira®), certolizumab pegol (Cimzia®), and golimumab (Simponi®); (2) non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/ or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate) or a pharmaceutically acceptable salt thereof (e.g., salmeterol xinafoate and fluticasone propionate).

For the treatment of cancer a compound of Formula (I) may be combined with an one or more additional therapeutic agents which are anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anticancer agents include, but are not limited to, the following: (1) an estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) an androgen receptor modulator such as finasteride and other 5α-reductase inhibitors, nilutamide, flutamide, bicalutamide, liarozole, and abiraterone acetate; (4) a retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) an antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) a prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) an HMG-CoA reductase inhibitor such as lovastatin, simvastatin, pravastatin, atorvastatin, fluvastatin and rosuvastatin; (8) an angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl) phenyl]-methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl) methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) an inhibitor of inherent multidrug resistance including inhibitors of p-glycoprotein (P-gp), such as LY335979, XR9576, OC144-093, R101922, VX853 and PSC833 (valspodar); (10) an inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) an agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; and (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable additional therapeutic agents used in cancer therapy that may be combined with compounds of Formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

These combinations are of particular interest in respiratory diseases and are conveniently adapted for inhaled or intranasal delivery.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the disease or condition mediated by Syk.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:
Me=methyl; Et=ethyl; Pr=propyl; iPr=isopropyl, Bu=butyl; t-Bu=tert-butyl; Ph=phenyl, and Ac=acetyl
μl=microliters
AcOH or HOAc=acetic acid
APCI=atmospheric-pressure chemical ionization
aq=aqueous
Bn=benzyl
Boc or BOC=tert-butoxycarbonyl
Bz=benzoyl
Boc=tert-butoxycarbonyl
Cbz=benyzloxycarbonyl
DCM=dichloromethane:
DMAP=4-Dimethylaminopyridine
DIBAL=diisobutylaluminum hydride
DIEA or Hünig's Base=N,N-diisopropylethylamine
DMA=1,2-dimethylacetamide
DMF=dimethylformamide
DMSO=dimethyl sulfoxide
DTT=dithiothreitol
EDC=1-ethyl-3-(3-dimethylaminopropyl)carbodiimide
EDTA=ethylenediamine tetraacetic acid
ESI=electrospray ionization
EtOAc=ethyl acetate
g=grams
GST=glutathione S-transferase
h=hour
HMDS=1,1,1,3,3,3-hexamethyldisilazane
HATU=N,N,N',N-tetramethyl-O-(7-azabenzotriazol-1-yl)uronium hexafluorophosphate
HEX=hexanes
HPLC=high-performance liquid chromatography
HOBt=1-hydroxybenzotriazole
LDA=lithium diisopropylamide
LCMS=liquid chromatography mass spectrometry
min=minute
mg=milligrams
mL=milliliters
mmol=millimoles
Me=methyl
MeOH: methanol
MS=mass spectrometry
NBS=N-bromosuccimide
NMR=nuclear magnetic resonance spectroscopy
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine (Et$_3$N)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
General Methods Compounds of the Formula (I) can be prepared according to one of the general synthetic schemes procedures set forth in Schemes 1-28 below, and/or by methods similar to those described in the Examples below.

Scheme 1

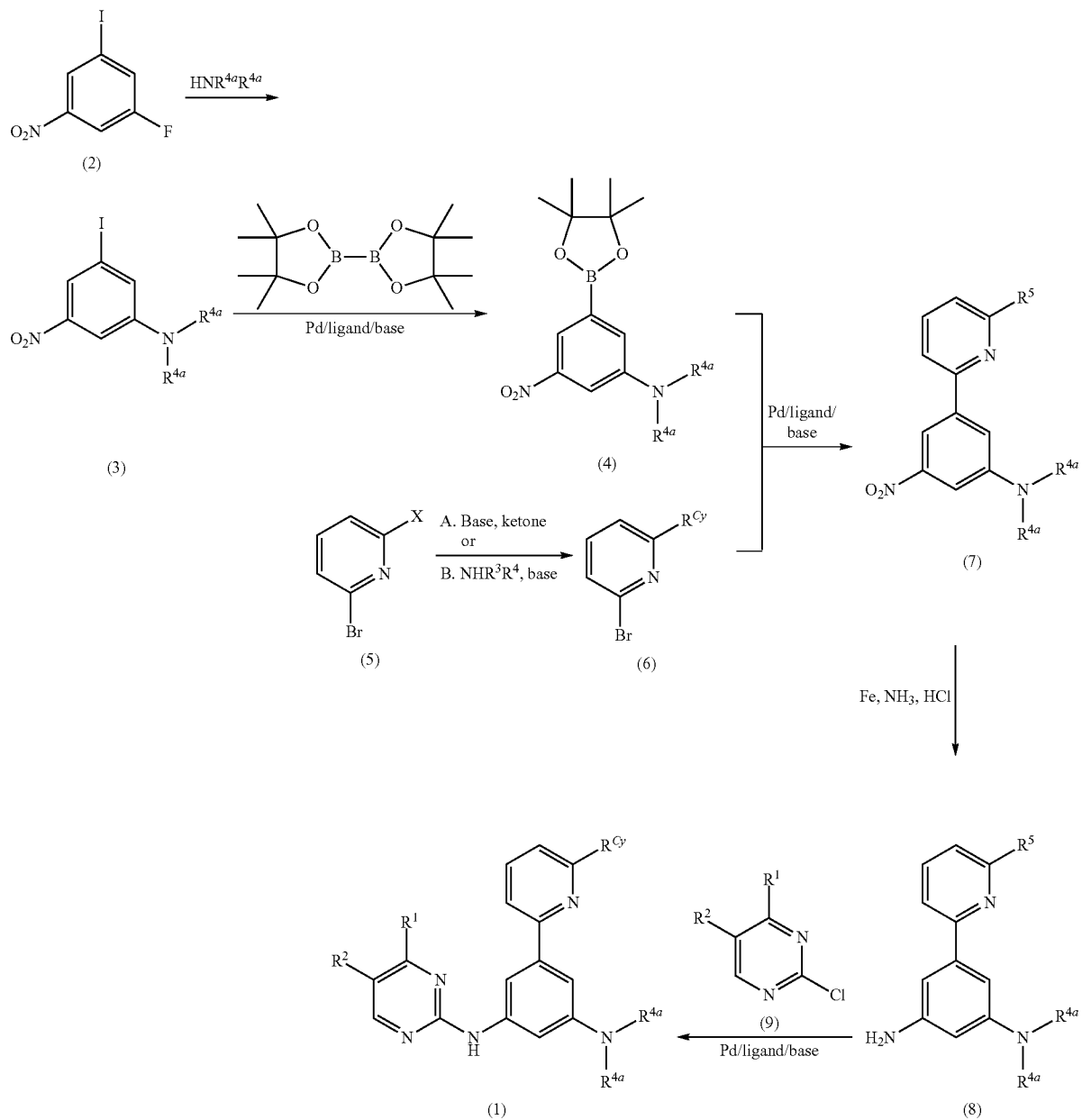

Compounds (3) are prepared by S$_N$Ar displacement of 1-fluoro-3-iodo-5-nitrobenzene (2) with commercially available amines. Miyaura coupling of (3) with bis(pinacolato) diboron provides boronic esters (4). Preparation of functionalized bromopyridines begins with dihalopyridine (5), either via selective lithiation and addition to an electophile or S$_N$Ar displacement by an amine provides bromide (6). Suzuki coupling of compounds (4) and (6) yields nitroarenes (7). Reduction with iron and ammonium chloride provides anilines (8). Buchwald coupling of compound (8) with substituted pyrimidines (9) results in compounds with the general structure of (1).

Scheme 2

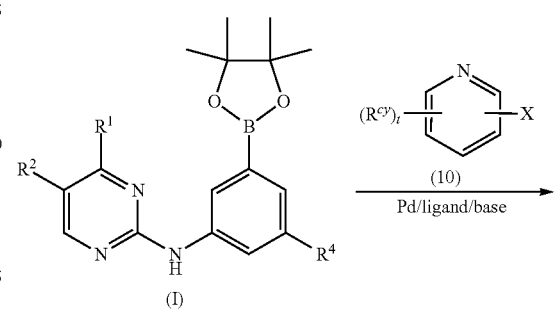

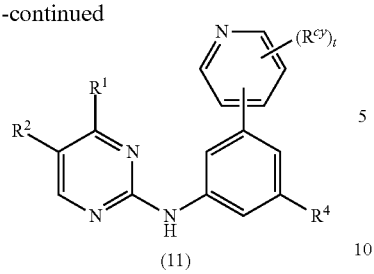

As shown in Scheme 2, the compounds (11) are prepared by Suzuki coupling of arylhalides (10) and intermediate I.

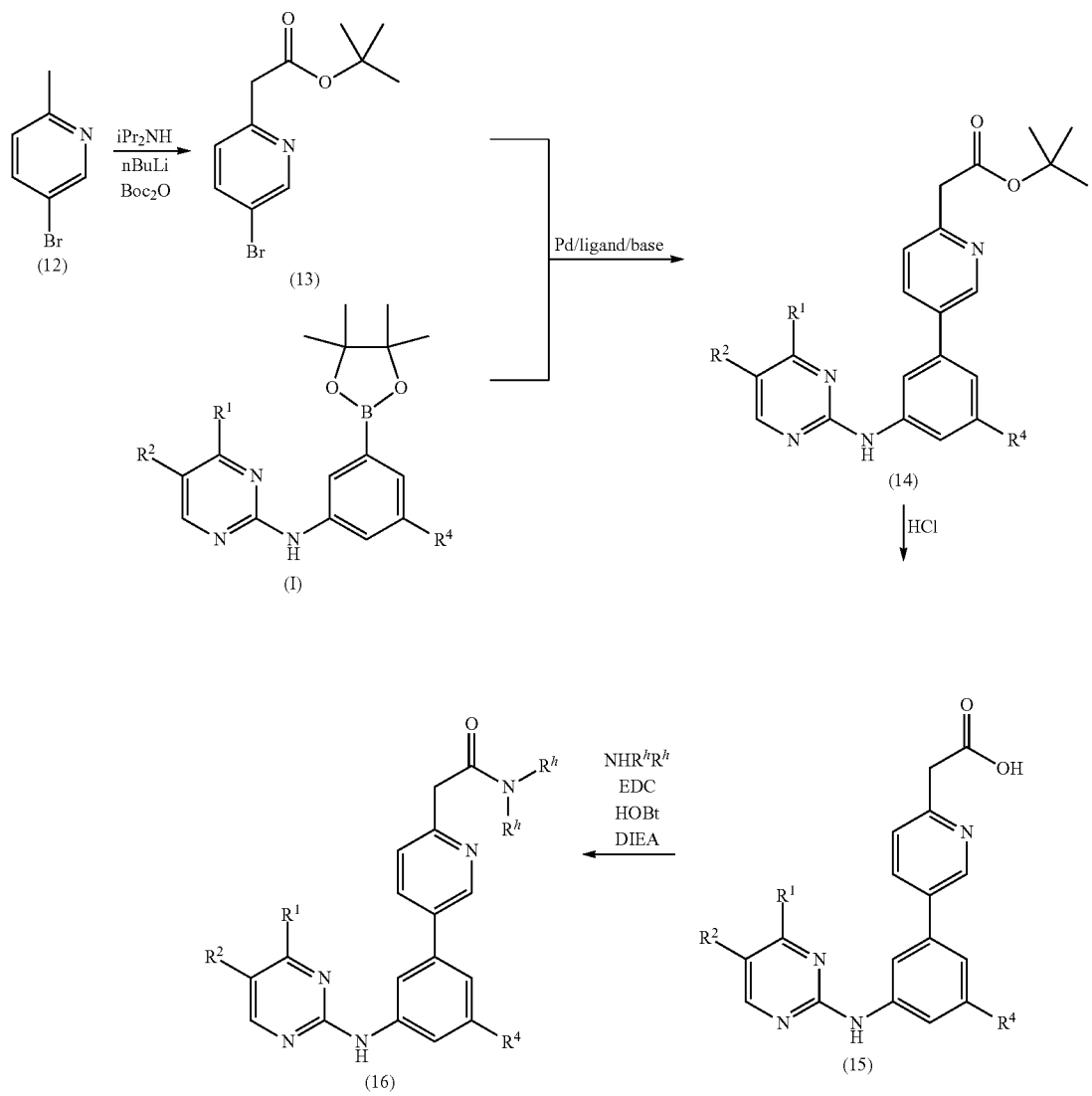

As shown in Scheme 3, Compound (13) is prepared by treating 5-bromo-2-methylpyridine (12) with LDA followed by BOC$_2$O. Suzuki coupling of bromide (13) and Intermediate I provides tricyclic compound (14) which is hydrolyzed into acid (15). Amide coupling of (15) with dimethylamine affords amide (16).

Scheme 4
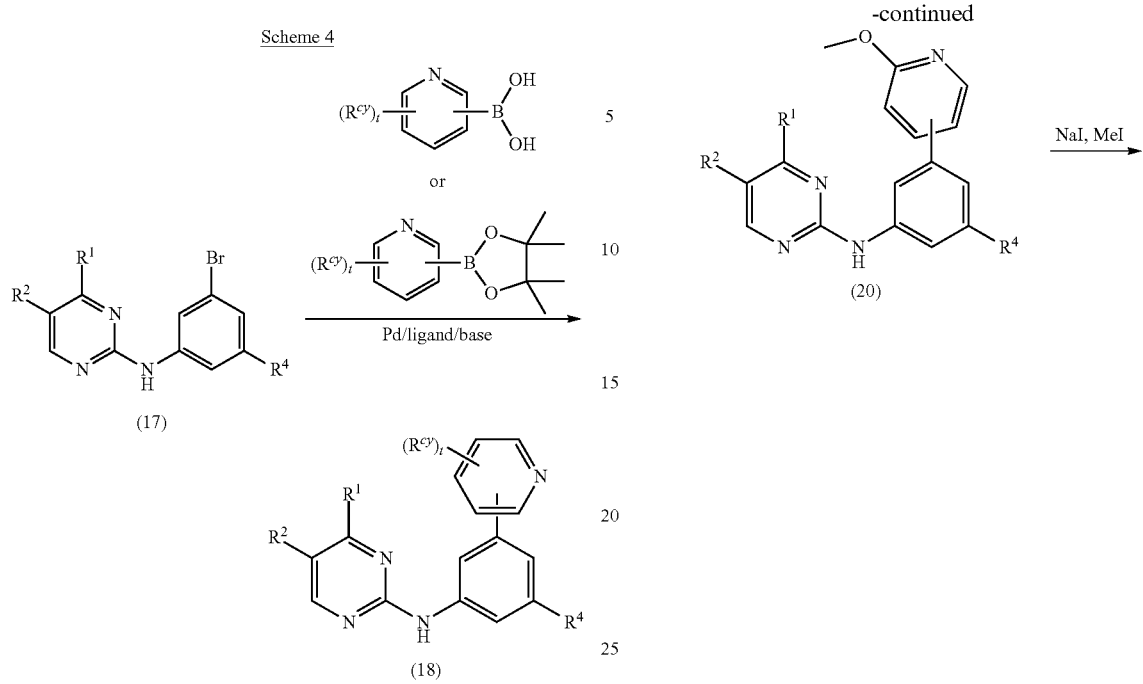
Compounds 18 are prepared by Suzuki coupling of aryl-halides (17) with boronic acids or esters.
Scheme 5
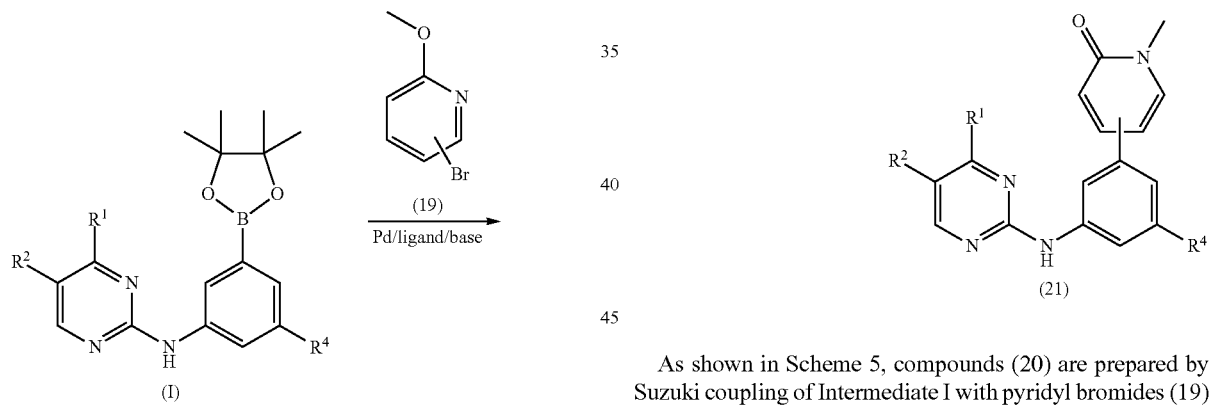
As shown in Scheme 5, compounds (20) are prepared by Suzuki coupling of Intermediate I with pyridyl bromides (19) followed by the de-methylation/methylation sequence.
Scheme 6
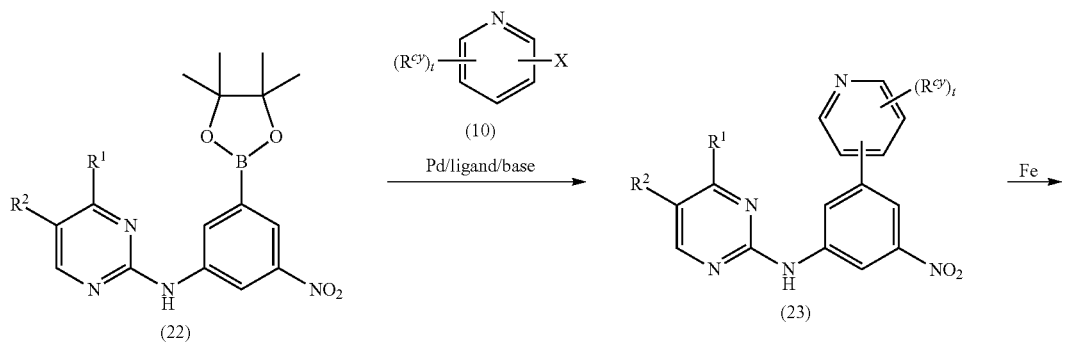

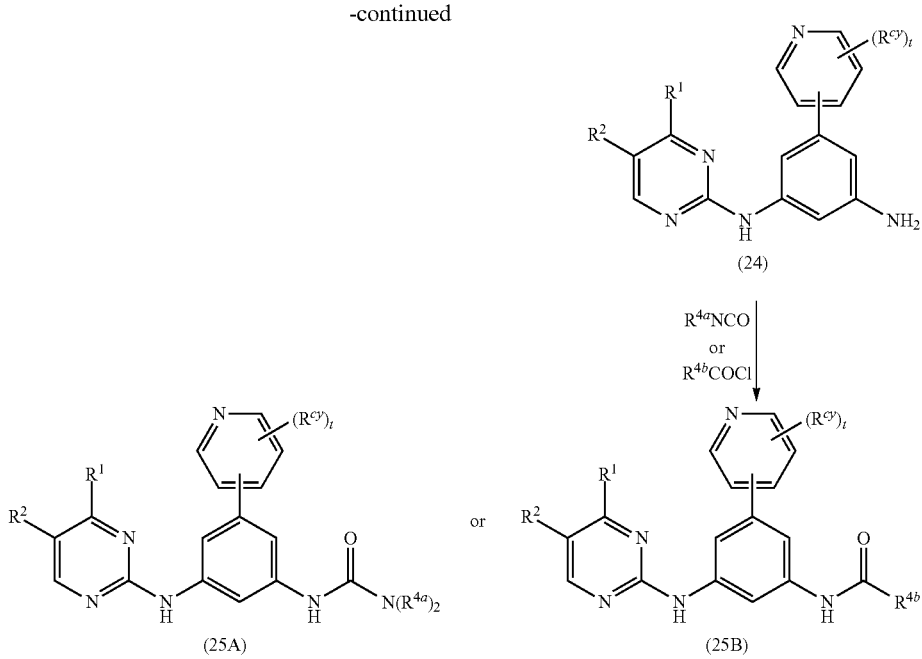

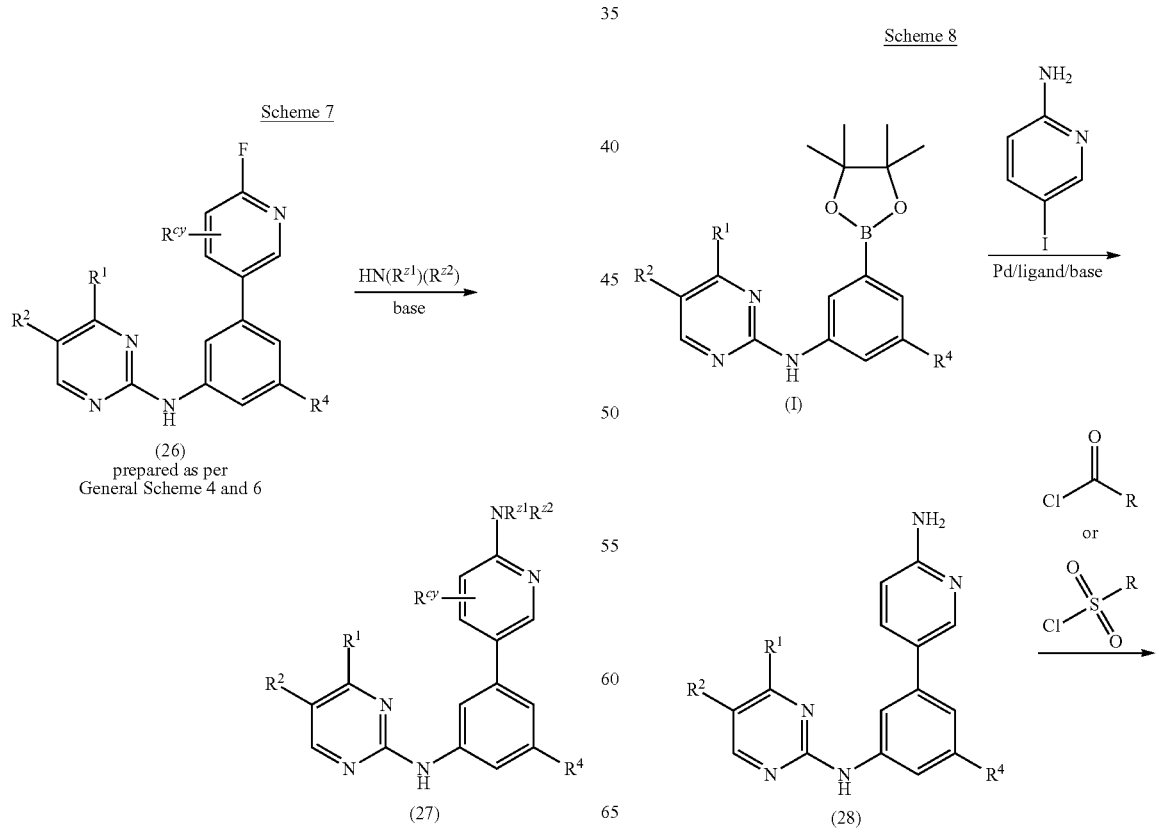

Compounds 23 are prepared by Suzuki coupling of boronic esters (22) and heteroaryl bromides (10) as shown in Scheme 6 above. Iron-mediated reduction of nitroarenes (23) results in anilines (24). Subsequent reaction with commercially available isocyanates or acyl chlorides provides compounds of the general structure of (25A) and (25B).

As shown in Scheme 7, compounds 27 are prepared by $S_NAr$ reaction of 26 with known or commercially available amines, wherein $R^{z1}$ and $R^{z2}$ are various amino substituents, e.g., alkyl.

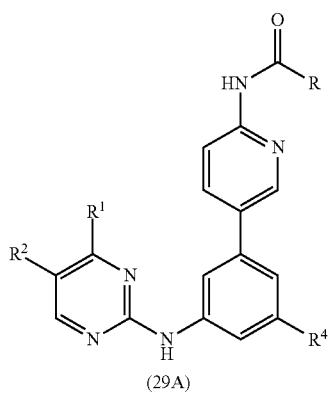
(29A)
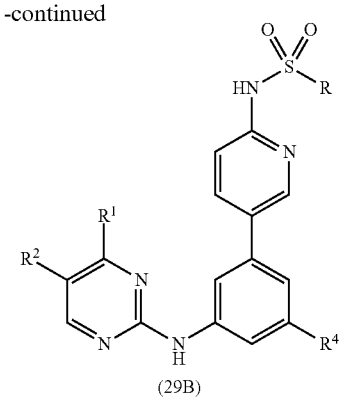
(29B)
Compounds (29A) and (29B) are prepared by Suzuki coupling with commercially available 5-iodopyridin-2-amine yields tricyclic compounds (28) followed by acylation/sulfonylation with known or commercially available acyl or sulfonyl chlorides.
Scheme 9
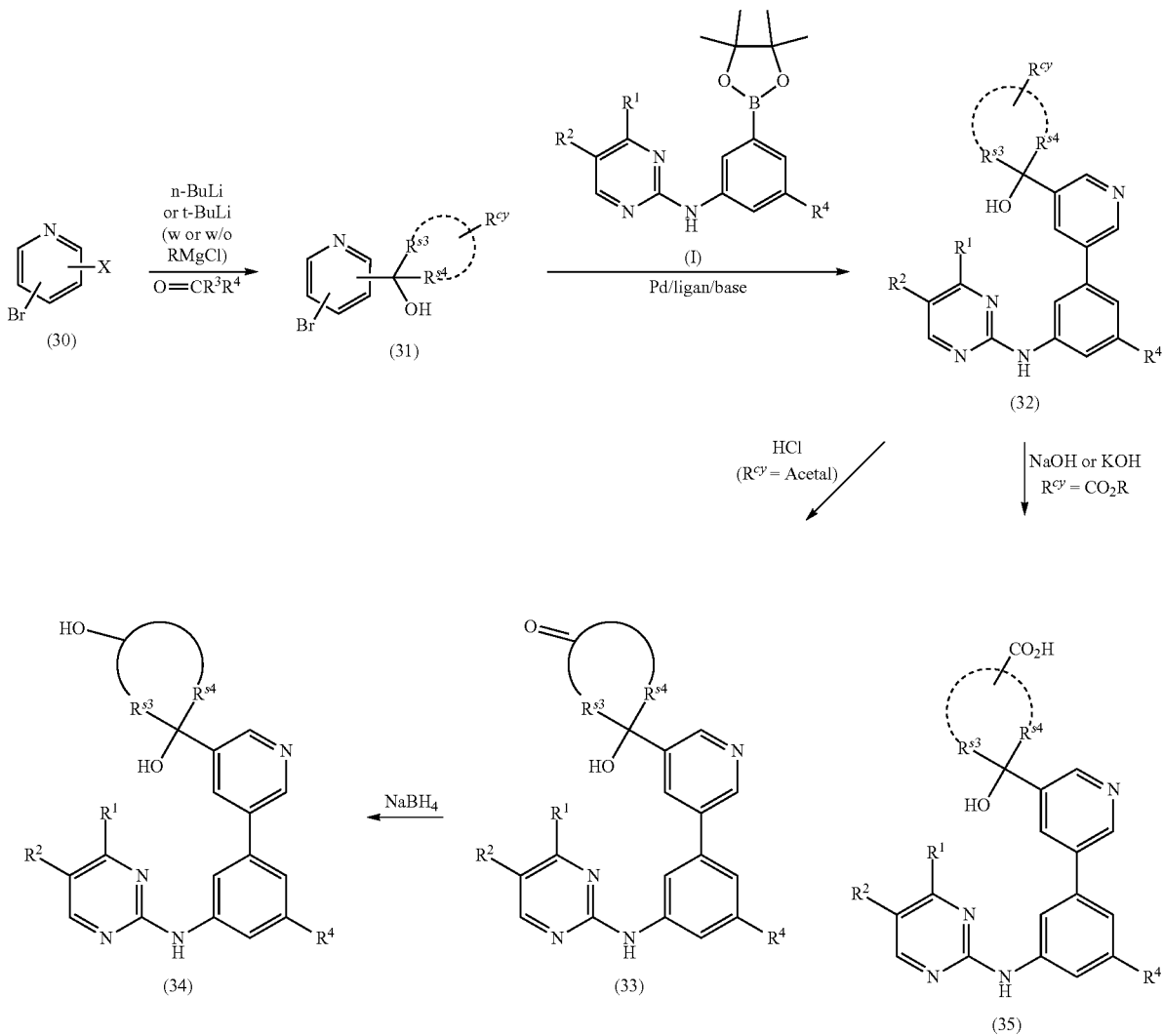

Compounds (32) are prepared by selective lithiation of dihalopyridine (30) with known or commercially available ketones to afford alcohols (31) followed by Suzuki coupling with Intermediate I. Compounds (32) ($R^{cy}$=acetal) are further modified into ketones (33) by removal of acetal group and subsequent reduction affords alcohol (34). Alternatively, acids (35) are prepared by the saponification of compound (32) ($R^{cy}$=$CO_2R$).

Scheme 10

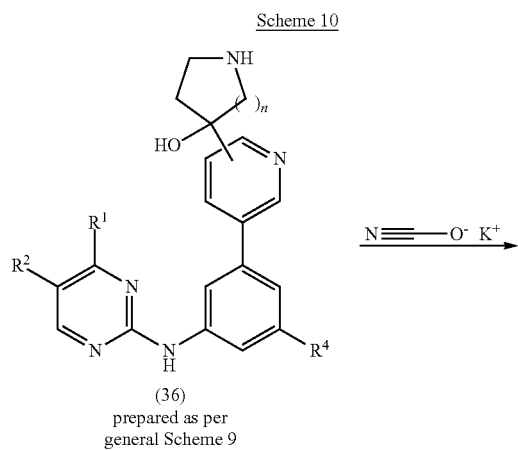

(36)
prepared as per
general Scheme 9

Compounds (37) are prepared by treating amines (36) with potassium cyanate.

Scheme 11

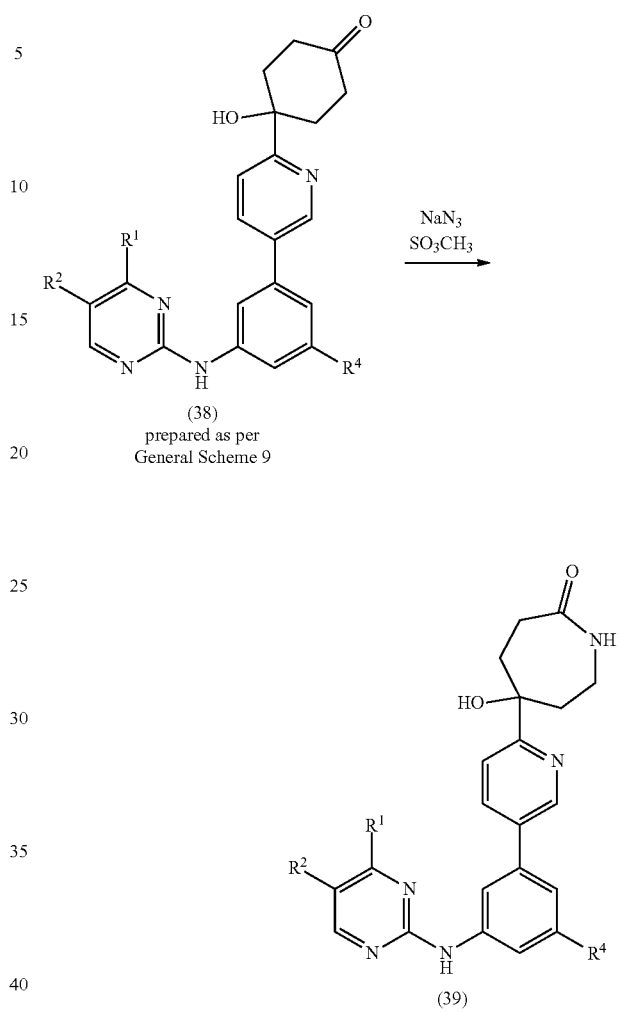

(38)
prepared as per
General Scheme 9

(39)

As shown in Scheme 11, compounds (39) are prepared by azido-Schmidt reaction of compounds (38).

Scheme 12

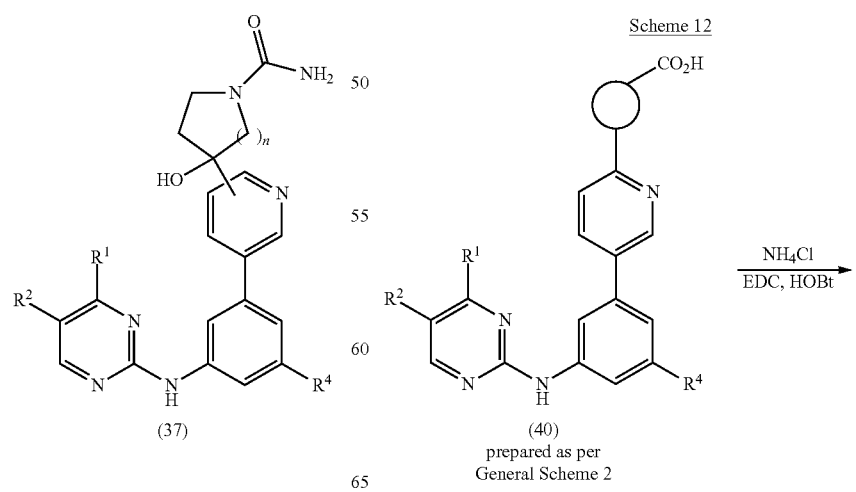

(37)

(40)
prepared as per
General Scheme 2

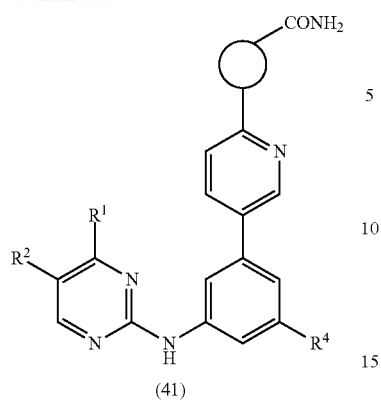
Amides (41) are formed by treatment of acids (40) with NH₄Cl and amide coupling reagents, such as EDC and HOBt.
Scheme 13
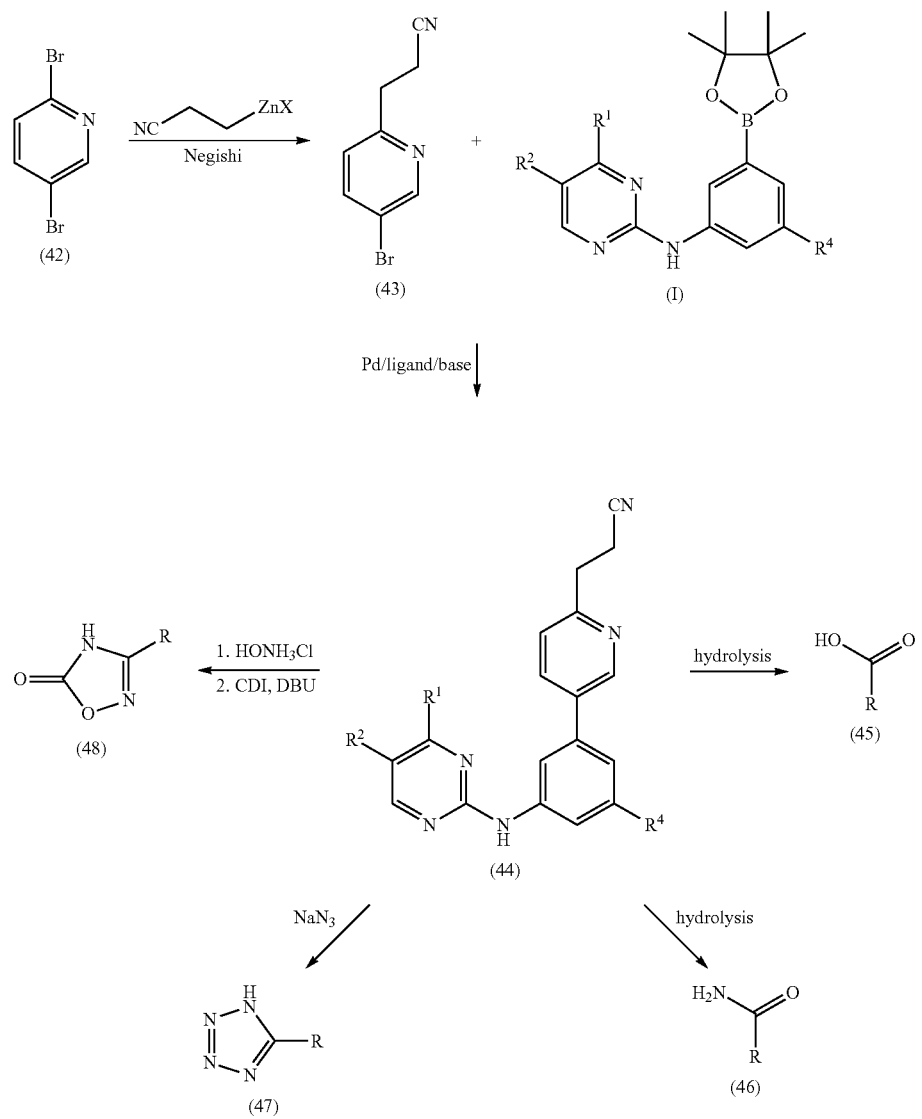

where R =

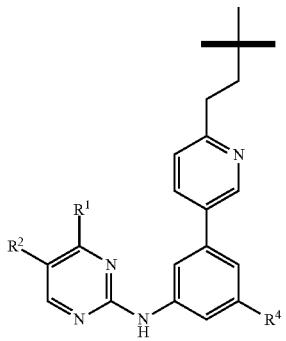

Preparation of the general core (44) in Scheme 13 begins with 2,5-dibromopyridine (42), which is carried forward in a selective Negishi coupling reaction to provide compound (43). Suzuki coupling of bromide 43 with Intermediate I yields compound (44). Nitrile (44) is then a key intermediate for the formation of compounds with the general structure of (45)-(48), which all contain the same basic core (R=N-[3-(6-ethylpyridin-3-yl)-5-methylphenyl]-4-(trifluoromethyl)pyrimidin-2-amine).

Scheme 14

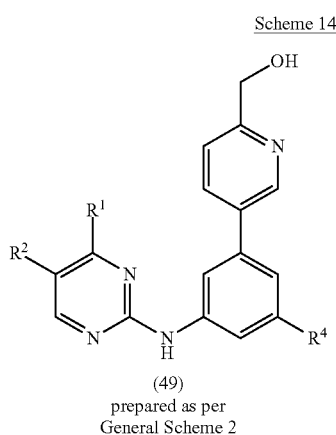

(49)
prepared as per
General Scheme 2

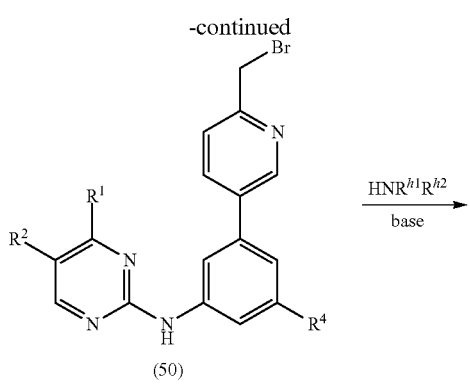

(50)

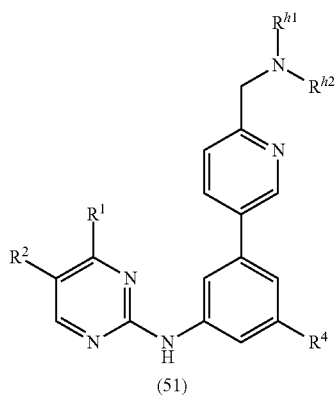

(51)

Compounds 51 are prepared by bromination of benzyl alcohols (49) to afford bromides (50) followed by displacement with known or commercially available amines or amides.

Scheme 15
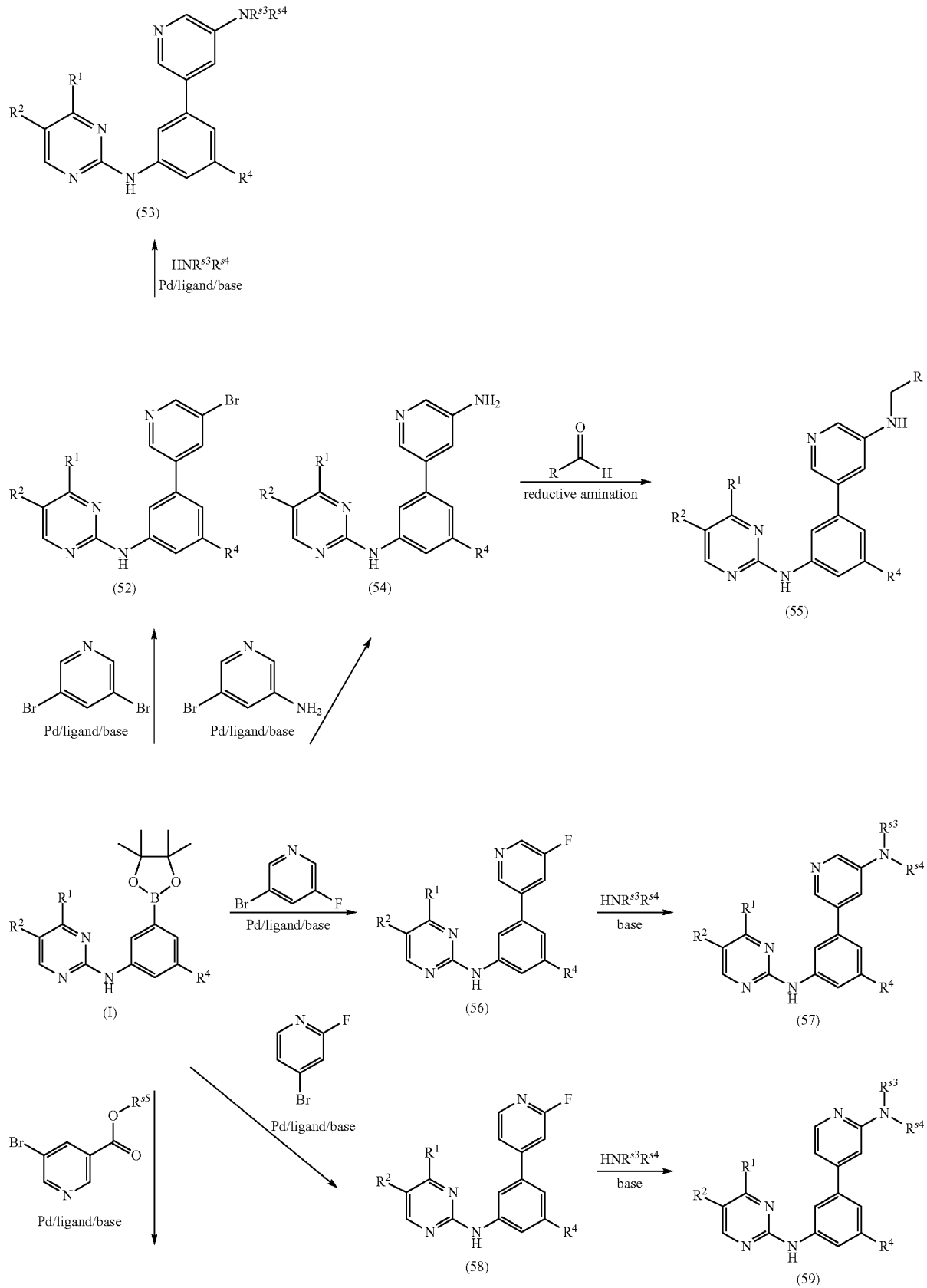

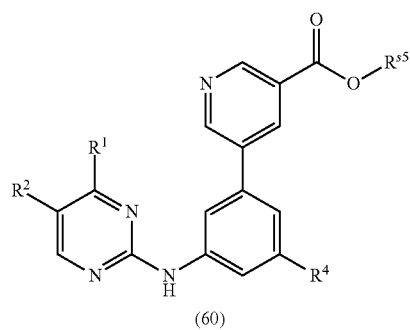

(60)

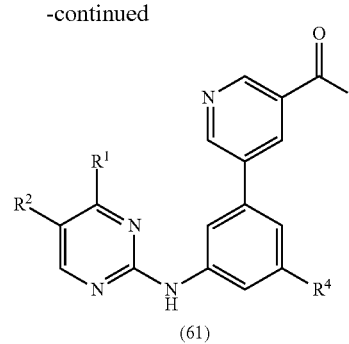

(61)

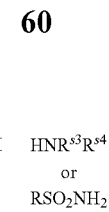

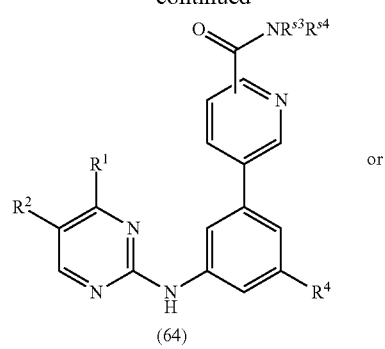

(62)

Compounds (52), (54), (56), (58), and (60) are prepared by Suzuki coupling of Intermediate I with corresponding pyridyl bromides. Buchwald-Hartwig amination of bromides (52) provides amines (53). $S_NAr$ reaction of bromides (56) and (58) with known or commercially available amines gives amines (57) and (59), respectively. Amines (55) are prepared by reductive amination of compounds (54) with commercially available aldehydes. Amides (62) are formed by saponification of esters (60) followed by amide coupling with commercially available amines.

-continued

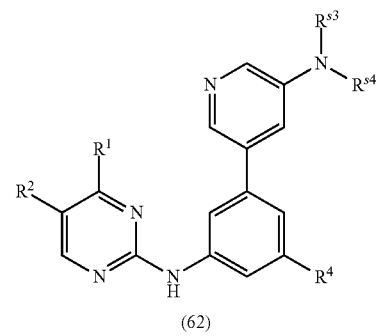

(64)

or

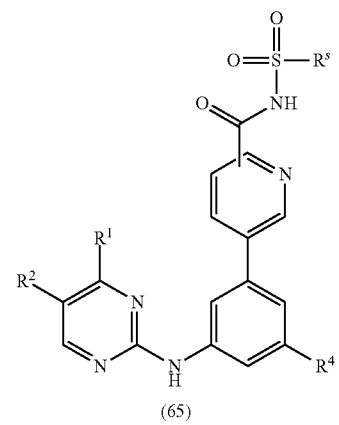

(65)

Scheme 16

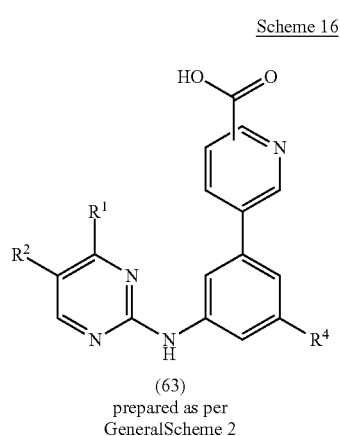

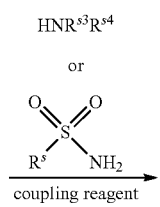

(63)
prepared as per
GeneralScheme 2

Compounds (64) and (65) are prepared by treating acids (63) with known or commercially available amines or sulfonamides in the presence of coupling reagents such as CDI and HOBt.

Scheme 17
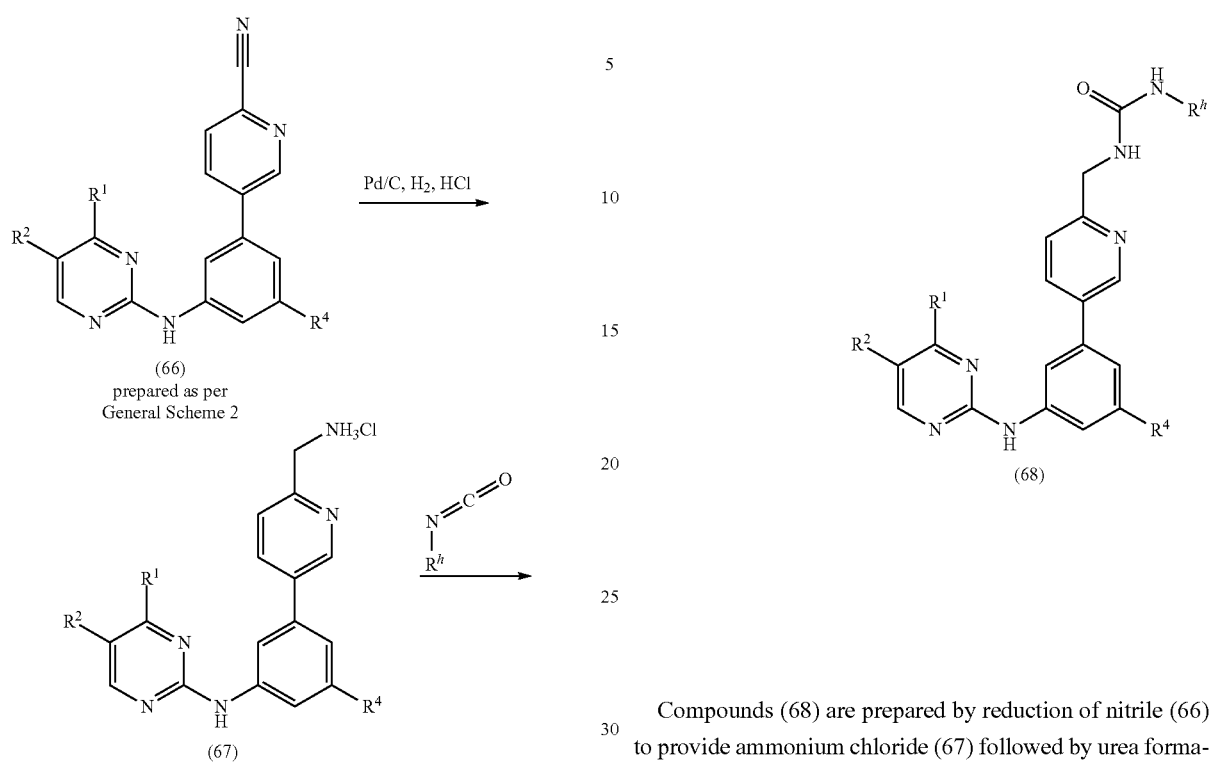
Compounds (68) are prepared by reduction of nitrile (66) to provide ammonium chloride (67) followed by urea formation with commercially available isocyanates.
Scheme 18
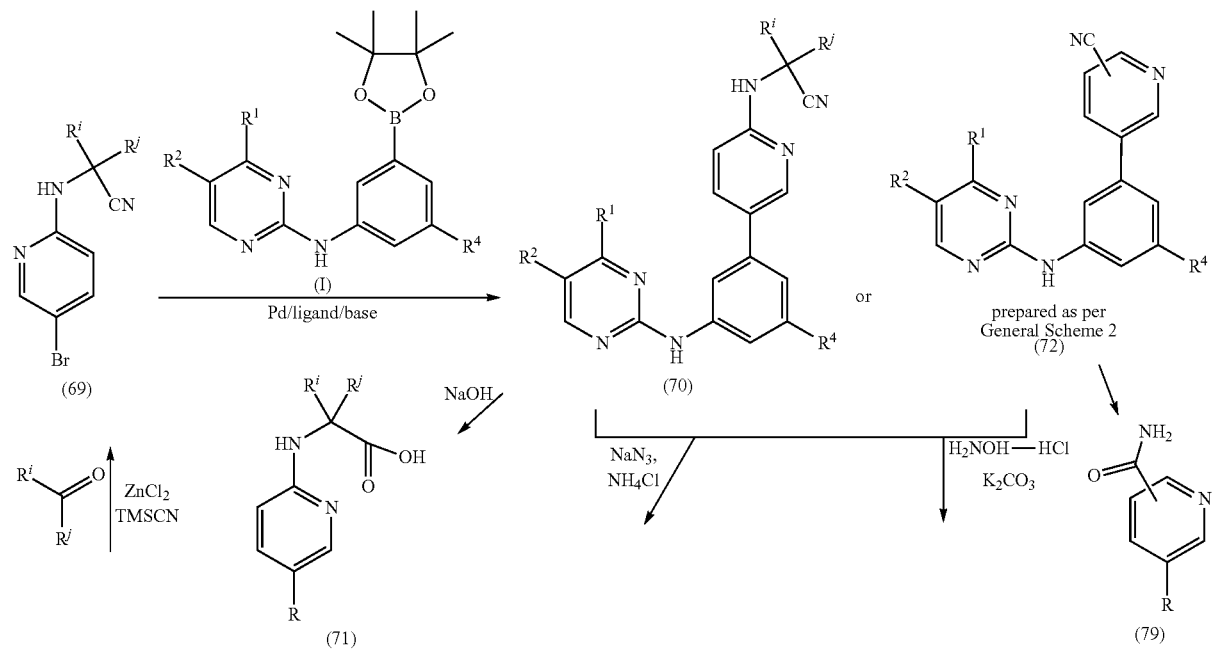

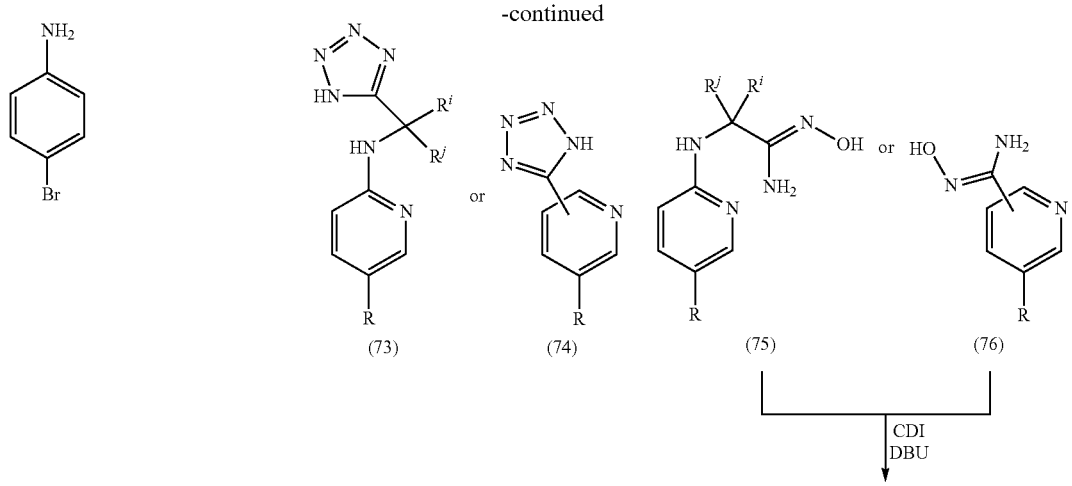

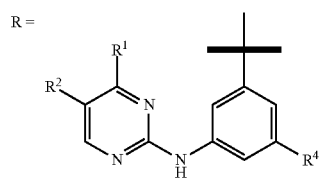

Preparation of the general core (70) in Scheme 18 begins with a Strecker reaction using 5-bromopyridin-2-amine and commercially available ketones to afford nitriles (69) followed by a palladium-mediated coupling reaction of nitriles (69) with Intermediate I. The compound (70) is then used a key intermediate for the formation of compounds with the general structures of (71), (73), (75) and (77). In a similar fashion, a key intermediate (72) (prepared as per Scheme 2) is transformed into the general structures of (74), (76), (78) and (79).

Scheme 19

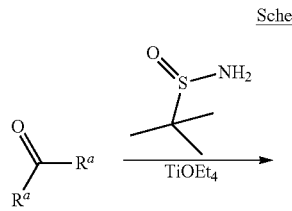

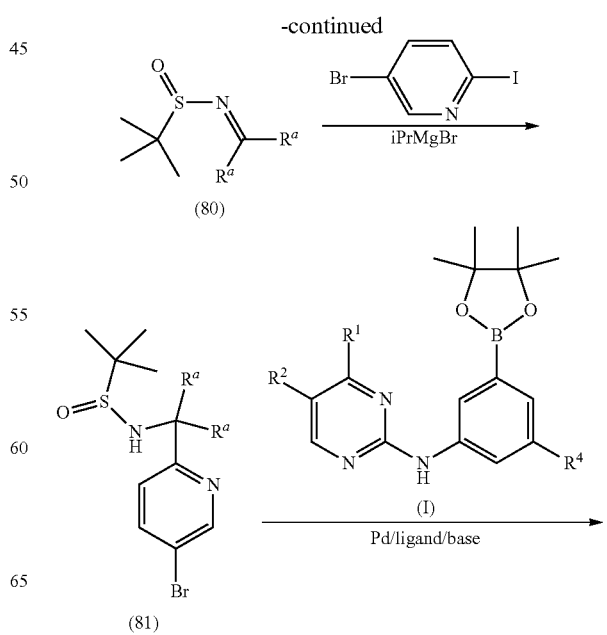

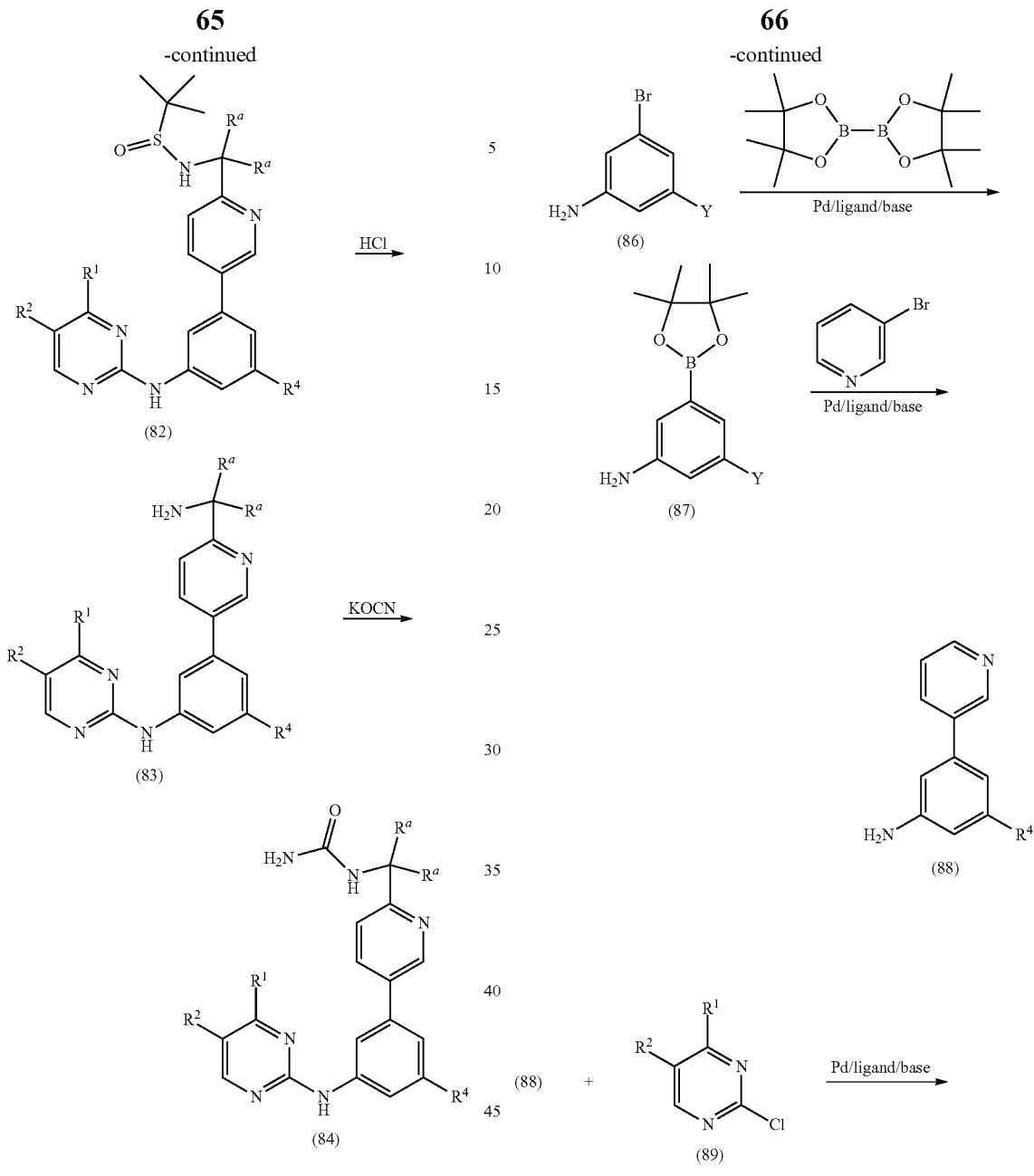

The formation of sulfimines (80) is accomplished by condensation of known ketones with 2-methylpropane-2-sulfinamide. Compound (80) is reacted with a prepared Grignard to yield compound (81). Suzuki reaction of (81) with Intermediate I yields adduct (82). Deprotection and reaction with potassium isocyanate provides ureas with the general structure of (84).

Scheme 20

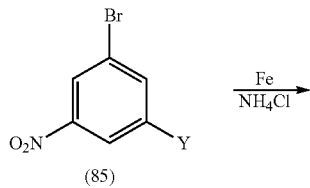

Iron-mediated reduction of nitroarenes (85) yields anilines (86). Miyuara coupling with bis(pinacolato)diboron produces boronic esters (87). Suzuki coupling of compound (87) and 3-bromopyridine yields compounds (88). Buchwald coupling of anilines (88) with prepared or known functionalized chloropyrimidines (89) generated compounds of the general structure of (90).

Scheme 21
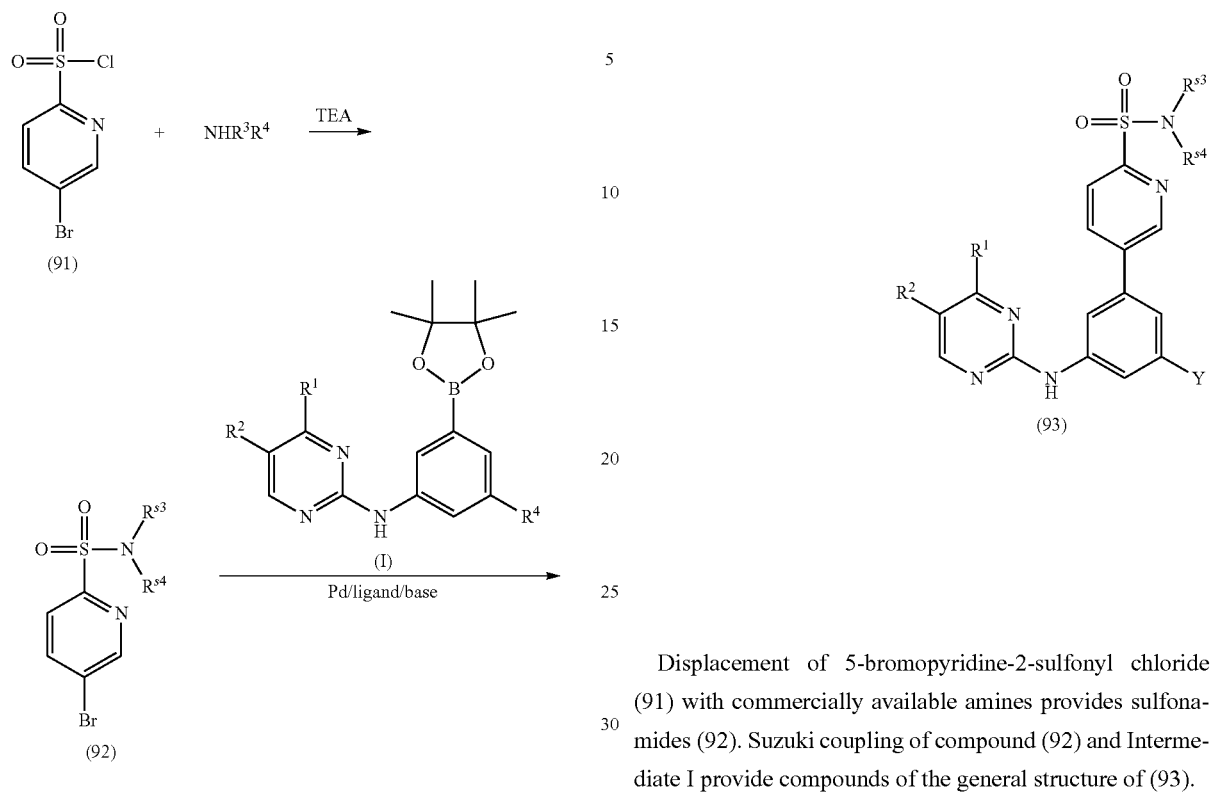
Displacement of 5-bromopyridine-2-sulfonyl chloride (91) with commercially available amines provides sulfonamides (92). Suzuki coupling of compound (92) and Intermediate I provide compounds of the general structure of (93).
Scheme 22
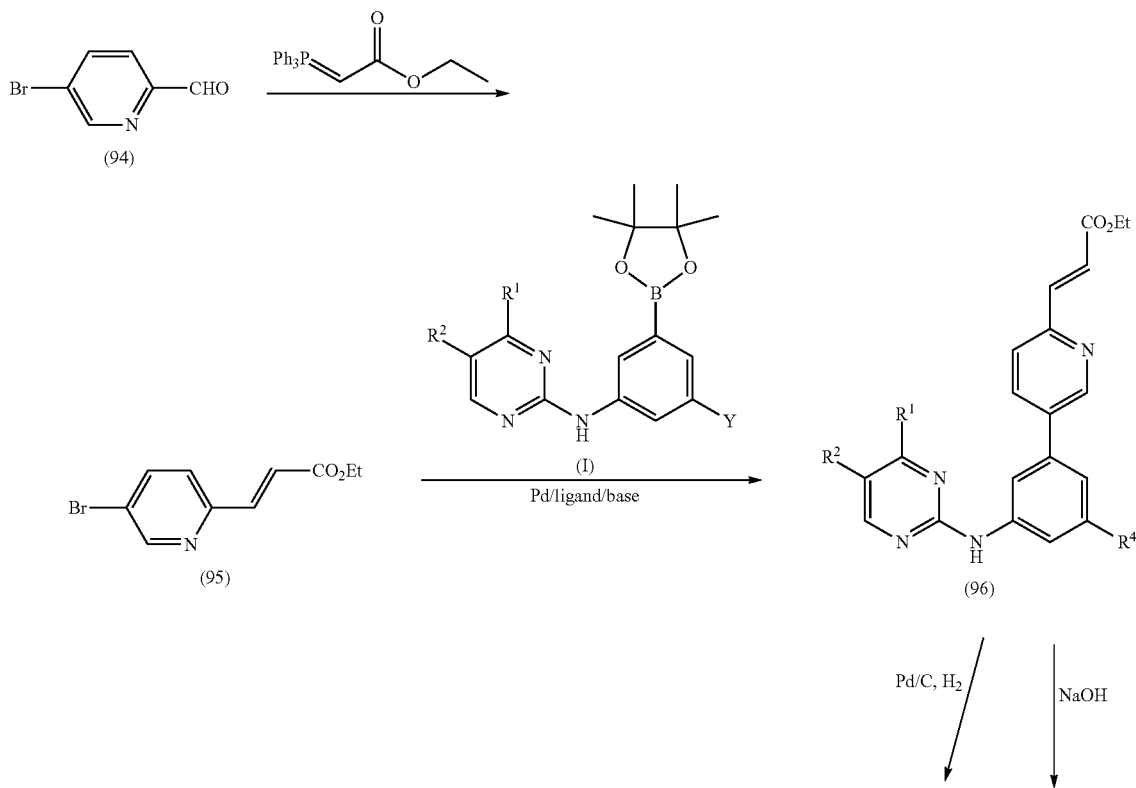

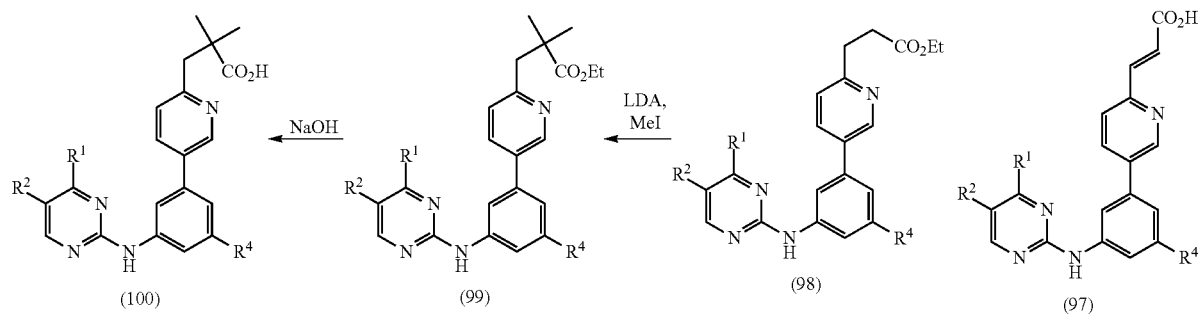

Preparation of the general core (96) in Scheme 23 begins with commercially available 5-bromopyridine-2-carbaldehyde (94). Homologation via Wittig reaction provides compound (95). Suzuki coupling of compound (95) and Intermediate I provides compound (96), which is either saponified to acid (97) or reduced to (98). Bis-alkylation of compound (99) and subsequent saponification provides compound (100).

Scheme 23

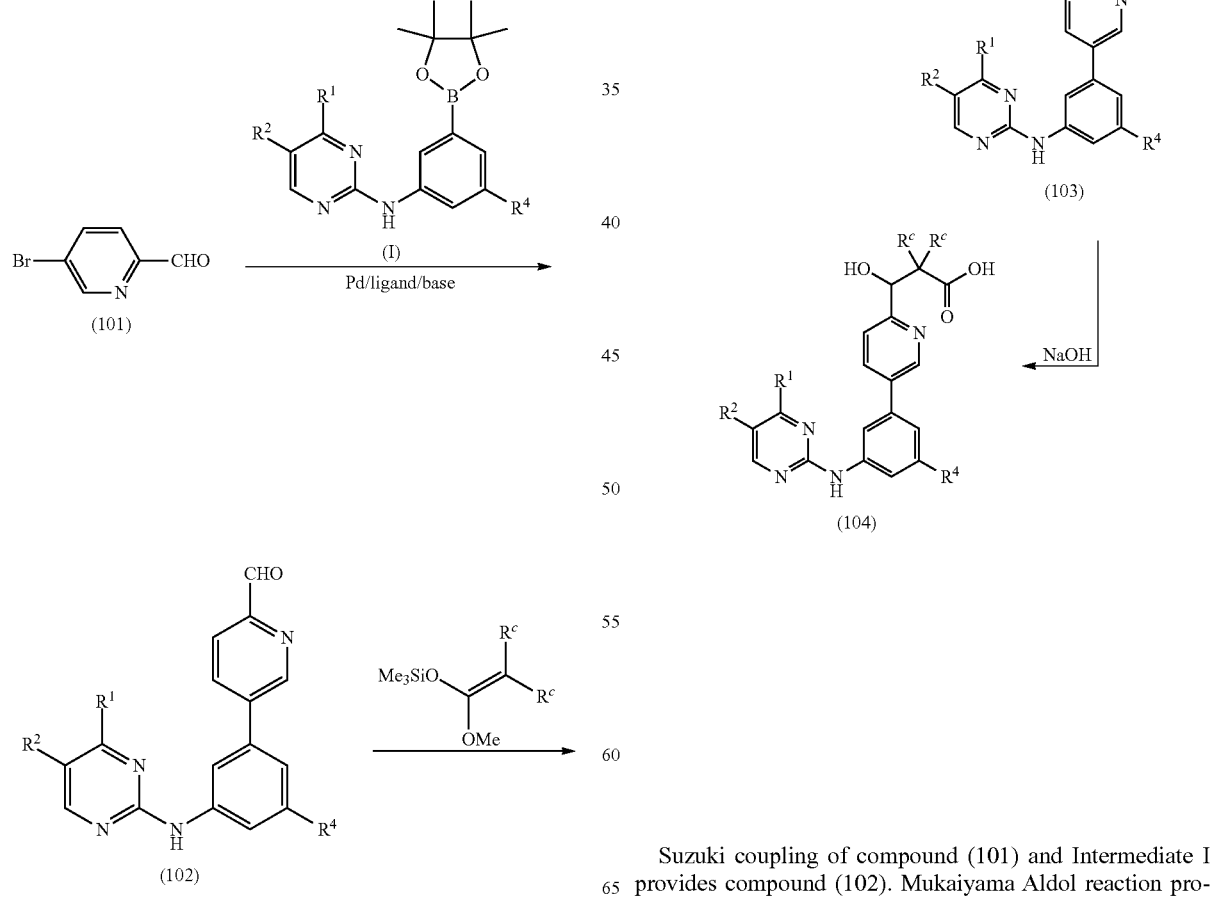

Suzuki coupling of compound (101) and Intermediate I provides compound (102). Mukaiyama Aldol reaction provides compound (103) which is subsequently saponified to provide compound (104).

Scheme 24
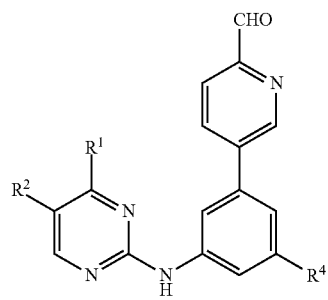 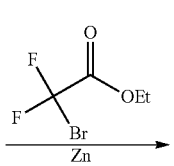
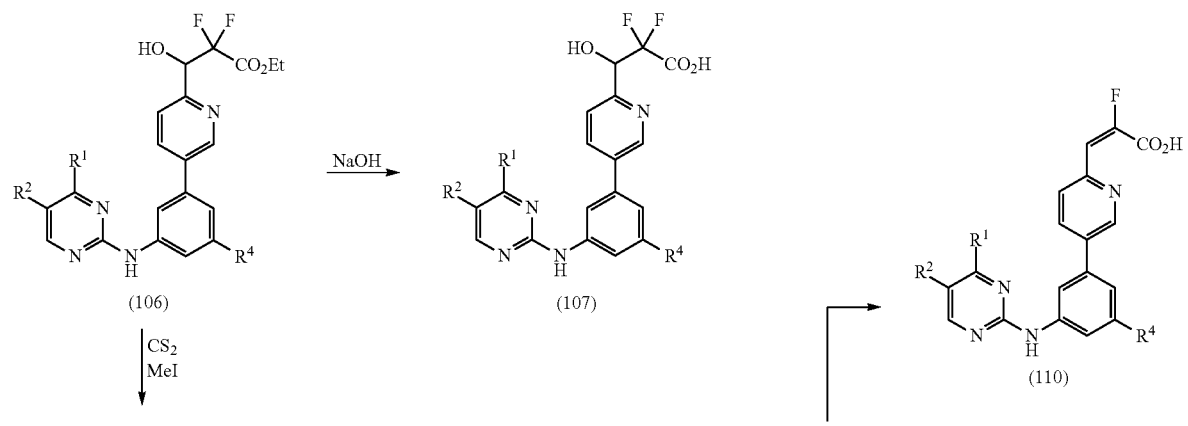
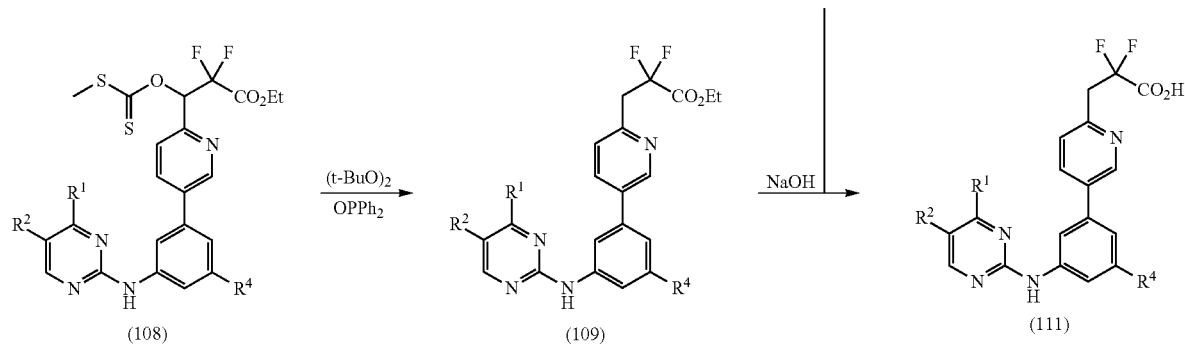

Preparation of the general core (106) in Scheme 24 begins with compound (105), which was synthesized using the method outlined in General Scheme 2. A Reformatsky reaction of aldehyde (105) with ethyl bromodifluoroacetate provides product (106). Compound (106) is saponified to acid (107) or alternatively the adjacent hydroxyl group is eliminated in a two-step process to yield compound (109). Saponification of compound (109) leads to the formation of compounds (110) and (111).

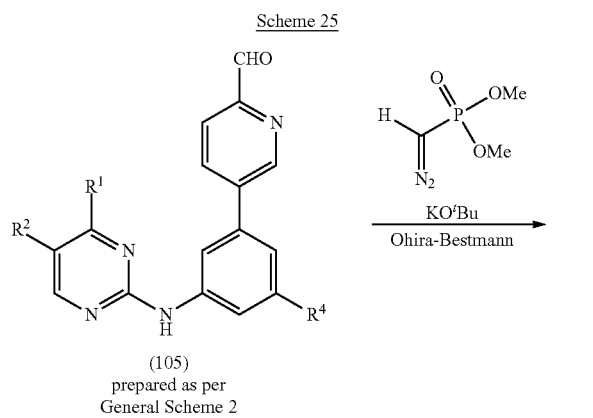

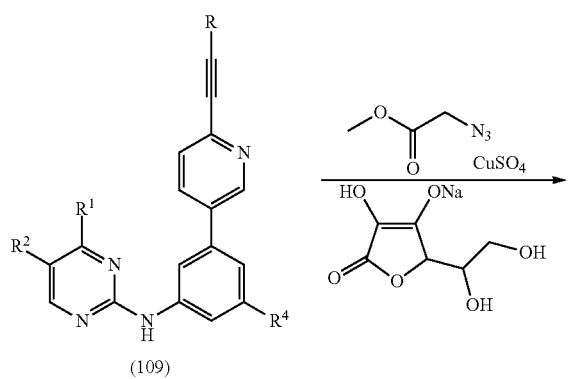

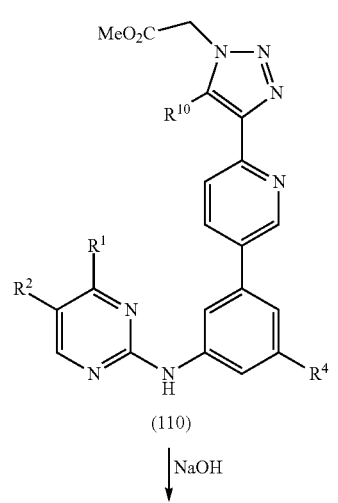

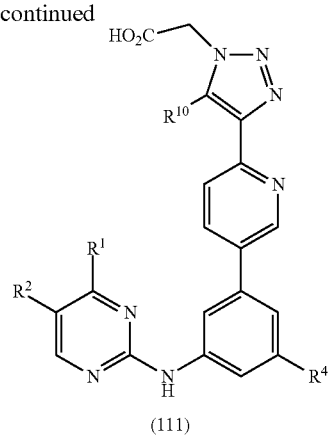

An Ohira-Bestmann reaction of aldehydes (105) provides acetylenes (109). In a one-pot reaction, compounds (109) are transformed into triazoles (110). Saponification of compounds (110) leads to the formation of compounds (111).

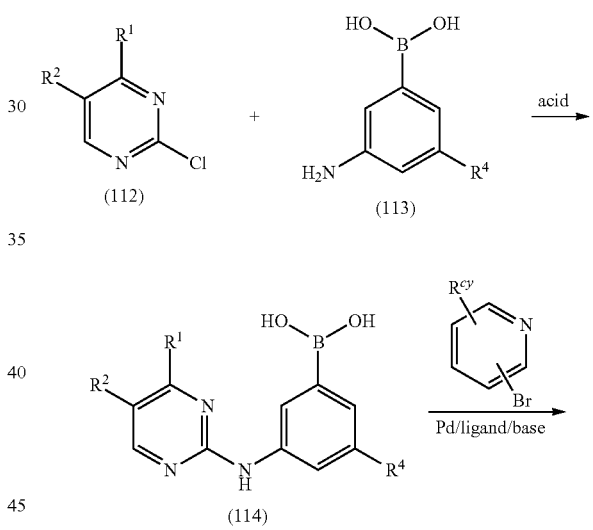

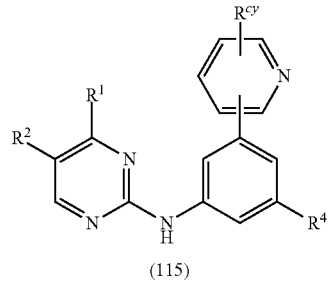

Compounds (114) are prepared by $S_NAr$ reaction of commercially available or prepared pyrimidines (112) with boronic acids (113). Subsequent Suzuki coupling reaction of compounds (114) with commercially available functionalized bromopyridines provides compounds of the general structure of (115).

Scheme 27
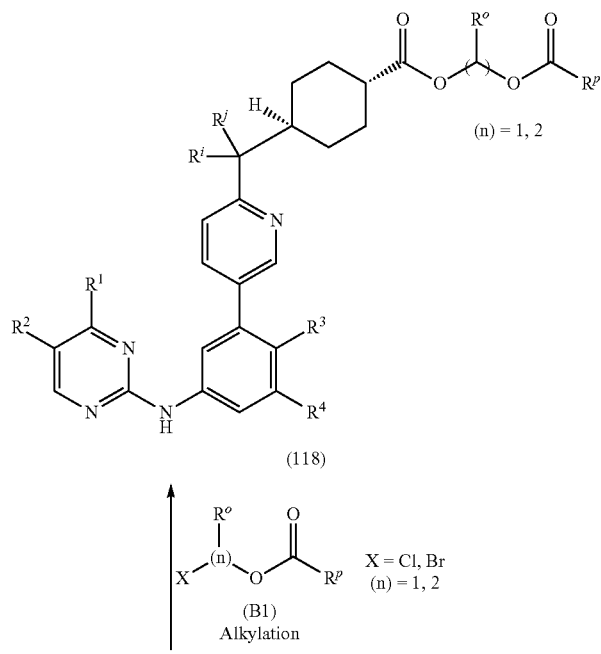
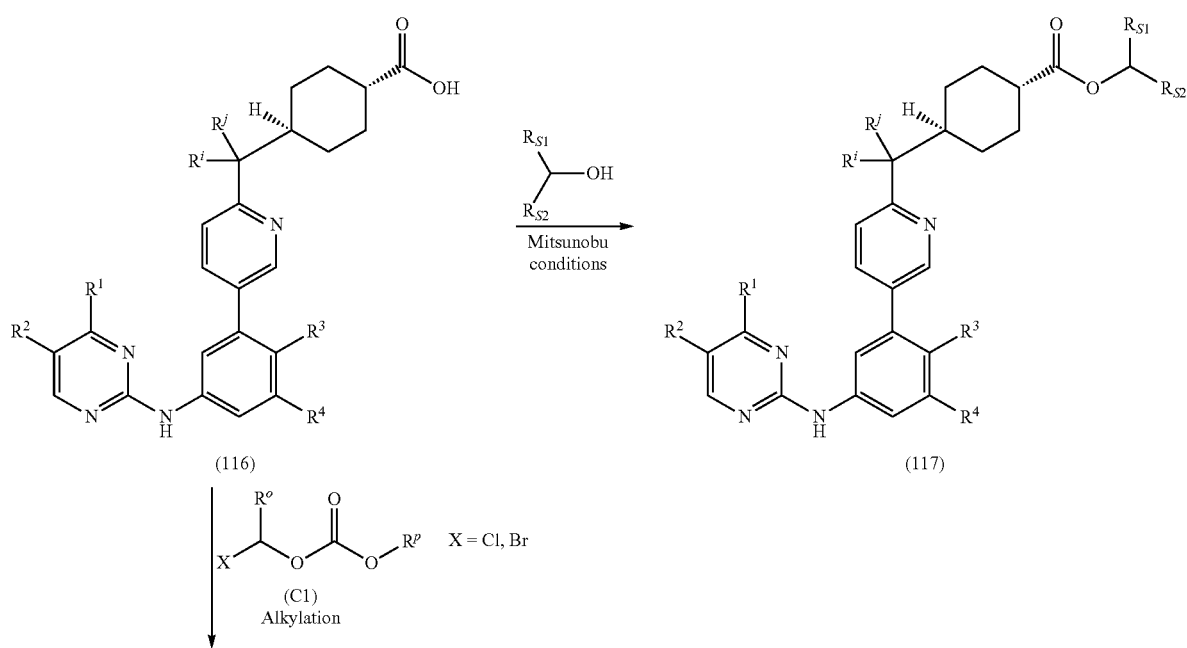

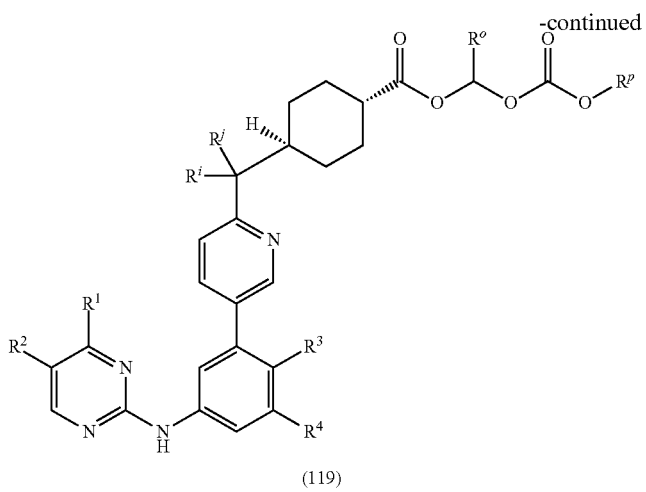

(119)

As shown in Scheme 27, compounds of structural subtype (117) are prepared from the trans-cyclohexane carboxylic acid (116) by a Mitsunobu reaction with various primary and secondary alcohols. Compounds of structural subtype (118) are prepared by the alkylation of the trans-cyclohexane carboxylic acid (116) by alkyl halides of formula (B1). Compounds of structural subtype (119) are prepared by the alkylation of the trans-cyclohexane carboxylic acid (116) by alkyl halides of formula (C1).

Scheme 28

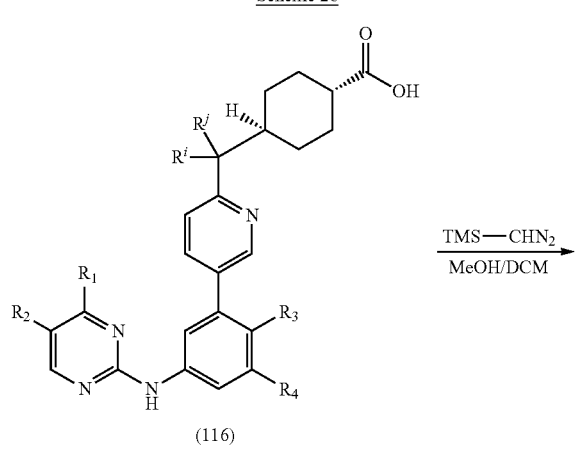

(116)

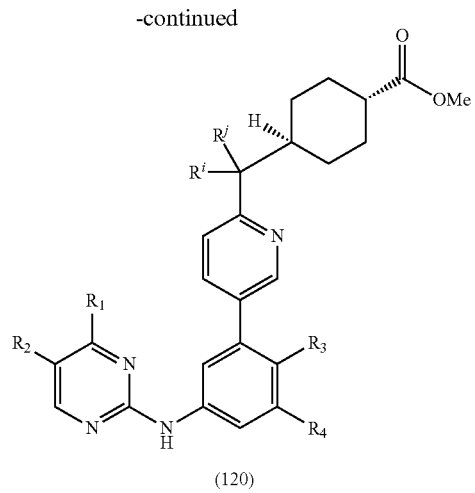

(120)

As shown in Scheme 28, compounds of structural subtype (120) are prepared by the reaction of the trans-cyclohexane carboxylic acid (116) with trimethylsilyldiazomethane and methanol.

For ease of reference, various intermediates are referred in the Examples below as precursors of various moieties of Compounds of the Formula (I). These moieties are illustrated in the structural formula below.

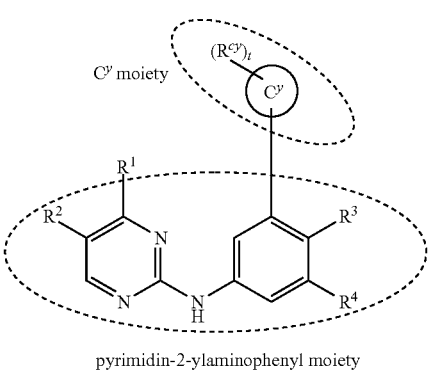

pyrimidin-2-ylaminophenyl moiety

The starting materials and reagents used in preparing compounds described are either available from commercial suppliers or were prepared by literature methods known to those skilled in the art.

These examples are being provided to further illustrate the present invention. The examples provided below are for illustrative purposes only; the scope of the invention is not to be considered limited in any way thereby.

Where the compounds in the examples include the designations "(R) or (S)" or "(R or S)" for a given chiral center in the molecule such designations mean that the compounds were isolated as single enantiomers and the stereochemical configurations of such compounds were not determined. Similarly, when a compound includes the designation "1R,4S or 1S,4R", this designation means that the compound has been isolated as a single diastereomer of unknown absolute configuration.

Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies stationary phase such as OJ-H or OJ column (stationary phase with particle size of 5 or 10 micron) with a mobile phase of $CO_2$ and a lower alcohol such as methanol or isopropanol.

EXAMPLES

Preparative Example 1

Preparation of Pyrimidin-2-ylaminophenyl Precursors Suitable for Coupling with C$^y$ Precursors Preparative Example 1.1

N-[3-methyl-5-(4,4,5,5-tetramethyl-1,3,2-dioxaborolan-2-yl)phenyl]-4-(trifluoromethyl)pyrimidin-2-amine

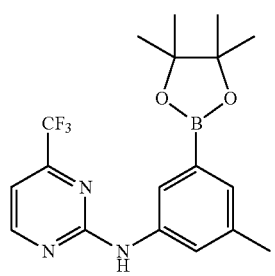

PrepEx-1.1

Step 1:

A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with 2 L of water, then adjusted to pH 7-8 with aqueous saturated sodium bicarbonate solution, followed by extraction with EtOAc (2×2 L). The organic layers were combined, washed with water (2×2 L), dried over anhydrous sodium sulfate and concentrated in vacuo to afford N-(3-bromo-5-methylphenyl)-4-(trifluoromethyl)pyrimidin-2-amine as a light yellow solid. MS ESI calc'd for $C_{12}H_{10}BrF_3N_3$ $[M+H]^+$ 332, 334. found 332, 334. $^1$H NMR (400 MHz, CDCl$_3$): δ 8.68 (d, J=4.9 Hz, 1H), 7.79 (s, 1H), 7.33-7.23 (m, 2H), 7.10-7.06 (m, 2H), 2.36 (s, 3H).

Step 2:

To a solution of N-(3-bromo-5-methylphenyl)-4-(trifluoromethyl)pyrimidin-2-amine (250 g, 753.01 mmol) in 1,4-dioxane (3 L) were added 4,4,5,5-tetramethyl-2-(4,4,5,5-tetramethyl-1,3,2-dioxaborolan-2-yl)-1,3,2-dioxaborolane (225 g, 885.83 mmol), KOAc (225 g, 2.30 mol) and Pd(dppf)Cl2 (19 g, 25.23 mmol). The resulting solution was heated to reflux overnight. The solid was filtered and the filtrate was decolorized by passing through a silica gel column. The fractions were collected and concentrated in vacuo. This resulted in a portion of purified product and a portion of crude product. The crude product was decolorized again with active carbon to provide an additional aliquot of product. The two portions of purified product were combined to afford N-[3-methyl-5-(4,4,5,5-tetramethyl-1,3,2-dioxaborolan-2-yl)phenyl]-4-(trifluoromethyl)pyrimidin-2-amine as a white solid. MS ESI calc'd for $C_{18}H_{22}BF_3N_3O_2$ $[M+H]^+$ 380. found 380. 1H NMR (400 MHz, CDCl$_3$) δ 8.61 (d, J=5.2, 1H), 7.75 (s, 1H), 7.64 (s, 1H), 7.40-7.30 (m, 2H), 7.00 (d, J=5.2, 1 H), 2.39 (s, 3H), 1.35 (s, 12H).

Preparative Example 1.2

N-(3-bromo-5-methylphenyl)-4-cyclopropylpyrimidin-2-amine

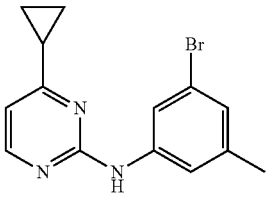

PrepEx. 1.2

To a solution of 2-chloro-4-cyclopropyl-pyrimidine (12.5 g, 81 mmol) and 3-bromo-5-methylaniline (18.1 g, 97 mmol) in 1,4-dioxane (100 mL) was added pivalic acid (9.3 mL, 81 mmol). The resulting mixture was heated to reflux and left stirring for 10 hours. The mixture was allowed to cool to room temperature and hexanes were added (80 mL). The slurry was filtered and the filtrate was washed with MeOH to afford a portion of N-(3-bromo-5-methylphenyl)-4-cyclopropylpyrimidin-2-amine. The mother liquors were concentrated, absorbed on silica gel and purified by silica gel column chromatography (EtOAc/Hex) to afford additional N-(3-bromo- 5-methylphenyl)-4-cyclopropylpyrimidin-2-amine as a white solid. MS ESI calc'd for $C_{14}H_{15}BrN_3$ [M+H]$^+$ 304 and 306. found 304 and 306.

Preparative Example 1.3

5-Fluoro-4-methoxy-N-[3-methyl-5-(4,4,5,5-tetramethyl-1,3,2-dioxaborolan-2-yl)phenyl]pyrimidin-2-amine

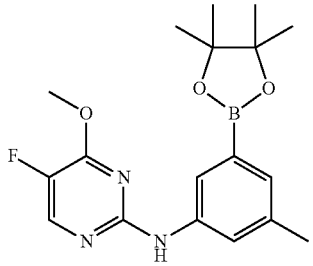

PrepEx. 1.3

A solution of 2-chloro-5-fluoro-4-methoxypyrimidine (0.32 g, 1.97 mmol) and 3-methyl-5-(4,4,5,5-tetramethyl-1,3,2-dioxaborolan-2-yl)aniline (0.40 g, 1.72 mmol) in dioxane (17 mL) and methanesulfonic acid (0.13 mL, 1.97 mmol) was heated to 100° C. overnight. The reaction was then cooled to room temperature, diluted with ethyl acetate, washed with water, dried over magnesium sulfate, filtered and concentrated in reduced pressure. The residue was purified by chromatography on silica gel to afford 5-fluoro-4-methoxy-N-[3-methyl-5-(4,4,5,5-tetramethyl-1,3,2-dioxaborolan-2-yl)phenyl]pyrimidin-2-amine. MS ESI calc'd for $C_{18}H_{24}BFN_3O_3$ [M+H]$^+$ 360. found 360. $^1$H NMR (500 MHz, DMSO-d$_6$) δ 9.51 (s, 1H), 8.27 (d, J=3.2, 1H), 8.00 (s, 1H), 7.57 (s, 1H), 7.07 (s, 1H), 4.01 (s, 3H), 2.25 (s, 3H), 1.26 (s, 12H).

The following intermediates were prepared using the route shown in Intermediate X.

Preparative Example 2

Preparation of C$^y$ Precursors Suitable for Coupling with Pyrimidin-2-ylaminophenyl Precursors Preparative Example 2.1

4-(5-Bromopyridin-2-yl)-1,4-diazepan-2-one

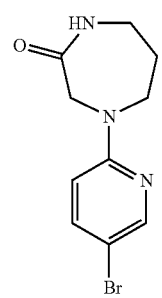

PrepEx 2.1

A solution of 3-bromo-6-fluoropyridine (315 mg, 1.79 mmol), 1,4-diazepan-2-one (200 mg, 1.75 mmol), and triethylamine (0.269 ml, 1.93 mmol) in N,N-dimethylacetamide (3 mL) was irradiated in a microwave reactor for twenty minutes at 220° C. The reaction mixture was diluted with ethyl acetate (35 mL) and then washed with saturated aqueous sodium bicarbonate (15 mL), water (3×10 mL), and brine (15 mL). The organic layer was dried over sodium sulfate, filtered, and concentrated under reduced pressure. The residue was purified by chromatography on silica gel (0.5-8.5% methanol/dichloromethane) to afford 4-(5-bromopyridin-2-yl)-1,4-diazepan-2-one. MS ESI calc'd. for $C_{10}H_{13}BrN_3O$ [M+H]+ 270 and 272. found 270 and 272. $^1$H NMR (500 MHz, DMSO-d$_6$): δ 8.14 (d, J=2.4 Hz, 1H), 7.68 (dd, J=9.1,

| Prep Ex No. | Structure | Name | Exact Mass [M + H]$^+$ |
|---|---|---|---|
| 1.4 | 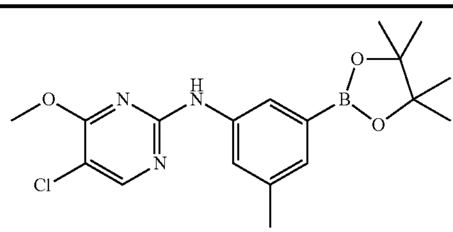 | 5-chloro-4-methoxy-N-[3-methyl-5-(4,4,5,5-tetramethyl-1,3,2-dioxaborolan-2-yl)phenyl]pyrimidin-2-amine | Calc'd 376, found 376 |
| 1.5 | 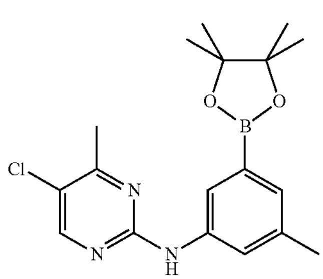 [SMILES: Cc1cc(Nc2ncc(Cl)c(C)n2)cc(B2OC(C)(C)C(C)(C)O2)c1] | 5-chloro-4-methyl-N-[3-methyl-5-(4,4,5,5-tetramethyl-1,3,2-dioxaborolan-2-yl)phenyl]pyrimidin-2-amine | Calc'd 360, found 360 |

2.7 Hz, 1H), 7.48 (m, 1H), 6.70 (d, J=9.1 Hz, 1H), 4.11 (s, 2H), 3.85 (s, 2H), 3.18 (m, 2H), 1.62 (m, 2H).

Preparative Example 2.2

Ethyl 4-[(5-bromopyridin-2-yl)oxy]cyclohexanecarboxylate

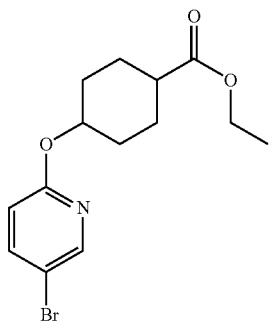

PrepEx 2.2

NaH (0.250 g, 6.25 mmol) was added to a mixture of ethyl 4-hydroxycyclohexanoate (0.916 ml, 5.68 mmol), and 5-bromo-2-fluoropyridine (0.585 mL, 5.68 mmol) in DMF (15 mL) at room temperature under an Argon atmosphere. The reaction mixture was heated to 80° C. for 2.5 hours. Upon cooling, the reaction mixture was diluted with saturated NaHCO$_3$ (50 mL), and extracted with ethyl acetate (50 mL) and diethyl ether (50 mL). The organic layer was washed with water, brine, dried over sodium sulfate, filtered, concentrated in vacuo and purified by silica gel chromatography (hexanes/ethyl Acetate) to afford ethyl 4-[(5-bromopyridin-2-yl)oxy]cyclohexanecarboxylate. MS ESI calc'd. for C$_{14}$H$_{19}$BrNO$_3$ [M+H]$^+$ 328 and 330. found 328 and 330.

Preparative Example 2.3

2-(5-Bromopyridin-3-yl)-1,1,1-trifluoropropan-2-ol

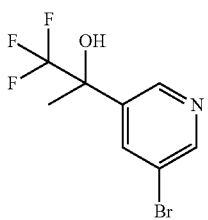

PrepEx 2.3

Tetrabutylammonium fluoride (1.0 M in THF, 33 µl, 0.033 mmol) was added to a solution of 1-(5-bromopyridin-3-yl)ethanone (65 mg, 0.33 mmol) and trimethyl(trifluoromethyl)silane (92 mg, 0.65 mmol) in THF (1.1 mL) at ambient temperature. After 30 minutes, the reaction mixture was diluted with water and extracted with DCM, dried over sodium sulfate, filtered, and concentrated under reduced pressure. The residue was purified by silica gel chromatography (0-30% ethyl acetate/hexanes, linear gradient) to afford 2-(5-bromopyridin-3-yl)-1,1,1-trifluoropropan-2-ol. MS ESI calc'd. for C$_8$H$_8$BrF$_3$NO [M+H]$^+$ 270 and 272. found 270 and 272. $^1$H NMR (500 MHz, CDCl$_3$) δ 8.72 (s, 1H), 8.69 (d, J=2.5 Hz, 1H), 8.10-8.08 (m, 1H), 2.58 (s, 1H), 1.82 (s, 3H).

Preparative Example 2.4

Trans-4-[(5-bromopyridin-2-yl)amino]cyclohexanecarboxylic acid

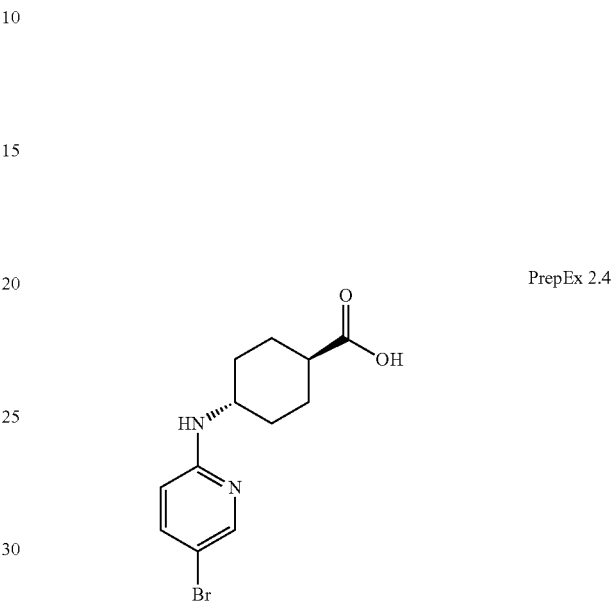

PrepEx 2.4

A mixture of trans-4-aminocyclohexanecarboxylic acid hydrochloride (2.00 g, 11.1 mmol), 5-bromo-2-fluoropyridine (2.29 mL, 22.3 mmol), potassium carbonate (3.08 g, 22.3 mmol), DIEA (3.89 mL, 22.3 mmol) in NMP (50 mL) was heated to 130° C. overnight. The reaction was cooled to room temperature, filtered through a pad of CELITE, and washed with NMP (50 mL). The reaction mixture was concentrated under reduced pressure. The residue was purified by silica gel chromatography (CH$_2$Cl$_2$/MeOH, 0-10%) to afford trans-4-[(5-bromopyridin-2-yl)amino]cyclohexanecarboxylic acid as a off-white solid. MS ESI calc'd for C$_{12}$H$_{16}$BrN$_2$O$_2$ [M+H]$^+$ 299 and 301. found 299 and 301.

Preparative Example 2.5

N-(5-bromopyridin-2-yl)-2-cyanoacetamide

BOP (3.07 g, 6.94 mmol) and DIEA (606 µl, 3.47 mmol) were added to a mixture of 5-bromo-2-fluoropyridine (400 mg, 2.312 mmol) and cyanoacetic acid (201 mg, 2.358 mmol) in DMF (11.6 mL). The reaction mixture was stirred at room temperature overnight, diluted with ethyl acetate and washed with water (2×). The organic layer was concentrated under reduced pressure and the residue was purified by silica gel chromatography (ethyl Acetate/hexanes) to afford N-(5-bromopyridin-2-yl)-2-cyanoacetamide. MS ESI calc'd for $C_8H_7BrN_3O$ [M+H]$^+$ 240 and 242. found 240.

Preparative Example 2.6

Ethyl 3-(4-bromopyridin-2-yl)propanoate

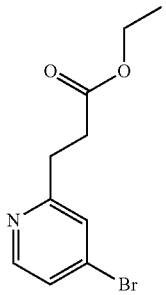
PrepEx 2.6

Nitrogen was bubbled through a solution of 2,4-dibromopyridine (0.25 g, 1.06 mmol) in THF (2 ml) for ~10 minutes. Tetrakis(triphenylphosphine)palladium(0) (0.122 g, 0.106 mmol) was added and the flask sealed with a septa. Bromo (3-ethoxy-3-oxopropyl)zinc (3.17 ml, 1.58 mmol) was added slowly via syringe and the reaction mixture was heated at 85° C. for 16 hours. Upon cooling, the reaction mixture was partitioned between DCM and brine. The organic layer was dried ($Na_2SO_4$), concentrated under reduced pressure and the residue was purified by silica gel chromatography (gradient elution with EtOAc/Hexanes 7 to 60%) to give ethyl 3-(4-bromopyridin-2-yl)propanoate as a pale yellow oil. MS ESI calc'd. for $C_{10}H_{13}BrNO_2$ [M+H]$^+$ 258 and 260. found 258 and 260. $^1$H NMR (500 MHz, CDCl$_3$) δ 8.33 (d, J=5.1 Hz, 1H), 7.39 (bs, 1H), 7.30 (dd, J=5.2, 1.7 Hz, 1H), 4.12 (q, J=6.7 Hz, 2H), 3.08 (t, J=6.5 Hz, 2H), 2.79 (t, J=6.4 Hz, 2H), 1.23 (t, J=6.8 Hz, 3H).

Preparative Example 2.7

Ethyl 3-[5-(4,4,5,5-tetramethyl-1,3,2-dioxaborolan-2-yl)pyridin-3-yl]propanoate

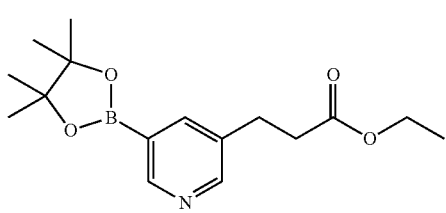
PrepEx 2.7

Step 1:
(Carbethoxymethylene)triphenylphosphorane (1.56 g, 4.49 mmol) was added to a solution of 5-bromopyridine-3-carbaldehyde (0.50 mg, 2.69 mmol) in DMF (5 mL) and the mixture was stirred at room temperature for one hour. The reaction was poured into ice water and then ethyl acetate was added. The organic layer was separated, washed with brine, dried over magnesium sulfate, filtered and concentrated under reduced pressure. The residue was dissolved in ethyl acetate and then hexanes were added until solid crashed out. The mixture was filtered and then the filtrate was concentrated in vacuo. The residue was purified by silica gel chromatography to afford an ~4:1 mixture of ethyl (2E)-3-(5-bromopyridin-3-yl)prop-2-enoate and ethyl (2Z)-3-(5-bromopyridin-3-yl)prop-2-enoate. MS ESI calc'd. for $C_{10}H_{11}BrNO_2$ [M+H]$^+$ 256 and 258. found 256 and 258. $^1$H NMR data for the major (2E) isomer: $^1$H NMR (500 MHz, DMSO-d$_6$) δ 8.87 (d, J=1.7 Hz, 1H), 8.70 (d, J=2.2 Hz, 1H), 8.51 (t, J=2.0 Hz, 1H), 7.64 (d, J=16.2 Hz, 1H), 6.88 (d, J=16.2 Hz, 1H), 4.19 (q, J=7.1 Hz, 2H), 1.25 (t, J=7.1 Hz, 3H).

Step 2:
To a solution of ethyl (2E)-3-(3-bromophenyl)prop-2-enoate and ethyl (2Z)-3-(5-bromopyridin-3-yl)prop-2-enoate (4:1 ratio of isomers, 332 mg, 1.30 mmol) in methanol (10 mL) and water (2.5 mL) was added copper (I) chloride (257 mg, 2.59 mmol) and sodium borohydride (98 mg, 2.59 mmol). After 15 minutes, the reaction was diluted with ethyl acetate and filtered through CELITE. The filtrate was washed with water, dried over magnesium sulfate, filtered and concentrated in vacuo. The residue was purified by silica gel chromatography to afford ethyl 3-(5-bromopyridin-3-yl)propanoate. MS ESI calc'd. for $C_{10}H_{13}BrNO_2$ [M+H]$^+$ 258 and 260. found 258 and 260. $^1$H NMR (500 MHz, DMSO-d$_6$) δ 8.52 (d, J=2.2 Hz, 1H), 8.44 (d, J=1.8 Hz, 1H), 7.96 (t, J=2.0 Hz, 1H), 4.02 (q, J=7.1 Hz, 2H), 2.84 (t, J=7.5 Hz, 2H), 2.67 (t, J=7.5 Hz, 2H), 1.12 (t, J=7.1 Hz, 3H).

Step 3:
A mixture of ethyl 3-(5-bromopyridin-3-yl)propanoate (1.64 g, 6.35 mmol), bis(pinacolato)diboron (1.78 g, 6.99 mmol), Pd$_2$(dba)$_3$ (291 mg, 0.318 mmol), tricyclohexylphosphine (178 mg, 0.635 mmol) and potassium acetate (998 mg, 10.2 mmol) in degassed dioxane (64 mL) was evacuated/purged 5 times with argon. The reaction was heated to 95° C. for 14 hours. The reaction was then allowed to cool to room temperature, diluted with water, extracted with ethyl acetate, dried over magnesium sulfate, filtered and concentrated in vacuo. The residue was purified by silica gel chromatography to afford ethyl 3-[5-(4,4,5,5-tetramethyl-1,3,2-dioxaborolan-2-yl)pyridin-3-yl]propanoate. $^1$H NMR (500 MHz, CDCl$_3$) δ 8.85 (s, 1H), 8.62 (s, 1H), 8.36 (s, 1H), 4.12 (q, J=7.1 Hz, 2H), 3.07 (t, J=7.3 Hz, 2H), 2.70 (t, J=7.3 Hz, 2H), 1.35 (s, 12H), 1.26-1.20 (m, 3H).

Preparative Example 2.8

Ethyl 3-(5-bromopyridin-2-yl)propanoate

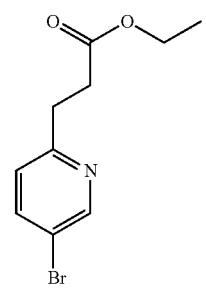
PrepEx 2.8

Argon was bubbled through a solution of 2,5-dibromopyridine (3.00 g, 12.7 mmol) in THF (25.3 ml) for ~10 minutes. Palladium Tetrakis (1.46 g, 1.27 mmol) was added quickly to the reaction mixture, and then [(3-ethoxy-3-oxopropyl)-λ$^3$-bromanylidene]zinc (38.0 ml, 19.0 mmol) was added slowly. The reaction mixture was heated to 85° C. overnight. The cooled reaction mixture was filtered through a CELITE pad and washed with DCM (3×). The filtrate was diluted with water, extracted with DCM (3×) and the combined organic layers were dried under reduced pressure. The residue was purified by silica gel chromatography (ethyl acetate/hexanes) to afford ethyl 3-(5-bromopyridin-2-yl)propanoate. MS ESI calc'd for $C_{10}H_{13}BrNO_2$ [M+H]$^+$ 258 and 260. found 258 and 260.

Preparative Example 2.9

3-(6-Bromopyridin-3-yl)propanoate

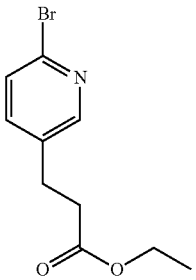

PrepEx 2.9

Palladium tetrakis (1.64 g, 1.41 mmol) was added to a solution of 2-bromo-4-iodopyridine (4.00 g, 14.1 mmol) in THF (28.2 ml) under an argon atmosphere. The mixture was cooled to 0° C., 3-ethoxy-3-oxopropylzinc bromide (36.6 mL, 18.3 mmol) was slowly added to the reaction mixture and stirred for 1 hour. The mixture was then allowed to warm to room temperature overnight. An aqueous ammonium chloride was added to the reaction mixture and stirred for 5 minutes. pH was then adjusted to ~8 with aqueous sodium bicarbonate and product was extracted with ethyl acetate (3×). The combined organic layers were dried over anhydrous magnesium sulfate, and concentrated under reduced pressure. The residue was purified by silica gel chromatography (ethyl acetate/hexanes) to afford ethyl 3-(6-bromopyridin-3-yl)propanoate. MS ESI calc'd for $C_{10}H_{13}BrNO_2$ [M+H]$^+$ 258 and 260. found 258 and 260.

Preparative Example 2.10

Ethyl 4-[(5-bromopyridin-2-yl)oxy]cyclohexanecarboxylate

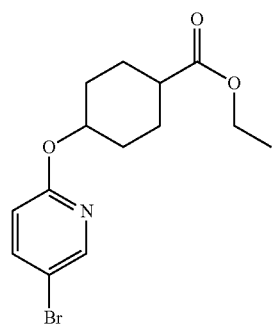

PrepEx 2.10

NaH (0.250 g, 6.25 mmol) was added to a mixture of ethyl 4-hydroxycyclohexanoate (0.916 ml, 5.68 mmol), and 5-bromo-2-fluoropyridine (0.585 mL, 5.68 mmol) in DMF (15 mL) at room temperature under an argon atmosphere. The reaction mixture was heated to 80° C. for 2.5 hours. Upon cooling, the reaction mixture was diluted with saturated NaHCO$_3$ (50 mL), extracted with ethyl acetate (50 mL) and diethyl ether (50 mL), washed with water, brine, dried over sodium sulfate, filtered, and concentrated in vacuo. The residue was purified by silica gel chromatography (hexanes/ethyl acetate) to afford ethyl 4-[(5-bromopyridin-2-yl)oxy]cyclohexanecarboxylate. MS ESI calc'd for $C_{14}H_{19}BrNO_3$ [M+H]$^+$ 328 and 330. found 328 and 330.

Example 1

Preparation of Compounds of Formula (I) Using the General Methods Illustrated in Scheme 1

Example 1.1

1-{6-[3-(Morpholin-4-yl)-5-{[4-(trifluoromethyl)pyrimidin-2-yl]amino}phenyl]pyridin-2-yl}cyclobutanol

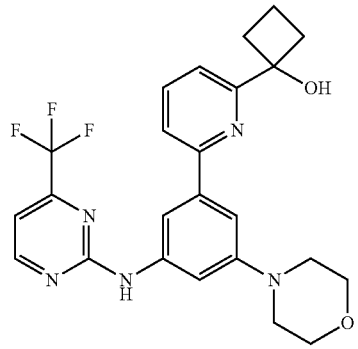

1.1

Step 1:
Morpholine (2.53 mL, 28.1 mmol) was added to a solution of 1-fluoro-3-iodo-5-nitrobenzene (3 g, 11.2 mmol) in DMSO (22.5 mL) under nitrogen. The reaction was heated at 120° C. for 2 hours, then cooled to room temperature and diluted with a mixture of ether and ethyl acetate. The organic layer was washed with water (2×) and concentrated under reduced pressure. The residue was purified by silica gel chromatography (ethyl acetate:hexanes) to afford 4-(3-iodo-5-nitrophenyl)morpholine as deep yellow solid.

Step 2:
Bis(pinacolato)diboron (2.72 g, 10.7 mmol), Pd(dppf)Cl$_2$-dichloromethane adduct (397 mg, 0.486 mmol) and potassium acetate (2.86 g, 29.2 mmol) were added to a solution of 4-(3-iodo-5-nitrophenyl)morpholine (3.25 g, 9.73 mmol) in dioxane (19.5 mL) and the reaction mixture was purged and flushed with N$_2$(g) (3×). The reaction mixture was heated to 120° C. overnight, then cooled to room temperature, diluted with ether, extracted with water (2×), dried over sodium sulfate, filtered and concentrated under reduced pressure. The crude product, 4-[3-nitro-5-(4,4,5,5-tetramethyl-1,3,2-dioxaborolan-2-yl)phenyl]morpholine, which was used without further purification. $^1$H NMR (500 MHz, CDCl$_3$) δ 8.13 (s, 1H), 7.79 (s, 1H), 7.63 (d, J=1.9, 1H), 4.02-3.80 (m, 4H), 3.46-3.17 (m, 4H), 1.38 (s, 12H).

Step 3a:
Preparation of 1-(6-Bromopyridin-2-yl)cyclobutanol: n-Butyllithium (6.85 mL, 11.0 mmol) was added to a suspension of 2,6-dibromopyridine (2.36 g, 9.96 mmol) in dichloromethane (60 mL) at −78° C. The reaction mixture was stirred for 15 minutes and cyclobutanone (0.838 g, 12.0 mmol) was added in one portion at −78° C. The reaction was stirred for an additional 30 minutes before pouring the reaction into a mixture of saturated aqueous NH$_4$Cl and dichloromethane. The organic layer was concentrated to dryness and was purified by flash chromatography to yield 1-(6-bromopyridin-2-yl)cyclobutanol as a light yellow oil. MS ESI calc'd. for C$_9$H$_{11}$BrNO [M+H]$^+$ 228 and 230. found 228 and 230.

Step 3:

Pd(dppf)Cl$_2$-dichloromethane adduct (40.8 mg, 0.05 mmol) and sodium carbonate (2 N, 1.5 mL, 3.0 mmol) were added to 1-(6-bromopyridin-2-yl)cyclobutanol (228 mg, 1.0 mmol) and 4-[3-nitro-5-(4,4,5,5-tetramethyl-1,3,2-dioxaborolan-2-yl)phenyl]morpholine (0.2 N in DMF, 5.0 mL, 1.0 mmol) and the reaction mixture was purged and flushed with N$_2$(g) (3x). The reaction mixture was heated to 100° C. for 4 hours, then cooled to room temperature, diluted with water, extracted with diethyl ether, washed with brine, dried over sodium sulfate, filtered an concentrated under reduced pressure. The crude product was purified by silica gel chromatography (ethyl acetate:hexanes) to afford 1-{6-[3-(morpholin-4-yl)-5-nitrophenyl]pyridin-2-yl}cyclobutanol. $^1$H NMR (500 MHz, CDCl$_3$) δ 8.30-8.23 (m, 1H), 7.98-7.95 (m, 1H), 7.93, (t, J=7.2 Hz 1H), 7.79 (t, J=2.2, 1H), 7.74 (d, J=7.8, 1H), 7.66 (d, J=7.8, 1H), 5.36 (s, 1H), 4.03-3.84 (m, 4H), 3.46-3.29 (m, 4H), 2.82-2.47 (m, 4H), 2.27-2.09 (m, 1H), 2.05-1.91 (m, 1H).

Step 4:

Ammonium chloride (22.6 mg, 0.422 mmol) and iron (216 mg, 3.57 mmol) were added to a solution of 1-{6-[3-(morpholin-4-yl)-5-nitrophenyl]pyridin-2-yl}cyclobutanol (250 mg, 0.703 mmol) in ethanol (4.69 mL) and water (2.36 mmol). The reaction mixture was heated to 85° C. for 1 hour, then cooled to room temperature. The reaction was filtered, diluted with water, extracted with ethyl acetate, dried over sodium sulfate, filtered and concentrated under reduced pressure. The residue was purified by silica gel chromatography (7:3 ethyl acetate:hexanes, then 100% ethyl acetate) to afford 1-{6-[3-amino-5-(morpholin-4-yl)phenyl]pyridin-2-yl}cyclobutanol as an off-white solid. $^1$H NMR (500 MHz, CDCl$_3$) δ 7.83 (s, 1H), 7.66-7.58 (m, 1H), 7.56 (d, J=7.5, 1H), 7.36-7.23 (m, 2H), 7.01 (s, 1H), 6.90 (s, 1H), 6.34 (s, 1H), 5.81 (s, 1H), 3.90 (m, 4H), 3.23 (m, 4H), 2.64-2.54 (m, 4H), 2.14-2.08 (m, 1H), 1.96-1.92 (m, 1H).

Step 5:

Xantphos (93 mg, 0.161 mmol), palladium(II) acetate (24.2 mg, 0.108 mmol), and cesium carbonate (350 mg, 1.08 mmol) were added to a degassed solution of 2-chloro-4-(trifluoromethyl)pyrimidine (103 mg, 0.565 mmol), 1-{6-[3-amino-5-(morpholin-4-yl)phenyl]pyridin-2-yl}cyclobutanol (175 mg, 0.538 mmol) in dioxane (45.3 mL) and the reaction mixture was heated to 100° C. for 2 hours and then for 5 hours at 115° C. Then, the reaction mixture was cooled to room temperature, diluted with water, extracted with ethyl acetate, washed with brine, dried over sodium sulfate, filtered and concentrated under reduced pressure. The crude product was purified by silica gel chromatography (ethyl acetate:hexanes) to afford 1-{6-[3-(morpholin-4-yl)-5-{[4-(trifluoromethyl)pyrimidin-2-yl]amino}phenyl]pyridin-2-yl}cyclobutanol as an off-white solid. MS APCI calc'd for C$_{24}$H$_{25}$F$_3$N$_5$O$_2$ [M+H]$^+$ 472. found 472. $^1$H NMR (NMR Hz 400 MHz, Acetone-d$_6$): δ 9.26 (s, 1H), 8.82 (d, J=4.8 Hz, 1H), 8.16 (s, 1H), 7.90 (t, J=7.8 Hz, 1H), 7.84-7.77 (m, 2H), 7.66 (d, J=7.8 Hz, 1H), 7.53 (s, 1H), 7.23 (d, J=4.9 Hz, 1H), 3.86 (t, J=4.4 Hz, 4H), 3.30 (t, J=4.4 Hz, 4H), 2.74-2.63 (m, 2H), 2.43 (m, 2H), 2.04 (m, 2H).

The following examples in Table 1 were prepared in an analogous manner to that described in general scheme 1 using commercially available amines in step 1.

TABLE 1

| Ex. | R$^{Cy}$ | Name | [M + H]$^+$ Calc'd | [M + H]$^+$ Obsv'd | Form(s) |
|---|---|---|---|---|---|
| 1.2 | —H | N-(3-morpholin-4-yl-5-pyridin-2-ylphenyl)-4-(trifluoromethyl)pyrimidin-2-amine | 402 | 402 | Free Base |
| 1.3 | 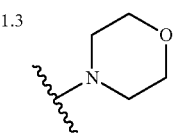 | N-[3-morpholin-4-yl-5-(6-morpholin-4-ylpyridin-2-yl)phenyl]-4-(trifluoromethyl)pyrimidin-2-amine | 487 | 487 | Free Base |

TABLE 1-continued

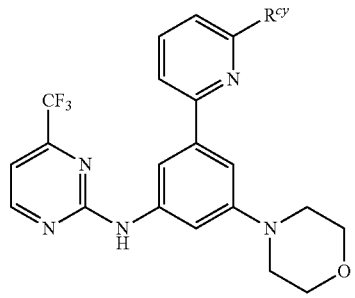

| Ex. | $R^{cy}$ | Name | [M + H]+ Calc'd | [M + H]+ Obsv'd | Form(s) |
|---|---|---|---|---|---|
| 1.4 | OH, N(CH2CH2OH)2 group | 2,2'-{[6-(3-morpholin-4-yl-5-{[4-(trifluoromethyl)pyrimidin-2-yl]amino}phenyl)pyridin-2-yl]imino}diethanol | 505 | 505 | Free Base |

Example 2

Preparation of Compounds of Formula (I) Using the General Methods Illustrated in Scheme 2

Example 2.1

5-(3-Methyl-5-{[4-(trifluoromethyl)pyrimidin-2-yl]amino}phenyl)pyridine-2-carboxylic acid

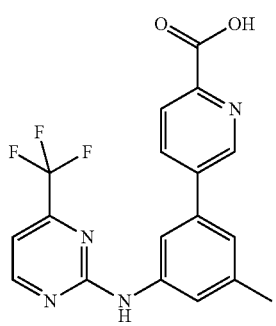

2.1

A mixture of N-[3-methyl-5-(4,4,5,5-tetramethyl-1,3,2-dioxaborolan-2-yl)phenyl]-4-(trifluoromethyl)pyrimidin-2-amine (6.5 g, 17.1 mmol), 5-bromopyridine-2-carboxylic acid (3.92 g, 19.4 mmol), aqueous sodium carbonate (2M, 17.1 mL, 34.3 mmol) in dioxanes (57.1 mL) was flushed and purged with Ar(g) (3×). PdCl$_2$(dppf)-dichloromethane adduct (646 mg, 0.791 mmol) was then added to the reaction mixture and heated at 130° C. for 10 hours. Upon cooling, the reaction mixture was filtered through a CELITE pad and washed with dioxane. The crude reaction mixture was concentrated under reduced pressure and diluted with 90% MeCN and 10% 2M HCl (aq). The crude solid was isolated by filtration and was recrystallized from dichloromethane to yield 5-(3-methyl-5-{[4-(trifluoromethyl)pyrimidin-2-yl]amino}phenyl)pyridine-2-carboxylic acid as an off-white powder. MS APC calc'd for $C_{18}H_{14}F_3N_4O_2$ [M+H]+ 375. found 375. $^1$H NMR (500 MHz, DMSO-d6) δ 10.32 (s, 1H), 8.95 (s, 1H), 8.84 (d, J=5.4, 1H), 8.18 (d, J=9.6, 1H), 8.12 (d, J=9.3, 1H), 8.05 (s, 1H), 7.28 (s, 2H), 2.38 (s, 3H).

Example 2.2

Methyl 3-(6-(3-((4-methoxypyrimidin-2-yl)amino)-5-methylphenyl)pyridin-2-yl)propanoate

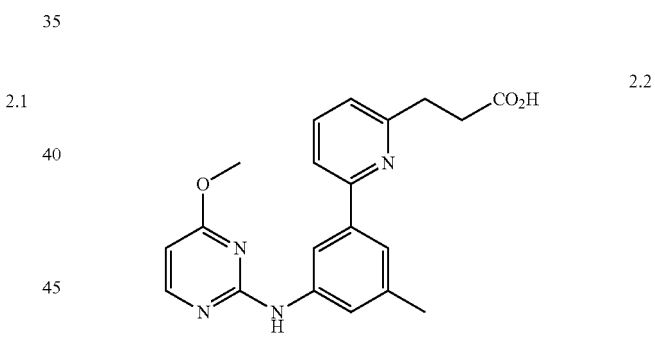

2.2

A mixture of 4-methoxy-N-(3-methyl-5-(4,4,5,5-tetramethyl-1,3,2-dioxaborolan-2-yl)phenyl)pyrimidin-2-amine (0.045 g, 0.13 mmol), ethyl 3-(6-bromopyridin-2-yl)propanoate (0.037 g, 0.15 mmol), PdCl$_2$(dppf)-CH$_2$Cl$_2$ (0.016 g, 0.020 mmol), and Na$_2$CO$_3$ (2.0 M in water, 0.13 mL, 0.26 mmol) in dioxane (0.75 mL) was purged with argon and heated to 110° C. for 12 hours. Upon cooling, NaOH (1.0 M in water, 0.50 mL) and MeOH (0.50 mL) were added to the reaction mixture and irradiated in a microwave reactor for 10 minutes at 110° C. Silica Supported-DMT (0.088 g, 0.13 mmol, 0.57 mmol/g) was added to the reaction mixture and shaken for 5 hours at ambient temperature. The reaction was passed through a syringe filter and the eluent was evaporated under reduced pressure. The residue was suspended in DMSO (1.5 mL) and was purified by reverse phase preparative HPLC (0:100 to 95:5 acetonitrile:water: 0.1% v/v formic acid modifier) to afford methyl 3-(6-(3-((4-methoxypyrimidin-2-yl)amino)-5-methylphenyl)pyridin-2-yl)propanoate. LRMS (ESI) calc'd for $C_{20}H_{21}N_4O_3$ [M+H]+: 365. Found:

365. $^1$H NMR (600 MHz, DMSO-d$_6$) δ 9.54 (s, 1H), 8.33 (s, 1H), 8.18 (d, J=5.6, 1H), 7.73 (t, J=7.7, 1H), 7.64 (d, J=7.8, 1H), 7.61 (s, 1H), 7.44 (s, 1H), 7.19 (d, J=7.6, 1H), 6.25 (d, J=5.6, 1H), 3.93 (s, 3H), 2.99 (t, J=7.4, 2H), 2.71 (t, J=7.4, 2H), 2.33 (s, 3H).

The following examples in Tables 2A-2D were prepared in an analogous manner to that described in general scheme 2 using known (e.g., Mallet, M.; Branger, G.; Marsais, F.; Queguiner, G. *J. Organometallic Chem* 1990, 382, 319-32), intermediates described above, or commercially available iodides, bromides, or chlorides. In some cases, ester hydrolysis and palladium scavenging steps were omitted.

TABLE 2A

| Ex. | R¹ | R^cy1 | R^cy2 | R^cy3 | R⁴ | Name | [M+H]⁺ Calc'd | [M+H]⁺ Obsv'd | Form |
|---|---|---|---|---|---|---|---|---|---|
| 2.3 | —CF₃ | —OCH₃ | —H | —H | —H | N-[3-(6-methoxypyridin-2-yl)phenyl]-4-(trifluoromethyl)pyrimidin-2-amine | 347 | 347 | Free Base |
| 2.4 | —CF₃ | 1-ethyl-1-hydroxycyclobutyl | —H | —H | —H | 3-[6-(3-{[4-(trifluoromethyl)pyrimidin-2-yl]amino}phenyl)pyridin-2-yl]pentan-3-ol | 403 | 403 | Free Base |
| 2.5 | —CF₃ | —H | ethyl acetate group | —H | —H | ethyl [6-(3-{[4-(trifluoromethyl)pyrimidin-2-yl]amino}phenyl)pyridin-3-yl]acetate | 403 | 403 | Free Base |
| 2.6 | —CF₃ | —H | —S(O)₂CH₃ | —H | —H | N-[3-[5-(methylsulfonyl)pyridin-2-yl]phenyl]-4-(trifluoromethyl)pyrimidin-2-amine | 395 | 395 | Free Base |
| 2.7 | —CF₃ | —H | —H | —C(O)NH₂ | —H | 2-(3-{[4-(trifluoromethyl)pyrimidin-2-yl]amino}phenyl)pyridine-4-carboxamide | 360 | 360 | Free Base |
| 2.8 | —CF₃ | —H | —C(O)NH₂ | —H | —H | 6-(3-{[4-(trifluoromethyl)pyrimidin-2-yl]amino}phenyl)pyridine-3-carboxamide | 360 | 360 | Free Base |

TABLE 2A-continued

| Ex. | R[1] | R[cy1] | R[cy2] | R[cy3] | R[4] | Name | [M+H]+ Calc'd | [M+H]+ Obsv'd | Form |
|---|---|---|---|---|---|---|---|---|---|
| 2.9 | —CF₃ | —H | 4-methylphenylsulfonamide group (Tol-SO₂-NH-) | —H | —H | 4-methyl-N-[6-(3-{[4-(trifluoromethyl)pyrimidin-2-yl]amino}phenyl)pyridin-3-yl]benzenesulfonamide | 486 | 486 | Free Base |
| 2.10 | —CF₃ | —OH | —NH₂ | —H | —CH₃ | 3-amino-6-(3-methyl-5-{[4-(trifluoromethyl)pyrimidin-2-yl]amino}phenyl)pyridin-2-ol | 362 | 362 | TFA Salt |
| 2.11 | —CF₃ | —H | —H | —C(O)OH | —H | 2-(3-{[4-(trifluoromethyl)pyrimidin-2-yl]amino}phenyl)pyridine-4-carboxylic acid | 361 | 361 | Formate Salt |
| 2.12 | —CF₃ | —C(O)OH | —H | —H | —H | 6-(3-{[4-(trifluoromethyl)pyrimidin-2-yl]amino}phenyl)pyridine-2-carboxylic acid | 361 | 361 | Formate Salt |
| 2.13 | —CF₃ | —C(O)OH | —H | —H | —CH₃ | 6-(3-methyl-5-{[4-(trifluoromethyl)pyrimidin-2-yl]amino}phenyl)pyridine-2-carboxylic acid | 375 | 375 | Formate Salt |
| 2.14 | —CF₃ | ethyl propanoate (—CH₂CH₂C(O)OCH₂CH₃) | —H | —H | —H | ethyl 3-[6-(3-{[4-(trifluoromethyl)pyrimidin-2-yl]amino}phenyl)pyridin-2-yl]propanoate | 417 | 417 | Formate Salt |

TABLE 2A-continued

| Ex. | R¹ | R^cy1 | R^cy2 | R^cy3 | R⁴ | Name | $[M+H]^+$ Calc'd | $[M+H]^+$ Obsv'd | Form |
|---|---|---|---|---|---|---|---|---|---|
| 2.15 | —CF₃ | —H | —H | ethyl propanoate linker | —H | ethyl 3-[2-(3-{[4-(trifluoromethyl)pyrimidin-2-yl]amino}phenyl)pyridin-4-yl]propanoate | 417 | 417 | Formate Salt |
| 2.16 | —CF₃ | —H | propanoic acid linker | —H | —H | 3-[6-(3-{[4-(trifluoromethyl)pyrimidin-2-yl]amino}phenyl)pyridin-3-yl]propanoic acid | 389 | 389 | Formate Salt |
| 2.17 | —CF₃ | propanoic acid linker | —H | —H | —H | 3-[6-(3-{[4-(trifluoromethyl)pyrimidin-2-yl]amino}phenyl)pyridin-2-yl]propanoic acid | 389 | 389 | Formate Salt |

TABLE 2A-continued

| Ex. | R¹ | R^cy1 | R^cy2 | R^cy3 | R⁴ | Name | [M+H]⁺ Calc'd | [M+H]⁺ Obsv'd | Form |
|---|---|---|---|---|---|---|---|---|---|
| 2.18 | —CF₃ | —H | —H | propanoic acid (CH₂CH₂COOH) | —H | 3-[2-(3-{[4-(trifluoromethyl)phenyl]amino}phenyl)pyrimidin-2-yl]pyridin-4-yl]propanoic acid | 389 | 389 | Formate Salt |
| 2.19 | —OCH₃ | —H | ethyl propanoate (CH₂CH₂COOCH₂CH₃) | —H | —CH₃ | ethyl 3-(6-{3-[(4-methoxypyrimidin-2-yl)amino]-5-methylphenyl}pyridin-3-yl)propanoate | 393 | 393 | Formate Salt |
| 2.20 | —OCH₃ | propanoic acid (CH₂CH₂COOH) | —H | —H | —CH₃ | 3-(6-{3-[(4-methoxypyrimidin-2-yl)amino]-5-methylphenyl}pyridin-2-yl)propanoic acid | 365 | 365 | Formate Salt |

TABLE 2A-continued

| Ex. | R¹ | R$^{cy1}$ | R$^{cy2}$ | R$^{cy3}$ | R⁴ | Name | [M + H]⁺ Calc'd | [M + H]⁺ Obsv'd | Form |
|---|---|---|---|---|---|---|---|---|---|
| 2.21 | —OCH₃ | —H | —H | ~~~~COOH | —CH₃ | 3-(2-{3-[(4-methoxypyrimidin-2-yl)amino]-5-methylphenyl}pyridin-4-yl)propanoic acid | 365 | 365 | Formate Salt |
| 2.22 | —CF₃ | —H | —H | ~~~~COOH | —CH₃ | 3-[2-(3-methyl-5-{[4-(trifluoromethyl)pyrimidin-2-yl]amino}phenyl)pyridin-4-yl]propanoic acid | 403 | 403 | Ammonium Salt |
| 2.23 | —CH₃ | —H | —H | ~~~~COOH | —CH₃ | 3-(2-{3-methyl-5-[(4-methylpyrimidin-2-yl)amino]phenyl}pyridin-4-yl)propanoic acid | 349 | 349 | Ammonium Salt |

TABLE 2A-continued

| Ex. | R¹ | R^cy1 | R^cy2 | R^cy3 | R⁴ | Name | [M+H]⁺ Calc'd | [M+H]⁺ Obsv'd | Form |
|---|---|---|---|---|---|---|---|---|---|
| 2.24 | cyclopropyl | —H | —H | (propanoic acid chain) | —CH₃ | 3-(2-{3-[(4-cyclopropylpyrimidin-2-yl)amino]-5-methylphenyl}pyridin-4-yl)propanoic acid | 375 | 375 | Ammonium Salt |
| 2.25 | —OCH₃ | (ethyl propanoate chain, OCH₂CH₃) | —H | —H | —CH₃ | ethyl 3-(6-{3-[(4-methoxypyrimidin-2-yl)amino]-5-methylphenyl}pyridin-2-yl)propanoate | 393 | 393 | Free Base |
| 2.26 | —OCH₃ | —H | (propanoic acid chain, OH) | —H | —CH₃ | 3-(6-{3-[(4-methoxypyrimidin-2-yl)amino]-5-methylphenyl}pyridin-3-yl)propanoic acid | 365 | 365 | Ammonium Salt |
| 2.27 | —CF₃ | —H | (ethyl propanoate chain) | —H | —CH₃ | ethyl 3-[6-(3-methyl-5-{[4-(trifluoromethyl)pyrimidin-2-yl]amino}phenyl)pyridin-3-yl]propanoate | 431 | 431 | Formate Salt |

TABLE 2A-continued

| Ex. | R[1] | R[cy1] | R[cy2] | R[cy3] | R[4] | Name | [M+H]+ Calc'd | [M+H]+ Obsv'd | Form |
|---|---|---|---|---|---|---|---|---|---|
| 2.28 | —CF₃ | (propanoate ethyl ester chain, OCH₂CH₃) | —H | —H | —CH₃ | ethyl 3-[6-(3-methyl-5-{[4-(trifluoromethyl)pyrimidin-2-yl]amino}phenyl)pyridin-2-yl]propanoate | 431 | 431 | Formate Salt |
| 2.29 | —CF₃ | —H | —H | (propanoate ethyl ester chain) | —CH₃ | ethyl 3-[2-(3-methyl-5-{[4-(trifluoromethyl)pyrimidin-2-yl]amino}phenyl)pyridin-4-yl]propanoate | 431 | 431 | Formate Salt |
| 2.30 | —CF₃ | —H | —H | (propanoic acid chain, OH) | —CH₃ | 3-[6-(3-methyl-5-{[4-(trifluoromethyl)pyrimidin-2-yl]amino}phenyl)pyridin-3-yl]propanoic acid | 403 | 403 | Formate Salt |

TABLE 2A-continued

| Ex. | R¹ | R^cy1 | R^cy2 | R^cy3 | R⁴ | Name | [M + H]⁺ Calc'd | [M + H]⁺ Obsv'd | Form |
|---|---|---|---|---|---|---|---|---|---|
| 2.31 | —CF₃ | OH (propanoic acid chain) | —H | —H | —CH₃ | 3-[6-(3-methyl-5-{[4-(trifluoromethyl)pyrimidin-2-yl]amino}phenyl)pyridin-2-yl]propanoic acid | 403 | 403 | Formate Salt |
| 2.32 | —CH₃ | OCH₂CH₃ (propanoate chain) | —H | —H | —CH₃ | ethyl 3-(6-{3-methyl-5-[(4-methylpyrimidin-2-yl)amino]phenyl}pyridin-2-yl)propanoate | 377 | 377 | Formate Salt |
| 2.33 | —CH₃ | —H | —H | ethyl propanoate chain | —CH₃ | ethyl 3-(2-{3-methyl-5-[(4-methylpyrimidin-2-yl)amino]phenyl}pyridin-4-yl)propanoate | 377 | 377 | Formate Salt |

TABLE 2A-continued

| Ex. | R¹ | R^cy1 | R^cy2 | R^cy3 | R⁴ | Name | [M + H]⁺ Calc'd | [M + H]⁺ Obsv'd | Form |
|---|---|---|---|---|---|---|---|---|---|
| 2.34 | —CH₃ | HOOC-CH₂CH₂- | —H | —H | —CH₃ | 3-(6-{3-methyl-5-[(4-methylpyrimidin-2-yl)amino]phenyl}pyridin-3-yl)propanoic acid | 349 | 349 | Formate Salt |
| 2.35 | —CH₃ | —H | HOOC-CH₂CH₂- | —H | —CH₃ | 3-(6-{3-methyl-5-[(4-methylpyrimidin-2-yl)amino]phenyl}pyridin-2-yl)propanoic acid | 349 | 349 | Formate Salt |
| 2.36 | —CH₃ | —H | EtOOC-CH₂CH₂- | —H | —CH₃ | ethyl 3-(6-{3-methyl-5-[(4-methylpyrimidin-2-yl)amino]phenyl}pyridin-3-yl)propanoate | 377 | 377 | Formate Salt |

TABLE 2A-continued

| Ex. | R¹ | R$^{cy1}$ | R$^{cy2}$ | R$^{cy3}$ | R⁴ | Name | [M + H]⁺ Calc'd | [M + H]⁺ Obsv'd | Form |
|---|---|---|---|---|---|---|---|---|---|
| 2.37 | cyclopropyl | —H | ethyl propanoate | —H | —CH₃ | ethyl 3-(6-{3-[(4-cyclopropylpyrimidin-2-yl)amino]-5-methylphenyl}pyridin-3-yl)propanoate | 403 | 403 | Formate Salt |
| 2.38 | cyclopropyl | ethyl propanoate with OCH₂CH₃ | —H | —H | —CH₃ | ethyl 3-(6-{3-[(4-cyclopropylpyrimidin-2-yl)amino]-5-methylphenyl}pyridin-2-yl)propanoate | 403 | 403 | Formate Salt |
| 2.39 | cyclopropyl | —H | —H | ethyl propanoate | —CH₃ | ethyl 3-(2-{3-[(4-cyclopropylpyrimidin-2-yl)amino]-5-methylphenyl}pyridin-4-yl)propanoate | 403 | 403 | Formate Salt |

TABLE 2A-continued

| Ex. | R[1] | R[cy1] | R[cy2] | R[cy3] | R[4] | Name | [M + H]+ Calc'd | [M + H]+ Obsv'd | Form |
|---|---|---|---|---|---|---|---|---|---|
| 2.40 | cyclopropyl | —H | -CH2CH2-COOH | —H | —CH3 | 3-(6-{3-[(4-cyclopropylpyrimidin-2-yl)amino]-5-methylphenyl}pyridin-3-yl)propanoic acid | 375 | 375 | Formate Salt |

TABLE 2B

| Ex. | R$^1$ | R$^{cy1}$ | R$^{cy2}$ | R$^{cy3}$ | R$^{cy4}$ | R$^4$ | Name | [M + H]$^+$ Calc'd | [M + H]$^+$ Obsv'd | Form |
|---|---|---|---|---|---|---|---|---|---|---|
| 2.41 | —CF$_3$ | —OCH$_3$ | —H | —H | —H | —H | N-[3-(6-methoxypyridin-3-yl)phenyl]-4-(trifluoromethyl)pyrimidin-2-amine | 347 | 347 | Free Base |
| 2.42 | —CF$_3$ | phenyl-CH(OH)— (racemic) | —H | —H | —H | —H | phenyl [5-(3-{[4-(trifluoromethyl)pyrimidin-2-yl]amino}phenyl)pyridin-2-yl]methanol | 423 | 423 | Free Base |
| 2.43 | —CF$_3$ | —OH | —H | —H | —H | —H | 5-(3-{[4-(trifluoromethyl)pyrimidin-2-yl]amino}phenyl)pyridin-2-ol | 333 | 333 | Free Base |
| 2.44 | —CF$_3$ | 2-oxo-imidazolidin-yl (HN-C(O)-NH) | —H | —H | —H | —H | 6-(3-{[4-(trifluoromethyl)pyrimidin-2-yl]amino}phenyl)-1,3-dihydro-2H-imidazo[4,5-b]pyridin-2-one | 373 | 373 | Free Base |
| 2.45 | —CF$_3$ | —H | —H | —F | —H | —CH$_3$ | N-[3-(2-fluoropyridin-3-yl)-5-methylphenyl]-4-(trifluoromethyl)pyrimidin-2-amine | 349 | 349 | Formate Salt |
| 2.46 | —CF$_3$ | —CN | —H | —H | —H | —CH$_3$ | 5-(3-methyl-5-{[4-(trifluoromethyl)pyrimidin-2-yl]amino}phenyl)pyridine-2-carbonitrile | 356 | 356 | Formate Salt |
| 2.47 | —CF$_3$ | pyrrolidine-fused (NH); Ring juncture is [2,3-b] | —H | —H | —H | —CH$_3$ | N-[3-(2,3-dihydro-1H-pyrrolo[2,3-b]pyridin-5-yl)-5-methylphenyl]-4-(trifluoromethyl)pyrimidin-2-amine | 372 | 372 | Formate Salt |
| 2.48 | —CF$_3$ | —H | —C(O)CH$_3$ | —H | —H | —CH$_3$ | 1-[5-(3-methyl-5-{[4-(trifluoromethyl)pyrimidin-2-yl]amino}phenyl) | 373 | 373 | Formate Salt |

TABLE 2B-continued

[Structure: pyrimidine with R¹ at 4-position, NH linker to phenyl bearing R⁴, with pyridine substituent bearing R^{cy1}, R^{cy2}, R^{cy3}, R^{cy4}]

| Ex. | R¹ | R^{cy1} | R^{cy2} | R^{cy3} | R^{cy4} | R⁴ | Name | [M + H]⁺ Calc'd | [M + H]⁺ Obsv'd | Form |
|---|---|---|---|---|---|---|---|---|---|---|
| 2.49 | —CF₃ | —CH₂N(H)(CH₃) | —H | —H | —H | —CH₃ | pyridin-3-yl]ethanone N-(3-methyl-5-{6-[(methylamino)methyl]pyridin-3-yl}phenyl)-4-(trifluoromethyl)pyrimidin-2-amine | 374 | 374 | Formate Salt |
| 2.50 | —CF₃ | —CO₂H | —H | —H | —H | —CH₃ | 5-(3-methyl-5-{[4-(trifluoromethyl)pyrimidin-2-yl]amino}phenyl)pyridine-2-carboxylic acid | 375 | 375 | Formate Salt |
| 2.51 | —CF₃ | —OH | —NH₂ | —H | —CH₃ | —CH₃ | 3-amino-4-methyl-5-(3-methyl-5-{[4-(trifluoromethyl)pyrimidin-2-yl]amino}phenyl)pyridin-2-ol | 376 | 376 | Formate Salt |
| 2.52 | —CF₃ | morpholine (O, NH); Ring juncture is [3,2-b] | | —H | —H | —CH₃ | N-[3-(3,4-dihydro-2H-pyrido[3,2-b][1,4]oxazin-7-yl)-5-methylphenyl]-4-(trifluoromethyl)pyrimidin-2-amine | 388 | 388 | Formate Salt |
| 2.53 | —CF₃ | —H | —C(O)OCH₃ | —H | —H | —CH₃ | methyl 5-(3-methyl-5-{[4-(trifluoromethyl)pyrimidin-2-yl]amino}phenyl)pyridine-3-carboxylate | 389 | 389 | Formate Salt |
| 2.54 | —CF₃ | —H | —CF₃ | —H | —H | —CH₃ | N-{3-methyl-5-[5-(trifluoromethyl)pyridin-3-yl]phenyl}-4-(trifluoromethyl)pyrimidin-2-amine | 399 | 399 | Formate Salt |
| 2.558 | —CF₃ | morpholine (O, NCH₃); Ring juncture is [3,2-b] | | —H | —H | —CH₃ | N-[3-methyl-5-(4-methyl-3,4-dihydro-2H-pyrido[3,2-b][1,4]oxazin-7-yl)phenyl]-4-(trifluoromethyl)pyrimidin-2-amine | 402 | 402 | Formate Salt |

TABLE 2B-continued

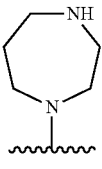

| Ex. | R¹ | $R^{cy1}$ | $R^{cy2}$ | $R^{cy3}$ | $R^{cy4}$ | R⁴ | Name | [M+H]⁺ Calc'd | [M+H]⁺ Obsv'd | Form |
|---|---|---|---|---|---|---|---|---|---|---|
| 2.56 | —CF₃ | —H | —CN | —H | —H | —CH₃ | 5-(3-methyl-5-{[4-(trifluoromethyl)pyrimidin-2-yl]amino}phenyl)pyridine-3-carbonitrile | 356 | 356 | Free Base, Formate Salt |
| 2.57 | —CF₃ | —H | —H | —H | —H | —CH₃ | N-(3-methyl-5-pyridin-3-ylphenyl)-4-(trifluoromethyl)pyrimidin-2-amine | 331 | 331 | TFA Salt |
| 2.58 | —CF₃ | —H | —OCH₃ | —H | —H | —CH₃ | N-[3-(5-methoxypyridin-3-yl)-5-methylphenyl]-4-(trifluoromethyl)pyrimidin-2-amine | 361 | 361 | Free Base |
| 2.59 | —CF₃ | 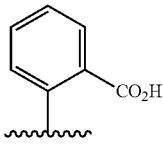 | —H | —H | —H | —CH₃ | N-{3-[6-(1,4-diazepan-1-yl)pyridin-3-yl]-5-methylphenyl}-4-(trifluoromethyl)pyrimidin-2-amine | 429 | 429 | TFA Salt |
| 2.60 | —CF₃ | 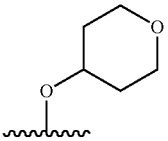 | —H | —H | —H | —CH₃ | 2-[5-(3-methyl-5-{[4-(trifluoromethyl)pyrimidin-2-yl]amino}phenyl)pyridin-2-yl]benzoic acid | 451 | 451 | TFA Salt |
| 2.61 | —CF₃ | 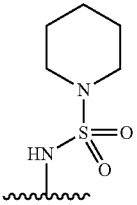 | —H | —H | —H | —CH₃ | N-{3-methyl-5-[6-(tetrahydro-2H-pyran-4-yloxy)pyridin-3-yl]phenyl}-4-(trifluoromethyl)pyrimidin-2-amine | 431 | 431 | TFA Salt |
| 2.62 | —CF₃ | (piperidin-1-ylsulfonylamino) | —H | —H | —H | —CH₃ | N-[5-(3-methyl-5-{[4-(trifluoromethyl)pyrimidin-2-yl]amino}phenyl)pyridin-2-yl]piperidine-1-sulfonamide | 493 | 493 | TFA Salt |
| 2.63 | —CF₃ | —CH₂NH₂ | —H | —H | —H | —CH₃ | N-{3-[6-(aminomethyl)pyridin-3-yl]-5- | 360 | 360 | TFA Salt |

TABLE 2B-continued

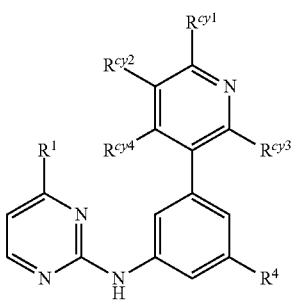

| Ex. | R¹ | R$^{cy1}$ | R$^{cy2}$ | R$^{cy3}$ | R$^{cy4}$ | R⁴ | Name | [M + H]⁺ Calc'd | [M + H]⁺ Obsv'd | Form |
|---|---|---|---|---|---|---|---|---|---|---|
| | | | | | | | methylphenyl}-4-(trifluoromethyl)pyrimidin-2-amine | | | |
| 2.64 | —CF₃ | —C(O)CH₃ | —H | —H | —H | —CH₃ | 1-[5-(3-methyl-5-{[4-(trifluoromethyl)pyrimidin-2-yl]amino}phenyl)pyridin-2-yl]ethanone | 373 | 373 | Free Base, Formate Salt |
| 2.65 | —CF₃ | —C(O)OCH₃ | —H | —H | —H | —CH₃ | methyl 5-(3-methyl-5-{[4-(trifluoromethyl)pyrimidin-2-yl]amino}phenyl)pyridine-2-carboxylate | 389 | 389 | Free Base, Formate Salt |
| 2.66 | —CF₃ | —H | —CH₂OH | —H | —H | —CH₃ | [5-(3-methyl-5-{[4-(trifluoromethyl)pyrimidin-2-yl]amino}phenyl)pyridin-3-yl]methanol | 361 | 361 | Free Base |
| 2.67 | —CF₃ | —H | —CN | —H | —H | —CH₃ | 5-(3-methyl-5-{[4-(trifluoromethyl)pyrimidin-2-yl]amino}phenyl)pyridine-3-carbonitrile | 356 | 356 | Free Base, Formate Salt |
| 2.68 | —CF₃ | —H | —C(O)OCH₂CH₃ | —H | —H | —CH₃ | ethyl 5-(3-methyl-5-{[4-(trifluoromethyl)pyrimidin-2-yl]amino}phenyl)pyridine-3-carboxylate | 403 | 403 | Free Base |
| 2.69 | —CF₃ | —H | —C(O)OH | —H | —H | —CH₃ | 5-(3-methyl-5-{[4-(trifluoromethyl)pyrimidin-2-yl]amino}phenyl)pyridine-3-carboxylic acid | 375 | 375 | Free Base |
| 2.70 | —CF₃ | 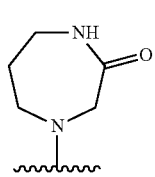 [SMILES: *N1CCCNC(=O)C1] | —H | —H | —H | —CH₃ | 4-[5-(3-methyl-5-{[4-(trifluoromethyl)pyrimidin-2-yl]amino}phenyl)pyridin-2-yl]-1,4-diazepan-2-one | 443 | 443 | Free Base |

TABLE 2B-continued

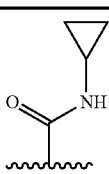

| Ex. | R¹ | R$^{cy1}$ | R$^{cy2}$ | R$^{cy3}$ | R$^{cy4}$ | R⁴ | Name | [M + H]⁺ Calc'd | [M + H]⁺ Obsv'd | Form |
|---|---|---|---|---|---|---|---|---|---|---|
| 2.71 | —CF₃ | 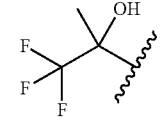 | —H | —H | —H | —CH₃ | N-cyclopropyl-5-(3-methyl-5-{[4-(trifluoromethyl)pyrimidin-2-yl]amino}phenyl)pyridine-2-carboxamide | 414 | 414 | Free Base |
| 2.72 | —CF₃ | —N(CH₃)₂ | —C(O)OH | —H | —H | —CH₃ | 2-(dimethylamino)-5-(3-methyl-5-{[4-(trifluoromethyl)pyrimidin-2-yl]amino}phenyl)pyridine-3-carboxylic acid | 418 | 418 | TFA Salt |
| 2.73 | —CF₃ | —H | —C(O)OH | —H | —H | —H | 5-(3-{[4-(trifluoromethyl)pyrimidin-2-yl]amino}phenyl)pyridine-3-carboxylic acid | 361 | 361 | Formate Salt |
| 2.74 | —CF₃ | —N(H)(CH₃) | —C(O)OH | —H | —H | —CH₃ | 2-(methylamino)-5-(3-methyl-5-{[4-(trifluoromethyl)pyrimidin-2-yl]amino}phenyl)pyridine-3-carboxylic acid | 404 | 404 | TFA Salt |
| 2.75 | —CF₃ | —H | 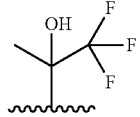 | —H | —H | —CH₃ | 1,1,1-trifluoro-2-[5-(3-methyl-5-{[4-(trifluoromethyl)pyrimidin-2-yl]amino}phenyl)pyridin-3-yl]propan-2-ol | 443 | 443 | No salt |
| 2.76 | —CF₃ | 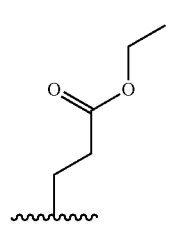 [SMILES: *CCC(=O)OCC] | —H | —H | —H | —CH₃ | 1,1,1-trifluoro-2-[5-(3-methyl-5-{[4-(trifluoromethyl)pyrimidin-2-yl]amino}phenyl)pyridin-2-yl]propan-2-ol | 443 | 443 | TFA Salt |
| 2.77 | —CF₃ | | —H | —H | —H | —H | ethyl 3-[5-(3-{[4-(trifluoromethyl)pyrimidin-2-yl]amino}phenyl)pyridin-2-yl]propanoate | 417 | 417 | Formate Salt |

TABLE 2B-continued

| Ex. | R¹ | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|
| 2.78 | —CF₃ | —H | ethyl propanoate group | —H | —H | —H | ethyl 3-[5-(3-{[4-(trifluoromethyl)pyrimidin-2-yl]amino}phenyl)pyridin-3-yl]propanoate | 417 | 417 | Formate Salt |
| 2.79 | —CF₃ | —H | propanoic acid group | —H | —H | —H | 3-[5-(3-{[4-(trifluoromethyl)pyrimidin-2-yl]amino}phenyl)pyridin-3-yl]propanoic acid | 389 | 389 | Formate Salt |
| 2.80 | —OCH₃ | ethyl propanoate group | —H | —H | —H | —CH₃ | ethyl 3-(5-{3-[(4-methoxy-pyrimidin-2-yl)amino]-5-methylphenyl}pyridin-2-yl)propanoate | 393 | 393 | Formate Salt |
| 2.81 | —OCH₃ | —H | ethyl propanoate group | —H | —H | —CH₃ | ethyl 3-(5-{3-[(4-methoxy-pyrimidin-2-yl)amino]-5-methylphenyl}pyridin-3-yl)propanoate | 393 | 393 | Formate Salt |
| 2.82 | —CF₃ | propanoic acid group | —H | —H | —H | —H | 3-[5-(3-{[4-(trifluoromethyl)pyrimidin-2-yl]amino}phenyl)pyridin-2-yl]propanoic acid | 389 | 389 | Ammonium Salt |

TABLE 2B-continued

| Ex. | R¹ | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|
| 2.83 | —OCH₃ | HOOC-CH₂-CH₂- | —H | —H | —H | —CH₃ | 3-(5-{3-[(4-methoxy-pyrimidin-2-yl)amino]-5-methylphenyl}pyridin-2-yl)propanoic acid | 365 | 365 | Ammonium Salt |
| 2.84 | —OCH₃ | —H | HOOC-CH₂-CH₂- | —H | —H | —CH₃ | 3-(5-{3-[(4-methoxy-pyrimidin-2-yl)amino]-5-methylphenyl}pyridin-3-yl)propanoic acid | 365 | 365 | Ammonium Salt |
| 2.85 | —CF₃ | —H | EtOOC-CH₂-CH₂- | —H | —H | —CH₃ | ethyl 3-[5-(3-methyl-5-{[4-(trifluoromethyl)pyrimidin-2-yl]amino}phenyl)pyridin-3-yl]propanoate | 431 | 431 | Formate Salt |
| 2.86 | —CF₃ | —H | HOOC-CH₂-CH₂- | —H | —H | —CH₃ | 3-[5-(3-methyl-5-{[4-(trifluoromethyl)pyrimidin-2-yl]amino}phenyl)pyridin-3-yl]propanoic acid | 403 | 403 | Formate Salt |
| 2.87 | —CH₃ | EtOOC-CH₂-CH₂- | —H | —H | —H | —CH₃ | ethyl 3-(5-{3-methyl-5-[(4-methylpyrimidin-2-yl)amino]phenyl}pyridin-2-yl)propanoate | 377 | 377 | Formate Salt |

TABLE 2B-continued

| Ex. | R¹ | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|
| 2.88 | —CH₃ | —H | (ethyl propanoate group) | —H | —H | —CH₃ | ethyl 3-(5-{3-methyl-5-[(4-methylpyrimidin-2-yl)amino]phenyl}pyridin-3-yl)propanoate | 377 | 377 | Formate Salt |
| 2.89 | —CH₃ | (propanoic acid group) | —H | —H | —H | —CH₃ | 3-(5-{3-methyl-5-[(4-methylpyrimidin-2-yl)amino]phenyl}pyridin-2-yl)propanoic acid | 349 | 349 | Formate Salt |
| 2.90 | —CH₃ | —H | (propanoic acid group) | —H | —H | —CH₃ | 3-(5-{3-methyl-5-[(4-methylpyrimidin-2-yl)amino]phenyl}pyridin-3-yl)propanoic acid | 349 | 349 | Formate Salt |
| 2.100 | (cyclopropyl) | —H | (ethyl propanoate group) | —H | —H | —CH₃ | ethyl 3-(5-{3-[(4-cyclopropyl-pyrimidin-2-yamino]-5-methylphenyl}pyridin-3-yl)propanoate | 403 | 403 | Formate Salt |
| 2.101 | (cyclopropyl) | (propanoic acid group) | —H | —H | —H | —CH₃ | 3-(5-{3-[(4-cyclopropyl-pyrimidin-2-yl)amino]-5-methylphenyl}pyridin-2-yl)propanoic acid | 375 | 375 | Formate Salt |

TABLE 2B-continued

[Structure: pyridine (with R^cy1, R^cy2, R^cy3, R^cy4 substituents) linked to a phenyl ring (bearing R^4) which is linked via NH to a pyrimidine bearing R^1]

| Ex. | R¹ | R^cy1 | R^cy2 | R^cy3 | R^cy4 | R⁴ | Name | [M+H]⁺ Calc'd | [M+H]⁺ Obsv'd | Form |
|---|---|---|---|---|---|---|---|---|---|---|
| 2.102 | cyclopropyl | —H | -CH₂CH₂-COOH | —H | —H | —CH₃ | 3-(5-{3-[(4-cyclopropyl-pyrimidin-2-yl)amino]-5-methylphenyl}pyridin-3-yl)propanoic acid | 375 | 375 | Formate Salt |
| 2.103 | cyclopropyl | -CH₂CH₂-C(O)OEt | —H | —H | —H | —CH₃ | ethyl 3-(5-{3-[(4-cyclopropyl-pyrimidin-2-yl)amino]-5-methylphenyl}pyridin-2-yl)propanoate | 403 | 403 | Formate Salt |
| 2.104 | cyclopropyl | trans-4-(HN-)cyclohexyl-CO₂H | —H | —H | —H | —CH₃ | trans-4-[(5-{3-[(4-cyclopropyl-pyrimidin-2-yl)amino]-5-methylphenyl}pyridin-2-yl)amino]cyclohexanecarboxylic acid | 444 | 444 | Sodium Salt |
| 2.105 | —OCH₃ | trans-4-(HN-)cyclohexyl-CO₂H | —H | —H | —H | —CH₃ | trans-4-[(5-{3-[(4-methoxy-pyrimidin-2-yl)amino]-5-methylphenyl}pyridin-2-yl)amino]cyclohexanecarboxylic acid | 434 | 434 | Sodium Salt |
| 2.106 | —CH₃ | trans-4-(HN-)cyclohexyl-CO₂H | —H | —H | —H | —CH₃ | trans-4-[(5-{3-methyl-5-[(4-methylpyrimidin-2-yl)amino]phenyl}pyridin-2-yl)amino]cyclohexanecarboxylic acid | 418 | 418 | Formate Salt |
| 2.107 | —CH₃ | trans-4-(HN-)cyclohexyl-CO₂H | —H | —H | —H | —CH₃ | trans-4-[(5-{3-[(4-methylpyrimidin-2-yl)amino]phenyl}pyridin-2-yl)amino]cyclohexanecarboxylic acid | 404 | 404 | Formate Salt |

TABLE 2B-continued

| Ex. | R¹ | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|
| 2.108 | —C(H)(CH₃)₂ | trans-4-aminocyclohexanecarboxylic acid group (trans) | —H | —H | —H | —CH₃ | trans-4-{[5-(3-methyl-5-{[4-(1-methylethyl)pyrimidin-2-yl]amino}phenyl)pyridin-2-yl]amino}cyclohexanecarboxylic acid | 446 | 446 | Formate Salt |
| 2.109 | —CF₃ | cyanoacetamide group | —H | —H | —H | —CH₃ | 2-cyano-N-[5-(3-methyl-5-{[4-(trifluoromethyl)pyrimidin-2-yl]amino}phenyl)pyridin-2-yl]acetamide | 413 | 413 | Free Base |
| 2.110 | —CF₃ | 4-oxycyclohexanecarboxylic acid (cis) or (trans) | —H | —H | —H | —CH₃ | 4-{[5-(3-methyl-5-{[4-(trifluoromethyl)pyrimidin-2-yl]amino}phenyl)pyridin-2-yl]oxy}cyclohexanecarboxylic acid | 473 | 473 | Free Base |
| 2.111 | —CF₃ | 4-oxycyclohexanecarboxylic acid (cis) or (trans) | —H | —H | —H | —CH₃ | 4-{[5-(3-methyl-5-{[4-(trifluoromethyl)pyrimidin-2-yl]amino}phenyl)pyridin-2-yl]oxy}cyclohexanecarboxylic acid | 473 | 473 | Free Base |
| 2.112 | —CF₃ | 4-oxybenzoic acid group | —H | —H | —H | —CH₃ | 4-{[5-(3-methyl-5-{[4-(trifluoromethyl)pyrimidin-2-yl]amino}phenyl)pyridin-2-yl]oxy}benzoic acid | 467 | 467 | Free Base |
| 2.113 | —CF₃ | —C(O)CH₃ | —H | —H | —H | —CH₃ | 1-[5-(3-methyl-5-{[4-(trifluoromethyl)pyrimidin-2-yl]amino}phenyl)pyridin-2-yl]ethanone | 373 | 373 | Free Base, Formate Salt |

TABLE 2B-continued

| Ex. | R¹ | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|
| 2.115 | —CF₃ | (CF₃)(CH₃)C(OH)CH₂— racemic | —H | —H | —H | —CH₃ | 1,1,1-trifluoro-2-[5-(3-methyl-5-{[4-(trifluoromethyl)pyrimidin-2-yl]amino}phenyl)pyridin-2-yl]propan-2-ol | 443 | 443 | TFA Salt |
| 2.116 | —CF₃ | F₂C(CO₂H)— | —H | —H | —H | —CH₃ | difluoro[5-(3-methyl-5-{[4-(trifluoromethyl)pyrimidin-2-yl]amino}phenyl)pyridin-2-yl]acetic acid | 425 | 425 | TFA Salt |
| 2.117 | —CF₃ | F₂C(CH₂OH)— | —H | —H | —H | —CH₃ | 2,2-difluoro-2-[5-(3-methyl-5-{[4-(trifluoromethyl)pyrimidin-2-yl]amino}phenyl)pyridin-2-yl]ethanol | 411 | 411 | Free Base |

TABLE 2C

| Ex. | R¹ | R² | R^cy1 | R^cy2 | R^cy3 | R^cy4 | R⁴ | Name | [M + H]⁺ Calc'd | [M + H]⁺ Obsv'd | Form |
|---|---|---|---|---|---|---|---|---|---|---|---|
| 2.118 | —OCH₃ | —Cl | trans-4-(HN-)cyclohexyl-CO₂H | —H | —H | —H | —CH₃ | trans-4-[(5-{3-[(5-chloro-4-methoxypyrimidin-2-yl)amino]-5-methylphenyl}pyridin-2-yl)amino]cyclohexanecarboxylic acid | 468 | 468 | Formate Salt |

TABLE 2C-continued

[Structure: pyrimidine with R1, R2 substituents linked via NH to a phenyl (with R4) bearing a pyridine with Rcy1, Rcy2, Rcy3, Rcy4 substituents]

| Ex. | R¹ | R² | R$^{cy1}$ | R$^{cy2}$ | R$^{cy3}$ | R$^{cy4}$ | R⁴ | Name | [M + H]⁺ Calc'd | [M + H]⁺ Obsv'd | Form |
|---|---|---|---|---|---|---|---|---|---|---|---|
| 2.119 | —CH₃ | —Cl | trans-4-(NH—)cyclohexane-CO₂H | —H | —H | —H | —CH₃ | trans-4-[(5-{3-[(5-chloro-4-methylpyrimidin-2-yl)amino]-5-methylphenyl}pyridin-2-yl)amino]cyclohexane-carboxylic acid | 452 | 452 | Formate Salt |
| 2.120 | —CH₃ | —F | trans-4-(NH—)cyclohexane-CO₂H | —H | —H | —H | —CH₃ | trans-4-[(5-{3-[(5-fluoro-4-methylpyrimidin-2-yl)amino]-5-methylphenyl}pyridin-2-yl)amino]cyclohexane-carboxylic acid | 436 | 436 | Formate Salt |
| 2.121 | —OCH₃ | —F | trans-4-(NH—)cyclohexane-CO₂H | —H | —H | —H | —CH₃ | trans-4-[(5-{3-[(5-fluoro-4-methoxypyrimidin-2-yl)amino]-5-methylphenyl}pyridin-2-yl)amino]cyclohexane-carboxylic acid | 452 | 452 | Formate Salt |

TABLE 2D

[Structure: pyrimidine with R¹ linked via NH to phenyl (with R⁴) bearing a pyridine with Rcy]

| Ex. | R¹ | R$^{cy}$ | R⁴ | Name | [M + H]⁺ Calc'd | [M + H]⁺ Obsv'd | Form |
|---|---|---|---|---|---|---|---|
| 2.122 | —CF₃ | —OCH₃ | —H | N-[3-(2-methoxypyridin-4-yl)phenyl]-4-(trifluoromethyl)pyrimidin-2-amine | 347 | 347 | Free Base |
| 2.123 | —CF₃ | —CF₃ | —CH₃ | N-{3-methyl-5-[2-(trifluoromethyl)pyridin-4-yl]phenyl}-4-(trifluoromethyl)pyrimidin-2-amine | 399 | 399 | Formate Salt |
| 2.124 | —CF₃ | —H | —CH₃ | N-(3-methyl-5-pyridin-4-ylphenyl)-4-(trifluoromethyl)pyrimidin-2-amine | 331 | 331 | Free Base |

TABLE 2D-continued

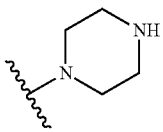 [SMILES: *N1CCNCC1]

| Ex. | R¹ | R^cy | R⁴ | Name | [M + H]⁺ Calc'd | [M + H]⁺ Obsv'd | Form |
|---|---|---|---|---|---|---|---|
| 2.125 | —CF₃ | —OH | —CH₃ | 4-(3-methyl-5-{[4-(trifluoromethyl)pyrimidin-2-yl]amino}phenyl)pyridin-2-ol | 347 | 347 | TFA Salt |
| 2.126 | —CF₃ | 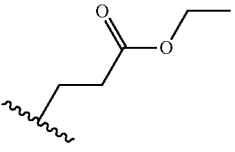 [SMILES: *CCC(=O)OCC] | —CH₃ | N-[3-methyl-5-(2-piperazin-1-ylpyridin-4-yl)phenyl]-4-(trifluoromethyl)pyrimidin-2-amine | 415 | 415 | Formate Salt |
| 2.127 | —CF₃ | —Br | | N-[3-(2-bromopyridin-4-yl)-5-methylphenyl]-4-(trifluoromethyl)pyrimidin-2-amine | 409 | 409 | Free Base |
| 2.128 | —CF₃ | —C(O)OH | —H | 4-(3-{[4-(trifluoromethyl)pyrimidin-2-yl]amino}phenyl)pyridine-2-carboxylic acid | 361 | 361 | Formate Salt |
| 2.129 | —CF₃ | —CH₂CH₂CO₂H | —H | 3-[4-(3-{[4-(trifluoromethyl)pyrimidin-2-yl]amino}phenyl)pyridin-2-yl]propanoic acid | 389 | 389 | Formate Salt |
| 2.130 | —OCH₃ | 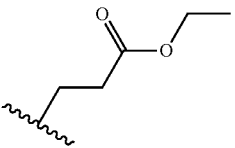 [SMILES: *CCC(=O)OCC] | | ethyl 3-(4-{3-[(4-methoxypyrimidin-2-yl)amino]-5-methylphenyl}pyridin-2-yl)propanoate | 393 | 393 | Formate Salt |
| 2.131 | —OCH₃ | —CH₂CH₂CO₂H | —CH₃ | 3-(4-{3-[(4-methoxypyrimidin-2-yl)amino]-5-methylphenyl}pyridin-2-yl)propanoic acid | 365 | 365 | Formate Salt |
| 2.132 | —CF₃ | 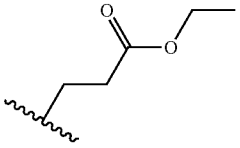 [SMILES: *CCC(=O)OCC] | —CH₃ | ethyl 3-[4-(3-methyl-5-{[4-(trifluoromethyl)pyrimidin-2-yl]amino}phenyl)pyridin-2-yl]propanoate | 431 | 431 | Formate Salt |
| 2.133 | —CF₃ | —CH₂CH₂CO₂H | —CH₃ | 3-[4-(3-methyl-5-{[4-(trifluoromethyl)pyrimidin-2-yl]amino}phenyl)pyridin-2-yl]propanoic acid | 403 | 403 | Formate Salt |
| 2.134 | —CH₃ |  | —CH₃ | ethyl 3-(4-{3-methyl-5-[(4-methylpyrimidin-2-yl)amino]phenyl}pyridin-2-yl)propanoate | 377 | 377 | Formate Salt |
| 2.135 | —CH₃ | —CH₂CH₂CO₂H | —CH₃ | 3-(4-{3-methyl-5-[(4-methylpyrimidin-2-yl)amino]phenyl}pyridin-2-yl)propanoic acid | 349 | 349 | Formate Salt |

TABLE 2D-continued

| Ex. | R[1] | R[cy] | R[4] | Name | [M + H]+ Calc'd | [M + H]+ Obsv'd | Form |
|---|---|---|---|---|---|---|---|
| 2.136 | cyclopropyl | —C(O)OCH₂CH₃ (ethyl propanoate linker) | —CH₃ | ethyl 3-(4-{3-[(4-cyclopropylpyrimidin-2-yl)amino]-5-methylphenyl}pyridin-2-yl)propanoate | 403 | 403 | Formate Salt |
| 2.137 | cyclopropyl | —CH₂CH₂CO₂H | —CH₃ | 3-(4-{3-[(4-cyclopropylpyimidin-2-yl)amino]-5-methylphenyl}pyridin-2-yl)propanoic acid | 375 | 375 | Formate Salt |

Example 2.138

1-[5-(3-Methyl-5-{[4-(trifluoromethyl)pyrimidin-2-yl]amino}phenyl)pyridin-2-yl]ethanol

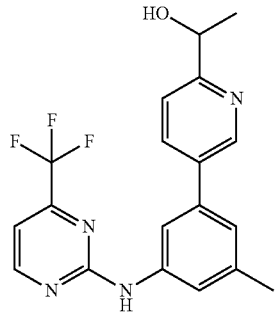

2.138

Sodium borohydride (46 mg, 1.2 mmol) was added to a solution of 1-[5-(3-methyl-5-{[4-(trifluoromethyl)pyrimidin-2-yl]amino}phenyl)pyridin-2-yl]ethanone (45 mg, 0.12 mmol) in tetrahydrofuran (300 μl) and methanol (300 μl) and then the reaction mixture was stirred at ambient temperature for 30 minutes. The reaction mixture was quenched with saturated aqueous potassium sodium tartrate (2 mL) and diluted with dichloromethane (3 mL). The mixture was stirred for 16 hours, filtered through a CELITE pad, dried over sodium sulfate, filtered, and concentrated under reduced pressure. The residue was purified by silica gel chromatography (10-40% acetone/hexanes, linear gradient) to afford 1-[5-(3-methyl-5-{[4-(trifluoromethyl)pyrimidin-2-yl]amino}phenyl)pyridin-2-yl]ethanol. MS ESI calc'd. for $C_{19}H_{18}F_3N_4O$ [M+H]+ 375. found 375. ¹H NMR (500 MHz, DMSO-d₆) δ 10.26 (s, 1H), 8.82 (s, 1H), 8.71 (s, 1H), 7.98 (d, J=7.5 Hz, 1H), 7.95 (s, 1H), 7.57 (d, J=7.5 Hz, 1H), 7.54 (s, 1H), 7.27 (s, 1H), 7.18 (s, 1H), 5.39 (s, 1H), 4.80-4.72 (m, 1H), 2.35 (s, 3H), 1.38 (d, J=5.5 Hz, 3H).

Example 3

Compounds of Formula (I) Using the General Methods Illustrated in Scheme 3

Examples 3.1 and 3.2

N,N-dimethyl-2-(5-(3-methyl-5-((4-(trifluoromethyl)pyrimidin-2-yl)amino)phenyl)pyridin-2-yl)acetamide

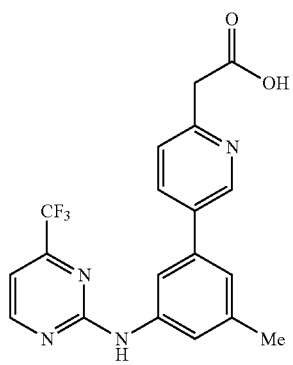

3.1

3.2

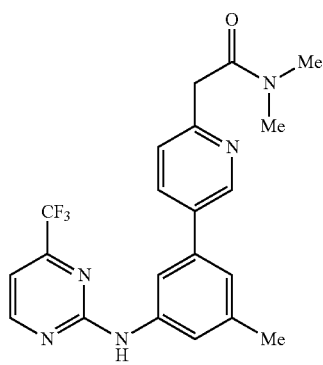

Step 1:
n-Butyllithium (2.2 ml, 3.52 mmol, 1.6 M) was added dropwise to a solution of diisopropylamine (500 μl, 3.51 mmol) in THF (5 ml) at −78° C. and the resulting solution was stirred at −78° C. for 30 minutes. A solution of 5-bromo-2-methylpyridine (500 mg, 2.91 mmol) in THF (1 mL) was added dropwise to LDA solution and the mixture was stirred for 1 hour. A solution of di-tert-butyl dicarbonate (742 μl, 3.20 mmol) in THF (1 ml) was added to the reaction mixture and warmed to room temperature over a period of 2 hours. The mixture was quenched with saturated ammonium chloride and extracted with ethyl acetate, washed with brine, dried, and concentrated under reduced pressure. The residue was purified by silica gel chromatography (ethyl acetate/hexanes) to afford tert-butyl 2-(5-bromopyridin-2-yl)acetate (151.8 mg, 0.558 mmol). MS ESI calc'd. for $C_{11}H_{14}BrNO_2$ [M+H]$^+$ 272 and 274. found 272 and 274.

Step 2:
A mixture of N-(3-methyl-5-(4,4,5,5-tetramethyl-1,3,2-dioxaborolan-2-yl)phenyl)-4-(trifluoromethyl)pyrimidin-2-amine (110 mg, 0.290 mmol), tert-butyl 2-(5-bromopyridin-2-yl)acetate (51.3 mg, 0.189 mmol), palladium(II) chloride (dppf) (28 mg, 0.038 mmol) and sodium carbonate (0.2 ml, 0.400 mmol, 2 M) in DMF (2 ml) was evacuated and purged with argon (3×), and then was irradiated in a microwave reactor for 10 minutes at 100° C. The mixture was filtered and purified on reversed phase HPLC to afford tert-butyl 2-(5-(3-methyl-5-((4-(trifluoromethyl)pyrimidin-2-yl)amino)phenyl)pyridin-2-yl)acetate (49.5 mg, 0.089 mmol). MS ESI calc'd. for $C_{23}H_{23}F_3N_4O_2$ [M+H]$^+$ 445. found 445.

Step 3:
tert-Butyl 2-(5-(3-methyl-5-((4-(trifluoromethyl)pyrimidin-2-yl)amino)phenyl)pyridin-2-yl)acetate (25 mg, 0.056 mmol) was added to HCl in dioxane (0.5 ml, 2.000 mmol, 4M). The mixture was stirred at room temperature for 1 hour. The solid was collected by the filtration and afforded 2-(5-(3-methyl-5-((4-(trifluoromethyl)pyrimidin-2-yl)amino)phenyl)pyridin-2-yl)acetic acid (14.1 mg, 0.033 mmol). MS ESI calc'd. for $C_{19}H_{16}F_3N_4O_2$ [M+H]$^+$ 389. found 389. $^1$H NMR (500 MHz, CD$_3$OD): δ 9.07 (d, J=1.5 Hz, 1H), 8.83 (dd, J=8.0, 1.5 Hz, 1H), 8.73 (d, J=5.0 Hz, 1H), 8.15-8.10 (m, 2H), 7.66 (s, 1H), 7.34 (s, 1H), 7.18 (d, J=5.0 Hz, 1H), 4.25 (s, 2H), 2.46 (s, 3H).

Step 4:
A mixture of 2-(5-(3-methyl-5-((4-(trifluoromethyl)pyrimidin-2-yl)amino)phenyl)pyridin-2-yl)acetic acid (8.4 mg, 0.020 mmol), dimethylamine (0.05 ml, 0.100 mmol, 2M), EDC (8.6 mg, 0.045 mmol), HOBT (7.8 mg, 0.051 mmol), DIEA (10 μl, 0.057 mmol) in 1,4-dioxane (0.8 ml) was stirred at room temperature for 16 hours. The mixture was purified by reversed phase HPLC to afford N,N-dimethyl-2-(5-(3-methyl-5-((4-(trifluoromethyl)pyrimidin-2-yl)amino)phenyl)pyridin-2-yl)acetamide (8.4 mg, 0.016 mmol). MS ESI calc'd. for $C_{21}H_{21}F_3N_5O$ [M+H]$^+$ 416. found 416. $^1$H NMR (600 MHz, CD$_3$OD): δ 8.97 (s, 1H), 8.71 (d, J=4.8 Hz, 1H), 8.62 (d, J=6.0 Hz, 1H), 8.09 (s, 1H), 7.89 (d, J=6.0 Hz, 1H), 7.60 (s, 1H), 7.26 (s, 1H), 7.13 (d, J=4.8 Hz, 1H), 4.25 (s, 2H), 3.18 (s, 3H), 3.00 (s, 3H), 2.43 (s, 3H).

Example 4

Compounds of Formula (I) Using the General Methods Illustrated in Scheme 4

Example 4.1

N-[3-(2-aminopyridin-4-yl)-5-methylphenyl]-4-methoxypyrimidin-2-amine

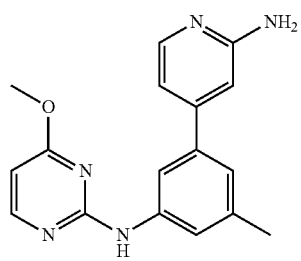

4.1

A mixture of N-(3-bromo-5-methylphenyl)-4-methoxypyrimidin-2-amine (125 mg, 0.425 mmol), 2-aminopyridine-4-boronic acid (103 mg, 0.467 mmol), PdCl$_2$(dppf)-CH$_2$Cl$_2$ adduct (35 mg, 0.042 mmol) and sodium carbonate (425 μL, 0.850 mmol) in dioxane (3 mL) was heated to 100° C. for 14 hours. The reaction mixture was filtered through a CELITE pad and washed with dioxane (3×). The filtrate was concentrated under reduced pressure and the residue was purified by silica gel chromatography (methanol/ethyl acetate) to give N-[3-(2-aminopyridin-4-yl)-5-methylphenyl]-4-methoxypyrimidin-2-amine as a tan solid. MS ESI calc'd for $C_{17}H_{18}N_5O$ [M+H]$^+$ 308. found 308. $^1$H NMR (500 MHz, DMSO-d$_6$) δ 9.59 (s, 1H), 8.20 (d, J=5.7 Hz, 1H), 7.95-7.88

(m, 2H), 7.61 (s, 1H), 7.00 (s, 1H), 6.69 (d, J=5.4 Hz, 1H), 6.64 (s, 1H), 6.28 (d, J=5.6 Hz, 1H), 5.95 (s, 2H), 3.92 (s, 3H), 2.32 (s, 3H).

Example 4.2

N-[3-(6-aminopyridin-3-yl)-5-methylphenyl]-4-(trifluoromethyl)pyrimidin-2-amine

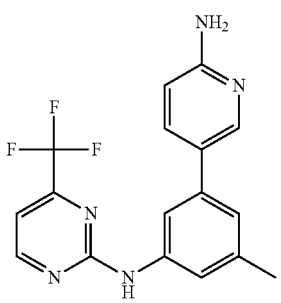

4.2

A mixture of N-(3-bromo-5-methylphenyl)-4-(trifluoromethyl)pyrimidin-2-amine (70 mg, 0.211 mmol), (3-ethoxyphenyl)boronic acid (70.1 mg, 0.422 mmol), $PdCl_2(dppf)$-$CH_2Cl_2$ adduct (34.4 mg, 0.042 mmol) and sodium carbonate (2 M in water) (211 µL, 0.422 mmol) in 2-methyl-tetrahydrofuran (1.05 mL) was heated to 60° C. for 12 hours. Si-dimercaptotriazine (222 mg, 0.126 mmol) and acetonitrile (3.0 mL) were added to the reaction mixture and stirred for 4 hours at room temperature to scavenge palladium. The reaction mixture was filtered, washed with DMSO (1.5 mL)) and concentrated under reduced pressure. The reaction mixture (still in 1.5 mL DMSO) was resubjected to filtration and the residue was purified by mass triggered reverse phase HPLC (57-91% Acetonitrile/Water (0.1% Formic Acid Modifier) to afford N-[3-(6-aminopyridin-3-yl)-5-methylphenyl]-4-(trifluoromethyl)pyrimidin-2-amine. MS APC calc'd for $C_{17}H_{15}F_3N_5$ $[M+H]^+$ 346. found 346. $^1H$ NMR (600 MHz, DMSO-d6) δ 10.12 (s, 1H), 8.78 (d, J=5.2, 1H), 8.16 (d, J=3.1, 1H), 7.79 (s, 1H), 7.60 (dd, J=2.7, 8.8, 1H), 7.39 (s, 1H), 7.22 (d, J=5.1, 1H), 7.01 (s, 1H), 6.55-6.41 (m, 1H), 6.03 (s, 2H), 2.29 (s, 3H).

The following examples in Tables 4A-4C were prepared in an analogous manner to that described in general scheme 4 using commercial boronic esters or acids.

TABLE 4A

| Ex. | $R^{cy1}$ | $R^{cy2}$ | Name | $[M + H]^+$ Calc'd | $[M + H]^+$ Obsv'd | Form(s) |
|---|---|---|---|---|---|---|
| 4.3 | —H | —F | N-[3-(5-fluoropyridin-3-yl)-5-methylphenyl]-4-(trifluoromethyl)pyrimidin-2-amine | 349 | 349 | Formate Salt |
| 4.4 | —F | —H | N-[3-(6-fluoropyridin-3-yl)-5-methylphenyl]-4-(trifluoromethyl)pyrimidin-2-amine | 349 | 349 | Formate Salt |
| 4.5 | —OCH₃ | —H | N-[3-(6-methoxypyridin-3-yl)-5-methylphenyl]-4-(trifluoromethyl)pyrimidin-2-amine | 361 | 361 | Formate Salt |
| 4.6 | —CF₃ | —H | N-{3-methyl-5-[6-(trifluoromethyl)pyridin-3-yl]phenyl}-4-(trifluoromethyl)pyrimidin-2-amine | 399 | 399 | Formate Salt |
| 4.7 | —CH₂OH | —H | [5-(3-methyl-5-{[4-(trifluoromethyl)pyrimidin-2-yl]amino}phenyl)pyridin-2-yl]methanol | 361 | 361 | Formate Salt |
| 4.8 | —OH | —H | 5-(3-methyl-5-{[4-(trifluoromethyl)pyrimidin-2-yl]amino}phenyl)pyridin-2-ol | 347 | 347 | Formate Salt |

TABLE 4B

| Ex. | R^cyl | Name | [M + H]+ Calc'd | [M + H]+ Obsv'd | Form(s) |
|---|---|---|---|---|---|
| 4.9 | —OCH₃ | N-[3-(6-methoxypyridin-2-yl)-5-methylphenyl]-4-(trifluoromethyl)pyrimidin-2-amine | 361 | 361 | Formate Salt |

TABLE 4C

| Ex. | R^cy | Name | [M + H]+ Calc'd | [M + H]+ Obsv'd | Form(s) |
|---|---|---|---|---|---|
| 4.10 | —OCH₃ | N-[3-(2-methoxypyridin-4-yl)-5-methylphenyl]-4-(trifluoromethyl)pyrimidin-2-amine | 361 | 361 | Formate Salt |

Example 5

Compounds of Formula (I) Using the General Methods Illustrated in Scheme 5

Example 5.1

1-Methyl-5-(3-{[4-(trifluoromethyl)pyrimidin-2-yl]amino}phenyl)pyridin-2(1H)-one

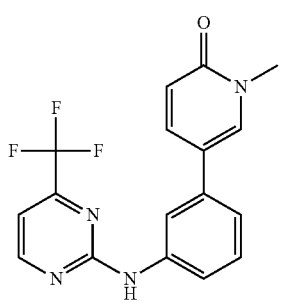

Step 1:

N-[3-(4,4,5,5-tetramethyl-1,3,2-dioxaborolan-2-yl)phenyl]-4-(trifluoromethyl)pyrimidin-2-amine (150 mg, 0.411 mmol) and potassium fluoride (71.6 mg, 1.23 mmol) were added to 3.00 mL of a stock solution of palladium(II) acetate (4.61 mg, 0.021 mmol) and butyl[di-(3S,5S,7S)-tricyclo[3.3.1.1^{3,7}]dec-1-yl]phosphane (14.7 mg, 0.041 mmol) in THF (3.00 mL) under nitrogen. 5-Bromo-2-methoxypyridine (0.069 mL, 0.534 mmol) and water (1.00 mL) were then added to the reaction mixture and was heated to 75° C. for 17 hours. Upon cooling to room temperature, the reaction mixture was quenched by the addition of 25% aqueous NH₄OAc. The aqueous layer was extracted with ethyl acetate (2×) and the combined organic layers were washed sequentially with water and brine, dried over Na₂SO₄ and concentrated under reduced pressure. The residue was purified by silica gel chromatography (ethyl acetate/dichloromethane) to afford N-[3-(6-methoxypyridin-3-yl)phenyl]-4-(trifluoromethyl)pyrimidin-2-amine as a beige solid. MS APC calc'd for C₁₇H₁₄F₃N₄O [M+H]+ 347. found 347.

Step 2:

Iodomethane (0.063 mL, 1.007 mmol) and sodium iodide (151 mg, 1.007 mmol) were added to a solution of N-[3-(6-methoxypyridin-3-yl)phenyl]-4-(trifluoromethyl)pyrimidin-2-amine (109 mg, 0.315 mmol) in MeCN (3.1 mL) at room temperature under nitrogen. The mixture was heated to 45° C. for 72 hours, then cooled to room temperature and concentrated in vacuo. The residue was diluted with water and extracted with ethyl acetate (2×). The combined organic layers were washed with brine, dried over Na₂SO₄ and concentrated under reduced pressure. The residue was purified by silica gel chromatography (ethyl acetate/hexanes) to afford 1-methyl-5-(3-{[4-(trifluoromethyl)pyrimidin-2-yl]amino}phenyl)pyridin-2(1H)-one as an off-white solid. MS APC calc'd for C₁₇H₁₄F₃N₄O [M+H]+ 347. found 347. Check LCMS data. ¹H NMR (400 MHz, Acetone-d₆): δ 9.31 (s, 1H); 8.83 (d, J=4.9 Hz, 1H); 8.72 (s, 1H); 7.96 (d, J=8.2 Hz, 1H); 7.84 (d, J=7.8 Hz, 1H); 7.79 (t, J=7.8 Hz, 1H); 7.54 (d, J=7.4 Hz, 1H); 7.48 (t, J=7.9 Hz, 1H); 7.24 (d, J=4.9 Hz, 1H); 6.76 (d, J=8.2 Hz, 1H); 4.04 (s, 3H). APCI: [M+H]+ m/z 347.1.

The following examples in Table 5 were prepared in an analogous manner to that described in general scheme 5.

TABLE 5

[Structure: pyrimidine with CF3 and NH linker to phenyl with CH3 and C^y substituent]

| Ex. | C^y | Name | [M + H]+ Calc'd | [M + H]+ Obsv'd | Form(s) |
|-----|-----|------|-----------------|------------------|---------|
| 5.2 | [1-methyl-pyridin-2(1H)-one-4-yl] | 1-methyl-4-(3-{[4-(trifluoromethyl)pyrimidin-2-yl]amino}phenyl)pyridin-2(1H)-one | 347 | 347 | Free Base |
| 5.3 | [1-methyl-pyridin-2(1H)-one-6-yl] | 1-methyl-6-(3-{[4-(trifluoromethyl)pyrimidin-2-yl]amino}phenyl)pyridin-2(1H)-one | 347 | 347 | Free Base |

Example 6

Compounds of Formula (I) Using the General Methods Illustrated in Scheme 6

Example 6.1

1-Methyl-3-[3-(pyridin-3-yl)-5-{[4-(trifluoromethyl)pyrimidin-2-yl]amino}phenyl]urea

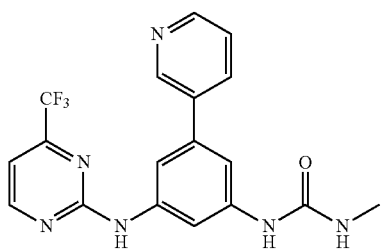

6.1

Step 1:

A mixture of N-[3-nitro-5-(4,4,5,5-tetramethyl-1,3,2-dioxaborolan-2-yl)phenyl]-4-(trifluoromethyl)pyrimidin-2-amine (250 mg, 0.610 mmol), 2-Me-THF (1.6 mL, 0.610 mmol), 3-bromopyridine (116 mg, 0.732 mmol) and sodium carbonate (0.610 mL, 1.22 mmol) was purged and flushed with Ar(g) (3×). PdCl$_2$(dppf)-dichloromethane adduct (24.9 mg, 0.030 mmol) was added to the reaction mixture and heated to 60° C. overnight. The reaction mixture was cooled to room temperature, and the product was collected by filtration. Crude N-[3-nitro-5-(pyridin-3-yl)phenyl]-4-(trifluoromethyl)pyrimidin-2-amine was carried forward without further purification. MS APC calc'd for C$_{16}$H$_{11}$F$_3$N$_5$O$_2$ [M+H]+ 362. found 362.

Step 2:

Ammonium chloride (333 mg, 6.23 mmol), ethanol (6.64 mL) and water (1.66 mL) was added to N-[3-nitro-5-(pyridin-3-yl)phenyl]-4-(trifluoromethyl)pyrimidin-2-amine (150 mg, 0.415 mmol) and was purged and flushed with Ar(g) (3×). Iron (69.6 mg, 1.25 mmol) was added to the reaction mixture and heated to 75° C. for 1.5 hours. The reaction mixture was cooled to room temperature, filtered through a CELITE pad and washed with chloroform. The organic layer was washed with saturated aqueous NH$_4$Cl, dried over sodium sulfate and concentrating under reduced pressure. Crude 5-(pyridin-3-yl)-N-[4-(trifluoromethyl)pyrimidin-2-yl]benzene-1,3-diamine was carried forward without further purification. MS APC calc'd for C$_{16}$H$_{13}$F$_3$N$_5$ [M+H]+ 332. found 332.

Step 3:

Triethylamine (44.2 µL, 0.317 mmol) followed by methyl isocyanate (18.1 mg, 0.317 mmol was added to a solution of 5-(pyridin-3-yl)-N-[4-(trifluoromethyl)pyrimidin-2-yl]benzene-1,3-diamine (35 mg, 0.106 mmol) in THF (264 µL). The reaction mixture was heated to 40° C. for 4 hours, then cooled to room temperature and concentrated under reduced pressure. The solid was diluted with diethyl ether (5.00 mL) and was filtered to isolate 1-methyl-3-[3-(pyridin-3-yl)-5-{[4-(trifluoromethyl)pyrimidin-2-yl]amino}phenyl]urea as a tan powder. The product was further dried under reduced pressure. MS APC calc'd for C$_{18}$H$_{16}$F$_3$N$_6$O [M+H]+ 389. found 389. $^1$H NMR (500 MHz, DMSO-d$_6$) δ 10.26 (s, 1H), 8.81 (s, 1H), 8.75 (s, 1H), 8.63 (s, 1H), 8.56 (s, 1H), 7.92 (d, J=8.5 Hz, 1H), 7.70 (s, 1H), 7.63 (s, 1H), 7.55 (s, 1H), 7.49 (s, 1H), 7.26 (s, 1H), 6.06 (s, 1H), 2.64 (s, 3H).

The following examples in Table 6 were prepared in an analogous manner to that described in general scheme 6 using commercially available bromides in step 1 and commercially available acyl chlorides and isocyanates in step 3. In some cases, step 3 was omitted*.

TABLE 6

| Ex. | C^y | R^4 | Name | [M + H]+ Calc'd | [M + H]+ Obsv'd | Form |
|---|---|---|---|---|---|---|
| 6.2 | pyridin-3-yl | —N(H)—C(O)CH₃ | N-(3-pyridin-3-yl-5-{[4-(trifluoromethyl)pyrimidin-2-yl]amino}phenyl)acetamide | 374 | 374 | Free Base |
| 6.3 | pyridin-3-yl | —N(H)—C(O)—N(H)CH₂CH₃ | 1-ethyl-3-(3-pyridin-3-yl-5-{[4-(trifluoromethyl)pyrimidin-2-yl]amino}phenyl)urea | 403 | 403 | TFA Salt |
| 6.4* | pyridin-4-yl | —NH₂ | 5-pyridin-4-yl-N-[4-(trifluoromethyl)pyrimidin-2-yl]benzene-1,3-diamine | 332 | 332 | TFA Salt |
| 6.5 | pyridin-4-yl | —N(H)—C(O)CH₃ | N-(3-pyridin-4-yl-5-{[4-(trifluoromethyl)pyrimidin-2-yl]amino}phenyl)acetamide | 374 | 374 | TFA Salt |
| 6.6 | 2-CO₂H-pyridin-5-yl | —N(H)—C(O)—N(H)CH₂CH₃ | 5-(3-[(ethylcarbamoyl)amino]-5-{[4-(trifluoromethyl)pyrimidin-2-yl]amino}phenyl)pyridine-2-carboxylic acid | 447 | 447 | TFA Salt |

Example 7

Compounds of Formula (I) Using the General Methods Illustrated in Scheme 7

Example 7.1

N-{5-[3-(acetylamino)-5-{[4-(trifluoromethyl)pyrimidin-2-yl]amino}phenyl]pyridin-2-yl}-2-methylalanine

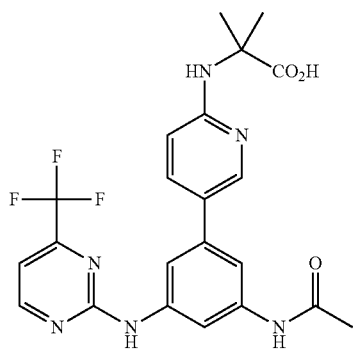

7.1

A mixture of N-[3-(6-fluoropyridin-3-yl)-5-{[4-(trifluoromethyl)pyrimidin-2-yl]amino}phenyl]acetamide (75.0 mg, 0.192 mmol), 2-methylalanine (39.5 mg, 0.383 mmol), and tripotassium phosphate (81.0 mg, 0.383 mmol) in DMSO (479 μL) was heated to 130° C. for 1 hour. The mixture was cooled to room temperature, filtered and the residue was purified by HPLC (10-100% acetonitrile in water+0.5% TFA) to yield N-{5-[3-(acetylamino)-5-{[4-(trifluoromethyl)pyrimidin-2-yl]amino}phenyl]pyridin-2-yl}-2-methylalanine as the bis-TFA salt. MS APC calc'd for $C_{22}H_{22}F_3N_6O_3$ $[M+H]^+$ 475. found 475. $^1$H NMR (500 MHz, $CD_3OD$) δ 8.72 (d, J=4.9, 1H), 8.23 (d, J=7.4, 1H), 8.09 (s, 1H), 7.91 (s, 1H), 7.78 (s, 1H), 7.56 (s, 1H), 7.17-7.12 (m, 2H), 2.65 (s, 6H), 2.16 (s, 3H).

The following examples in Table 7A were prepared in an analogous manner to that described in general scheme 7.

TABLE 7A

| Example | $R^{cy}$ | Name | $[M+H]^+$ Calc'd | $[M+H]^+$ Obsv'd | Form(s) |
|---|---|---|---|---|---|
| 7.2 | (azetidine-CO₂H structure) | (2S)-1-{5-[3-(acetylamino)-5-{[4-(trifluoromethyl)pyrimidin-2-yl]amino}phenyl]pyridin-2-yl}azetidine-2-carboxylic acid | 473.1 | 473.1 | TFA Salt |
| 7.3 | (2-oxopyrrolidin-3-ylamino structure) | N-(3-{6-[(2-oxopyrrolidin-3-yl)amino]pyridin-3-yl}-5-{[4-(trifluoromethyl)pyrimidin-2-yl]amino}phenyl)acetamide | 472.3 | 472.2 | TFA Salt |
| 7.4 | (5-oxo-1,4-diazepan-1-yl structure) | N-(3-[6-(5-oxo-1,4-diazepan-1-yl)pyridin-3-yl]-5-{[4-(trifluoromethyl)pyrimidin-2-yl]amino}phenyl)acetamide | 486.2 | 486.2 | Free Base |

TABLE 7A-continued

| Example | R$^{cy}$ | Name | [M + H]$^+$ Calc'd | [M + H]$^+$ Obsv'd | Form(s) |
|---|---|---|---|---|---|
| 7.5 | 3-oxopiperazin-1-yl | N-(3-[6-(3-oxopiperazin-1-yl)pyridin-3-yl]-5-{[4-(trifluoromethyl)pyrimidin-2-yl]amino}phenyl)acetamide | 472.2 | 472.1 | Free Base |

Example 7.6

(2S)-1-[5-(3-methyl-5-{[4-(trifluoromethyl)pyrimidin-2-yl]amino}phenyl)pyridin-2-yl]azetidine-2-carboxylic acid

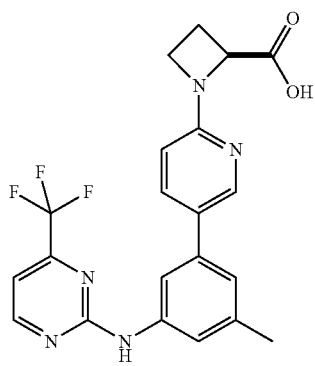

Step 1:
2-Methyl-THF (123 mL), sodium carbonate (2M, 18.5 mL, 36.9 mmol) and 5-bromo-2-fluoropyridine (7.15 g, 40.6 mmol) were added to N-[3-methyl-5-(4,4,5,5-tetramethyl-1,3,2-dioxaborolan-2-yl)phenyl]-4-(trifluoromethyl)pyrimidin-2-amine (14 g, 36.9 mmol) and the reaction mixture was purged and flushed with Ar(g) (3×) before adding PdCl$_2$(dppf)-dichloromethane adduct (1.51 g, 1.85 mmol). The reaction mixture was heated to 85° C. overnight. Another portion of 5-bromo-2-fluoropyridine (2.00 g) and PdCl$_2$(dppf)-dichloromethane adduct (300 mg, 0.368 mmol) were added to the reaction mixture and heated to 85° C. overnight. The reaction mixture was cooled to room temperature and concentrated under reduced pressure. A hot solution of 10% water, 20% DCM and 70% MeCN was added to the residue and the product was collected by filtration. The product was washed with cold DCM to yield N-[3-(6-fluoropyridin-3-yl)-5-methylphenyl]-4-(trifluoromethyl)pyrimidin-2-amine as a green-tinted solid. MS APC calc'd for C$_{17}$H$_{13}$F$_3$N$_4$ [M+H]$^+$ 349. found 349. $^1$H NMR (500 MHz, DMSO-d$_6$) δ 10.27 (s, 1H), 8.82 (d, J=4.8 Hz, 1H), 8.45 (s, 1H), 8.18 (td, J=2.4 Hz, 8.2 Hz, 1H), 7.93 (s, 1H), 7.56 (s, 1H), 7.31-7.24 (m, 2H), 7.18 (s, 1H), 3.32 (s, 3H).

Step 2:
N-[3-(6-Fluoropyridin-3-yl)-5-methylphenyl]-4-(trifluoromethyl)pyrimidin-2-amine (15.0 g, 43.1 mmol), (2S)-azetidine-2-carboxylic acid (5.23 g, 51.7 mmol) and tripotassium phosphate (18.3 g, 86.0 mmol) are flushed and purged with N$_2$(g) (3×) and DMSO (107 mL) was added. The reaction mixture was heated to 130° C. for 6 hours, then cooled to room temperature and was stirred overnight. The CELITE was added to the reaction mixture, filtered and precipitated by addition of acetonitrile (ca. 300 mL). The crude product was collected by filtration and purified by reverse phase chromatography to yield (2S)-1-[5-(3-methyl-5-{[4-(trifluoromethyl)pyrimidin-2-yl]amino}phenyl)pyridin-2-yl]azetidine-2-carboxylic acid. MS ESI calc'd for C$_{21}$H$_{19}$F$_3$N$_5$O$_2$ [M+H]$^+$ 430. found 430. $^1$H NMR (600 MHz, CDCl$_3$) δ 8.64 (d, J=4.7 Hz, 1H), 8.29 (s, 1H), 7.85 (d, J=8.5 Hz, 1H), 7.77 (s, 1H), 7.43 (s, 1H), 7.27 (s, 1H), 7.06-6.94 (m, 2H), 6.50 (d, J=8.6 Hz, 1H), 4.88 (t, J=8.1 Hz, 1H), 3.90 (dd, J=8.2 Hz, 16.3 Hz, 2H), 3.03-2.88 (m, 1H), 2.49 (d, J=8.3 Hz, 1H), 2.40 (s, 3H).

The following examples in Tables 7B-7C were prepared in an analogous manner to that described in general scheme 7 using known or commercially available amines in step 2.

TABLE 7B

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.7 | (2-methyl-2-aminopropanoic acid group) | —CH$_3$ | 2-methyl-N-[5-(3-methyl-5-{[4-(trifluoromethyl)pyrimidin-2-yl]amino}phenyl)pyridin-2-yl]alanine | 432 | 432 | Free Base, Formate Salt |
| 7.8 | (1,3-diazaspiro[5.5]undecan-2-one group) | —CH$_3$ | 9-[5-(3-methyl-5-{[4-(trifluoromethyl)pyrimidin-2-yl]amino}phenyl)pyridin-2-yl]-1,3-diazaspiro[5.5]undecan-2-one | 497 | 497 | Formate Salt |
| 7.9 | (2,8-diazaspiro[5.5]undecan-1-one group) racemic | —CH$_3$ | 8-[5-(3-methyl-5-{[4-(trifluoromethyl)pyrimidin-2-yl]amino}phenyl)pyridin-2-yl]-2,8-diazaspiro[5.5]undecan-1-one | 497 | 497 | Formate Salt |
| 7.10 | (1,9-diazaspiro[5.5]undecane group) | —CH$_3$ | N-{3-[6-(1,9-diazaspiro[5.5]undec-9-yl)pyridin-3-yl]-5-methylphenyl}-4-(trifluoromethyl)pyrimidin-2-amine | 483 | 483 | Formate Salt |
| 7.11 | (1-oxa-7-azaspiro[4.5]decane group) racemic | —CH$_3$ | N-{3-methyl-5-[6-(1-oxa-7-azaspiro[4.5]dec-7-yl)pyridin-3-yl]phenyl}-4-(trifluoromethyl)pyrimidin-2-amine | 470 | 470 | Formate Salt |

TABLE 7B-continued

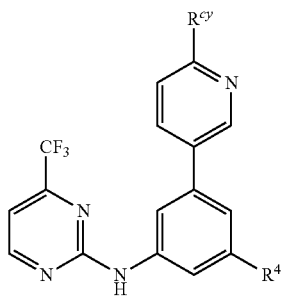

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.12 | (1,4-dioxa-7-azaspiro[4.5]dec-7-yl) | —CH$_3$ | N-{3-[6-(1,4-dioxa-7-azaspiro[4.5]dec-7-yl)pyridin-3-yl]-5-methylphenyl}-4-(trifluoromethyl)pyrimidin-2-amine | 472 | 472 | Formate Salt |
| 7.13 | (1-oxo-1,7-diazaspiro[4.5]decan-7-yl) racemic | —CH$_3$ | 7-[5-(3-methyl-5-{[4-(trifluoromethyl)pyrimidin-2-yl]amino}phenyl)pyridin-2-yl]-1,7-diazaspiro[4.5]decan-1-one | 483 | 483 | Formate Salt |
| 7.14 | (1-oxo-2-oxa-7-azaspiro[4.5]decan-7-yl) racemic | —CH$_3$ | 7-[5-(3-methyl-5-{[4-(trifluoromethyl)pyrimidin-2-yl]amino}phenyl)pyridin-2-yl]-2-oxa-7-azaspiro[4.5]decan-1-one | 484 | 484 | Formate Salt |
| 7.15 | (2-methyl-1-oxo-2,8-diazaspiro[4.5]decan-8-yl) | —CH$_3$ | 2-methyl-8-[5-(3-methyl-5-{[4-(trifluoromethyl)pyrimidin-2-yl]amino}phenyl)pyridin-2-yl]-2,8-diazaspiro[4.5]decan-1-one | 497 | 497 | Formate Salt |
| 7.16 | (5-(aminomethyl)pyrrolidin-2-one) racemic | —CH$_3$ | 5-({[5-(3-methyl-5-{[4-(trifluoromethyl)pyrimidin-2-yl]amino}phenyl)pyridin-2-yl]amino}methyl)pyrrolidin-2-one | 443 | 443 | Formate Salt |

TABLE 7B-continued

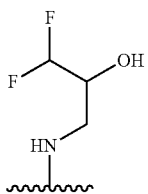

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.17 | 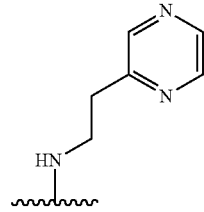 [SMILES: *NCCc1cnccn1]<br>racemic | —CH$_3$ | 1,1-difluoro-3-{[5-(3-methyl-5-{[4-(trifluoromethyl)pyrimidin-2-yl]amino}phenyl)pyridin-2-yl]amino}propan-2-ol | 440 | 440 | Formate Salt |
| 7.18 | 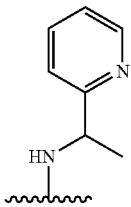 | —CH$_3$ | N-(3-methyl-5-{6-[(2-pyrazin-2-ylethyl)amino]pyridin-3-yl}phenyl)-4-(trifluoromethyl)pyrimidin-2-amine | 452 | 452 | Formate Salt |
| 7.19 | 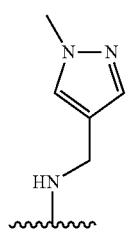 [SMILES: *NCc1cnn(C)c1]<br>racemic | —CH$_3$ | N-(3-methyl-5-{6-[(1-pyridin-2-ylethyl)amino]pyridin-3-yl}phenyl)-4-(trifluoromethyl)pyrimidin-2-amine | 451 | 451 | Formate Salt |
| 7.20 | | —CH$_3$ | N-[3-methyl-5-(6-{[(1-methyl-1H-pyrazol-4-yl)methyl]amino}pyridin-3-yl)phenyl]-4-(trifluoromethyl)pyrimidin-2-amine | 440 | 440 | Formate Salt |
| 7.21 | 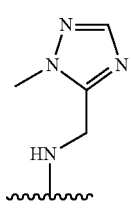 [SMILES: *NCc1ncnn1C] | —CH$_3$ | N-[3-methyl-5-(6-{[(1-methyl-1H-1,2,4-triazol-5-yl)methyl]amino}pyridin-3-yl)phenyl]-4-(trifluoromethyl)pyrimidin-2-amine | 441 | 441 | Formate Salt |

TABLE 7B-continued

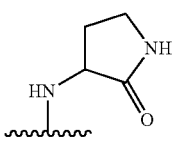

| Ex. | R^cy | R^4 | Name | [M + H]+ Calc'd | [M + H]+ Obsv'd | Form(s) |
| --- | --- | --- | --- | --- | --- | --- |
| 7.22 | 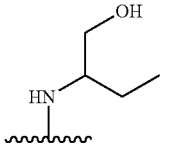<br>racemic | —CH$_3$ | 3-{[5-(3-methyl-5-{[4-(trifluoromethyl)pyrimidin-2-yl]amino}phenyl)pyridin-2-yl]amino}pyrrolidin-2-one | 429 | 429 | Formate Salt |
| 7.23 | 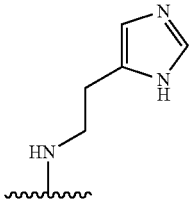 [SMILES: *NCCc1cnc[nH]1]<br>racemic | —CH$_3$ | 2-{[5-(3-methyl-5-{[4-(trifluoromethyl)pyrimidin-2-yl]amino}phenyl)pyridin-2-yl]amino}butan-1-ol | 418 | 418 | Formate Salt |
| 7.24 | 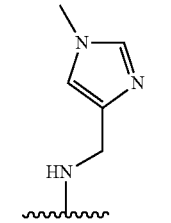 [SMILES: *NCc1cn(C)cn1] | —CH$_3$ | N-[3-(6-{[2-(1H-imidazol-4-yl)ethyl]amino}pyridin-3-yl)-5-methylphenyl]-4-(trifluoromethyl)pyrimidin-2-amine | 440 | 440 | Formate Salt |
| 7.25 | 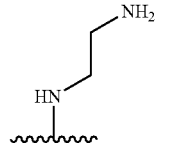 | —CH$_3$ | N-[3-methyl-5-(6-{[(1-methyl-1H-imidazol-4-yl)methyl]amino}pyridin-3-yl)phenyl]-4-(trifluoromethyl)pyrimidin-2-amine | 440 | 440 | Formate Salt |
| 7.25A | 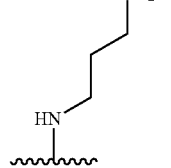 | —CH$_3$ | N-[5-(3-methyl-5-{[4-(trifluoromethyl)pyrimidin-2-yl]amino}phenyl)pyridin-2-yl]ethane-1,2-diamine | 389 | 389 | Formate Salt |
| 7.26 | | —CH$_3$ | N-[5-(3-methyl-5-{[4-(trifluoromethyl)pyrimidin-2-yl]amino}phenyl)pyridin-2-yl]propane-1,3-diamine | 403 | 403 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.27 | (4-oxo-1,4-diazepan-1-yl) | —CH$_3$ | 1-[5-(3-methyl-5-{[4-(trifluoromethyl)pyrimidin-2-yl]amino}phenyl)pyridin-2-yl]-1,4-diazepan-5-one | 443 | 433 | Formate Salt |
| 7.28 | N,N-dimethylglycinamide group | —CH$_3$ | N,N~2~-dimethyl-N~2~-[5-(3-methyl-5-{[4-(trifluoromethyl)pyrimidin-2-yl]amino}phenyl)pyridin-2-yl]glycinamide | 431 | 431 | Formate Salt |
| 7.29 | N-methylglycinamide group | —CH$_3$ | N-methyl-N~2~-[5-(3-methyl-5-{[4-(trifluoromethyl)pyrimidin-2-yl]amino}phenyl)pyridin-2-yl]glycinamide | 417 | 417 | Formate Salt |
| 7.30 | N-methyl-2-hydroxyethylamino group | —CH$_3$ | 2-{methyl[5-(3-methyl-5-{[4-(trifluoromethyl)pyrimidin-2-yl]amino}phenyl)pyridin-2-yl]amino}ethanol | 404 | 404 | Formate Salt |
| 7.31 | glycinamide group | —CH$_3$ | N~2~-[5-(3-methyl-5-{[4-(trifluoromethyl)pyrimidin-2-yl]amino}phenyl)pyridin-2-yl]glycinamide | 403 | 403 | Formate Salt |
| 7.32 | piperidine-4-carboxamide | —CH$_3$ | 1-[5-(3-methyl-5-{[4-(trifluoromethyl)pyrimidin-2-yl]amino}phenyl)pyridin-2-yl]piperidine-4-carboxamide | 457 | 457 | Formate Salt |
| 7.33 | 1-methylpiperazin-2-one group | —CH$_3$ | 1-methyl-4-[5-(3-methyl-5-{[4-(trifluoromethyl)pyrimidin-2-yl]amino}phenyl)pyridin-2-yl]piperazin-2-one | 443 | 443 | Formate Salt |

TABLE 7B-continued

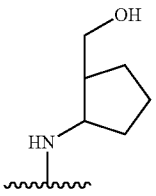

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.34 | 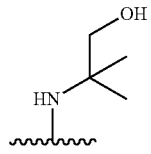 [SMILES: *NC(C)(C)CO] | —CH$_3$ | (1-{[5-(3-methyl-5-{[4-(trifluoromethyl)pyrimidin-2-yl]amino}phenyl)pyridin-2-yl]amino}cyclopentyl)methanol | 444 | 444 | Formate Salt |
| 7.35 | 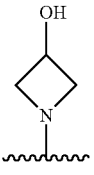 [SMILES: *N1CC(O)C1] | —CH$_3$ | 2-methyl-2-{[5-(3-methyl-5-{[4-(trifluoromethyl)pyrimidin-2-yl]amino}phenyl)pyridin-2-yl]amino}propan-1-ol | 418 | 418 | Formate Salt |
| 7.36 | 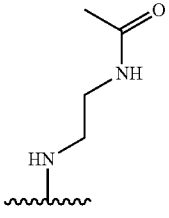 | —CH$_3$ | 1-[5-(3-methyl-5-{[4-(trifluoromethyl)pyrimidin-2-yl]amino}phenyl)pyridin-2-yl]azetidin-3-ol | 402 | 402 | Formate Salt |
| 7.37 | 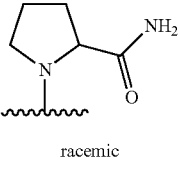 [SMILES: *N1CCCC1C(N)=O] | —CH$_3$ | N-(2-{[5-(3-methyl-5-{[4-(trifluoromethyl)pyrimidin-2-yl]amino}phenyl)pyridin-2-yl]amino}ethyl)acetamide | 431 | 431 | Formate Salt |
| 7.38 | 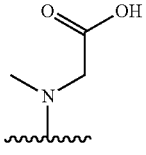 [SMILES: *N(C)CC(=O)O]<br>racemic | —CH$_3$ | 1-[5-(3-methyl-5-{[4-(trifluoromethyl)pyrimidin-2-yl]amino}phenyl)pyridin-2-yl]prolinamide | 443 | 443 | Formate Salt |
| 7.39 | | —CH$_3$ | N-methyl-N-[5-(3-methyl-5-{[4-(trifluoromethyl)pyrimidin-2-yl]amino}phenyl)pyridin-2-yl]glycine | 418 | 418 | Formate Salt, Formate Salt |
| 7.40 | 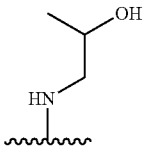 [SMILES: *NCC(C)O] | —CH$_3$ | 1-{[5-(3-methyl-5-{[4-(trifluoromethyl)pyrimidin-2-yl]amino}phenyl)pyridin-2-yl]amino}propan-2-ol | 404 | 404 | Formate Salt |

TABLE 7B-continued

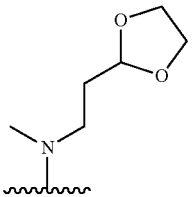 [SMILES: *N(C)CCC1OCCO1]

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.41 | 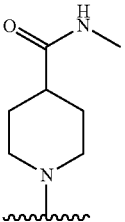 [SMILES: *N1CCC(C(=O)NC)CC1] | —CH$_3$ | N-[3-(6-{[2-(1,3-dioxolan-2-yl)ethyl](methyl)amino}pyridin-3-yl)-5-methylphenyl]-4-(trifluoromethyl)pyrimidin-2-amine | 460 | 460 | Formate Salt |
| 7.42 | 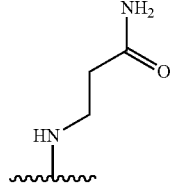 [SMILES: *NCCC(N)=O] | —CH$_3$ | N-methyl-1-[5-(3-methyl-5-{[4-(trifluoromethyl)pyrimidin-2-yl]amino}phenyl)pyridin-2-yl]piperidine-4-carboxamide | 471 | 471 | Formate Salt |
| 7.43 | 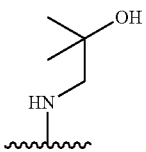 [SMILES: *NCC(C)(C)O] | —CH$_3$ | N~3~-[5-(3-methyl-5-{[4-(trifluoromethyl)pyrimidin-2-yl]amino}phenyl)pyridin-2-yl]-beta-alaninamide | 417 | 417 | Formate Salt |
| 7.44 | 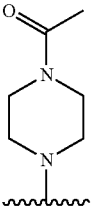 | —CH$_3$ | 2-methyl-1-{[5-(3-methyl-5-{[4-(trifluoromethyl)pyrimidin-2-yl]amino}phenyl)pyridin-2-yl]amino}propan-2-ol | 418 | 418 | Formate Salt |
| 7.45 | 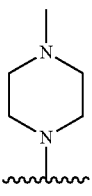 | —CH$_3$ | N-{3-[6-(4-acetylpiperazin-1-yl)pyridin-3-yl]-5-methylphenyl}-4-(trifluoromethyl)pyrimidin-2-amine | 457 | 457 | Formate Salt |
| 7.46 | | —CH$_3$ | N-{3-methyl-5-[6-(4-methylpiperazin-1-yl)pyridin-3-yl]phenyl}-4-(trifluoromethyl)pyrimidin-2-amine | 429 | 429 | Formate Salt |

TABLE 7B-continued

| Ex. | R<sup>cy</sup> | R<sup>4</sup> | Name | [M + H]⁺ Calc'd | [M + H]⁺ Obsv'd | Form(s) |
|---|---|---|---|---|---|---|
| 7.47 | (3-oxetanylamino) | —CH₃ | N-{3-methyl-5-[6-(oxetan-3-ylamino)pyridin-3-yl]phenyl}-4-(trifluoromethyl)pyrimidin-2-amine | 402 | 402 | Formate Salt |
| 7.48 | 4-(methylsulfonyl)piperazin-1-yl | —CH₃ | N-(3-methyl-5-{6-[4-(methylsulfonyl)piperazin-1-yl]pyridin-3-yl}phenyl)-4-(trifluoromethyl)pyrimidin-2-amine | 493 | 493 | Formate Salt |
| 7.49 | 4-ethylpiperazin-1-yl | —CH₃ | N-{3-[6-(4-ethylpiperazin-1-yl)pyridin-3-yl]-5-methylphenyl}-4-(trifluoromethyl)pyrimidin-2-amine | 443 | 443 | Formate Salt |
| 7.50 | (2-acetamidoethyl)(methyl)amino | —CH₃ | N-(2-{methyl[5-(3-methyl-5-{[4-(trifluoromethyl)pyrimidin-2-yl]amino}phenyl)pyridin-2-yl]amino}ethyl)acetamide | 445 | 445 | Formate Salt |
| 7.51 | (5R)-2-oxopiperidin-5-ylamino | —CH₃ | (5R)-5-{[5-(3-methyl-5-{[4-(trifluoromethyl)pyrimidin-2-yl]amino}phenyl)pyridin-2-yl]amino}piperidin-2-one | 443 | 443 | Formate Salt |
| 7.52 | (5S)-2-oxopiperidin-5-ylamino | —CH₃ | (5S)-5-{[5-(3-methyl-5-{[4-(trifluoromethyl)pyrimidin-2-yl]amino}phenyl)pyridin-2-yl]amino}piperidin-2-one | 443 | 443 | Formate Salt |
| 7.53 | 3,3-difluoropiperidin-1-yl | —CH₃ | N-{3-[6-(3,3-difluoropiperidin-1-yl)pyridin-3-yl]-5-methylphenyl}-4-(trifluoromethyl)pyrimidin-2-amine | 450 | 450 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.54 | 2-(methoxymethyl)pyrrolidin-1-yl (racemic) | —CH$_3$ | N-(3-{6-[2-(methoxymethyl)pyrrolidin-1-yl]pyridin-3-yl}-5-methylphenyl)-4-(trifluoromethyl)pyrimidin-2-amine | 444 | 444 | Formate Salt |
| 7.55 | 1,3-dimethyl-2-oxopiperazin-4-yl (racemic) | —CH$_3$ | 1,3-dimethyl-4-[5-(3-methyl-5-{[4-(trifluoromethyl)pyrimidin-2-yl]amino}phenyl)pyridin-2-yl]piperazin-2-one | 457 | 457 | Formate Salt |
| 7.56 | 4,4-difluoropiperidin-1-yl | —CH$_3$ | N-{3-[6-(4,4-difluoropiperidin-1-yl)pyridin-3-yl]-5-methylphenyl}-4-(trifluoromethyl)pyrimidin-2-amine | 450 | 450 | Formate Salt |
| 7.57 | L-prolinamide-1-yl | —CH$_3$ | 1-[5-(3-methyl-5-{[4-(trifluoromethyl)pyrimidin-2-yl]amino}phenyl)pyridin-2-yl]-L-prolinamide | 443 | 443 | Formate Salt |
| 7.58 | 3,5-dimethylpiperazin-1-yl (racemic) | —CH$_3$ | N-{3-[6-(3,5-dimethylpiperazin-1-yl)pyridin-3-yl]-5-methylphenyl}-4-(trifluoromethyl)pyrimidin-2-amine | 443 | 443 | Formate Salt |
| 7.59 | 4-acetyl-1,4-diazepan-1-yl | —CH$_3$ | N-{3-[6-(4-acetyl-1,4-diazepan-1-yl)pyridin-3-yl]-5-methylphenyl}-4-(trifluoromethyl)pyrimidin-2-amine | 471 | 471 | Formate Salt |

TABLE 7B-continued

| Ex. | R^cy | R^4 | Name | [M + H]+ Calc'd | [M + H]+ Obsv'd | Form(s) |
|---|---|---|---|---|---|---|
| 7.60 | (4-propyl-1,4-diazepan-1-yl) | —CH$_3$ | N-{3-methyl-5-[6-(4-propyl-1,4-diazepan-1-yl)pyridin-3-yl]phenyl}-4-(trifluoromethyl)pyrimidin-2-amine | 471 | 471 | Formate Salt |
| 7.61 | [3-(methoxymethyl)pyrrolidin-1-yl], racemic | —CH$_3$ | N-(3-{6-[3-(methoxymethyl)pyrrolidin-1-yl]pyridin-3-yl}-5-methylphenyl)-4-(trifluoromethyl)pyrimidin-2-amine | 444 | 444 | Formate Salt |
| 7.62 | N-methyl-beta-alaninamide group | —CH$_3$ | N-methyl-N~3~-[5-(3-methyl-5-{[4-(trifluoromethyl)pyrimidin-2-yl]amino}phenyl)pyridin-2-yl]-beta-alaninamide | 431 | 431 | Formate Salt |
| 7.63 | 3-propoxypiperidin-1-yl, racemic | —CH$_3$ | N-{3-methyl-5-[6-(3-propoxypiperidin-1-yl)pyridin-3-yl]phenyl}-4-(trifluoromethyl)pyrimidin-2-amine | 472 | 472 | Formate Salt |
| 7.64 | N-(3-aminopropyl)acetamide | —CH$_3$ | N-(3-{[5-(3-methyl-5-{[4-(trifluoromethyl)pyrimidin-2-yl]amino}phenyl)pyridin-2-yl]amino}propyl)acetamide | 445 | 445 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.65 | (N-methylpyrrolidine-2-carboxamide group) | —CH$_3$ | N-methyl-1-[5-(3-methyl-5-{[4-(trifluoromethyl)pyrimidin-2-yl]amino}phenyl)pyridin-2-yl)prolinamide | 457 | 457 | Formate Salt |
| 7.66 | (N,N-dimethylglycinamide group) | —CH$_3$ | N,N-dimethyl-N~2~-[5-(3-methyl-5-{[4-(trifluoromethyl)pyrimidin-2-yl]amino}phenyl)pyridin-2-yl]glycinamide | 431 | 431 | Formate Salt |
| 7.67 | (piperazin-2-one group) | —CH$_3$ | 4-[5-(3-methyl-5-{[4-(trifluoromethyl)pyrimidin-2-yl]amino}phenyl)pyridin-2-yl]piperazin-2-one | 429 | 429 | Formate salt |
| 7.68 | (3-aminopyrrolidin-2-one group) | —CH$_3$ | 3-{[5-(3-methyl-5-{[4-(trifluoromethyl)pyrimidin-2-yl]amino}phenyl)pyridin-2-yl]amino}pyrrolidin-2-one | 429 | 429 | Free Base |
| 7.69 | (serine group) | —CH$_3$ | N-[5-(3-methyl-5-{[4-(trifluoromethyl)pyrimidin-2-yl]amino}phenyl)pyridin-2-yl]serine | 434 | 434 | Formate Salt |
| 7.70 | (D-leucine group) | —CH$_3$ | N-[5-(3-methyl-5-{[4-(trifluoromethyl)pyrimidin-2-yl]amino}phenyl)pyridin-2-yl]-D-leucine | 460 | 460 | Free Base, Formate Salt, Ammonium Salt |
| 7.71 | (L-homoserine group) | —CH$_3$ | N-[5-(3-methyl-5-{[4-(trifluoromethyl)pyrimidin-2-yl]amino}phenyl)pyridin-2-yl]-L-homoserine | 448 | 448 | Free Base, Formate Salt, Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.72 | | —CH$_3$ | 4-{[5-(3-methyl-5-{[4-(trifluoromethyl)pyrimidin-2-yl]amino}phenyl)pyridin-2-yl]amino}piperidine-4-carboxylic acid | 473 | 473 | Formate Salt |
| 7.73 | | —CH$_3$ | N-[5-(3-methyl-5-{[4-(trifluoromethyl)pyrimidin-2-yl]amino}phenyl)pyridin-2-yl]-D-histidine | 484 | 484 | Free Base, Formate Salt, Ammonium Salt |
| 7.74 | | —CH$_3$ | (2S)-4-(methylsulfonyl)-2-{[5-(3-methyl-5-{[4-(trifluoromethyl)pyrimidin-2-yl]amino}phenyl)pyridin-2-yl]amino}butanoic acid | 510 | 510 | Formate Salt |
| 7.75 | | —CH$_3$ | N-(2-cyanoethyl)-N-[5-(3-methyl-5-{[4-(trifluoromethyl)pyrimidin-2-yl]amino}phenyl)pyridin-2-yl]glycine | 457 | 457 | Formate Salt |
| 7.76 | | —CH$_3$ | O-methyl-N-[5-(3-methyl-5-{[4-(trifluoromethyl)pyrimidin-2-yl]amino}phenyl)pyridin-2-yl]serine | 448 | 448 | Formate Salt |
| 7.77 | | —CH$_3$ | 3-methyl-N-[5-(3-methyl-5-{[4-(trifluoromethyl)pyrimidin-2-yl]amino}phenyl)pyridin-2-yl]-D-histidine | 498 | 498 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.78 | | —CH$_3$ | 1-{[5-(3-methyl-5-{[4-(trifluoromethyl)pyrimidin-2-yl]amino}phenyl)pyridin-2-yl]amino}cyclobutanecarboxylic acid | 444 | 444 | Formate Salt |
| 7.79 | | —CH$_3$ | 3-(1-benzothiophen-3-yl)-N-[5-(3-methyl-5-{[4-(trifluoromethyl)pyrimidin-2-yl]amino}phenyl)pyridin-2-yl]-D-alanine | 550 | 550 | Formate Salt |
| 7.80 | | —CH$_3$ | 1-{[5-(3-methyl-5-{[4-(trifluoromethyl)pyrimidin-2-yl]amino}phenyl)pyridin-2-yl]amino}cyclopentane-carboxylic acid | 458 | 458 | Formate Salt |
| 7.81 | | —CH$_3$ | 1-{[5-(3-methyl-5-{[4-(trifluoromethyl)pyrimidin-2-yl]amino}phenyl)pyridin-2-yl]amino}cyclopropanecarboxylic acid | 430 | 430 | Formate Salt |
| 7.82 | racemic | —CH$_3$ | 1-[5-(3-methyl-5-{[4-(trifluoromethyl)pyrimidin-2-yl]amino}phenyl)pyridin-2-yl]azetidine-2-carboxylic acid | 430 | 430 | Formate Salt |
| 7.83 | | —CH$_3$ | 1-[5-(3-methyl-5-{[4-(trifluoromethyl)pyrimidin-2-yl]amino}phenyl)pyridin-2-yl]-L-prolylglycine | 501 | 501 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.84 | (L-prolinyl) | —CH$_3$ | 1-[5-(3-methyl-5-{[4-(trifluoromethyl)pyrimidin-2-yl]amino}phenyl)pyridin-2-yl]-L-proline | 444 | 444 | Formate Salt, Ammonium Salt |
| 7.85 | (piperidine-2-carboxylic) | —CH$_3$ | (2R)-1-[5-(3-methyl-5-{[4-(trifluoromethyl)pyrimidin-2-yl]amino}phenyl)pyridin-2-yl]piperidine-2-carboxylic acid | 458 | 458 | Formate Salt |
| 7.86 | (L-alanine) | —CH$_3$ | N-[5-(3-methyl-5-{[4-(trifluoromethyl)pyrimidin-2-yl]amino}phenyl)pyridin-2-yl]-L-alanine | 418 | 418 | Free Base |
| 7.87 | (glycine) | —CH$_3$ | N-[5-(3-methyl-5-{[4-(trifluoromethyl)pyrimidin-2-yl]amino}phenyl)pyridin-2-yl]glycine | 404 | 404 | Ammonium Salt |
| 7.88 | (beta-alanine) | —CH$_3$ | N-[5-(3-methyl-5-{[4-(trifluoromethyl)pyrimidin-2-yl]amino}phenyl)pyridin-2-yl]-beta-alanine | 418 | 418 | Free Base |
| 7.89 | (D-alanine) | —CH$_3$ | N-[5-(3-methyl-5-{[4-(trifluoromethyl)pyrimidin-2-yl]amino}phenyl)pyridin-2-yl]-D-alanine | 418 | 418 | Ammonium Salt |
| 7.90 | (D-valine) | —CH$_3$ | N-[5-(3-methyl-5-{[4-(trifluoromethyl)pyrimidin-2-yl]amino}phenyl)pyridin-2-yl]-D-valine | 446 | 446 | Ammonium Salt |
| 7.91 | (L-valine) | —CH$_3$ | N-[5-(3-methyl-5-{[4-(trifluoromethyl)pyrimidin-2-yl]amino}phenyl)pyridin-2-yl]-L-valine | 446 | 446 | Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.92 | (threonine side chain, R,S) | —CH$_3$ | N-[5-(3-methyl-5-{[4-(trifluoromethyl)pyrimidin-2-yl]amino}phenyl)pyridin-2-yl]-L-threonine | 448 | 448 | Ammonium Salt |
| 7.93 | (asparagine side chain, R) | —CH$_3$ | N~2~-[5-(3-methyl-5-{[4-(trifluoromethyl)pyrimidin-2-yl]amino}phenyl)pyridin-2-yl]-D-asparagine | 461 | 461 | Ammonium Salt |
| 7.94 | (asparagine side chain, S) | —CH$_3$ | N~2~-[5-(3-methyl-5-{[4-(trifluoromethyl)pyrimidin-2-yl]amino}phenyl)pyridin-2-yl]-L-asparagine | 461 | 461 | Ammonium Salt |
| 7.95 | (methionine side chain) | —CH$_3$ | N-[5-(3-methyl-5-{[4-(trifluoromethyl)pyrimidin-2-yl]amino}phenyl)pyridin-2-yl]-L-methionine | 478 | 478 | Ammonium Salt |
| 7.96 | (phenylalanine side chain) | —CH$_3$ | N-[5-(3-methyl-5-{[4-(trifluoromethyl)pyrimidin-2-yl]amino}phenyl)pyridin-2-yl]-D-phenylalanine | 494 | 494 | Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.97 | | —CH₃ | N-[5-(3-methyl-5-{[4-(trifluoromethyl)pyrimidin-2-yl]amino}phenyl)pyridin-2-yl]-L-phenylalanine | 494 | 494 | Ammonium Salt |
| 7.98 | | —CH₃ | N-[5-(3-methyl-5-{[4-(trifluoromethyl)pyrimidin-2-yl]amino}phenyl)pyridin-2-yl]-L-tyrosine | 510 | 510 | Ammonium Salt |
| 7.99 | | —CH₃ | N-[5-(3-methyl-5-{[4-(trifluoromethyl)pyrimidin-2-yl]amino}phenyl)pyridin-2-yl]-D-tryptophan | 533 | 533 | Ammonium Salt |
| 7.100 | | —CH₃ | N-[5-(3-methyl-5-{[4-(trifluoromethyl)pyrimidin-2-yl]amino}phenyl)pyridin-2-yl]-L-tryptophan | 533 | 533 | Ammonium Salt |
| 7.101 | | —CH₃ | N-[5-(3-methyl-5-{[4-(trifluoromethyl)pyrimidin-2-yl]amino}phenyl)pyridin-2-yl]-D-isoleucine | 460 | 460 | Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.102 | (structure) | —CH$_3$ | 4-{[5-(3-methyl-5-{[4-(trifluoromethyl)pyrimidin-2-yl]amino}phenyl)pyridin-2-yl]amino}butanoic acid | 432 | 432 | Ammonium Salt |
| 7.103 | (structure) | —CH$_3$ | (2S)-2-{[5-(3-methyl-5-{[4-(trifluoromethyl)pyrimidin-2-yl]amino}phenyl)pyridin-2-yl]amino}butanoic acid | 432 | 432 | Ammonium Salt |
| 7.104 | (structure) | —CH$_3$ | N-methyl-N-[5-(3-methyl-5-{[4-(trifluoromethyl)pyrimidin-2-yl]amino}phenyl)pyridin-2-yl]-L-alanine | 432 | 432 | Ammonium Salt |
| 7.105 | (structure) | —CH$_3$ | (4R)-4-hydroxy-1-[5-(3-methyl-5-{[4-(trifluoromethyl)pyrimidin-2-yl]amino}phenyl)pyridin-2-yl]-L-proline | 460 | 460 | Ammonium Salt |
| 7.106 | (structure) | —CH$_3$ | 3-methyl-N-[5-(3-methyl-5-{[4-(trifluoromethyl)pyrimidin-2-yl]amino}phenyl)pyridin-2-yl]-L-valine | 460 | 460 | Ammonium Salt |
| 7.107 | (structure) | —CH$_3$ | N-[5-(3-methyl-5-{[4-(trifluoromethyl)pyrimidin-2-yl]amino}phenyl)pyridin-2-yl]-D-norvaline | 446 | 446 | Ammonium Salt |
| 7.108 | (structure) | —CH$_3$ | N-[5-(3-methyl-5-{[4-(trifluoromethyl)pyrimidin-2-yl]amino}phenyl)pyridin-2-yl]-D-serine | 434 | 434 | Ammonium Salt |
| 7.109 | (structure) | —CH$_3$ | N-[5-(3-methyl-5-{[4-(trifluoromethyl)pyrimidin-2-yl]amino}phenyl)pyridin-2-yl]-L-serine | 434 | 434 | Ammonium Salt |

TABLE 7B-continued

| Ex. | R$^{cy}$ | R$^4$ | Name | [M + H]$^+$ Calc'd | [M + H]$^+$ Obsv'd | Form(s) |
|---|---|---|---|---|---|---|
| 7.110 | (pyrrolidine-2-carboxylic acid, D) | —CH$_3$ | 1-[5-(3-methyl-5-{[4-(trifluoromethyl)pyrimidin-2-yl]amino}phenyl)pyridin-2-yl]-D-prolilne | 444 | 444 | Ammonium Salt |
| 7.111 | (leucine, L) | —CH$_3$ | N-[5-(3-methyl-5-{[4-(trifluoromethyl)pyrimidin-2-yl]amino}phenyl)pyridin-2-yl]-L-leucine | 460 | 460 | Ammonium Salt |
| 7.112 | (histidine, L) | —CH$_3$ | N-[5-(3-methyl-5-{[4-(trifluoromethyl)pyrimidin-2-yl]amino}phenyl)pyridin-2-yl]-L-histidine | 484 | 484 | Ammonium Salt |
| 7.113 | (3-hydroxypropylamino) | —CH$_3$ | 3-{[5-(3-methyl-5-{[4-(trifluoromethyl)pyrimidin-2-yl]amino}phenyl)pyridin-2-yl]amino}propan-1-ol | 404 | 404 | TFA Salt |
| 7.114 | (2-amino-2-methylpropanenitrile) | —CH$_3$ | 2-methyl-2-{[5-(3-methyl-5-{[4-(trifluoromethyl)pyrimidin-2-yl]amino}phenyl)pyridin-2-yl]amino}propanenitrile | 413 | 413 | Free Base |
| 7.115 | (racemic 2-amino-3,3-dimethylbutanenitrile) | —CH$_3$ | 2,3,3-trimethyl-2-{[5-(3-methyl-5-{[4-(trifluoromethyl)pyrimidin-2-yl]amino}phenyl)pyridin-2-yl]amino}butanenitrile | 455 | 455 | Free Base |

TABLE 7B-continued

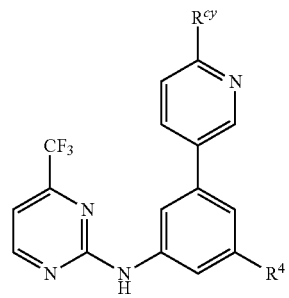

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.116 | (1-oxa-8-azaspiro[5.5]undecan-8-yl, racemic) | —CH$_3$ | N-{3-methyl-5-[6-(1-oxa-8-azaspiro[5.5]undec-8-yl)pyridin-3-yl]phenyl}-4-(trifluoromethyl)pyrimidin-2-amine | 484 | 484 | Formate Salt |
| 7.117 | (4,4,4-trifluoro-2-methyl-2-aminobutanenitrile, racemic) | —CH$_3$ | 4,4,4-trifluoro-2-methyl-2-{[5-(3-methyl-5-{[4-(trifluoromethyl)pyrimidin-2-yl]amino}phenyl)pyridin-2-yl]amino}butanenitrile | 481 | 481 | Free Base |
| 7.118 | (2-methyl-2-aminobutanenitrile, racemic) | —CH$_3$ | 2-methyl-2-{[5-(3-methyl-5-{[4-(trifluoromethyl)pyrimidin-2-yl]amino}phenyl)pyridin-2-yl]amino}butanenitrile | 427 | 427 | Free Base, TFA Salt |
| 7.119 | (proline, racemic) | —CH$_3$ | 1-[5-(3-methyl-5-{[4-(trifluoromethyl)pyrimidin-2-yl]amino}phenyl)pyridin-2-yl]proline | 444 | 444 | Free Base |
| 7.120 | (piperidine-2-carboxylic acid, 2S) | —CH$_3$ | (2S)-1-[5-(3-methyl-5-{[4-(trifluoromethyl)pyrimidin-2-yl]amino}phenyl)pyridin-2-yl]piperidine-2-carboxylic acid | 458 | 458 | Free Base |
| 7.121 | (2-methyl-L-proline) | —CH$_3$ | 2-methyl-1-[5-(3-methyl-5-{[4-(trifluoromethyl)pyrimidin-2-yl]amino}phenyl)pyridin-2-yl]-L-proline | 458 | 458 | TFA Salt |

TABLE 7B-continued

| Ex. | R^cy | R^4 | Name | [M + H]^+ Calc'd | [M + H]^+ Obsv'd | Form(s) |
|---|---|---|---|---|---|---|
| 7.122 | (pyrrolidine-2-carboxylic acid, (R) or (S)) | —CH_3 | 1-[5-(3-methyl-5-{[4-(trifluoromethyl)pyrimidin-2-yl]amino}phenyl)pyridin-2-yl]proline | 444 | 444 | Free Base |
| 7.123 | (2-methylalanine derivative) | —CH_3 | 2-methyl-N-[5-(3-methyl-5-{[4-(trifluoromethyl)pyrimidin-2-yl]amino}phenyl)-3-(trifluoromethyl)pyridin-2-yl]alanine | 500 | 500 | Free Base |
| 7.124 | (3-aminopyrrolidin-2-one, racemic) | —H | 3-{[5-(3-{[4-(trifluoromethyl)pyrimidin-2-yl]amino}phenyl)pyridin-2-yl]amino}pyrrolidin-2-one | 415 | 415 | Free Base |
| 7.125 | (2-methylalanine derivative) | —H | 2-methyl-N-[5-(3-{[4-(trifluoromethyl)pyrimidin-2-yl]amino}phenyl)pyridin-2-yl]alanine | 418 | 418 | TFA Salt |
| 7.126 | (azetidine-2-carboxylic acid) | —H | (2S)-1-[5-(3-{[4-(trifluoromethyl)pyrimidin-2-yl]amino}phenyl)pyridin-2-yl]azetidine-2-carboxylic acid | 416 | 416 | TFA Salt |
| 7.127 | (azetidine-2-carboxylic acid) | —F | (2S)-1-[5-(3-fluoro-5-{[4-(trifluoromethyl)pyrimidin-2-yl]amino}phenyl)pyridin-2-yl]azetidine-2-carboxylic acid | 434 | 434 | Chloride Salt |
| 7.128 | (4-aminopyrrolidin-2-one, racemic) | —CH_3 | 4-{[5-(3-methyl-5-{[4-(trifluoromethyl)pyrimidin-2-yl]amino}phenyl)pyridin-2-yl]amino}pyrrolidin-2-one | 429 | 429 | Formate Salt |

TABLE 7B-continued

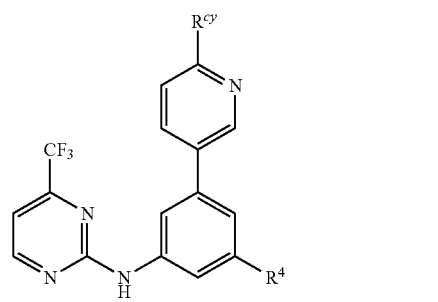

| Ex. | R$^{cy}$ | R$^4$ | Name | [M + H]$^+$ Calc'd | [M + H]$^+$ Obsv'd | Form(s) |
|---|---|---|---|---|---|---|
| 7.129 | (1-amino-cyclopropanecarboxylic acid group) | —CH$_3$ | 1-{[5-(3-methyl-5-{[4-(trifluoromethyl)pyrimidin-2-yl]amino}phenyl)pyridin-2-yl]amino}cyclopropanecarboxylic acid | 430 | 430 | Formate Salt |
| 7.130 | (4-aminobutanoic acid group) | —CH$_3$ | 4-{[5-(3-methyl-5-{[4-(trifluoromethyl)pyrimidin-2-yl]amino}phenyl)pyridin-2-yl]amino}butanoic acid | 432 | 432 | Ammonium Salt |
| 7.131 | (N-methyl-L-alanine group) | —CH$_3$ | N-methyl-N-[5-(3-methyl-5-{[4-(trifluoromethyl)pyrimidin-2-yl]amino}phenyl)pyridin-2-yl]-L-alanine | 432 | 432 | Ammonium Salt |
| 7.132 | (piperidin-2-yl acetic acid group) racemic | —CH$_3$ | {1-[5-(3-methyl-5-{[4-(trifluoromethyl)pyrimidin-2-yl]amino}phenyl)pyridin-2-yl]piperidin-2-yl}acetic acid | 472 | 472 | Formate Salt |
| 7.133 | (azetidine-3-carboxylic acid group) | —CH$_3$ | 1-[5-(3-methyl-5-{[4-(trifluoromethyl)pyrimidin-2-yl]amino}phenyl)pyridin-2-yl]azetidine-3-carboxylic acid | 430 | 430 | Formate Salt |
| 7.134 | (3S)-3-hydroxy-L-proline group | —CH$_3$ | (3S)-3-hydroxy-1-[5-(3-methyl-5-{[4-(trifluoromethyl)pyrimidin-2-yl]amino}phenyl)pyridin-2-yl]-L-proline | 460 | 460 | Formate Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.135 | (piperidine-3-carboxylic acid, racemic) | —CH$_3$ | 1-[5-(3-methyl-5-{[4-(trifluoromethyl)pyrimidin-2-yl]amino}phenyl)pyridin-2-yl]piperidine-3-carboxylic acid | 458 | 458 | Formate Salt |
| 7.136 | (piperidine-4-carboxylic acid) | —CH$_3$ | 1-[5-(3-methyl-5-{[4-(trifluoromethyl)pyrimidin-2-yl]amino}phenyl)pyridin-2-yl]piperidine-4-carboxylic acid | 458 | 458 | Formate Salt, TFA Salt |
| 7.137 | (1,3-thiazolidine-4-carboxylic acid, racemic) | —CH$_3$ | 3-[5-(3-methyl-5-{[4-(trifluoromethyl)pyrimidin-2-yl]amino}phenyl)pyridin-2-yl]-1,3-thiazolidine-4-carboxylic acid | 462 | 462 | Formate Salt |
| 7.138 | (glycylglycine) | —CH$_3$ | N-[5-(3-methyl-5-{[4-(trifluoromethyl)pyrimidin-2-yl]amino}phenyl)pyridin-2-yl]glycylglycine | 461 | 461 | Formate Salt |
| 7.139 | (4-aminobutanoic acid) | —CH$_3$ | 4-{4-[5-(3-methyl-5-{[4-(trifluoromethyl)pyrimidin-2-yl]amino}phenyl)pyridin-2-yl]piperazin-1-yl}butanoic acid | 501 | 501 | Formate Salt |
| 7.140 | (2-amino-2-methylpropanoic acid) | —CH$_3$ | {4-[5-(3-methyl-5-{[4-(trifluoromethyl)pyrimidin-2-yl]amino}phenyl)pyridin-2-yl]piperazin-1-yl}acetic acid | 473 | 473 | Formate Salt |

TABLE 7B-continued

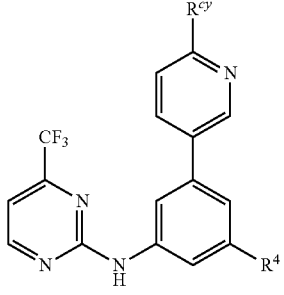

| Ex. | R^cy | R^4 | Name | [M + H]^+ Calc'd | [M + H]^+ Obsv'd | Form(s) |
|---|---|---|---|---|---|---|
| 7.141 | 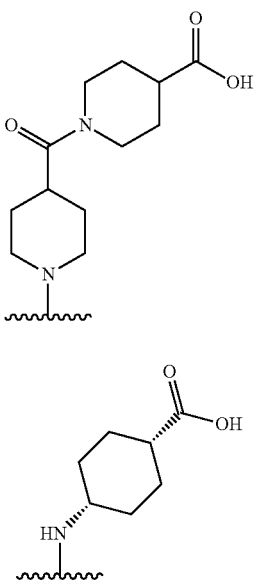 | —CH₃ | 1-({1-[5-(3-methyl-5-{[4-(trifluoromethyl)pyrimidin-2-yl]amino}phenyl)pyridin-2-yl]piperidin-4-yl}carbonyl)piperidine-4-carboxylic acid | 569 | 569 | Formate Salt |
| 7.142 | 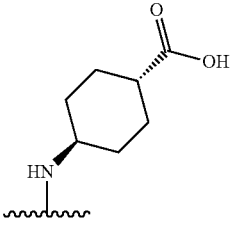 [SMILES: *N[C@H]1CC[C@H](C(=O)O)CC1] | —CH₃ | cis-4-{[5-(3-methyl-5-{[4-(trifluoromethyl)pyrimidin-2-yl]amino}phenyl)pyridin-2-yl]amino}cyclohexane-carboxylic acid | 472 | 472 | Ammonium Salt |
| 7.143 | | —CH₃ | trans-4-{[5-(3-methyl-5-{[4-(trifluoromethyl)pyrimidin-2-yl]amino}phenyl)pyridin-2-yl]amino}cyclohexane-carboxylic acid | 472 | 472 | Ammonium Salt |
| 7.144 | 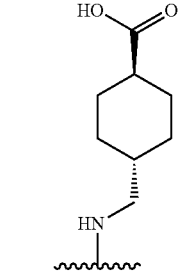 [SMILES: *NC[C@H]1CC[C@H](C(=O)O)CC1] | —CH₃ | trans-4-({[5-(3-methyl-5-{[4-(trifluoromethyl)pyrimidin-2-yl]amino}phenyl)pyridin-2-yl]amino}methyl)cyclohexanecarboxylic acid | 486 | 486 | Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.145 | (4-carboxycyclohexyl-azetidinyl) | —CH$_3$ | 4-{1-[5-(3-methyl-5-{[4-(trifluoromethyl)pyrimidin-2-yl]amino}phenyl)pyridin-2-yl]azetidin-3-yl}cyclohexanecarboxylic acid | 512 | 512 | Ammonium Salt |
| 7.146 | (3-carboxycyclohexyl-azetidinyl) (cis) or (trans) | —CH$_3$ | 3-{1-[5-(3-methyl-5-{[4-(trifluoromethyl)pyrimidin-2-yl]amino}phenyl)pyridin-2-yl]azetidin-3-yl}cyclohexanecarboxylic acid | 512 | 512 | Ammonium Salt |
| 7.147 | (1R,2S)-2-cyclohexyl-piperidinyl | —CH$_3$ | (1R,2S)-2-{1-[5-(3-methyl-5-{[4-(trifluoromethyl)pyrimidin-2-yl]amino}phenyl)pyridin-2-yl]piperidin-4-yl}cyclohexanecarboxylic acid | 540 | 540 | Ammonium Salt |
| 7.148 | 4-(aminomethyl)cyclohexane-carboxylic acid | —CH$_3$ | 4-({[5-(3-methyl-5-{[4-(trifluoromethyl)pyrimidin-2-yl]amino}phenyl)pyridin-2-yl]amino}methyl)cyclohexanecarboxylic acid | 486 | 486 | Ammonium Salt |

TABLE 7B-continued

| Ex. | R<sup>cy</sup> | R<sup>4</sup> | Name | [M + H]<sup>+</sup> Calc'd | [M + H]<sup>+</sup> Obsv'd | Form(s) |
|---|---|---|---|---|---|---|
| 7.149 | (piperidine-3-carbonyl-piperidine-3-carboxylic acid, 3R,3R) | —CH$_3$ | (3R)-1-({(3R)-1-[5-(3-methyl-5-{[4-(trifluoromethyl)pyrimidin-2-yl]amino}phenyl)pyridin-2-yl]piperidin-3-yl}carbonyl)piperidine-3-carboxylic acid | 569 | 569 | TFA Salt |
| 7.150 | (piperidine-3-carbonyl-piperidine-3-carboxylic acid, 3S,3R) | —CH$_3$ | (3S)-1-({(3R)-1-[5-(3-methyl-5-{[4-(trifluoromethyl)pyrimidin-2-yl]amino}phenyl)pyridin-2-yl]piperidin-3-yl}carbonyl)piperidine-3-carboxylic acid | 569 | 5769 | TFA Salt |
| 7.151 | (5-oxopyrrolidine-3-carboxylic acid attached to piperidin-4-yl) racemic | —CH$_3$ | 1-{1-[5-(3-methyl-5-{[4-(trifluoromethyl)pyrimidin-2-yl]amino}phenyl)pyridin-2-yl]piperidin-4-yl}-5-oxopyrrolidine-3-carboxylic acid | 541 | 541 | TFA Salt |
| 7.152 | (2-methylalanine-NH-) | —CH$_3$ | N-[5-(3-{[5-bromo-4-(trifluoromethyl)pyrimidin-2-yl]amino}-5-methylphenyl)pyridin-2-yl-2-methylalanine | 510 | 510, 512 | TFA Salt |
| 7.153 | (N-methylglycinamide) | —CH$_3$ | N~2~-methyl-N~2~-[5-(3-methyl-5-{[4-(trifluoromethyl)pyrimidin-2-yl]amino}phenyl)pyridin-2-yl]glycinamide | 417 | 417 | Free Base |

TABLE 7B-continued

| Ex. | R$^{cy}$ | R$^4$ | Name | [M + H]$^+$ Calc'd | [M + H]$^+$ Obsv'd | Form(s) |
|---|---|---|---|---|---|---|
| 7.154 | (structure: D-alanine fragment) | —CH$_3$ | N-[5-(3-methyl-5-{[4-(trifluoromethyl)pyrimidin-2-yl]amino}phenyl)pyridin-2-yl]-D-alanine | 418 | 418 | Ammonium Salt |
| 7.155 | (structure: L-phenylalanine fragment) | —CH$_3$ | N-[5-(3-methyl-5-{[4-(trifluoromethyl)pyrimidin-2-yl]amino}phenyl)pyridin-2-yl]-L-phenylalanine | 494 | 494 | Ammonium Salt |
| 7.156 | (structure: L-serine fragment) | —CH$_3$ | N-[5-(3-methyl-5-{[4-(trifluoromethyl)pyrimidin-2-yl]amino}phenyl)pyridin-2-yl]-L-serine | 434 | 434 | Ammonium Salt |
| 7.157 | (structure: pyrrolidin-2-one fragment, racemic) | —CH$_3$ | 3-{[5-(3-methyl-5-{[4-(trifluoromethyl)pyrimidin-2-yl]amino}phenyl)pyridin-2-yl]amino}pyrrolidin-2-one | 429 | 429 | Formate Salt |

TABLE 7C

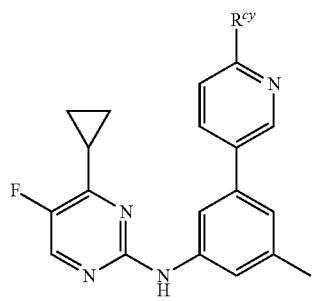

| Ex. | R^cy | Name | [M + H]+ Calc'd | [M + H]+ Obsv'd | Form(s) |
|---|---|---|---|---|---|
| 7.158 | (pyrrolidin-2-one with HN, racemic) | 3-[(5-{3-[(4-cyclopropyl-5-fluoropyrimidin-2-yl)amino]-5-methylphenyl}pyridin-2-yl)amino]pyrrolidin-2-one | 419 | 419 | Free Base |
| 7.159 | (2-methylalanine group) | N-(5-{3-[(4-cyclopropyl-5-fluoropyrimidin-2-yl)amino]-5-methylphenyl}pyridin-2-yl)-2-methylalanine | 422 | 422 | TFA Salt |
| 7.160 | (azetidine-2-carboxylic acid) | (2S)-1-(5-{3-[(4-cyclopropyl-5-fluoropyrimidin-2-yl)amino]-5-fluorophenyl}pyridin-2-yl)azetidine-2-carboxylic acid | 424 | 424 | Free Base |
| 7.161 | (azetidine-2-carboxylic acid) | (2S)-1-(5-{3-[(4-cyclopropyl-5-fluoropyrimidin-2-yl)amino]-5-methylphenyl}pyridin-2-yl)azetidine-2-carboxylic acid | 420 | 420 | TFA Salt |

Example 8

Compounds of Formula (I) Using the General Methods Illustrated in Scheme 8

Examples 8.1 and 8.2

Methyl {[5-(3-methyl-5-{[4-(trifluoromethyl)pyrimidin-2-yl]amino}phenyl)pyridin-2-yl]sulfamoyl}acetate and {[5-(3-Methyl-5-{[4-(trifluoromethyl)pyrimidin-2-yl]amino}phenyl)pyridin-2-yl]sulfamoyl}acetic acid

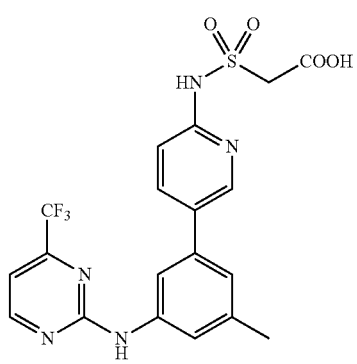

8.2

Step 1:

A mixture of N-[3-methyl-5-(4,4,5,5-tetramethyl-1,3,2-dioxaborolan-2-yl)phenyl]-4-(trifluoromethyl)pyrimidin-2-amine (1.29 g, 3.41 mmol), 5-iodopyridin-2-amine (500 mg, 2.27 mmol), PdCl$_2$(dppf) (333 mg, 0.455 mmol) and sodium carbonate (2.27 ml, 4.55 mmol) in dioxane (9.10 mL) was heated to 100° C. for 16 hours. The reaction mixture was then filtered through a CELITE plug and washed with 1:1 DCM: methanol. The residue was purified by silica gel chromatography (ethyl acetate/hexanes) to give N-[3-(6-aminopyridin-3-yl)-5-methylphenyl]-4-(trifluoromethyl)pyrimidin-2-amine as a colorless solid. MS APCI calc'd for C$_{17}$H$_{15}$F$_3$N$_5$ [M+H]$^+$ 346. found 346.

Step 2:

A solution of N-[3-(6-Aminopyridin-3-yl)-5-methylphenyl]-4-(trifluoromethyl)pyrimidin-2-amine (100 mg, 0.290 mmol) and methyl (chlorosulfonyl)acetate (60.0 mg, 0.348 mmol) in THF (2.90 mL) was cooled to −10° C. Triethylamine (0.13 mL, 0.933 mmol) was added dropwise (over 1 min) to the reaction mixture and stirred for 30 minutes at this temperature. An additional portion of methyl (chlorosulfonyl)acetate (60.0 mg, 0.348 mmol) and triethylamine (0.13 mL, 0.933 mmol) were added to the reaction mixture and was stirred at 0° C. for 6 hours. The reaction mixture was quenched at 0° C. with 1 mL water and was concentrated under reduced pressure. The residue was purified by reverse phase chromatography to yield methyl {[5-(3-methyl-5-{[4-(trifluoromethyl)pyrimidin-2-yl]amino}phenyl)pyridin-2-yl]sulfamoyl}acetate (Ex. 8.1) as a TFA salt. MS APCI calc'd for C$_{20}$H$_{19}$F$_3$N$_5$O$_4$S [M+H]$^+$ 482. found 482. $^1$H NMR (500 MHz, DMSO-d6) δ 11.16 (s, 1H), 10.25 (s, 1H), 8.83 (d, J=4.5 Hz, 1H), 8.42 (br s, 1H), 8.02 (s, 1H), 7.88 (s, 1H), 7.53 (s, 1H), 7.27 (d, J=5.3 Hz, 1H), 7.15 (s, 2H), 4.61 (br s, 2H), 3.64 (s, 3H), 2.34 (s, 3H).

Step 3:

Ethanol (1.00 mL) and aqueous sodium hydroxide (1 M, 0.075 mL, 0.075 mmol) were added to methyl {[5-(3-methyl-5-{[4-(trifluoromethyl)pyrimidin-2-yl]amino}phenyl)pyridin-2-yl]sulfamoyl}acetate (TFA salt, 20.0 mg, 0.034 mmol) and stirred at room temperature for 45 minutes. The reaction mixture was concentrated under reduced pressure. The residue was purified by reverse phase chromatography (10-80% acetonitrile in water+0.1% TFA) to give {[5-(3-methyl-5-{[4-(trifluoromethyl)pyrimidin-2-yl]amino}phenyl)pyridin-2-yl]sulfamoyl}acetic acid (TFA salt) as a colorless solid. MS APCI calc'd for C$_{19}$H$_{17}$F$_3$N$_5$O$_4$S [M+H]$^+$ 468. found 468. $^1$H NMR (500 MHz, DMSO-d6) δ 10.25 (s, 1H), 8.83 (d, J=5.2 Hz, 1H), 8.54-8.21 (m, 1H), 8.00 (s, 1H), 7.88 (s, 1H), 7.53 (s, 1H), 7.27 (d, J=5.1 Hz, 1H), 7.14 (s, 2H), 4.38-3.68 (m, 2H), 2.34 (s, 3H).

The following examples in Table 8 were prepared in an analogous manner to that described in general scheme 8 using known or commercially available acyl or sulfonyl chlorides in step 2. In some cases, step 3 was omitted*.

TABLE 8

| Ex. | R<sup>cy</sup> | Name | [M + H]⁺ Calc'd | [M + H]⁺ Obsv'd | Form(s) |
|---|---|---|---|---|---|
| 8.3* | | methyl 3-{[5-(3-methyl-5-{[4-(trifluoromethyl)pyrimidin-2-yl]amino}phenyl)pyridin-2-yl]amino}-3-oxopropanoate | 446 | 446 | Free Base |
| 8.4 | OH | 3-{[5-(3-methyl-5-{[4-(trifluoromethyl)pyrimidin-2-yl]amino}phenyl)pyridin-2-yl]amino}-3-oxopropanoic acid | 432 | 432 | TFA Salt |

Example 9

Compounds of Formula (I) Using the General Methods Illustrated in Scheme 9

Procedure A

Example 9.1

2-[5-(3-Methyl-5-{[4-(trifluoromethyl)pyrimidin-2-yl]amino}phenyl)pyridin-2-yl]propane-1,2-diol

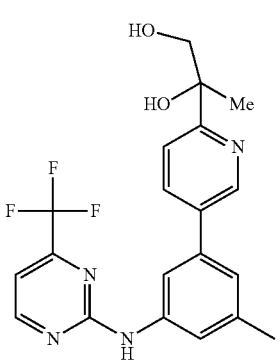

9.1

Step 1:

For a literature procedure to carry out a selective mono-lithiation of 2,5-dibromopyridine, see: Wang, X.; Rabbat, P.; O'Shea, P.; Tillyer, R.; Grabowski, E. J. J.; Reider, P. J. *Tetrahedron Lett.* 2000, 41, 4335-4338. n-BuLi (3.17 mL, 5.07 mmol) was added to 2,5-dibromopyridine (1.00 g, 4.22 mmol) in toluene (49.7 mL) at −78° C. and stirred for 2 hours at −78° C. 1-{[tert-Butyl(dimethyl)silyl]oxy}propan-2-one (1.22 mL, 6.33 mmol) was added dropwise to the reaction mixture over 15 minutes. Upon addition, the reaction mixture was warmed to room temperature overnight. The reaction mixture was quenched with a saturated aqueous NH₄Cl (2.00 mL) and the solvent was removed under reduced pressure. The resultant residue was diluted with dichloromethane (20.0 mL) and was partitioned with a saturated aqueous solution of NH₄Cl (20.0 mL). The organic layer was dried over sodium sulfate, concentrated under reduced pressure and purified by silica gel chromatography (ethyl acetate/hexanes) to yield 2-(5-bromopyridin-2-yl)-1-{[tert-butyl(dimethyl)silyl]oxy}propan-2-ol. MS APCI calc'd for $C_{14}H_{25}BrNO_2Si$ [M+H]⁺ 346. found 346 and 348.

Step 2:

2-Methyl-THF (1.48 mL), sodium carbonate (2M, 223 μL, 0.446 mmol) and 2-(5-bromopyridin-2-yl)-1-{[tert-butyl(dimethyl)silyl]oxy}propan-2-ol (170 mg, 0.490 mmol) were added to N-[3-methyl-5-(4,4,5,5-tetramethyl-1,3,2-dioxaborolan-2-yl)phenyl]-4-(trifluoromethyl)pyrimidin-2-amine (169 mg, 0.446 mmol) and purged and flushed with Ar(g) (3×). PdCl₂(dppf)-dichloromethane adduct (18.2 mg, 0.022 mmol) was added to the reaction mixture, purged and flushed with Ar(g) (3×) and heated to 85° C. for 2 hours. The reaction was cooled to room temperature and was diluted with water (5.00 mL), extracted with DCM (5.00 mL), dried over sodium sulfate, and concentrated under reduced pressure. The residue was purified by silica gel chromatography (acetone/hexanes) to yield 1-{[tert-butyl(dimethyl)silyl]oxy}-2-[5-(3-methyl-5-{[4-(trifluoromethyl)pyrimidin-2-yl]

amino}phenyl)pyridin-2-yl]propan-2-ol. The isolated intermediate was dissolved in neat TFA (1.00 mL) and stirring for 20 minutes at room temperature. The excess TFA was removed under reduced pressure and the resultant residue was partitioned with dichloromethane (5.00 mL) and 1M NaOH (aq) (5.00 mL). The organic layer was washed with brine (5.00 mL), dried over sodium sulfate and concentrated under reduced pressure. The residue was purified by silica gel chromatography (acetone/hexanes) to yield 2-[5-(3-methyl-5-{[4-(trifluoromethyl)pyrimidin-2-yl]amino}phenyl)pyridin-2-yl]propane-1,2-diol. MS APCI calc'd for $C_{20}H_{20}F_3N_4O_2$ [M+H]$^+$ 405. found 405. $^1$H NMR (500 MHz, DMSO-d6) δ 10.27 (s, 1H), 8.83 (d, J=5.5 Hz, 1H), 8.72 (s, 1H), 7.96 (d, J=16.2 Hz, 1H), 7.70 (d, J=9.2 Hz, 1H), 7.55 (s, 1H), 7.27 (d, J=5.5 Hz, 1H), 7.18 (s, 1H), 5.13 (s, 1H), 4.64 (s, 1H), 3.57 (d, J=7.6 Hz, 2H), 2.36 (s, 3H), 1.40 (s, 3H).

Procedure B

Example 9.2

4-Hydroxy-4-[4-(3-methyl-5-{[4-(trifluoromethyl)pyrimidin-2-yl]amino}phenyl)pyridin-2-yl]cyclohexanone

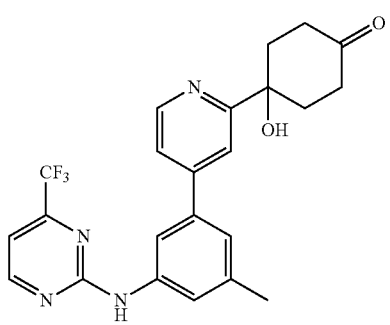

Step 1:
2,4-Dibromopyridine (250 mg, 1.06 mmol) in toluene (8 mL) was cooled to −78° C., and n-buthyl lithium (0.791 ml, 1.266 mmol) was added dropwise. The reaction mixture was stirred for 1 hour at −78° C. 1,4-Cyclohanedione mono-ethylene ketal (165 mg, 1.055 mmol) in toluene (2 mL) was added to the reaction mixture and allowed to warm to room temperature. The reaction mixture was quenched with saturated aqueous ammonium chloride, extracted with $CH_2Cl_2$ (3×), dried over $Na_2SO_4$ and concentrated under reduced pressure. The residue was purified by silica gel column chromatography (ethyl acetate/hexanes) to afford 8-(4-bromopyridin-2-yl)-1,4-dioxaspiro[4.5]decan-8-ol as a pale yellow oil. MS ESI calc'd for $C_{13}H_{17}BrNO_3$ [M+H]$^+$ 314 and 316. found 314 and 316.

Step 2:
PdCl$_2$(dppf)-dichloromethane adduct (32.2 mg, 0.039 mmol) and N-[3-methyl-5-(4,4,5,5-tetramethyl-1,3,2-dioxaborolan-2-yl)phenyl]-4-(trifluoromethyl)pyrimidin-2-amine (299 mg, 0.789 mmol) were combined in a flask, and the contents were evacuated and backfilled (3×) with nitrogen. Dioxane (5 ml), 8-(4-bromopyridin-2-yl)-1,4-dioxaspiro[4.5]decan-8-ol (248 mg, 0.789 mmol), and sodium carbonate (1.18 ml, 2.37 mmol) were added to the reaction mixture and then heated to 100° C. for 2 hours. Upon cooling, the reaction mixture was diluted with water and extracted with ethyl acetate (2×). The combined organic layers were washed with saturated aqueous NaHCO$_3$ and brine, dried over Na$_2$SO$_4$ and concentrated under reduced pressure. The residue was purified by silica gel chromatography (ethyl acetate/hexanes) to provide 8-[4-(3-methyl-5-({[4-(trifluoromethyl)pyrimidin-2-yl]amino}phenyl)pyridin-2-yl]-1,4-dioxaspiro[4.5]decan-8-ol as a white foam. MS ESI calc'd for $C_{25}H_{26}F_3N_4O_3$ [M+H]$^+$ 487. found 487.

Step 3:
Hydrochloric acid (1.75 mL, 10.5 mmol, 6.0 M in dioxane) was added to a solution of 8-[4-(3-Methyl-5-{[4-(trifluoromethyl)pyrimidin-2-yl]amino}phenyl)pyridin-2-yl]-1,4-dioxaspiro[4.5]decan-8-ol (255 mg, 0.524 mmol) in THF (3 mL). The reaction mixture was stirred for 1 hour at room temperature, then brought to pH 8 with saturated aqueous sodium bicarbonate. The reaction mixture was extracted with EtOAc (3×), and the combined organic layers were washed with saturated aqueous sodium bicarbonate. The organic layer was dried over Na$_2$SO$_4$, filtered, and concentrated under reduced pressure. The residue was purified by silica gel chromatography (ethyl acetate/hexanes) to afford 4-hydroxy-4-[4-(3-methyl-5-{[4-(trifluoromethyl)pyrimidin-2-yl]amino}phenyl)pyridin-2-yl]cyclohexanone as a white foam. MS ESI calc'd for $C_{23}H_{22}F_3N_4O_2$ [M+H]$^+$ 443. found 443. $^1$H NMR (500 MHz, DMSO-d$_6$) δ 10.30 (s, 1H), 8.83 (d, J=4.9 Hz, 1H), 8.56 (d, J=5.1 Hz, 1H), 8.05 (s, 1H), 8.00 (d, J=1.1 Hz, 1H), 7.62 (s, 1H), 7.49 (dd, J=5.1, 1.8 Hz, 1H), 7.29-7.26 (m, 2H), 5.68 (s, 1H), 2.77 (td, J=14.1, 6.2 Hz, 2H), 2.46-2.36 (m, 2H), 2.37 (s, 3H), 2.18 (d, J=14.5 Hz, 2H), 2.02-1.91 (m, 2H).

Procedure C

Example 9.3

Cis-1-[4-(3-methyl-5-{[4-(trifluoromethyl)pyrimidin-2-yl]amino}phenyl)pyridine-2-yl]cyclohexane-1,4-diol

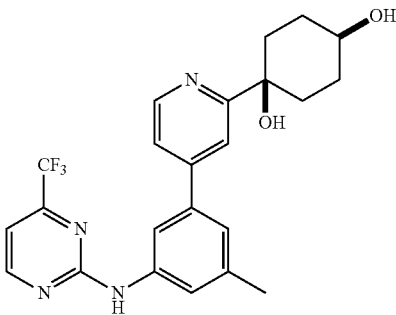

A solution of 4-hydroxy-4-[4-(3-methyl-5-{[4-(trifluoromethyl)pyrimidin-2-yl]amino}phenyl)pyridin-2-yl]cyclohexanone (52 mg, 0.118 mmol) in methanol (1 mL) was cooled to 0° C. Sodium borohydride (6.67 mg, 0.176 mmol) was added to the reaction mixture and stirred for 20 minutes at 0° C. The reaction mixture was diluted with water, warmed to room temperature and extracted with ethyl acetate (3×). The combined organic layers were dried over Na$_2$SO$_4$, filtered, and concentrated under reduced pressure. The residue was purified by silica gel chromatography (ethyl acetate/hexanes) to afford cis-1-[4-(3-methyl-5-{[4-(trifluoromethyl)pyrimidin-2-yl]amino}phenyl)pyridine-2-yl]cyclohexane-1,4-diol as a colorless oil. MS ESI calc'd for $C_{23}H_{24}F_3N_4O_2$ [M+H]+ 445. found 445. ¹H NMR (500 MHz, $CD_3OD$) δ 8.70 (d, J=4.9 Hz, 1H), 8.49 (d, J=5.2 Hz, 1H), 8.02 (s, 1H), 7.95 (d, J=15.0 Hz, 1H), 7.58 (s, 1H), 7.49 (d, J=5.1 Hz, 1H), 7.23 (s, 1H), 7.11 (d, J=4.9 Hz, 1H), 3.77-3.66 (m, 1H), 2.41 (s, 3H), 2.18-2.08 (m, 2H), 1.89-1.82 (m, 4H), 1.76 (br d, J=12.3 Hz, 2H).

Procedure D

Example 9.4

(1S,4R or 1R,4S)-4-[5-(3-fluoro-5-{[4-(trifluoromethyl)pyrimidin-2-yl]amino}phenyl)pyridin-2-yl]-4-hydroxy-2,2-dimethylcyclohexanecarboxylic acid

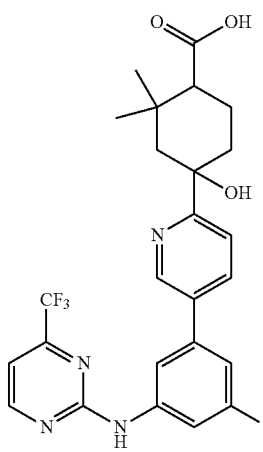

9.4

Step 1:

n-BuLi was added dropwise to a solution of 2,5-dibromopyridine in toluene (30 mL) at −78° C. The reaction mixture was stirred for 1 hour at −78° C., then a solution of methyl 2,2-dimethyl-4-oxocyclohexanecarboxylate in toluene (5 mL) was added. The reaction mixture was warm to room temperature, quenched with saturated aqueous ammonium chloride, extracted with $CH_2Cl_2$ (3×), dried over $Na_2SO_4$ and concentrated under reduced pressure. The residue was purified by silica gel chromatography (ethyl acetate/hexanes) to afford methyl 4-(5-bromopyridin-2-yl)-4-hydroxy-2,2-dimethylcyclohexanecarboxylate as a colorless oil. MS ESI calc'd for $C_{15}H_{21}BrNO_3$ [M+H]+ 342 and 344. found 342 and 344.

Step 2:

$PdCl_2$(dppf)-$CH_2Cl_2$ (9.19 mg, 0.011 mmol) and N-[3-fluoro-5-(4,4,5,5-tetramethyl-1,3,2-dioxaborolan-2-yl)phenyl]-4-(trifluoromethyl)pyrimidin-2-amine (86.0 mg, 0.225 mmol) were combined in a flask and were evacuated and back-filled with nitrogen (3×). Dioxane (3 mL), methyl 4-(5-bromopyridin-2-yl)-4-hydroxy-2,2-dimethylcyclohexanecarboxylate (77.0 mg, 0.225 mmol), and sodium carbonate (2M, 0.337 mL, 0.675 mmol) were added sequentially to the reaction mixture and heated to 100° C. for 15 hours. The reaction mixture was cooled to room temperature, then diluted with water and extracted with ethyl acetate EtOAc (2×). The combined organic layers were washed with saturated aqueous $NaHCO_3$, then brine, dried over $Na_2SO_4$ and concentrated under reduced pressure. The residue was purified by silica gel chromatography (ethyl acetate/hexanes) to afford methyl (1,4-cis)-4-[5-(3-fluoro-5-{[4-(trifluoromethyl)pyrimidin-2-yl]amino}phenyl)pyridin-2-yl]-4-hydroxy-2,2-dimethylcyclohexanecarboxylate as a colorless oil. MS ESI calc'd for $C_{26}H_{27}F_4N_4O_3$ [M+H]+ 519. found 519.

Step 3:

NaOH (424 μL, 0.424 mmol, 1 M) was added to a solution of methyl (1,4-cis)-4-[5-(3-fluoro-5-{[4-(trifluoromethyl)pyrimidin-2-yl]amino}phenyl)pyridin-2-yl]-4-hydroxy-2,2-dimethylcyclohexanecarboxylate (22 mg, 0.042 mmol) in MeOH (500 μL). The reaction mixture was irradiated in a microwave reactor for 10 minutes at 110° C. The reaction mixture was cooled to room temperature and 1 M HCl was added until the pH of the solution reached 3-4. The reaction mixture was diluted with water and extracted with 10% IPA:$CHCl_3$ (2×). The combined organic layers were washed with water, dried over $Na_2SO_4$, filtered, and concentrated under reduced pressure to provide a crude product. SFC separation of the stereoisomers provided (1S,4R or 1R,4S)-4-[5-(3-fluoro-5-{[4-(trifluoromethyl)pyrimidin-2-yl]amino}phenyl)pyridin-2-yl]-4-hydroxy-2,2-dimethylcyclohexanecarboxylic acid as a white solid. MS ESI calc'd for $C_{25}H_{25}F_4N_4O_3$ [M+H]+ 505. found 505. ¹H NMR (500 MHz, DMSO-$d_6$) δ10.56 (s, 1H), 8.89 (d, J=4.9 Hz, 1H), 8.76 (d, J=2.1 Hz, 1H), 8.06-7.97 (m, 1H), 7.89 (s, 1H), 7.78-7.72 (m, 2H), 7.36 (d, J=4.9 Hz, 1H), 7.23 (d, J=9.6 Hz, 1H), 2.18-2.03 (m, 2H), 2.01-1.92 (m, 1H), 1.89 (d, J=14.0 Hz, 1H), 1.66-1.52 (m, 2H), 1.43 (d, J=13.5 Hz, 2H), 1.14 (s, 3H), 0.99 (s, 3H).

Procedure E

Example 9.5

3-Hydroxy-3-[5-(3-methyl-5-{[4-(trifluoromethyl)pyrimidin-2-yl]amino}phenyl)pyridin-3-yl]cyclopentanecarboxylic acid

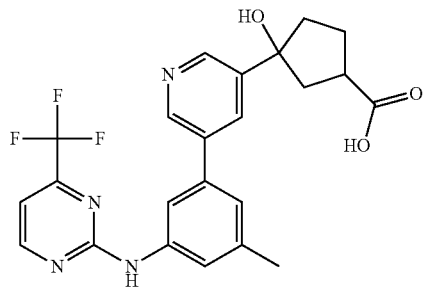

9.5

Step 1:

A solution of THF:toluene (2.11 mL:2.11 mL) and n-BuLi (0.923 ml, 1.48 mmol) was cooled to −10° C. The reaction mixture was purged/filled with argon (3×). n-Butyl magnesium chloride (0.369 ml, 0.739 mmol) was added to the reaction mixture and stirred for 30 minutes. 3,5-Dibromopyridine (0.5 g, 2.111 mmol) was added to the reaction mixture over the course of 30 minutes, keeping bath below −10° C. and stirred for 1 hour. Ethyl 3-oxocyclopentanecarboxylate (0.330 g, 2.111 mmol) was added to the reaction mixture and stirred at −10° C. for ~5 minutes. The reaction mixture was warmed to room temperature, diluted with saturated ammonium, extracted DCM (3×), and combined organic layers were concentrated under reduced pressure. The residue was purified by silica gel chromatography (ethyl acetate/hexanes) to afford ethyl 3-(5-bromopyridin-3-yl)-3-hydroxycyclopentanecarboxylate. MS ESI calc'd for $C_{13}H_{17}BrNO_3$ [M+H]$^+$ 314 and 316. found 314 and 316.

Step 2:

A mixture of N-[3-methyl-5-(4,4,5,5-tetramethyl-1,3,2-dioxaborolan-2-yl)phenyl]-4-(trifluoromethyl)pyrimidin-2-amine (211 mg, 0.557 mmol), ethyl 3-(5-bromopyridin-3-yl)-3-hydroxycyclopentanecarboxylate (175 mg, 0.557 mmol), and sodium carbonate (2 M, 557 µl, 1.11 mmol) in 2-methyl THF (2785 µl) was purged with argon for 10 minutes. PdCl$_2$(dppf)-CH$_2$Cl$_2$ adduct (22.7 mg, 0.028 mmol) was added to the reaction mixture and heated to 85° C. overnight. Upon cooling, the reaction was diluted with water and extracted with DCM (3×). The combined organic layers were dried under reduced pressure and purified by silica gel chromatography (ethyl acetate/hexanes) to afford ethyl 3-hydroxy-3-[5-(3-methyl-5-{[4-(trifluoromethyl)pyrimidin-2-yl]amino}phenyl)pyridin-3-yl]cyclopentanecarboxylate. MS ESI calc'd for $C_{25}H_{26}F_3N_4O_3$ [M+H]$^+$ 487. found 487.

Step 3:

A solution of KOH in MeOH (1 M, 2 mL, 2.00 mmol) was added to the 3-hydroxy-3-[5-(3-methyl-5-{[4-(trifluoromethyl)pyrimidin-2-yl]amino}phenyl)pyridin-3-yl]cyclopentanecarboxylate (60 mg, 0.123 mmol). The reaction mixture was stirred at room temperature, overnight, diluted with 2N HCl and extracted with DCM (3×). The combined organic layers were dried under reduced pressure to give 3-hydroxy-3-[5-(3-methyl-5-{[4-(trifluoromethyl)pyrimidin-2-yl]amino}phenyl)pyridin-3-yl]cyclopentanecarboxylic acid. MS ESI calc'd for $C_{23}H_{22}F_3N_4O_3$ [M+H]$^+$ 459. found 459. $^1$H NMR (500 MHz, MeOD) δ 9.01 (s, 1H), 8.92 (d, J=6.0 Hz, 1H), 8.74 (d, J=5.0 Hz, 1H), 8.19 (s, 1H), 7.63 (s, 2H), 7.35 (s, 1H), 7.17 (d, J=5.0 Hz, 1H), 2.51-2.00 (m, 7H), 1.19 (s, 3H).

Procedure F

Example 9.6 trans-4-(1-(5-(3-(4-cyclopropylpyrimidin-2-ylamino)-5-methylphenyl)pyridin-2-yl)-1-hydroxyethyl)cyclohexanecarboxylic acid 9.6

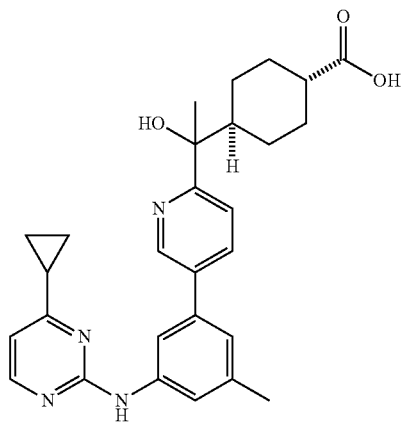

Step 1:

t-BuLi (0.950 mL, 1.52 mmol) was added dropwise to a cooled solution of 2-bromo-5-chloropyridine (225 mg, 1.17 mmol) in DCM (11 mL) at −78° C. over 2 minutes. The reaction mixture was stirred for 2 hours at −78° C. and a solution of butyl trans-4-acetylcyclohexanecarboxylate (291 mg, 1.286 mmol) in DCM (1 mL) was added dropwise at −78° C. The reaction mixture was slowly warmed to room temperature over a period of 16 hours. The reaction mixture was quenched with saturated aqueous NH$_4$Cl and extracted with DCM (3×). The combined organic layers were washed with brine, dried over Na$_2$SO$_4$, filtered and concentrated under reduced pressure. The residue was purified by silica gel chromatography (ethyl acetate/hexanes) to afford trans-butyl 4-(1-(5-chloropyridin-2-yl)-1-hydroxyethyl)cyclohexanecarboxylate as a brown oil. MS ESI calc'd for $C_{18}H_{27}ClNO_3$ [M+H]$^+$ 340. found 340.

Step 2:

A mixture of trans-butyl 4-(1-(5-chloropyridin-2-yl)-1-hydroxyethyl)cyclohexanecarboxylate (110 mg, 0.324 mmol), 4-cyclopropyl-N-[3-methyl-5-(4,4,5,5-tetramethyl-1,3,2-dioxaborolan-2-yl)phenyl]pyrimidin-2-amine (114 mg, 0.324 mmol), BrettPhos Precatalyst (13.0 mg, 0.016 mmol), BrettPhos (18.0 mg, 0.034 mmol) and sodium carbonate (330 µl, 0.660 mmol) in dioxane (1618 µl) was heated to 100° C. for 2 hours. The reaction mixture was cooled to room temperature and TFA (0.5 mL) was added. The reaction mixture was purified directly by preparative HPLC Reverse phase (C-18), eluting with Acetonitrile/Water+0.1% TFA (45-80%). The major peak was collected and lyophilized to give trans-butyl 4-(1-(5-(3-(4-cyclopropylpyrimidin-2-ylamino)-5-methylphenyl)pyridin-2-yl)-1-hydroxyethyl)cyclohexanecarboxylate as a colorless solid. MS ESI calc'd for $C_{32}H_{41}N_4O_3$ [M+H]$^+$ 529. found 529.

Step 3:

A solution of trans-butyl 4-(1-(5-(3-(4-cyclopropylpyrimidin-2-ylamino)-5-methylphenyl)pyridin-2-yl)-1-hydroxyethyl)cyclohexanecarboxylate (61.0 mg, 0.095 mmol) and NaOH (1 M, 0.480 ml, 0.480 mmol) in MeOH (1 mL) was heated to 80° C. for 1 hour. The reaction mixture was cooled to room temperature, acidified with aqueous 1N HCl and diluted with 9:1 CHCl$_3$:IPA. The mixture was then diluted with water and extracted with 9:1 CHCl$_3$:IPA (3×). The combined organic layers were dried over sodium sulfate, filtered and concentrated under reduced pressure to afford trans-4-(1-(5-(3-(4-cyclopropylpyrimidin-2-ylamino)-5-methylphenyl)pyridin-2-yl)-1-hydroxyethyl)cyclohexanecarboxylic acid. MS ESI calc'd for $C_{28}H_{33}N_4O_3$ [M+H]$^+$ 473. found 473. $^1$H NMR (500 MHz, DMSO-d6) δ 9.57 (s, 1H), 8.75 (s, 1H), 8.49 (br s, 1H), 8.27 (d, J=5.0 Hz, 1H), 8.00 (br s, 1H), 7.97 (s, 1H), 7.66 (s, 1H), 7.19 (s, 1H), 6.82 (d, J=5.0 Hz, 1H), 5.74 (s, 1H), 2.35 (s, 3H), 2.04-1.73 (m, 5H), 1.56 (s, 3H), 1.30-1.22 (m, 5H), 1.05-1.01 (m, 5H).

Procedure G

Example 9.7

4-[5-(3-Methyl-5-{[4-(trifluoromethyl)pyrimidin-2-yl]amino}phenyl)pyridin-3-yl]piperidin-4-ol

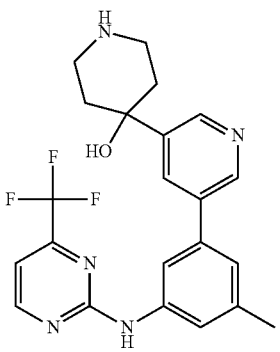

9.7

Step 1:

Literature procedure was used to for the selective monosubstitution of dibromoarenes, see: Iida, T.; Wada, T.; Tomimoto, K.; Mase, T. *Tetrahedron Lett.* 2001, 42, 4841-4844. n-Butylmagnesium chloride in THF (2 M, 0.739 mL, 1.48 mmol) was added to a solution of 1:1 THF:toluene (4.22 mL) and n-BuLi in hexanes (1.6M, 1.85 mL, 2.95 mmol) at −10° C. and stirred for 30 minutes. A solution of 3,5-dibromopyridine (1.00 g, 4.22 mmol) in 1:1 THF:toluene (4.22 mL) was added dropwise over 30 minutes to the reaction mixture and stirred for 1 hour at −10° C. A solution of tert-butyl 4-oxopiperidine-1-carboxylate (0.841 g, 4.22 mmol) in THF (1.00 mL) was added dropwise to the reaction mixture at −10° C. and warmed to room temperature. The reaction mixture was diluted with saturated aqueous NH$_4$Cl and extracted with dichloromethane. The combined organic layers were dried over sodium sulfate and concentrating under reduced pressure. The crude residue was purified by silica gel chromatography (ethyl acetate/hexanes) to yield tert-butyl 4-(5-bromopyridin-3-yl)-4-hydroxypiperidine-1-carboxylate. MS APCI calc'd for $C_{15}H_{22}BrN_2O_3$ [M+H]$^+$ 357 and 359. found 357 and 359.

Step 2:

Dioxane (2.70 mL), tert-butyl 4-(5-bromopyridin-3-yl)-4-hydroxypiperidine-1-carboxylate (207 mg, 0.580 mmol), and sodium carbonate (2 M, 791 μL, 1.58 mmol) was added to N-[3-methyl-5-(4,4,5,5-tetramethyl-1,3,2-dioxaborolan-2-yl)phenyl]-4-(trifluoromethyl)pyrimidin-2-amine (200 mg, 0.527 mmol) and purged and flushed with Ar(g) (3×). PdCl$_2$(dppf)-dichloromethane adduct (21.5 mg, 0.026 mmol) was added to the reaction mixture and heated to 100° C. for 8 hours. The reaction mixture was cooled to room temperature, filtered through CELITE, washed with dichloromethane and extracted with water. The organic layer was dried over sodium sulfate, and was concentrated under reduced pressure. The residue was purified by silica gel chromatography (acetone/hexanes) to yield tert-butyl 4-hydroxy-4-[5-(3-methyl-5-{[4-(trifluoromethyl)pyrimidin-2-yl]amino}phenyl)pyridin-3-yl]piperidine-1-carboxylate. MS APCI calc'd for $C_{27}H_{31}F_3N_5O_3$ [M+H]$^+$ 530. found 530.

Step 3:

Trifluoroacetic acid (262 μL, 3.40 mmol) was added to a solution of tert-butyl 4-hydroxy-4-[5-(3-methyl-5-{[4-(trifluoromethyl)pyrimidin-2-yl]amino}phenyl)pyridin-3-yl]piperidine-1-carboxylate (180 mg, 0.340 mmol) in dichloromethane (1.70 mL). The reaction mixture was stirred for 2 hours, diluted with 10% aqueous NH$_4$OH (1.00 mL) and the precipitated solid was collected by filtration to yield 4-[5-(3-methyl-5-{[4-(trifluoromethyl)pyrimidin-2-yl]amino}phenyl)pyridin-3-yl]piperidin-4-ol as a TFA salt. MS APCI calc'd for $C_{22}H_{23}F_3N_5O$ [M+H]$^+$ 430. found 430. $^1$H NMR (500 MHz, DMSO-d6) δ 8.82 (d, J=5.2 Hz, 1H), 8.66 (s, 2H), 8.01 (s, 1H), 7.98 (s, 1H), 7.56 (s, 1H), 7.26 (d, J=5.0 Hz, 1H), 7.20 (s, 1H), 3.04-2.92 (m, 2H), 2.76 (br m, 2H), 2.36 (s, 3H), 1.99-1.75 (br m, 2H), 1.69-1.49 (br m, 2H).

The following examples in Tables 9A-9C were prepared in an analogous manner to that described in general Scheme 9 using commercially available or known ketones using the procedures A-G as described above.

TABLE 9A

| Ex. | R<sup>cy</sup> | R<sup>1</sup> | R<sup>4</sup> | Name | [M+H]+ Calc'd | [M+H]+ Obsv'd | Form(s) | Procedure |
|---|---|---|---|---|---|---|---|---|
| 9.8 | 2,2-dimethyl-4-hydroxy-cyclohexanecarboxylic acid (cis) | —CF₃ | —CH₃ | (1S,4R or 1R,4S)-4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid | 501 | 501 | Free Base | B |
| 9.9 | 5,5-dimethyl-2-oxabicyclo[2.2.2]octan-3-one (cis) | —CF₃ | —CH₃ | (1R,4S or 1S,4R)-5,5-dimethyl-1-[5-(3-methyl-5-{[4-(trifluoromethyl)pyrimidin-2-yl]amino}phenyl)pyridin-2-yl]-2-oxabicyclo[2.2.2]octan-3-one | 483 | 483 | Free Base | B |
| 9.10 | 5,5-dimethyl-2-oxabicyclo[2.2.2]octan-3-one (cis) | —CF₃ | —CH₃ | (1S,4R or 1R,4S) 5,5-dimethyl-1-[5-(3-methyl-5-{[4-(trifluoromethyl)pyrimidin-2-yl]amino}phenyl)pyridin-2-yl]-2-oxabicyclo[2.2.2]octan-3-one | 483 | 483 | Free Base | B |
| 9.11 | 4-hydroxy-1-methylcyclohexanecarboxylic acid (cis) | —CF₃ | —CH₃ | cis-4-hydroxy-1-methyl-4-[5-(3-methyl-5-{[4-(trifluoromethyl)pyrimidin-2-yl]amino}phenyl)pyridin-2-yl]cyclohexanecarboxylic acid | 487 | 487 | Free Base | B |
| 9.12 | 4-hydroxy-1-methylcyclohexanecarboxylic acid (cis) | —CF₃ | —C(H)F₂ | cis-4-{5-[3-(difluoromethyl)-5-{[4-(trifluoromethyl)pyrimidin-2-yl]amino}phenyl]pyridin-2-yl}-4-hydroxy-1-methylcyclohexanecarboxylic acid | 523 | 523 | Free Base | B |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.13 | 2,2-dimethyl-4-hydroxy-4-carboxy-cyclohexyl (cis) | —CF$_3$ | —C(H)F$_2$ | (1S,4R or 1R,4S)-4-{5-[3-(difluoromethyl)-5-{[4-(trifluoromethyl)pyrimidin-2-yl]amino}phenyl]pyridin-2-yl}-4-hydroxy-2,2-dimethylcyclohexanecarboxylic acid | 537 | | Free Base | B |
| 9.14 | 2,2-dimethyl-4-hydroxy-4-carboxy-cyclohexyl (cis) | —CF$_3$ | —F | (1R,4S or 1S,4R)-4-[5-(3-fluoro-5-{[4-(trifluoromethyl)pyrimidin-2-yl]amino}phenyl)pyridin-2-yl]-4-hydroxy-2,2-dimethylcyclohexanecarboxylic acid | 505 | 505 | Free Base | B |
| 9.15 | 2,2-dimethyl-4-hydroxy-4-carboxy-cyclohexyl (cis) | —CF$_3$ | —CH$_3$ | (1R,4S or 1S,4R)-4-hydroxy-2,2-dimethyl-4-[4-(3-methyl-5-{[4-(trifluoromethyl)pyrimidin-2-yl]amino}phenyl)pyridin-2-yl]cyclohexanecarboxylic acid | 501 | 501 | Free Base | B |
| 9.16 | 2,2-dimethyl-4-hydroxy-4-carboxy-cyclohexyl (cis) | —CF$_3$ | —CH$_3$ | (1R,4S or 1S,4R)-4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid | 501 | 501 | Free Base | B |
| 9.17 | trans-4-(2-hydroxypropan-2-yl)cyclohexanecarboxylic acid (R) or (S) | —OCH$_3$ | —CH$_3$ | trans-4-[(1R or 1S)-1-hydroxy-1-(5-{3-[(4-methoxypyrimidin-2-yl)amino]-5-methylphenyl}pyridin-2-yl)ethyl]cyclohexanecarboxylic acid | 463 | 463 | Free Base | D |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.18 | (4-carboxycyclohexyl)(2-hydroxypropan-2-yl), trans, (R) or (S) | —cPr | —CH$_3$ | trans-4-[(1R or 1S)-1-(5-{3-[(4-cyclopropylpyrimidin-2-yl)amino]-5-methylphenyl}pyridin-2-yl)-1-hydroxyethyl]cyclohexanecarboxylic acid | 473 | 473 | Free Base | D |
| 9.19 | (4-carboxycyclohexyl)(2-hydroxypropan-2-yl), trans, (R) or (S) | —cPr | —CH$_3$ | trans-4-[(1R or 1S)-1-(5-{3-[(4-cyclopropylpyrimidin-2-yl)amino]-5-methylphenyl}pyridin-2-yl)-1-hydroxyethyl]cyclohexanecarboxylic acid | 473 | 473 | Free Base | D |
| 9.20 | 4-(2-hydroxypropan-2-yl)benzoic acid, racemic | —CF$_3$ | —CH$_3$ | 4-{1-hydroxy-1-[5-(3-methyl-5-{[4-(trifluoromethyl)pyrimidin-2-yl]amino}phenyl)pyridin-2-yl]ethyl}benzoic acid | 495 | 495 | Free Base | C (with iPrMgCl) |
| 9.21 | 3-hydroxy-3-cyclohexanecarboxylic acid, racemic | —CF$_3$ | —CH$_3$ | 3-hydroxy-3-[5-(3-methyl-5-{[4-(trifluoromethyl)pyrimidin-2-yl]amino}phenyl)pyridin-2-yl]cyclohexanecarboxylic acid | 473 | 473 | Free Base | B |
| 9.22 | 3-hydroxy-2,2-dimethyl-cyclopentanecarboxylic acid, racemic | —CF$_3$ | —CH$_3$ | 3-hydroxy-2,2-dimethyl-3-[5-(3-methyl-5-{[4-(trifluoromethyl)pyrimidin-2-yl]amino}phenyl)pyridin-2-yl]cyclopentanecarboxylic acid | 487 | 487 | | C |

TABLE 9A-continued

| Ex. | R<sup>cy</sup> | R<sup>1</sup> | R<sup>4</sup> | Name | [M + H]+ Calc'd | [M + H]+ Obsv'd | Form(s) | Procedure |
|---|---|---|---|---|---|---|---|---|
| 9.23 | racemic (cyclohexane with OH, COOH, C(CH$_3$)(OH)) | —CH$_3$ | —CH$_3$ | trans-4-[1-hydroxy-1-(5-{3-methyl-5-[(4-methylpyrimidin-2-yl)amino]phenyl}pyridin-2-yl)ethyl]cyclohexanecarboxylic acid | 447 | 447 | TFA Salt | D |
| 9.24 | racemic | —cPr | —CH$_3$ | trans-4-[1-(5-{3-[(4-cyclopropylpyrimidin-2-yl)amino]-5-methylphenyl}pyridin-2-yl)-1-hydroxyethyl]cyclohexanecarboxylic acid | 473 | 473 | Free Base | D |
| 9.25 | racemic | —OCH$_3$ | —CH$_3$ | trans-4-[1-hydroxy-1-(5-{3-[(4-methoxypyrimidin-2-yl)amino]-5-methylphenyl}pyridin-2-yl)ethyl]cyclohexanecarboxylic acid | 463 | 463 | Free Base | D |
| 9.26 | (R) or (S) | —CH$_3$ | —CH$_3$ | trans-4-[(1R or 1S)-1-hydroxy-1-(5-{3-methyl-5-[(4-methylpyrimidin-2-yl)amino]phenyl}pyridin-2-yl)ethyl]cyclohexanecarboxylic acid | 447 | 447 | Free Base | D |
| 9.27 | (R) or (S) | —CH$_3$ | —CH$_3$ | cis-4-[(1S or 1R)-1-hydroxy-1-(5-{3-methyl-5-[(4-methylpyrimidin-2-yl)amino]phenyl}pyridin-2-yl)ethyl]cyclohexanecarboxylic acid | 447 | 447 | Free Base | D |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.28 | trans-4-hydroxymethyl-cyclohexyl (R) or (S) | —OCH₃ | —CH₃ | trans-4-[(1R or 1S)-1-hydroxy-1-(5-{3-[(4-methoxypyrimidin-2-yl)amino]-5-methylphenyl}pyridin-2-yl)ethyl]cyclohexanecarboxylic acid | 463 | 463 | Free Base, TFA Salt | D |
| 9.29 | trans-4-hydroxymethyl-cyclohexyl (R) or (S) | —C(H)F₂ | —CH₃ | trans-4-{(1R or 1S)-1-[5-(3-{[4-(difluoromethyl)pyrimidin-2-yl]amino}-5-methylphenyl)pyridin-2-yl]-1-hydroxyethyl}cyclohexanecarboxylic acid | 483 | 483 | TFA Salt | D |
| 9.30 | trans-4-hydroxymethyl-cyclohexyl (R) or (S) | —CH₃ | —CH₃ | trans-4-{(1R or 1S)-1-hydroxy-1-[5-(3-methyl-5-{[4-(trifluoromethyl)pyrimidin-2-yl]amino}phenyl)pyridin-2-yl]ethyl}cyclohexanecarboxylic acid | 501 | 501 | TFA Salt | D |
| 9.31 | trans-4-hydroxymethyl-cyclohexyl (R) or (S) | —C(H)F₂ | —CH₃ | trans-4-{(1R or 1S)-1-[5-(3-{[4-(difluoromethyl)pyrimidin-2-yl]amino}-5-methylphenyl)pyridin-2-yl]-1-hydroxyethyl}cyclohexanecarboxylic acid | 483 | 483 | TFA Salt | D |
| 9.32 | 2,2-dimethyl-5-hydroxy-1,3-dioxan-5-yl | —CF₃ | —CH₃ | 2,2-dimethyl-5-[5-(3-methyl-5-{[4-(trifluoromethyl)pyrimidin-2-yl]amino}phenyl)pyridin-2-yl]-1,3-dioxan-5-ol | 461 | 461 | Free Base | A |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.33 | HOCH2-C(OH)(CH2OH)- (propane-1,2,3-triol) | —CF3 | —CH3 | 2-[5-(3-methyl-5-{[4-(trifluoromethyl)pyrimidin-2-yl]amino}phenyl)pyridin-2-yl]propane-1,2,3-triol | 421 | 421 | Free Base | A |
| 9.34 | cis-4-hydroxy-4-carboxycyclohexyl | —CF3 | —CH3 | cis-4-hydroxy-4-[5-(3-methyl-5-{[4-(trifluoromethyl)pyrimidin-2-yl]amino}phenyl)pyridin-2-yl]cyclohexanecarboxylic acid | 473 | 473 | Free Base | C (replaced with iPrMgCl) |
| 9.35 | trans-4-hydroxy-4-carboxycyclohexyl | —CF3 | —CH3 | trans 4-hydroxy-4-[5-(3-methyl-5-{[4-(trifluoromethyl)pyrimidin-2-yl]amino}phenyl)pyridin-2-yl]cyclohexanecarboxylic acid | 473 | 473 | Free Base | C (replaced with iPrMgCl) |
| 9.36 | trans-4-hydroxy-4-carboxycyclohexyl | —OCH3 | —CH3 | trans-4-hydroxy-4-(5-{3-[(4-methoxypyrimidin-2-yl)amino]-5-methylphenyl}pyridin-2-yl)cyclohexanecarboxylic acid | 435 | 435 | Free Base | C (replaced with iPrMgCl) |
| 9.37 | cis-4-hydroxy-4-carboxycyclohexyl | —CH3 | —CH3 | cis-4-hydroxy-4-(5-{3-methyl-5-[(4-methylpyrimidin-2-yl)amino]phenyl}pyridin-2-yl)cyclohexanecarboxylic acid | 419 | 419 | Free Base | C (replaced with iPrMgCl) |
| 9.38 | trans-4-hydroxy-4-carboxycyclohexyl | —CH3 | —CH3 | trans-4-hydroxy-4-(5-{3-methyl-5-[(4-methylpyrimidin-2-yl)amino]phenyl}pyridin-2-yl)cyclohexanecarboxylic acid | 419 | 419 | TFA Salt | C (replaced with iPrMgCl) |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.39 | 4-hydroxy-2,2-dimethyl-4-carboxycyclohexyl (Racemic) | —CH$_3$ | —CH$_3$ | 4-hydroxy-2,2-dimethyl-4-(5-{3-methyl-5-[(4-methylpyrimidin-2-yl)amino]phenyl}pyridin-2-yl)cyclohexanecarboxylic acid | 447 | 447 | Ammonium Salt | B |
| 9.40 | ethyl ester analog (Racemic) | —CH$_3$ | —CH$_3$ | ethyl 4-hydroxy-2,2-dimethyl-4-(5-{3-methyl-5-[(4-methylpyrimidin-2-yl)amino]phenyl}pyridin-2-yl)cyclohexanecarboxylate | 475 | 475 | Free Base | B |
| 9.41 | methyl ester analog (racemic) | —CF$_3$ | —CH$_3$ | methyl 4-hydroxy-2,2-dimethyl-4-[5-(3-methyl-5-{[4-(trifluoromethyl)pyrimidin-2-yl]amino}phenyl)pyridin-2-yl]cyclohexanecarboxylate | 515 | 515 | Free Base | B |
| 9.42 | ethyl ester analog (Racemic) | —CF$_3$ | —CH$_3$ | ethyl 4-hydroxy-2,2-dimethyl-4-[5-(3-methyl-5-{[4-(trifluoromethyl)pyrimidin-2-yl]amino}phenyl)pyridin-2-yl]cyclohexanecarboxylate | 529 | 529 | Formate Salt | B |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.43 | 4-hydroxy-2,2-dimethyl-4-carboxylic acid cyclohexyl group (Racemic) | —CF$_3$ | —H | 4-hydroxy-2,2-dimethyl-4-[5-(3-{[4-(trifluoromethyl)pyrimidin-2-yl]amino}phenyl)pyridin-2-yl]cyclohexanecarboxylic acid | 487 | 487 | Formate Salt | B |
| 9.44 | ethyl 4-hydroxy-1-methyl cyclohexanecarboxylate | —CF$_3$ | —CH$_3$ | ethyl 4-hydroxy-1-methyl-4-[5-(3-methyl-5-{[4-(trifluoromethyl)pyrimidin-2-yl]amino}phenyl)pyridin-2-yl]cyclohexanecarboxylate | 515 | 515 | Free Base | B |
| 9.45 | methyl 4-hydroxy-2,2-dimethyl cyclohexanecarboxylate (cis, racemic) | —CF$_3$ | —CH$_3$ | methyl 4-hydroxy-2,2-dimethyl-4-[4-(3-methyl-5-{[4-(trifluoromethyl)pyrimidin-2-yl]amino}phenyl)pyridin-2-yl]cyclohexanecarboxylate | 515 | 515 | Free Base | B |
| 9.46 | 4-hydroxy-2,2-dimethyl cyclohexanecarboxylic acid (Racemic) | —CF$_3$ | —CH$_3$ | 4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid | 501 | 501 | Formate Salt | B |
| 9.47 | ethyl 3-hydroxy-2,2-dimethyl cyclopentanecarboxylate (racemic) | —CF$_3$ | —CH$_3$ | ethyl 3-hydroxy-2,2-dimethyl-3-[5-(3-methyl-5-{[4-(trifluoromethyl)pyrimidin-2-yl]amino}phenyl)pyridin-2-yl]cyclopentanecarboxylate | 515 | 515 | Free Base | C |

TABLE 9A-continued

| Ex. | R^cy | R¹ | R⁴ | Name | [M + H]+ Calc'd | [M + H]+ Obsv'd | Form(s) | Procedure |
|---|---|---|---|---|---|---|---|---|
| 9.48 | (cyclohexane with HO-CH- and -COOH, racemic) | —CPr | —CH$_3$ | butyl trans-4-[1-(5-{3-[(4-cyclopropylpyrimidin-2-yl)amino]-5-methylphenyl}pyridin-2-yl)-1-hydroxyethyl]cyclohexanecarboxylate | 529 | 529 | TFA Salt | D |
| 9.49 | (butyl ester cyclohexane with HO-CH-, racemic) | —OCH$_3$ | —CH$_3$ | butyl trans-4-[1-hydroxy-1-(5-{3-[(4-methoxypyrimidin-2-yl)amino]-5-methylphenyl}pyridin-2-yl)ethyl]cyclohexanecarboxylate | 519 | 519 | TFA Salt | D |
| 9.50 | (butyl ester cyclohexane with HO-CH-, (R) or (S)) | —OCH$_3$ | —H | butyl trans-4-[(1R or 1S)-1-hydroxy-1-(5-{3-[(4-methoxypyrimidin-2-yl)amino]-5-methylphenyl}pyridin-2-yl)ethyl]cyclohexanecarboxylate | 519 | 519 | TFA Salt | D |
| 9.51 | (butyl ester cyclohexane with HO-CH-, (R) or (S)) | —C(H)F$_2$ | —CH$_3$ | butyl trans-4-{(1R or 1S)-1-[5-(3-{[4-(difluoromethyl)pyrimidin-2-yl]amino}-5-methylphenyl)pyridin-2-yl]-1-hydroxyethyl}cyclohexanecarboxylate | 539 | 539 | TFA Salt | D |
| 9.52 | (butyl ester cyclohexane with HO-CH-, (R) or (S)) | —CF$_3$ | —CH$_3$ | butyl trans-4-{(1R or 1S)-1-hydroxy-1-[5-(3-methyl-5-{[4-(trifluoromethyl)pyrimidin-2-yl]amino}phenyl)pyridin-2-yl]ethyl}cyclohexanecarboxylate | 557 | 557 | TFA Salt | D |

TABLE 9A-continued

| Ex. | R^cy | R^1 | R^4 | Name | [M + H]+ Calc'd | [M + H]+ Obsv'd | Form(s) | Procedure |
|---|---|---|---|---|---|---|---|---|
| 9.53 | butyl trans-4-hydroxycyclohexanecarboxylate-derived group (R) or (S) | —CH$_3$ | —CH$_3$ | butyl trans-4-[(1R or 1S)-1-(5-{3-[(5-chloro-4-methylpyrimidin-2-yl)amino]-5-methylphenyl}pyridin-2-yl)-1-hydroxyethyl]cyclohexanecarboxylate | 537 | 537 | TFA Salt | D |
| 9.54 | 4-hydroxycyclohexanone | —CF$_3$ | —CH$_3$ | 4-hydroxy-4-[5-(3-methyl-5-{[4-(trifluoromethyl)pyrimidin-2-yl]amino}phenyl)pyridin-2-yl]cyclohexanone | 443 | 443 | TFA Salt | A |
| 9.55 | 3-hydroxyoxetane | —CF$_3$ | —CH$_3$ | 3-[5-(3-methyl-5-{[4-(trifluoromethyl)pyrimidin-2-yl]amino}phenyl)pyridin-2-yl]oxetan-3-ol | 403 | 403 | Free Base | A |
| 9.56 | 2-methylpropane-1,2-diol (R) or (S) | —CF$_3$ | —CH$_3$ | 2-[5-(3-methyl-5-{[4-(trifluoromethyl)pyrimidin-2-yl]amino}phenyl)pyridin-2-yl]propane-1,2-diol | 405 | 405 | Free Base | A |
| 9.57 | 2-methylpropane-1,2-diol (R) or (S) | —CF$_3$ | —CH$_3$ | 2-[5-(3-methyl-5-{[4-(trifluoromethyl)pyrimidin-2-yl]amino}phenyl)pyridin-2-yl]propane-1,2-diol | 405 | 405 | Free Base | A |
| 9.58 | cis-cyclohexane-1,4-diol | —CF$_3$ | —CH$_3$ | cis-1-[5-(3-methyl-5-{[4-(trifluoromethyl)pyrimidin-2-yl]amino}phenyl)pyridin-2-yl]cyclohexane-1,4-diol | 445 | 445 | TFA Salt | A |

TABLE 9B

| Ex. | R^cy | R^1 | R^4 | Name | [M + H]+ Calc'd | [M + H]+ Obsv'd | Form(s) | Procedure |
|---|---|---|---|---|---|---|---|---|
| 9.59 | 2,2-dimethyl-4-hydroxy-4-cyclohexanecarboxylic acid (cis) | —CF$_3$ | —CH$_3$ | (1S,4R or 1R,4S)-4-hydroxy-2,2-dimethyl-4-[4-(3-methyl-5-{[4-(trifluoromethyl)pyrimidin-2-yl]amino}phenyl)pyridin-2-yl]cyclohexanecarboxylic acid | 501 | 501 | Free Base | B |
| 9.60 | 1-hydroxycyclobutyl | —CF$_3$ | —CH$_3$ | 1-[4-(3-methyl-5-{[4-(trifluoromethyl)pyrimidin-2-yl]amino}phenyl)pyridin-2-yl]cyclobutanol | 401 | 401 | Free Base | A |
| 9.61 | 2-hydroxypropan-2-yl | —CF$_3$ | —CH$_3$ | 2-[4-(3-methyl-5-{[4-(trifluoromethyl)pyrimidin-2-yl]amino}phenyl)pyridin-2-yl]propan-2-ol | 389 | 389 | Free Base | A |
| 9.62 | 2,2-dimethyl-5-hydroxy-1,3-dioxan-5-yl | —CF$_3$ | —CH$_3$ | 2,2-dimethyl-5-[4-(3-methyl-5-{[4-(trifluoromethyl)pyrimidin-2-yl]amino}phenyl)pyridin-2-yl]-1,3-dioxan-5-ol | 461 | 461 | Free Base | A |
| 9.63 | 8-hydroxy-1,4-dioxaspiro[4.5]dec-8-yl | —CF$_3$ | —CH$_3$ | 8-[4-(3-methyl-5-{[4-(trifluoromethyl)pyrimidin-2-yl]amino}phenyl)pyridin-2-yl]-1,4-dioxaspiro[4.5]decan-8-ol | 487 | 487 | Free Base | A |
| 9.64 | 1,2-dihydroxy-2-methylpropyl | —CF$_3$ | —CH$_3$ | 2-[4-(3-methyl-5-{[4-(trifluoromethyl)pyrimidin-2-yl]amino}phenyl)pyridine-2-yl]propane-1,2-diol | 405 | 405 | Free Base | A |
| 9.65 | 1,3-dihydroxy-2-(hydroxymethyl)propan-2-yl | —CF$_3$ | —CH$_3$ | 2-[4-(3-methyl-5-{[4-(trifluoromethyl)pyrimidin-2-yl]amino}phenyl)pyridine-2-yl]propane-1,2,3-triol | 421 | 421 | Free Base | A |

TABLE 9C

| Ex. | R^cy | R^1 | R^4 | Name | [M+H]+ Calc'd | [M+H]+ Obsv'd | Form(s) | Procedure |
|---|---|---|---|---|---|---|---|---|
| 9.66 | 3-carboxy-cyclohexyl with OH (racemic) | —CF$_3$ | —CH$_3$ | 3-hydroxy-3-[5-(3-methyl-5-{[4-(trifluoromethyl)pyrimidin-2-yl]amino}phenyl)pyridin-3-yl]cyclohexanecarboxylic acid | 473 | 473 | Chloride Salt | B |
| 9.67 | 3-carboxy-cyclopentyl with OH (racemic) | —CF$_3$ | —CH$_3$ | 3-hydroxy-3-[5-(3-methyl-5-{[4-(trifluoromethyl)pyrimidin-2-yl]amino}phenyl)pyridin-3-yl]cyclopentanecarboxylic acid | 459 | 459 | Chloride Salt | C |
| 9.68 | HOCH$_2$-C(OH)(CH$_3$)- (racemic) | —CF$_3$ | —CH$_3$ | 2-[5-(3-methyl-5-{[4-(trifluoromethyl)pyrimidin-2-yl]amino}phenyl)pyridin-3-yl]propane-1,2-diol | 405 | 405 | Free Base | A |
| 9.69 | cis-4-carboxy-4-hydroxy-cyclohexyl | —CF$_3$ | —CH$_3$ | cis-4-hydroxy-4-[5-(3-methyl-5-{[4-(trifluoromethyl)pyrimidin-2-yl]amino}phenyl)pyridin-3-yl]cyclohexanecarboxylic acid | 473 | 473 | Free Base | E |
| 9.70 | trans-4-carboxy-4-hydroxy-cyclohexyl | —CF$_3$ | —CH$_3$ | trans-4-hydroxy-4-[5-(3-methyl-5-{[4-(trifluoromethyl)pyrimidin-2-yl]amino}phenyl)pyridin-3-yl]cyclohexanecarboxylic acid | 473 | 473 | Free Base | E |
| 9.71 | —C(CH$_3$)$_2$OH | —C(H)(OH)CH$_3$ | —CH$_3$ | 2-[5-(3-methyl-5-{[4-(trifluoromethyl)pyrimidin-2-yl]amino}phenyl)pyridin-3-yl]propan-2-ol | 389 | 389 | Free Base | E |

TABLE 9C-continued

| Ex. | R<sup>cy</sup> | R<sup>1</sup> | R<sup>4</sup> | Name | [M + H]+ Calc'd | [M + H]+ Obsv'd | Form(s) | Procedure |
|---|---|---|---|---|---|---|---|---|
| 9.72 | (3-hydroxy-3-methyl-2-oxobutyl), racemic | —CF$_3$ | —CH$_3$ | 3-hydroxy-3-[5-(3-methyl-5-{[4-(trifluoromethyl)pyrimidin-2-yl]amino}phenyl)pyridin-3-yl]butan-2-one | 417 | 417 | Free Base | E |
| 9.73 | (2,3-dihydroxy-3-methylbutyl), racemic | —CF$_3$ | —CH$_3$ | 2-[5-(3-methyl-5-{[4-(trifluoromethyl)pyrimidin-2-yl]amino}phenyl)pyridin-3-yl]butane-2,3-diol | 419 | 419 | Free Base | E (then NaBH$_4$ reduction) |
| 9.74 | (1,3-dihydroxy-2-(hydroxymethyl)propan-2-yl) | —cPr | —CH$_3$ | 2-(5-{3-[(4-cyclopropylpyrimidin-2-yl)amino]-5-methylphenyl}pyridin-3-yl)propane-1,2,3-triol | 393 | 393 | TFA Salt | E |
| 9.75 | (1,3-dihydroxy-2-(hydroxymethyl)propan-2-yl) | —CH$_3$ | —CH$_3$ | 2-(5-{3-methyl-5-[(4-methylpyrimidin-2-yl)amino]phenyl}pyridin-3-yl)propane-1,2,3-triol | 367 | 367 | TFA Salt | E |
| 9.76 | (4-hydroxycyclohexyl) | —CF$_3$ | —CH$_3$ | 1-[5-(3-methyl-5-{[4-(trifluoromethyl)pyrimidin-2-yl]amino}phenyl)pyridin-3-yl]cyclohexane-1,4-diol | 445 | 445 | TFA Salt | E |
| 9.77 | (ethyl 3-hydroxycyclohexanecarboxylate), racemic | —CF$_3$ | —CH$_3$ | ethyl 3-hydroxy-3-[5-(3-methyl-5-{[4-(trifluoromethyl)pyrimidin-2-yl]amino}phenyl)pyridin-3-yl]cyclohexanecarboxylate | 501 | 501 | Free Base | B |
| 9.78 | (2,2-dimethyl-5-hydroxy-1,3-dioxan-5-yl) | —CF$_3$ | —CH$_3$ | 2,2-dimethyl-5-[5-(3-methyl-5-{[4-(trifluoromethyl)pyrimidin-2-yl]amino}phenyl)pyridin-3-yl]-1,3-dioxan-5-ol | 461 | 461 | Free Base | E |

TABLE 9C-continued

| Ex. | R<sup>cy</sup> | R<sup>1</sup> | R<sup>4</sup> | Name | [M + H]+ Calc'd | [M + H]+ Obsv'd | Form(s) | Procedure |
|---|---|---|---|---|---|---|---|---|
| 9.79 | 3-hydroxyoxetan-3-yl | —CF$_3$ | —CH$_3$ | 3-[5-(3-methyl-5-{[4-(trifluoromethyl)pyrimidin-2-yl]amino}phenyl)pyridin-3-yl]oxetan-3-ol | 403 | 403 | Free Base | E |
| 9.80 | 1,3-dihydroxy-2-(hydroxymethyl)propan-2-yl | —CF$_3$ | —CH$_3$ | 2-[5-(3-methyl-5-{[4-(trifluoromethyl)pyrimidin-2-yl]amino}phenyl)pyridin-3-yl]propane-1,2,3-triol | 421 | 421 | Free Base | E |
| 9.81 | 1,1,1-trifluoro-2-hydroxypropan-2-yl | —CF$_3$ | —CH$_3$ | 1,1,1-trifluoro-2-[5-(3-methyl-5-{[4-(trifluoromethyl)pyrimidin-2-yl]amino}phenyl)pyridin-3-yl]propan-2-ol | 443 | 443 | Free Base | E |

TABLE 9D

[Structure shown at top of table: pyrimidine with R¹, R², linked via NH to phenyl bearing R⁴ and pyridine with R^cy]

| Ex. | R^cy | R¹ | R² | R⁴ | Name | [M + H]+ Calc'd | [M + H]+ Obsv'd | Form(s) | Procedure |
|---|---|---|---|---|---|---|---|---|---|
| 9.82 | [cyclohexanecarboxylic acid with CH(OH) substituent, (R) or (S)] | —CH₃ | —Cl | —CH₃ | trans-4-[(1R or 1S)-1-(5-{3-[(5-chloro-4-methylpyrimidin-2-yl)amino]-5-methylphenyl}pyridin-2-yl)-1-hydroxyethyl]cyclohexanecarboxylic acid | 481 | 481 | TFA Salt | D |
| 9.83 | [cyclohexanecarboxylic acid with CH(OH) substituent, (R) or (S)] | —CH₃ | —F | —CH₃ | trans-4-[(1R or 1S)-1-(5-{3-[(5-fluoro-4-methylpyrimidin-2-yl)amino]-5-methylphenyl}pyridin- 2-yl)-1-hydroxyethyl]cyclohexanecarboxylic acid | 465 | 465 | TFA Salt | D |

Example 10

Compounds of Formula (I) Using the General Methods Illustrated in Scheme 10

Example 10.1

4-Hydroxy-4-[5-(3-methyl-5-{[4-(trifluoromethyl)pyrimidin-2-yl]amino}phenyl)pyridin-3-yl]piperidine-1-carboxamide

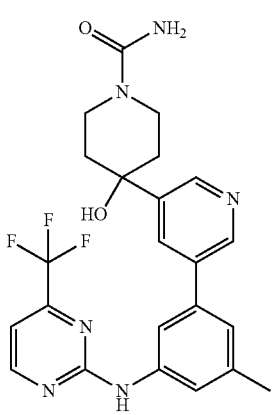

10.1

Potassium cyanate (11.9 mg, 0.147 mmol) and HCl (138 µL, 0.138 mmol) was added to the 4-[5-(3-methyl-5-{[4-(trifluoromethyl)pyrimidin-2-yl]amino}phenyl)pyridin-3-yl]piperidin-4-ol (50.0 mg, 0.092 mmol) in THF (383 µL) and water (1.15 mL) and heated to 50° C. for 4 hours. The reaction mixture was cooled to room temperature and neutralize with aqueous 10% NH₄OH. The resulting precipitate was collected by filtration to yield 4-hydroxy-4-[5-(3-methyl-5-{[4-(trifluoromethyl)pyrimidin-2-yl]amino}phenyl)pyridin-3-yl]piperidine-1-carboxamide. MS APCI calc'd for $C_{23}H_{24}F_3N_6O_2$ [M+H]⁺ 473. found 473. ¹H NMR (500 MHz, DMSO-d6) δ 10.25 (s, 1H), 8.82 (d, J=5.2 Hz, 1H), 8.68 (dd, J=2.4 Hz, 6.3 Hz, 2H), 8.02 (s, 1H), 7.97 (s, 1H), 7.56 (s, 1H), 7.25 (d, J=10.2 Hz, 1H), 7.22 (s, 1H), 5.92 (s, 2H), 3.85 (d, J=16.4 Hz, 2H), 3.09 (t, J=14.5 Hz, 2H), 2.36 (s, 3H), 1.88 (t, J=15.9 Hz, 2H), 1.63 (d, J=14.3 Hz, 2H).

The following examples in Table 10 were prepared in an analogous manner to that described in general Scheme 10 using compounds synthesized from the procedure found in general Scheme 9 using amine-containing ketones in step 1.

TABLE 10

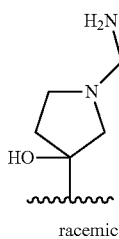

| Ex. | R<sup>cy1</sup> | R<sup>cy2</sup> | Name | [M + H]<sup>+</sup> Calc'd | [M + H]<sup>+</sup> Obsv'd | Form(s) |
|---|---|---|---|---|---|---|
| 10.2 | —H | 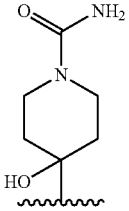<br>racemic | 3-hydroxy-3-[5-(3-methyl-5-{[4-(trifluoromethyl)pyrimidin-2-yl]amino}phenyl)pyridin-3-yl]pyrrolidine-1-carboxamide | 459.2 | 459.1 | TFA Salt |
| 10.3 | 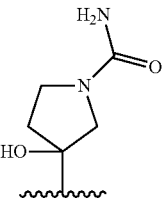 | —H | 4-hydroxy-4-[5-(3-methyl-5-{[4-(trifluoromethyl)pyrimidin-2-yl]amino}phenyl)pyridin-2-yl]piperidine-1-carboxamide | 473.2 | 473.1 | Free Base |
| 10.4 | <br>racemic | —H | 3-hydroxy-3-[5-(3-methyl-5-{[4-(trifluoromethyl)pyrimidin-2-yl]amino}phenyl)pyridin-2-yl]pyrrolidine-1-carboxamide | 459.2 | 459.1 | Free Base |

Example 11

Compounds of Formula (I) Using the General Methods Illustrated in Scheme 11

Example 11.1

5-Hydroxy-5-[5-(3-methyl-5-{[4-(trifluoromethyl)pyrimidin-2-yl]amino}phenyl)pyridin-2-yl]azepan-2-one

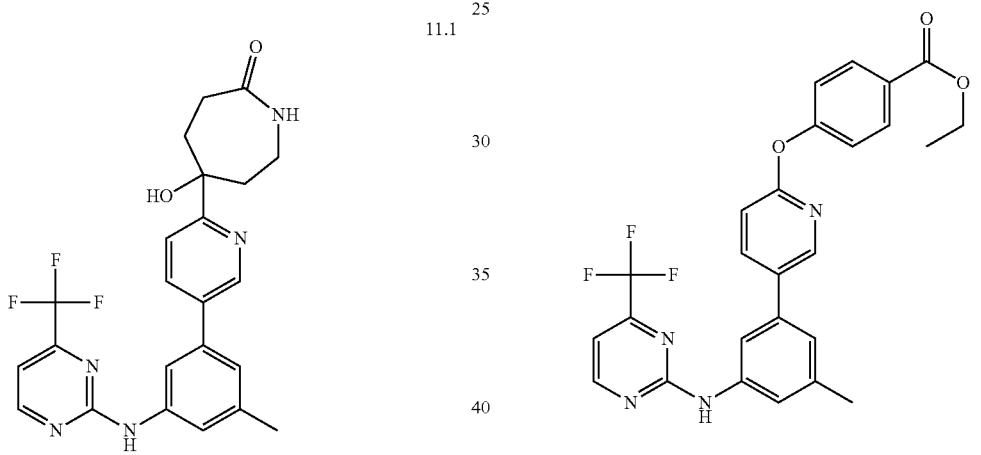

Methanesulfonic acid (53.4 µL, 0.822 mmol) and sodium azide (16.0 mg, 0.247 mmol) were added to a solution of 4-hydroxy-4-[5-(3-methyl-5-{[4-(trifluoromethyl)pyrimidin-2-yl]amino}phenyl)pyridin-2-yl]cyclohexanone (40.0 mg, 0.082 mmol) in chloroform (411 µL) and heated to 65° C. for 2 hours. The reaction mixture was cooled to room temperature and concentrated under reduced pressure. The residue was purified by reverse phase chromatography (10-95% acetonitrile in water+0.5% TFA) to yield 5-hydroxy-5-[5-(3-methyl-5-{[4-(trifluoromethyl)pyrimidin-2-yl]amino}phenyl)pyridin-2-yl]azepan-2-one as a TFA salt. MS APCI calc'd for $C_{23}H_{23}F_3N_5O_2$ [M+H]$^+$ 458. found 458. $^1$H NMR (500 MHz, DMSO-d6) δ 10.30 (s, 1H), 8.88 (s, 1H), 8.83 (d, J=5.5, 1H), 8.10 (d, J=8.0 Hz, 1H), 7.98 (s, 1H), 7.67 (s, 2H), 7.58 (s, 1H), 7.52 (d, J=8.7, 1H), 7.28 (d, J=5.5, 1H), 7.21 (s, 1H), 3.42 (br s, 1H), 2.81 (m, 1H), 2.66-2.49 (m, 5H), 2.37 (s, 3H), 2.33-2.26 (m, 1H).

Example 12

Compounds of Formula (I) Using the General Methods Illustrated in Scheme 12

Example 12.1

Ethyl-4-{[5-(3-methyl-5-{[4-(trifluoromethyl)pyrimidin-2-yl]amino}phenyl)pyridin-2-yl]oxy}benzoate Step 1:

Ethyl-4-hydroxy benzoate (157 mg, 0.947 mmol) was added to a stirred solution of N-[3-(6-fluoropyridin-3-yl)-5-methylphenyl]-4-(trifluoromethyl)pyrimidin-2-amine (300 mg, 0.861 mmol) and potassium carbonate (238 mg, 1.72 mmol) in DMSO (4.0 mL). The reaction mixture was heated to 150° C. for 16 hours. The reaction was cooled to room temperature, diluted with water and extracted with ethyl acetate (3×). The combined organic layers were dried with magnesium sulfate, filtered, and concentrated under reduced pressure. The residue was purified by reverse phase chromatography (60-100% MeCN/Water, with 0.1% TFA). The fractions were combined and neutralized with saturated sodium bicarbonate and the aqueous layer extracted with ethyl acetate (3×). The combined organic layers were dried, filtered, and concentrated under reduced pressure to give ethyl-4-{[5-(3-methyl-5-{[4-(trifluoromethyl)pyrimidin-2-yl]amino}phenyl)pyridin-2-yl]oxy}benzoate (349 mg, 0.706 mmol) as an off white solid. MS ESI calc'd for $C_{26}H_{22}F_3N_4O_3$ [M+H]$^+$ 495. found 495.

Example 12.2

4-{[5-(3-Methyl-5-{[4-(trifluoromethyl)pyrimidin-2-yl]amino}phenyl)pyridin-2-yl]oxy}benzoic acid

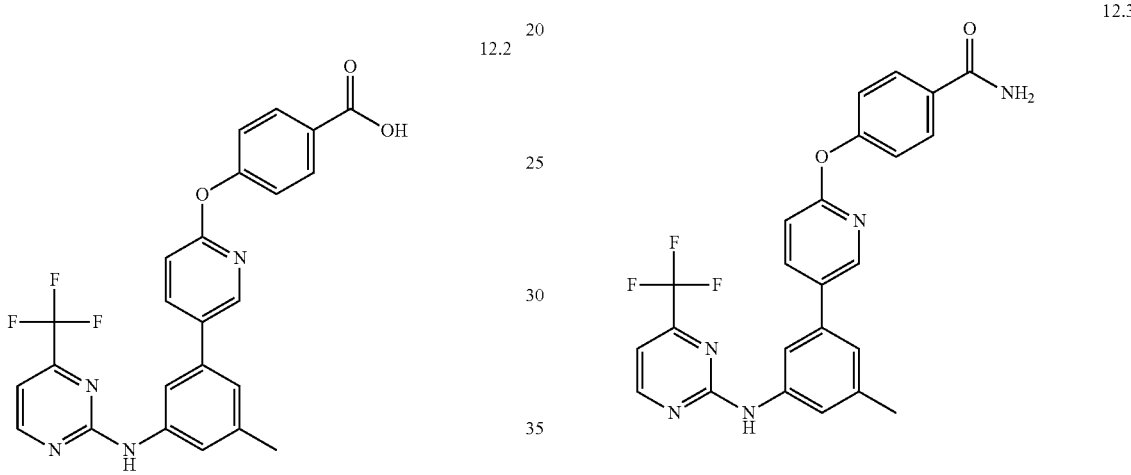

Step 2:

Sodium hydroxide (1 M in water, 1.41 mL, 1.41 mmol) was added to a solution of ethyl-4-{[5-(3-methyl-5-{[4-(trifluoromethyl)pyrimidin-2-yl]amino}phenyl)pyridin-2-yl]oxy}benzoate (349 mg, 0.706 mmol) in methanol (3.53 mL) and stirred at 60° C. for 16 hours. THF (5 mL) was added to the reaction mixture and heated at 60° C. for 6 hours. The reaction was cooled to room temperature and acidified with aqueous 1N HCl. The aqueous layer was extracted with 3:1 CHCl$_3$:isopropanol (3×). The combined organic layers were dried with magnesium sulfate, filtered, and concentrated under reduced pressure. The residue was purified by silica gel chromatography (MeOH/DCM) to afford 4-{[5-(3-methyl-5-{[4-(trifluoromethyl)pyrimidin-2-yl]amino}phenyl)pyridin-2-yl]oxy}benzoic acid (114 mg, 0.244 mmol) as a white solid. MS ESI calc'd for $C_{24}H_{18}F_3N_4O_3$ [M+H]$^+$ 467. found 467.

$^1$H NMR (500 MHz, DMSO-d6) δ 10.25 (s, 1H), 8.81 (d, J=4.5 Hz, 1H), 8.41 (d, J=2.0 Hz, 1H), 8.09 (dd, J=2.5 Hz, 10.5 Hz, 1H), 7.96 (d, J=8.5 Hz, 2H), 7.89 (s, 1H), 7.54 (s, 1H), 7.26 (d, J=5.0 Hz, 1H), 7.22-7.18 (m, 2H), 7.16 (s, 1H), 2.34 (s, 3H).

Example 12.3

4-{[5-(3-Methyl-5-{[4-(trifluoromethyl)pyrimidin-2-yl]amino}phenyl)pyridin-2-yl]oxy}benzamide Ammonium chloride (39 mg, 0.733 mmol) was added to a stirred solution of 4-{[5-(3-methyl-5-{[4-(trifluoromethyl)pyrimidin-2-yl]amino}phenyl)pyridin-2-yl]oxy}benzoic acid (114 mg, 0.244 mmol), EDC (94 mg, 0.489 mmol), HOBt (99 mg, 0.733 mmol), and diisopropylethyl amine (0.256 mL, 1.47 mmol) in DMF (4 mL). The reaction mixture was stirred at room temperature for 16 hours, diluted with water and extracted with ethyl acetate (3×). The combined organics were washed with saturated sodium bicarbonate and then brine. The organic layer was dried with magnesium sulfate, filtered, and concentrated under reduced pressure. The residue was purified by silica gel chromatography (MeOH/DCM) to afford 4-{[5-(3-methyl-5-{[4-(trifluoromethyl)pyrimidin-2-yl]amino}phenyl)pyridin-2-yl]oxy}benzamide (89 mg, 0.191 mmol) as a white solid. MS ESI calc'd for $C_{24}H_{19}F_3N_5O_3$ [M+H]$^+$ 466. found 466. $^1$H NMR (500 MHz, DMSO-d6) δ 10.25 (s, 1H), 8.81 (d, J=5.0 Hz, 1H), 8.39 (d, J=2.0 Hz, 1H), 8.08 (dd, J=8.8, 1.8 Hz, 1H), 7.96 (s, 1H), 7.92 (d, J=8.0 Hz, 2H), 7.89 (s, 1H), 7.53 (s, 1H), 7.34 (s, 1H), 7.26 (d, J=4.5 Hz, 1H), 7.21 (d, J=8.0 Hz, 2H), 7.17 (d, J=8.5 Hz, 1H), 7.15 (s, 1H), 2.34 (s, 3H).

The following examples in Table 12 were prepared in an analogous manner to that described in Examples 12.1-12.3 and general scheme 12.

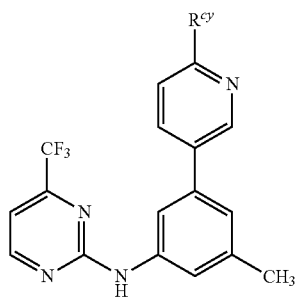

| Ex. | R^cy | Name | [M + H]+ Calc'd | [M + H]+ Obsv'd | Form(s) |
|---|---|---|---|---|---|
| 12.4 | (4-carbamoylphenyl-C(OH)(CH3)- group, racemic) | 4-{1-hydroxy-1-[5-(3-methyl-5-{[4-(trifluoromethyl)pyrimidin-2-yl]amino}phenyl)pyridin-2-yl]ethyl}benzamide | 494 | 494 | Formate Salt |
| 12.5 | (3-methyl-2-oxopiperazine-1-carbonyl, racemic) | 3-methyl-4-{[5-(3-methyl-5-{[4-(trifluoromethyl)pyrimidin-2-yl]amino}phenyl)pyridin-2-yl]carbonyl}piperazin-2-one | 471 | 471 | TFA Salt |
| 12.6 | (carboxamide) | 5-(3-methyl-5-{[4-(trifluoromethyl)pyrimidin-2-yl]amino}phenyl)pyridine-2-carboxamide | 374 | 374 | TFA Salt |
| 12.7 | (glycylglycinamide) | N-[5-(3-methyl-5-{[4-(trifluoromethyl)pyrimidin-2-yl]amino}phenyl)pyridin-2-yl]glycylglycinamide | 460 | 460 | Free Base |
| 12.8 | (1-aminocyclopropanecarboxamide) | 1-{[5-(3-methyl-5-{[4-(trifluoromethyl)pyrimidin-2-yl]amino}phenyl)pyridin-2-yl]amino}cyclopropanecarboxamide | 429 | 429 | Free Base |
| 12.9 | ((2S)-azetidine-2-carboxylic acid) | (2S)-1-[5-(3-methyl-5-{[4-(trifluoromethyl)pyrimidin-2-yl]amino}phenyl)pyridin-2-yl]azetidine-2-carboxamide | 429 | 429 | Free Base |

Example 13

Compounds of Formula (I) Using the General Methods Illustrated in Scheme 13

Example 13.1

3-[5-(3-Methyl-5-{[4-(trifluoromethyl)pyrimidin-2-yl]amino}phenyl)pyridin-2-yl]propanenitrile

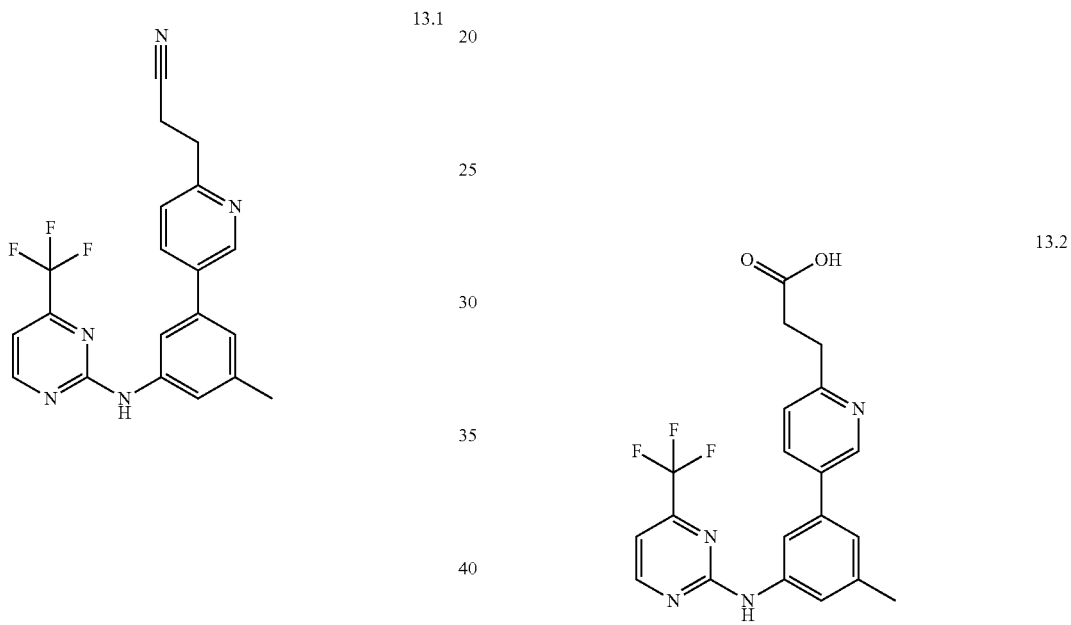

Step 1:

A solution of 2,5-dibromopyridine (100 mg, 0.422 mmol) in tetrahydrofuran (844 µL) was purged and flushed with Ar(g) (3×). Pd(PPh$_3$)$_4$ (48.8 mg, 0.042 mmol) was added to the reaction mixture and purged and flushed (3×) with Ar(g). Bromo(2-cyanoethyl)zinc (1270 µL, 0.633 mmol) was added dropwise to the reaction mixture and heated to 85° C. Upon the reaction completion (as deemed by LCMS analysis) was cooled to room temperature, filtered through CELITE, washed with dichloromethane and diluted with water. The organic layer was extracted, dried over sodium sulfate, and concentrated under reduced pressure. The residue was purified by silica gel chromatography (acetone/exanes) to yield 3-(5-bromopyridin-2-yl)propanenitrile. MS APCI calc'd for C$_8$H$_8$BrN$_2$ [M+H]$^+$ 211 and 213. found 211 and 213.

Step 2:

2-Methyl tetrahydrofuran (1.32 mL) and sodium carbonate (2M, 396 µL, 0.791 mmol) was added to N-[3-methyl-5-(4,4,5,5-tetramethyl-1,3,2-dioxaborolan-2-yl)phenyl]-4-(trifluoromethyl)pyrimidin-2-amine (150 mg, 0.396 mmol) and was purged and flushed with Ar(g) (3×). PdCl$_2$(dppf)-dichloromethane adduct (16.2 mg, 0.020 mmol) was added to the reaction mixture and heated to 90° C. for 10 hours. The reaction mixture was cooled to room temperature, filtered through CELITE, washed with dichloromethane, and diluted with water. The organic layer was extracted, dried over sodium sulfate, and was concentrated under reduced pressure. The residue was purified by silica gel chromatography (acetone/hexanes) to yield 3-[5-(3-methyl-5-{[4-(trifluoromethyl)pyrimidin-2-yl]amino}phenyl)pyridin-2-yl]propanenitrile. MS APCI calc'd for C$_{20}$H$_{17}$F$_3$N$_5$ [M+H]$^+$ 384. found 384. $^1$H NMR (500 MHz, DMSO-d6) δ 10.27 (s, 1H), 8.83 (d, J=4.9 Hz, 1H), 8.77 (d, J=2.1 Hz, 1H), 7.97 (dd, J=2.4, 7.9 Hz, 2H), 7.54 (s, 1H), 7.44 (d, J=8.1 Hz, 1H), 7.27 (d, J=4.9 Hz, 1H), 7.19 (s, 1H), 3.10 (t, J=7.1 Hz, 2H), 2.94 (t, J=7.1 Hz, 2H), 2.35 (s, 3H).

Example 13.2

3-[5-(3-Methyl-5-{[4-(trifluoromethyl)pyrimidin-2-yl]amino}phenyl)pyridin-2-yl]propanoic acid Sodium hydroxide (4 M, 261 µL, 1.04 mmol) and methanol (348 µL) were added to 3-[5-(3-methyl-5-{[4-(trifluoromethyl)pyrimidin-2-yl]amino}phenyl)pyridin-2-yl]propanenitrile (40 mg, 0.104 mmol) and the reaction mixture was heated to 80° C. overnight. The reaction mixture was cooled to room temperature and was neutralized with aqueous 6 M HCl. The precipitate was collected by filtration, diluted with 1.5 mL DMSO:methanol (1:1) and was purified by reverse phase chromatography (10-80% MeCN in water+0.05% TFA) to yield 3-[5-(3-methyl-5-{[4-(trifluoromethyl)pyrimidin-2-yl]amino}phenyl)pyridin-2-yl]propanoic acid as the TFA salt. MS APCI calc'd for C$_{20}$H$_{18}$F$_3$N$_4$O$_2$ [M+H]$^+$ 403. found 403. $^1$H NMR (500 MHz, DMSO-d6). $^1$H NMR (500 MHz, DMSO) δ 10.29 (s, 1H), 8.82 (s, 2H), 8.15 (s, 1H), 7.96 (s, 1H), 7.57 (s, 2H), 7.25 (d, J=29.5 Hz, 2H), 3.65-3.26 (m, 1H), 3.07 (s, 2H), 2.74 (s, 2H), 2.36 (s, 3H).

Example 13.3

3-[5-(3-Methyl-5-{[4-(trifluoromethyl)pyrimidin-2-yl]amino}phenyl)pyridin-2-yl]propanamide

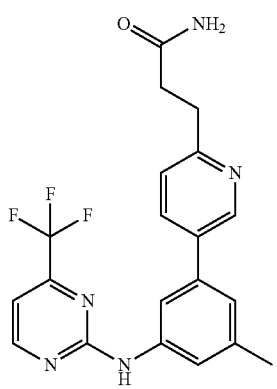

13.3

3-[5-(3-Methyl-5-{[4-(trifluoromethyl)pyrimidin-2-yl]amino}phenyl)pyridin-2-yl]propanenitrile (40 mg, 0.104 mmol) was added to a solution of sodium hydroxide (4 M, 54.8 µL, 0.219 mmol) and hydrogen peroxide (30%, 16.0 µL, 0.157 mmol) in DMSO (209 µL). The reaction mixture was stirred at room temperature for 8 hours. The reaction mixture was diluted with 1:1 DMSO:methanol solution (2 mL), filtered, and purified by reverse phase chromatography (20-95% MeCN in water with 0.5% TFA) to yield 3-[5-(3-methyl-5-{[4-(trifluoromethyl)pyrimidin-2-yl]amino}phenyl)pyridin-2-yl]propanamide as the TFA salt. MS APCI calc'd for $C_{20}H_{19}F_3N_5O$ [M+H]$^+$ 402. found 402. $^1$H NMR (500 MHz, DMSO-d6) δ 10.29 (s, 1H), 8.83 (d, J=4.8 Hz, 2H), 8.21-8.09 (m, 1H), 7.97 (s, 1H), 7.57 (s, 2H), 7.42-7.35 (m, 1H), 7.28 (d, J=4.9 Hz, 1H), 7.22 (s, 1H), 6.88-6.79 (m, 1H), 3.05 (t, 2H), 2.57 (t, 2H), 2.36 (s, 3H).

Example 13.4

N-(3-Methyl-5-{6-[2-(1H-tetrazol-5-yl)ethyl]pyridin-3-yl}phenyl)-4-(trifluoromethyl)pyrimidin-2-amine

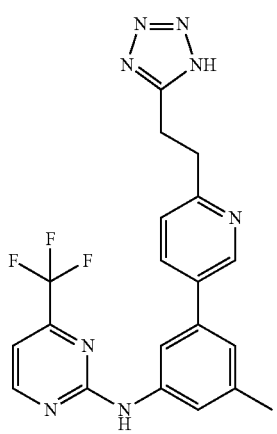

13.4

Sodium azide (13.7 mg, 0.210 mmol) and ammonium chloride (11.3 mg, 0.210 mmol) were added to a solution of 3-[5-(3-methyl-5-{[4-(trifluoromethyl)pyrimidin-2-yl]amino}phenyl)pyridin-2-yl]propanenitrile (62.0 mg, 0.162 mmol) in DMF (539 µL). The reaction mixture was heated to 80° C. overnight. Two additional equivalents of sodium azide and ammonium chloride were added to the reaction mixture and heated at 100° C. for 10 hours. The reaction mixture was cooled to room temperature, diluted with 1:1 DMSO:methanol solution (2.00 mL), filtered and directly purified by reverse phase chromatography (10-90% MeCN in water with 0.5% TFA) to yield N-(3-methyl-5-{6-[2-(1H-tetrazol-5-yl)ethyl]pyridin-3-yl}phenyl)-4-(trifluoromethyl)pyrimidin-2-amine as a TFA salt. MS APCI calc'd for $C_{20}H_{18}F_3N_8$ [M+H]$^+$ 427. found 427. $^1$H NMR (500 MHz, DMSO-d6). δ 10.27 (s, 1H), 8.82 (d, J=4.7, 1H), 8.78 (s, 1H), 8.02 (s, 1H), 7.95 (s, 1H), 7.55 (s, 1H), 7.47 (d, J=8.1, 1H), 7.27 (d, J=4.9 Hz, 1H), 7.19 (s, 1H), 3.37 (d, J=20.5 Hz, 2H), 3.28 (t, J=7.2 Hz, 2H), 2.35 (s, 3H).

Example 13.5

3-{2-[5-(3-Methyl-5-{[4-(trifluoromethyl)pyrimidin-2-yl]amino}phenyl)pyridin-2-yl]ethyl}-1,2,4-oxadiazol-5(4H)-one

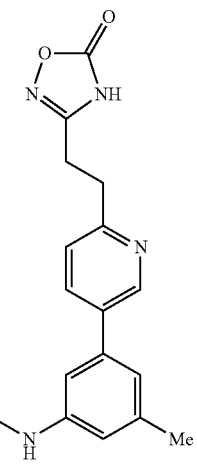

13.5

Hydroxylamine hydrochloride (147 mg, 2.11 mmol) and potassium carbonate (292 mg, 2.11 mmol) were added to 3-[5-(3-methyl-5-{[4-(trifluoromethyl)pyrimidin-2-yl]amino}phenyl)pyridin-2-yl]propanenitrile (135 mg, 0.352 mmol) in ethanol (587 µL). The reaction mixture was heated to 80° C. overnight. The reaction mixture was cooled to room temperature and concentrated under reduced pressure. The resultant reside was diluted with dichloromethane (2.00 mL), filtered through a short silica get pad and was concentrated under reduced pressure to yield crude N'-hydroxy-3-[5-(3-methyl-5-{[4-(trifluoromethyl)pyrimidin-2-yl]amino}phenyl)pyridin-2-yl]propanimidamide. The crude oxime was diluted with dioxane (1.00 mL) and CDI (57.1 mg, 0.352 mmol), then DBU (106 µL, 0.704 mmol) were added. The reaction mixture was stirred at room temperature for 2 hours, concentrated under reduced pressure, diluted with 1:1 DMSO:methanol (2.00 mL) and filtered. The residue was direct purification by reverse phase chromatography (10-80% MeCN in water+0.5% TFA, linear gradient) to yield 3-{2-[5-

(3-methyl-5-{[4-(trifluoromethyl)pyrimidin-2-yl]amino}phenyl)pyridin-2-yl]ethyl}-1,2,4-oxadiazol-5(4H)-one as the TFA salt. MS APCI calc'd for $C_{21}H_{18}F_3N_6O_2$ [M+H]$^+$ 443. found 443. $^1$H NMR (500 MHz, DMSO-d6) δ 10.28 (s, 1H), 8.87-8.71 (m, J=18.2 Hz, 2H), 8.11-8.00 (m, 1H), 7.96 (s, 1H), 7.56 (s, 1H), 7.53-7.44 (m, 1H), 7.28 (d, 1H), 7.21 (s, 1H), 3.16 (t, 2H), 2.99 (t, 2H), 2.36 (s, 3H).

Example 14

Compounds of Formula (I) Using the General Methods Illustrated in Scheme 14

Example 14.1

1-{[5-(3-Methyl-5-{[4-(trifluoromethyl)pyrimidin-2-yl]amino}phenyl)pyridin-2-yl]methyl}pyrrolidin-2-one

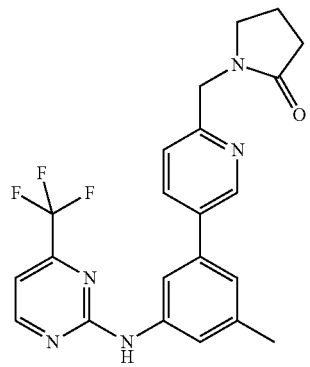

14.1

Step 1:
Dichloromethane (3.24 mL) and triphenylphosphine (0.459 g, 1.75 mmol) was added to [5-(3-methyl-5-{[4-(trifluoromethyl)pyrimidin-2-yl]amino}phenyl)pyridin-2-yl]methanol (0.35 g, 0.971 mmol). Carbon tetrabromide (0.451 g, 1.36 mmol) was added slowly to the reaction mixture and stirred for 8 hours at room temperature. The reaction mixture was diluted with 10% sodium thiosulfate (5.00 mL) and the organic layer was separated, dried over sodium sulfate, and concentrated under reduced pressure. The residue was purified by silica gel chromatography (ethyl acetate/hexanes) to yield N-{3-[6-(bromomethyl)pyridin-3-yl]-5-methylphenyl}-4-(trifluoromethyl)pyrimidin-2-amine. MS APCI calc'd for $C_{18}H_{15}BrF_3N_4$ [M+H]$^+$ 423 and 425. found 423 and 425.
Step 2:
n-BuLi (1.6 M, 303 μL, 0.484 mmol) was added to diisopropylamine (67.3 μL, 0.473 mmol) in THF (394 μL) at −78° C. The reaction was warmed to −40° C. and was stirred for 1 hour. The reaction mixture was cooled back to −78° C. and a solution of pyrrolidin-2-one (15.1 mg, 0.177 mmol) in THF (100 μL) was added dropwise. The reaction mixture was warmed to −40° C. and stirred for 1 hour. The reaction mixture was cooled back to −78° C. and a solution of N-{3-[6-(bromomethyl)pyridin-3-yl]-5-methylphenyl}-4-(trifluoromethyl)pyrimidin-2-amine (50.0 mg, 0.118 mmol) in THF (300 μL) was added. The reaction mixture was slowly warmed to room temperature and quenched with saturated aqueous ammonium chloride (1.00 mL) and THF was removed under reduced pressure. The reaction mixture was extracted with dichloromethane and the organic was dried over sodium sulfate and concentration under reduced pressure. The residue was purified by reverse phase prep HPLC (10-80% MeCN in water with 0.5% TFA) to yield 1-{[5-(3-methyl-5-{[4-(trifluoromethyl)pyrimidin-2-yl]amino}phenyl)pyridin-2-yl]methyl}pyrrolidin-2-on. MS APCI calc'd for $C_{22}H_{21}F_3N_5O$ [M+H]$^+$ 428. found 428. $^1$H NMR (500 MHz, DMSO-d6) δ 10.28 (s, 1H), 8.82 (d, J=4.9 Hz, 1H), 8.78 (d, J=2.0, 1H), 8.04 (dd, J=2.3 Hz, 8.1 Hz, 1H), 7.95 (s, 1H), 7.56 (s, 1H), 7.38 (d, J=8.1, 1H), 7.27 (d, J=4.9 Hz, 1H), 7.20 (s, 1H), 4.52 (s, 3H), 4.38 (br s, 2H), 3.37 (t, J=7.0 Hz, 2H), 2.31 (t, J=8.1 Hz, 2H), 1.96 (q, J=7.6 Hz, 15.1 Hz, 2H).

Example 15

Compounds of Formula (I) Using the General Methods Illustrated in Scheme 15

Example 15.1

N-(3-{5-[(2-Methoxyethyl)amino]pyridin-3-yl}-5-methylphenyl)-4-(trifluoromethyl)pyrimidin-2-amine

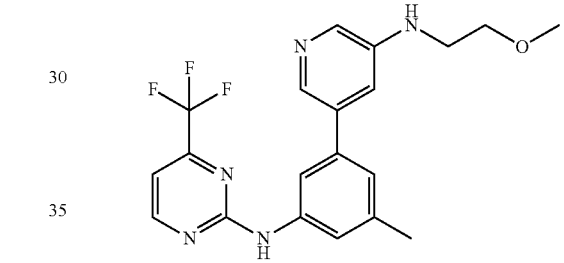

15.1

Step 1:
A mixture of N-[3-methyl-5-(4,4,5,5-tetramethyl-1,3,2-dioxaborolan-2-yl)phenyl]-4-(trifluoromethyl)pyrimidin-2-amine (2.00 g, 5.27 mmol), 3,5-dibromopyridine (4.37 g, 18.5 mmol) and Pd(dppf)Cl$_2$—CH$_2$Cl$_2$ (0.215 g, 0.264 mmol) in 1,4-dioxane (26.4 mL, 0.2 M), and Na$_2$CO$_3$ (5.27 mL, 2.00 M) was purged with argon and heated to 80° C. for 4 hours. The reaction mixture was filtered through a CELITE plug and washed with dichloromethane. The eluent was diluted with water and extracted with dichloromethane (3×). The combined organic layers were concentrated in vacuo and the residue was purified by silica gel chromatography (ethyl acetate/hexanes) to afford N-[3-(5-bromopyridin-3-yl)-5-methylphenyl]-4-(trifluoromethyl)pyrimidin-2-amine. MS APCI calc'd for $C_{17}H_{13}BrF_3N_4$ [M+H]$^+$ 409 and 411. found 409 and 411.
Step 2:
A mixture of N-[3-(5-bromopyridin-3-yl)-5-methylphenyl]-4-(trifluoromethyl)pyrimidin-2-amine (35.0 mg, 0.128 mmol), 2-methoxyethanamine (9.61 mg, 0.128 mmol), Pd$_2$(dba)$_3$ (7.83 mg, 0.0086 mmol), Xantphos (14.9 mg, 0.026 mmol), and Cs$_2$CO$_3$ (69.7 mg, 0.214 mmol) in 1,4-dioxane (0.855 mL, 0.1 M) was purged with argon and heated to 90° C. for 12 hours. The reaction mixture was cooled to room temperature and DMSO (1.00 mL) and Si-Thiol (23.4 mg, 1.84 mmol/g) were added to the reaction mixture. The reaction mixture was stir at room temperature for 4 hours and then passed through a filter, concentrated in vacuo, and the crude residue was purified by reverse phase preparative HPLC (0:100 to 95:5 acetonitrile:water: 0.1% v/v formic acid modifier) to afford N-(3-{5-[(2-methoxyethyl)amino]pyridin-3-yl}-5-methylphenyl)-4-(trifluoromethyl)pyrimidin-2-amine as the formic acid salt. MS APCI calc'd for $C_{20}H_{21}F_3N_4O$ [M+H]$^+$ 404. found 404. $^1$H NMR (600 MHz, DMSO-d6) δ 10.20 (s, 1H), 8.80 (d, J=4.9 Hz, 1H), 7.97 (d, J=5.6 Hz, 2H), 7.87 (s, 1H), 7.50 (s, 1H), 7.24 (d, J=4.9 Hz, 1H), 7.09 (d, J=6.1 Hz, 2H), 3.49 (t, J=5.5 Hz, 2H), 3.33-3.22 (m, 5H), 2.32 (s, 3H).

The following examples in Table 15A were prepared in an analogous manner to that described in to Example 15.1 and in general Scheme 15 using known or commercially available amines in step 2.

TABLE 15A

| Ex. | R$^{cy}$ | Name | [M + H]$^+$ Calc'd | [M + H]$^+$ Obsv'd | Form(s) |
|-----|----------|------|--------------------|--------------------|---------|
| 15.2 | | 4-[5-(3-methyl-5-{[4-(trifluoromethyl)pyrimidin-2-yl]amino}phenyl)pyridin-3-yl]piperazin-2-one | 429 | 429 | Formate Salt |
| 15.3 | | 1-[5-(3-methyl-5-{[4-(trifluoromethyl)pyrimidin-2-yl]amino}phenyl)pyridin-3-yl]-1,4-diazepan-5-one | 443 | 443 | Formate Salt |
| 15.4 | | 1-[5-(3-methyl-5-{[4-(trifluoromethyl)pyrimidin-2-yl]amino}phenyl)pyridin-3-yl]azetidin-3-ol | 402 | 402 | Formate Salt |
| 15.5 | racemic | 1-[5-(3-methyl-5-{[4-(trifluoromethyl)pyrimidin-2-yl]amino}phenyl)pyridin-3-yl]pyrrolidin-3-ol | 416 | 416 | Formate Salt |
| 15.6 | | 1-methyl-4-[5-(3-methyl-5-{[4-(trifluoromethyl)pyrimidin-2-yl]amino}phenyl)pyridin-3-yl]piperazin-2-one | 443 | 443 | Formate Salt |

TABLE 15A-continued

| Ex. | R$^{cy}$ | Name | [M + H]$^+$ Calc'd | [M + H]$^+$ Obsv'd | Form(s) |
|---|---|---|---|---|---|
| 15.7 | | 3,3-dimethyl-4-[5-(3-methyl-5-{[4-(trifluoromethyl)pyrimidin-2-yl]amino}phenyl)pyridin-3-yl]piperazin-2-one | 457 | 457 | Formate Salt |
| 15.8 | | 1-[5-(3-methyl-5-{[4-(trifluoromethyl)pyrimidin-2-yl]amino}phenyl)pyridin-3-yl]-1,7-diazaspiro[4.4]nonan-6-one | 469 | 469 | Formate Salt |
| 15.9 | | 1-[5-(3-methyl-5-{[4-(trifluoromethyl)pyrimidin-2-yl]amino}phenyl)pyridin-3-yl]-1,7-diazaspiro[4.5]decan-6-one | 483 | 483 | Formate Salt |
| 15.10 | | 1-[5-(3-methyl-5-{[4-(trifluoromethyl)pyrimidin-2-yl]amino}phenyl)pyridin-3-yl]piperidine-4-carboxamide | 457 | 457 | Formate Salt |
| 15.11 | | N-(3-{5-[(cyclopropylmethyl)amino]pyridin-3-yl}-5-methylphenyl)-4-(trifluoromethyl)pyrimidin-2-amine | 400 | 400.1 | Formate Salt |
| 15.12 | | N-{3-[5-(isoxazol-3-yl amino)pyridin-3-yl]-5-methylphenyl}-4-(trifluoromethyl)pyrimidin-2-amine | 413 | 413 | Formate Salt |
| 15.13 | | N-{3-methyl-5-[5-(pyridin-4-ylamino)pyridin-3-yl]phenyl}-4-(trifluoromethyl)pyrimidin-2-amine | 423 | 423 | Formate Salt |

TABLE 15A-continued

| Ex. | R^cy | Name | [M + H]+ Calc'd | [M + H]+ Obsv'd | Form(s) |
|---|---|---|---|---|---|
| 15.14 | (pyridin-4-ylmethyl)amino | N-(3-methyl-5-{5-[(pyridin-4-ylmethyl)amino]pyridin-3-yl}phenyl)-4-(trifluoromethyl)pyrimidin-2-amine | 437 | 437 | Formate Salt |
| 15.15 | 4-methylpiperazin-1-yl | N-{3-methyl-5-[5-(4-methylpiperazin-1-yl)pyridin-3-yl]phenyl}-4-(trifluoromethyl)pyrimidin-2-amine | 429 | 429 | Formate Salt |
| 15.16 | (2-morpholin-4-ylethyl)amino | N-(3-methyl-5-{5-[(2-morpholin-4-ylethyl)amino]pyridin-3-yl}phenyl)-4-(trifluoromethyl)pyrimidin-2-amine | 459 | 459 | Formate Salt |
| 15.17 | 1,4-dioxa-8-azaspiro[4.5]dec-8-yl | N-{3-[5-(1,4-dioxa-8-azaspiro[4.5]dec-8-yl)pyridin-3-yl]-5-methylphenyl}-4-(trifluoromethyl)pyrimidin-2-amine | 472 | 472 | Formate Salt |
| 15.18 | morpholin-4-yl | N-[3-methyl-5-(5-morpholin-4-ylpyridin-3-yl)phenyl]-4-(trifluoromethyl)pyrimidin-2-amine | 416 | 416 | Formate Salt |
| 15.19 | 2-oxo-1,4-diazepan-4-yl | 4-[5-(3-methyl-5-{[4-(trifluoromethyl)pyrimidin-2-yl]amino}phenyl)pyridin-3-yl]-1,4-diazepan-2-one | 443 | | TFA Salt, Formate Salt |

Example 15.20

N-[5-(3-methyl-5-{[4-(trifluoromethyl)pyrimidin-2-yl]amino}phenyl)pyridin-3-yl]glycine

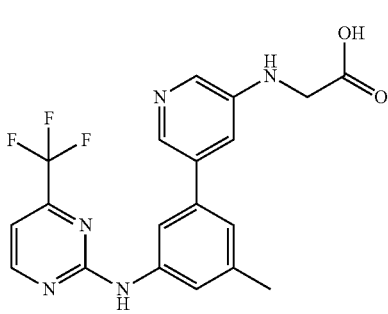

15.20 was stirred for 1 hour at room temperature. Si-cyanoborohydride (123 mg, 0.116 mmol, 0.94 g/mmol) was added to the reaction mixture and stir for 12 hours at room temperature. The reaction mixture was filtered, concentrated in vacuo and the residue was purified by reverse phase liquid chromatography (5:95 to 95:5, acetonitrile:water+0.1% v/v formic acid) afforded N-[5-(3-methyl-5-{[4-(trifluoromethyl)pyrimidin-2-yl]amino}phenyl)pyridin-3-yl]glycine as the formic acid salt. MS APCI calc'd for $C_{19}H_{17}F_3N_5O_2$ [M+H]$^+$ 404. found 404. $^1$H NMR (600 MHz, DMSO-d6) δ 10.24 (s, 1H), 8.82 (d, J=4.9 Hz, 1H), 8.02 (d, J=1.8 Hz, 1H), 7.96 (d, J=2.6 Hz, 1H), 7.89 (s, 1H), 7.53 (s, 1H), 7.26 (d, J=4.9 Hz, 1H), 7.11 (s, 1H), 7.05 (s, 2H), 3.91 (s, 2H), 2.34 (s, 3H).

The following example in Table 15B was prepared in an analogous manner to Example 15.20 to that described in general Scheme 15 using known or commercially available aldehydes in step 2.

TABLE 15B

| Ex. | R$^{cy}$ | Name | [M + H]$^+$ Calc'd | [M + H]$^+$ Obsv'd | Form(s) |
|---|---|---|---|---|---|
| 15.21 | | 3-({[5-(3-methyl-5-{[4-(trifluoromethyl)pyrimidin-2-yl]amino}phenyl)pyridin-3-yl]amino}methyl)pyridin-2(1H)-one | 453 | 453 | Formate Salt |

Step 1:

A mixture of N-[3-methyl-5-(4,4,5,5-tetramethyl-1,3,2-dioxaborolan-2-yl)phenyl]-4-(trifluoromethyl)pyrimidin-2-amine (4.00 g, 10.6 mmol), 5-bromopyridin-3-amine (2.01 g, 11.6 mmol), Pd(dppf)Cl$_2$—CH$_2$Cl$_2$ (0.431 g, 0.527 mmol) in 1,4-dioxane (52.7 mL, 0.2 M) and Na$_2$CO$_3$ (10.6 mL, 2 M) was purged with argon and heated to 80° C. for 4 hours. The reaction mixture was filtered through a CELITE plug and washed with dichloromethane. The eluent was diluted with water and extracted with dichloromethane (3×). The combined organic layers were concentrated in vacuo and purified by silica gel column chromatography (methanol/ethyl acetate) to afford N-[3-(5-aminopyridin-3-yl)-5-methylphenyl]-4-(trifluoromethyl)pyrimidin-2-amine. MS APCI calc'd for $C_{17}H_{15}F_3N_5$ [M+H]$^+$ 346. found 346.

Step 2:

A mixture of N-[3-(5-aminopyridin-3-yl)-5-methylphenyl]-4-(trifluoromethyl)pyrimidin-2-amine (20.0 mg, 0.058 mmol), oxoacetic acid (4.29 mg, 0.058 mmol) in DMF (0.579 mL, 0.1 M), and trifluoroacetic acid (8.92 μL, 0.116 mmol).

Example 15.22

2-{[5-(3-Methyl-5-{[4-(trifluoromethyl)pyrimidin-2-yl]amino}phenyl)pyridin-3-yl]amino}ethanol

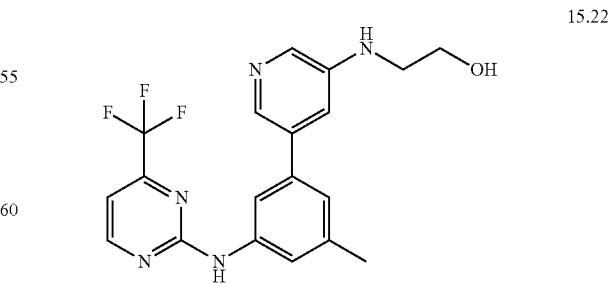

15.22

Step 1:

A mixture of N-[3-methyl-5-(4,4,5,5-tetramethyl-1,3,2-dioxaborolan-2-yl)phenyl]-4-(trifluoromethyl)pyrimidin-2- amine (1.00 g, 2.64 mmol), Na$_2$CO$_3$ (2.64 mL, 5.27 mmol, 2.0 M), and 3-bromo-5-fluoropyridine (0.511 g, 2.90 mmol) in 2-methyl tetrahydrofuran (13.0 mL) was purged with argon (3×), then Pd(dppf)Cl$_2$—CH$_2$Cl$_2$ (0.108 g, 0.132 mmol) was added. The reaction was purged with argon (3×) and heated to 80° C. The reaction was monitored by LC/MS and upon completion was cooled to ambient temperature. The reaction mixture was filtered through a CELITE plug and washed with dichloromethane. The eluent was diluted with water and the organic layer was extracted, dried over sodium sulfate, and concentrated in vacuo. The residue was purified by silica gel chromatography (acetone/hexanes) to afford N-[3-(5-fluoropyridin-3-yl)-5-methylphenyl]-4-(trifluoromethyl)pyrimidin-2-amine. MS APCI calc'd for C$_{17}$H$_{13}$F$_4$N$_4$ [M+H]$^+$ 349. found 349.

Step 2:

Ethanolamine (26.3 mg, 0.431 mmol) was added to a mixture of N-[3-(5-fluoropyridin-3-yl)-5-methylphenyl]-4-(trifluoromethyl)pyrimidin-2-amine (50.0 mg, 0.144 mmol) and sodium hydride (17.2 mg, 0.431 mmol) in THF (0.718 mL, 0.2 M). The reaction mixture was heated overnight at 80° C. The reaction mixture was quenched with saturated aqueous NH$_4$Cl and extracted with chloroform. The organic layer was concentrated in vacuo and purified by reverse phase liquid chromatography (10:90 to 60:40, acetonitrile:water) afforded 2-{[5-(3-methyl-5-{[4-(trifluoromethyl)pyrimidin-2-yl]amino}phenyl)pyridin-3-yl]amino}ethanol as the formic acid salt. MS APCI calc'd for C$_{19}$H$_{19}$F$_3$N$_5$O [M+H]$^+$ 390. found 390. $^1$H NMR (500 MHz, DMSO-d6) δ 10.28 (s, 1H), 8.83 (d, J=4.9 Hz, 1H), 8.48 (s, 1H), 8.34 (d, J=2.6 Hz, 1H), 7.99 (d, J=11.4 Hz, 3H), 7.59 (d, J=26.7 Hz, 2H), 7.34-7.12 (m, 2H), 4.33 (t, J=4.9 Hz, 2H), 3.77 (br s, 3H), 3.27 (t, J=5.3 Hz, 2H).

Example 15.23

1-{4-[4-(3-Methyl-5-{[4-(trifluoromethyl)pyrimidin-2-yl]amino}phenyl)pyridin-2-yl]piperazin-1-yl}ethanone

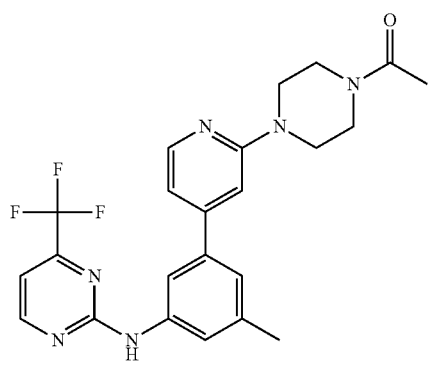

Step 1:

A mixture of N-[3-methyl-5-(4,4,5,5-tetramethyl-1,3,2-dioxaborolan-2-yl)phenyl]-4-(trifluoromethyl)pyrimidin-2-amine (8.00 g, 21.1 mmol), PdCl$_2$(dppf)-dichloromethane adduct (0.861 g, 1.06 mmol), 2-methyl-THF (70.0 mL), 2 M sodium carbonate (21.1 mL, 42.2 mmol), and 4-bromo-2-fluoro pyridine (2.40 mL, 23.2 mmol) was heated to 86° C. for 6 hours under an argon atmosphere. The reaction mixture was directly subjected to an extraction where the aqueous and organic layers were separated. The aqueous layer was extracted with ethyl acetate (50 mL). The combined organic layers were washed sequentially with saturated sodium bicarbonate (40 mL) and saturated aqueous sodium chloride (40 mL). The organic layer was dried over sodium sulfate, filtered and concentrated under reduced pressure. The crude residue was triturated with a mixture of ethyl acetate (15 mL), dichloromethane (5 mL), and methanol (2 mL) to afford N-[3-(2-fluoropyridin-4-yl)-5-methylphenyl]-4-(trifluoromethyl)pyrimidin-2-amine as an off-white solid. MS APCI calc'd for C$_{17}$H$_{13}$F$_4$N$_4$ [M+H]$^+$ 349. found 349. $^1$H NMR (500 MHz, DMSO-d6) δ 10.31 (s, 1H), 8.84 (d, J=4.9 Hz, 1H), 8.30 (d, J=5.3 Hz, 1H), 8.09 (s, 1H), 7.61 (d, J=6.2 Hz, 2H), 7.39 (s, 1H), 7.34 (s, 1H), 7.29 (d, J=4.9 Hz, 1H), 2.36 (s, 3H).

Step 2:

A mixture of N-[3-(2-fluoropyridin-4-yl)-5-methylphenyl]-4-(trifluoromethyl)pyrimidin-2-amine (50.0 mg, 0.144 mmol), 1-(piperazin-1-yl)ethanone (36.8 mg, 0.287 mmol), and tribasic potassium phosphate (60.9 mg, 0.287 mmol) in DMSO (250 µL) was heated at 130° C. for 48 hours. The reaction mixture was diluted with DMSO (600 µL) and filtered through a plug of CELITE. The residue was purified by mass triggered reverse phase HPLC (21-55% acetonitrile in water+0.1% formic acid) to afford 1-{4-[4-(3-methyl-5-{[4-(trifluoromethyl)pyrimidin-2-yl]amino}phenyl)pyridin-2-yl]piperazin-1-yl}ethanone as a tan solid. MS APCI calc'd for C$_{23}$H$_{24}$F$_3$N$_6$O [M+H]$^+$ 457. found 457. $^1$H NMR (600 MHz, DMSO-d6) δ10.20 (s, 1H), 8.80 (d, J=4.8 Hz, 1H), 8.15 (d, J=5.2 Hz, 1H), 7.99 (s, 1H), 7.53 (s, 1H), 7.24 (d, J=4.9 Hz, 1H), 7.22 (s, 1H), 6.98 (s, 1H), 6.88 (d, J=5.3 Hz, 1H), 3.62-3.56 (m, 2H), 3.52 (d, J=7.5 Hz, 6H), 2.34 (s, 3H), 2.02 (s, 3H).

The following examples in Table 15C were prepared in an analogous manner to that described in Example 15.23 and general scheme 15.

TABLE 15C

| Ex. | R^cy | Name | [M + H]+ Calc'd | [M + H]+ Obsv'd | Form(s) |
|---|---|---|---|---|---|
| 15.24 | (formyl piperazine) | 4-[4-(3-methyl-5-{[4-(trifluoromethyl)pyrimidin-2-yl]amino}phenyl)pyridin-2-yl]piperazine-1-carbaldehyde | 443 | 443 | Formate Salt |
| 15.25 | (1,9-diazaspiro[5.5]undecan-2-one) | 9-[4-(3-methyl-5-{[4-(trifluoromethyl)pyrimidin-2-yl]amino}phenyl)pyridin-2-yl]-1,9-diazaspiro[5.5]undecan-2-one | 497 | 497 | Formate Salt |
| 15.26 | (1-oxa-8-azaspiro[5.5]undecane) racemic | N-{3-methyl-5-[2-(1-oxa-8-azaspiro[5.5]undec-8-yl)pyridin-4-yl]phenyl}-4-(trifluoromethyl)pyrimidin-2-amine | 484 | 484 | Formate Salt |
| 15.27 | (2,8-diazaspiro[5.5]undecan-1-one) racemic | 8-[4-(3-methyl-5-{[4-(trifluoromethyl)pyrimidin-2-yl]amino}phenyl)pyridin-2-yl]-2,8-diazaspiro[5.5]undecan-1-one | 497 | 497 | Formate Salt |
| 15.28 | (1-oxa-7-azaspiro[4.5]decane) racemic | N-{3-methyl-5-[2-(1-oxa-7-azaspiro[4.5]dec-7-yl)pyridin-4-yl]phenyl}-4-(trifluoromethyl)pyrimidin-2-amine | 470 | 470 | Formate Salt |

TABLE 15C-continued

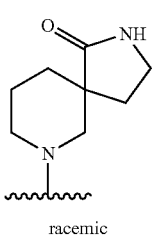 [SMILES: *N1CCCC2(CCNC2=O)C1]

| Ex. | R^cy | Name | [M + H]+ Calc'd | [M + H]+ Obsv'd | Form(s) |
|---|---|---|---|---|---|
| 15.29 | 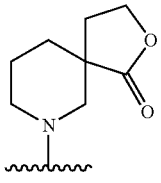<br>racemic | 7-[4-(3-methyl-5-{[4-(trifluoromethyl)pyrimidin-2-yl]amino}phenyl)pyridin-2-yl]-2,7-diazaspiro[4.5]decan-1-one | 483 | 483 | Formate Salt |
| 15.30 | 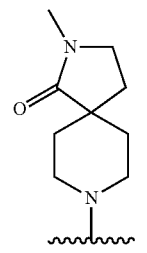 [SMILES: *N1CCC2(CC1)CCN(C)C2=O]<br>racemic | 7-[4-(3-methyl-5-{[4-(trifluoromethyl)pyrimidin-2-yl]amino}phenyl)pyridin-2-yl]-2-oxa-7-azaspiro[4.5]decan-1-one | 484 | 484 | Formate Salt |
| 15.31 | 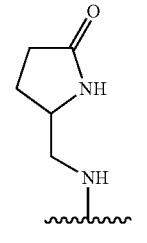 [SMILES: *NCC1CCC(=O)N1] | 2-methyl-8-[4-(3-methyl-5-{[4-(trifluoromethyl)pyrimidin-2-yl]amino}phenyl)pyridin-2-yl]-2,8-diazaspiro[4.5]decan-1-one | 497 | 497 | Formate Salt |
| 15.32 | 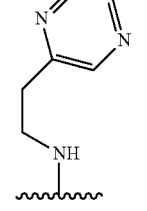 | 5-({[4-(3-methyl-5-{[4-(trifluoromethyl)pyrimidin-2-yl]amino}phenyl)pyridin-2-yl]amino}methyl)pyrrolidin-2-one | 443 | 443 | Formate Salt |
| 15.33 |  | N-(3-methyl-5-{2-[(2-pyrazin-2-ylethyl)amino]pyridin-4-yl}phenyl)-4-(trifluoromethyl)pyrimidin-2-amine | 452 | 452 | Formate Salt |

TABLE 15C-continued

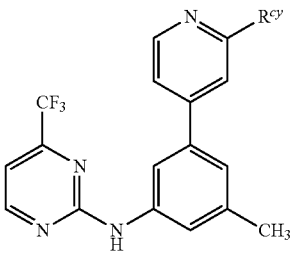

| Ex. | R<sup>cy</sup> | Name | [M + H]+ Calc'd | [M + H]+ Obsv'd | Form(s) |
|---|---|---|---|---|---|
| 15.34 | 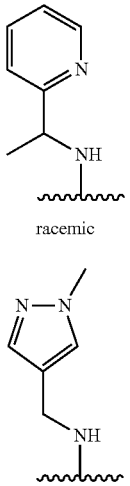<br>racemic | N-(3-methyl-5-{2-[(1-pyridin-2-ylethyl)amino]pyridin-4-yl}phenyl)-4-(trifluoromethyl)pyrimidin-2-amine | 451 | 451 | Formate Salt |
| 15.35 | 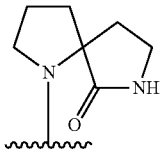 [SMILES: *N1CCCC12CCNC2=O] | N-[3-methyl-5-(2-{[(1-methyl-1H-pyrazol-4-yl)methyl]amino}pyridin-4-yl)phenyl]-4-(trifluoromethyl)pyrimidin-2-amine | 440 | 440 | Formate Salt |
| 15.36 | 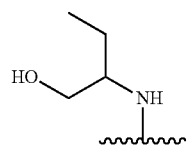 [SMILES: *NC(CC)CO] | 1-[4-(3-methyl-5-{[4-(trifluoromethyl)pyrimidin-2-yl]amino}phenyl)pyridin-2-yl]-1,7-diazaspiro[4.4]nonan-6-one | 469 | 469 | Formate Salt |
| 15.37 | 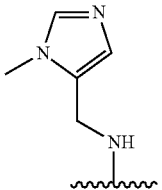 [SMILES: *NCc1cncn1C] | 2-{[4-(3-methyl-5-{[4-(trifluoromethyl)pyrimidin-2-yl]amino}phenyl)pyridin-2-yl]amino}butan-1-ol | 418 | 418 | Formate Salt |
| 15.38 | 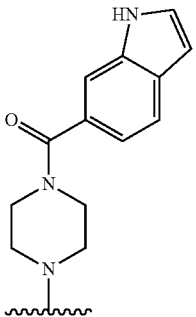 [SMILES: *N1CCN(C(=O)c2ccc3cc[nH]c3c2)CC1] | N-[3-methyl-5-(2-{[(1-methyl-1H-imidazol-5-yl)methyl]amino}pyridin-4-yl)phenyl]-4-(trifluoromethyl)pyrimidin-2-amine | 440 | 440 | Formate Salt |
| 15.39 |  | N-(3-{2-[4-(1H-indol-6-ylcarbonyl)piperazin-1-yl]pyridin-4-yl}-5-methylphenyl)-4-(trifluoromethyl)pyrimidin-2-amine | 558 | 558 | Formate Salt |

TABLE 15C-continued

| Ex. | R<sup>cy</sup> | Name | [M + H]⁺ Calc'd | [M + H]⁺ Obsv'd | Form(s) |
|---|---|---|---|---|---|
| 15.40 | (1-methyl-1H-imidazol-4-yl)methylamino group | N-[3-methyl-5-(2-{[(1-methyl-1H-imidazol-4-yl)methyl]amino}pyridin-4-yl)phenyl]-4-(trifluoromethyl)pyrimidin-2-amine | 440 | 440 | Formate Salt |
| 15.41 | H₂N-CH₂CH₂-NH- | N-[4-(3-methyl-5-{[4-(trifluoromethyl)pyrimidin-2-yl]amino}phenyl)pyridin-2-yl]ethane-1,2-diamine | 389 | 389 | Formate Salt |
| 15.42 | 1,4-diazepan-5-one | 1-[4-(3-methyl-5-{[4-(trifluoromethyl)pyrimidin-2-yl]amino}phenyl)pyridin-2-yl]-1,4-diazepan-5-one | 443 | 443 | Formate Salt |
| 15.43 | 2-methylalanine | 2-methyl-N-[4-(3-methyl-5-{[4-(trifluoromethyl)pyrimidin-2-yl]amino}phenyl)pyridin-2-yl]alanine | 432 | 432 | Formate Salt |
| 15.44 | piperazin-2-one | 4-[4-(3-methyl-5-{[4-(trifluoromethyl)pyrimidin-2-yl]amino}phenyl)pyridin-2-yl]piperazin-2-one | 429 | 429 | Formate Salt |
| 15.45 | HO-CH₂CH₂-N(CH₃)- | 2-{methyl[4-(3-methyl-5-{[4-(trifluoromethyl)pyrimidin-2-yl]amino}phenyl)pyridin-2-yl]amino}ethanol | 404 | 404 | Formate Salt |
| 15.46 | piperidine-4-carboxamide | 1-[4-(3-methyl-5-{[4-(trifluoromethyl)pyrimidin-2-yl]amino}phenyl)pyridin-2-yl]piperidine-4-carboxamide | 457 | 457 | Formate Salt |

TABLE 15C-continued

| Ex. | R$^{cy}$ | Name | [M + H]$^+$ Calc'd | [M + H]$^+$ Obsv'd | Form(s) |
|---|---|---|---|---|---|
| 15.47 | | 1-methyl-4-[4-(3-methyl-5-{[4-(trifluoromethyl)pyrimidin-2-yl]amino}phenyl)pyridin-2-yl]piperazin-2-one | 443 | 443 | Formate Salt |
| 15.48 | | (2S)-2-{[4-(3-methyl-5-{[4-(trifluoromethyl)pyrimidin-2-yl]amino}phenyl)pyridin-2-yl]amino}propan-1-ol | 404 | 404 | Formate Salt |
| 15.49 | | 2-methyl-2-{[4-(3-methyl-5-{[4-(trifluoromethyl)pyrimidin-2-yl]amino}phenyl)pyridin-2-yl]amino}propane-1,3-diol | 434 | 434 | Formate Salt |
| 15.50 | | (1-{[4-(3-methyl-5-{[4-(trifluoromethyl)pyrimidin-2-yl]amino}phenyl)pyridin-2-yl]amino}cyclopentyl)methanol | 444 | 444 | Formate Salt |
| 15.51 | | 2-methyl-2-{[4-(3-methyl-5-{[4-(trifluoromethyl)pyrimidin-2-yl]amino}phenyl)pyridin-2-yl]amino}propan-1-ol | 418 | 418 | Formate Salt |
| 15.52 | | (2R)-1-{[4-(3-methyl-5-{[4-(trifluoromethyl)pyrimidin-2-yl]amino}phenyl)pyridin-2-yl]amino}propan-2-ol | 404 | 404 | Formate Salt |
| 15.53 | | 1-[4-(3-methyl-5-{[4-(trifluoromethyl)pyrimidin-2-yl]amino}phenyl)pyridin-2-yl]azetidin-3-ol | 402 | 402 | Formate Salt |
| 15.54 | | N-(2-{[4-(3-methyl-5-{[4-(trifluoromethyl)pyrimidin-2-yl]amino}phenyl)pyridin-2-yl]amino}ethyl)acetamide | 431 | 431 | Formate Salt |

TABLE 15C-continued

| Ex. | R^Cy | Name | [M + H]+ Calc'd | [M + H]+ Obsv'd | Form(s) |
|---|---|---|---|---|---|
| 15.55 | pyrrolidine-2-carboxamide | 1-[4-(3-methyl-5-{[4-(trifluoromethyl)pyrimidin-2-yl]amino}phenyl)pyridin-2-yl]prolinamide | 443 | 443 | Formate Salt |
| 15.56 | 1-(hydroxymethyl)cyclopropylamino | (1-{[4-(3-methyl-5-{[4-(trifluoromethyl)pyrimidin-2-yl]amino}phenyl)pyridin-2-yl]amino}cyclopropyl)methanol | 416 | 416 | Formate Salt |
| 15.57 | N-methyl-N-[2-(1,3-dioxolan-2-yl)ethyl]amino | N-[3-(2-{[2-(1,3-dioxolan-2-yl)ethyl](methyl)amino}pyridin-4-yl)-5-methylphenyl]-4-(trifluoromethyl)pyrimidin-2-amine | 460 | 460 | Formate Salt |
| 15.58 | N-methylpiperidine-4-carboxamide | N-methyl-1-[4-(3-methyl-5-{[4-(trifluoromethyl)pyrimidin-2-yl]amino}phenyl)pyridin-2-yl]piperidine-4-carboxamide | 471 | 471 | Formate Salt |
| 15.59 | 3-aminopropanamide | N~3~-[4-(3-methyl-5-{[4-(trifluoromethyl)pyrimidin-2-yl]amino}phenyl)pyridin-2-yl]-beta-alaninamide | 417 | 417 | Formate Salt |
| 15.60 | 2-hydroxy-2-methylpropylamino | 2-methyl-1-{[4-(3-methyl-5-{[4-(trifluoromethyl)pyrimidin-2-yl]amino}phenyl)pyridin-2-yl]amino}propan-2-ol | 418 | 418 | Formate Salt |
| 15.61 | 4-methylpiperazin-1-yl | N-{3-methyl-5-[2-(4-methylpiperazin-1-yl)pyridin-4-yl]phenyl}-4-(trifluoromethyl)pyrimidin-2-amine | 429 | 429 | Formate Salt |
| 15.62 | oxetan-3-ylamino | N-{3-methyl-5-[2-(oxetan-3-ylamino)pyridin-4-yl]phenyl}-4-(trifluoromethyl)pyrimidin-2-amine | 402 | 402 | Formate Salt |

TABLE 15C-continued

| Ex. | R<sup>cy</sup> | Name | [M + H]<sup>+</sup> Calc'd | [M + H]<sup>+</sup> Obsv'd | Form(s) |
|---|---|---|---|---|---|
| 15.63 | | N-(3-methyl-5-{2-[4-(methylsulfonyl)piperazin-1-yl]pyridin-4-yl}phenyl)-4-(trifluoromethyl)pyrimidin-2-amine | 493 | 493 | Formate Salt |
| 15.64 | | N-{3-[2-(4-ethylpiperazin-1-yl)pyridin-4-yl]-5-methylphenyl}-4-(trifluoromethyl)pyrimidin-2-amine | 443 | 443 | Formate Salt |
| 15.65 | | N-(2-{methyl[4-(3-methyl-5-{[4-(trifluoromethyl)pyrimidin-2-yl]amino}phenyl)pyridin-2-yl]amino}ethyl)acetamide | 445 | 445 | Formate Salt |
| 15.66 | | (5R)-5-{[4-(3-methyl-5-{[4-(trifluoromethyl)pyrimidin-2-yl]amino}phenyl)pyridin-2-yl]amino}piperidin-2-one | 443 | 443 | Formate Salt |
| 15.67 | | (5S)-5-{[4-(3-methyl-5-{[4-(trifluoromethyl)pyrimidin-2-yl]amino}phenyl)pyridin-2-yl]amino}piperidin-2-one | 443 | 443 | Formate Salt |
| 15.68 | | N-{3-[2-(3,3-difluoropiperidin-1-yl)pyridin-4-yl]-5-methylphenyl}-4-(trifluoromethyl)pyrimidin-2-amine | 450 | 450 | Formate Salt |
| 15.69 | racemic | N-(3-{2-[2-(methoxymethyl)pyrrolidin-1-yl]pyridin-4-yl}-5-methylphenyl)-4-(trifluoromethyl)pyrimidin-2-amine | 444 | 444 | Formate Salt |

TABLE 15C-continued

| Ex. | R<sup>cy</sup> | Name | [M + H]⁺ Calc'd | [M + H]⁺ Obsv'd | Form(s) |
|---|---|---|---|---|---|
| 15.70 | (4,4-difluoropiperidin-1-yl) | N-{3-[2-(4,4-difluoropiperidin-1-yl)pyridin-4-yl]-5-methylphenyl}-4-(trifluoromethyl)pyrimidin-2-amine | 450 | 450 | Formate Salt |
| 15.71 | (3,5-dimethylpiperazin-1-yl) | N-{3-[2-(3,5-dimethylpiperazin-1-yl)pyridin-4-yl]-5-methylphenyl}-4-(trifluoromethyl)pyrimidin-2-amine | 443 | 443 | Formate Salt |
| 15.72 | (1-hydroxypropan-2-yl)amino, racemic | 1-{[4-(3-methyl-5-{[4-(trifluoromethyl)pyrimidin-2-yl]amino}phenyl)pyridin-2-yl]amino}propan-2-ol | 404 | 404 | Formate Salt |
| 15.73 | L-prolinamide | 1-[4-(3-methyl-5-{[4-(trifluoromethyl)pyrimidin-2-yl]amino}phenyl)pyridin-2-yl]-L-prolinamide | 443 | 443 | Formate Salt |
| 15.74 | (5-oxopyrrolidin-3-yl)amino, racemic | 4-{[4-(3-methyl-5-{[4-(trifluoromethyl)pyrimidin-2-yl]amino}phenyl)pyridin-2-yl]amino}pyrrolidin-2-one | 429 | 429 | Formate Salt |
| 15.75 | 4-acetyl-1,4-diazepan-1-yl | N-{3-[2-(4-acetyl-1,4-diazepan-1-yl)pyridin-4-yl]-5-methylphenyl}-4-(trifluoromethyl)pyrimidin-2-amine | 471 | 471 | Formate Salt |

TABLE 15C-continued

| Ex. | R<sup>cy</sup> | Name | [M + H]+ Calc'd | [M + H]+ Obsv'd | Form(s) |
|---|---|---|---|---|---|
| 15.76 | (4-propyl-1,4-diazepan-1-yl) | N-{3-methyl-5-[2-(4-propyl-1,4-diazepan-1-yl)pyridin-4-yl]phenyl}-4-(trifluoromethyl)pyrimidin-2-amine | 471 | 471 | Formate Salt |
| 15.77 | 3-(methoxymethyl)pyrrolidin-1-yl, racemic | N-(3-{2-[3-(methoxymethyl)pyrrolidin-1-yl]pyridin-4-yl}-5-methylphenyl)-4-(trifluoromethyl)pyrimidin-2-amine | 444 | 444 | Formate Salt |
| 15.78 | N-methyl-beta-alaninamide linker | N-methyl-N~3~-[4-(3-methyl-5-{[4-(trifluoromethyl)pyrimidin-2-yl]amino}phenyl)pyridin-2-yl]-beta-alaninamide | 431 | 431 | Formate Salt |
| 15.79 | 3-propoxypiperidin-1-yl, racemic | N-{3-methyl-5-[2-(3-propoxypiperidin-1-yl)pyridin-4-yl]phenyl}-4-(trifluoromethyl)pyrimidin-2-amine | 472 | 472 | Formate Salt |
| 15.80 | N-(3-acetamidopropyl)amino | N-(3-{[4-(3-methyl-5-{[4-(trifluoromethyl)pyrimidin-2-yl]amino}phenyl)pyridin-2-yl]amino}propyl)acetamide | 445 | 445 | Formate Salt |
| 15.81 | N-methylprolinamide, racemic | N-methyl-1-[4-(3-methyl-5-{[4-(trifluoromethyl)pyrimidin-2-yl]amino}phenyl)pyridin-2-yl]prolinamide | 457 | 457 | Formate Salt |
| 15.82 | N,N-dimethylglycinamide | N,N-dimethyl-N~2~-[4-(3-methyl-5-{[4-(trifluoromethyl)pyrimidin-2-yl]amino}phenyl)pyridin-2-yl]glycinamide | 431 | 431 | Formate Salt |

TABLE 15C-continued

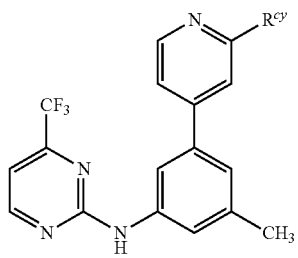

| Ex. | R<sup>cy</sup> | Name | [M + H]<sup>+</sup> Calc'd | [M + H]<sup>+</sup> Obsv'd | Form(s) |
|---|---|---|---|---|---|
| 15.83 | (racemic pyrrolidinone-CH2NH) | 5-({[4-(3-methyl-5-{[4-(trifluoromethyl)pyrimidin-2-yl]amino}phenyl)pyridin-2-yl]amino}methyl)pyrrolidin-2-one | 443 | 443 | Formate Salt |
| 15.84 | (racemic octahydropyrrolo[3,4-c]pyrrole-CH2OH) | {5-[4-(3-methyl-5-{[4-(trifluoromethyl)pyrimidin-2-yl]amino}phenyl)pyridin-2-yl]octahydropyrrolo[3,4-c]pyrrol-1-yl}methanol | 471 | 471 | Formate Salt |
| 15.85 | (3,5-dimethylpiperazinyl) | N-{3-[2-(3,5-dimethylpiperazin-1-yl)pyridin-4-yl]-5-methylphenyl}-4-(trifluoromethyl)pyrimidin-2-amine | 443 | 443 | Formate Salt |
| 15.86 | (L-prolinamide) | 1-[4-(3-methyl-5-{[4-(trifluoromethyl)pyrimidin-2-yl]amino}phenyl)pyridin-2-yl]-L-prolinamide | 443 | 443 | Formate Salt |
| 15.87 | (piperidine-4-carboxylic acid) | 1-[4-(3-methyl-5-{[4-(trifluoromethyl)pyrimidin-2-yl]amino}phenyl)pyridin-2-yl]piperidine-4-carboxylic acid | 458 | 458 | Formate Salt |
| 15.88 | (piperazinyl) | N-[3-methyl-5-(2-piperazin-1-ylpyridin-4-yl)phenyl]-4-(trifluoromethyl)pyrimidin-2-amine | 415 | 415 | Formate Salt |
| 15.89 | (piperazin-2-one) | 4-[4-(3-methyl-5-{[4-(trifluoromethyl)pyrimidin-2-yl]amino}phenyl)pyridin-2-yl]piperazin-2-one | 429 | 429 | Formate Salt |

Example 15.90

N-(2,3-dihydroxypropyl)-5-(3-methyl-5-{[4-(trifluoromethyl)pyrimidin-2-yl]amino}phenyl)pyridine-3-carboxamide

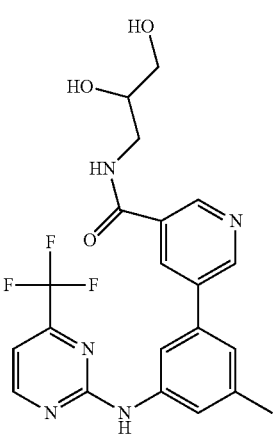

15.90

Step 1:

Methanol (1.0 mL) and aqueous sodium hydroxide (4 M in H$_2$O, 0.65 mL, 2.6 mmol) was added to a flask containing ethyl 5-(3-methyl-5-{[4-(trifluoromethyl)pyrimidin-2-yl]amino}phenyl)pyridine-3-carboxylate (210 mg, 0.052 mmol) and the reaction was heated to 60° C. for 1 hour. The mixture was allowed to cool to room temperature, acidified (2 N HCl) and the solid was isolated by filtration to yield 5-(3-methyl-5-{[4-(trifluoromethyl)pyrimidin-2-yl]amino}phenyl)pyridine-3-carboxylic acid. MS ESI calc'd for C$_{18}$H$_{14}$F$_3$N$_4$O$_2$ [M+H]$^+$ 375. found 375.

Step 2:

N,N-diisopropylamine (99 μL, 0.57 mmol), 3-aminopropane-1,2-diol (35 mg, 0.38 mmol) and benzotriazol-1-yloxy-tris(dimethylamino)phosphonium hexafluorophosphate (130 mg, 0.29 mmol) were added to a solution of 5-(3-methyl-5-{[4-(trifluoromethyl)pyrimidin-2-yl]amino}phenyl)pyridine-3-carboxylic acid (71 mg, 0.19 mmol) in DMF (0.6 mL) and the reaction mixture was stirred for 20 hours at room temperature. The reaction mixture was diluted with water and extracted with dichloromethane, dried over sodium sulfate, filtered and concentrated under reduced pressure. The residue was purified by reverse phase HPLC to afford N-(2,3-dihydroxypropyl)-5-(3-methyl-5-{[4-(trifluoromethyl)pyrimidin-2-yl]amino}phenyl)pyridine-3-carboxamide as a TFA salt. MS ESI calc'd for C$_{21}$H$_{21}$F$_3$N$_5$O$_3$ [M+H]$^+$ 448. found 448. $^1$H NMR (500 MHz, DMSO-d$_6$) δ 10.29 (s, 1H), 8.97 (s, 1H), 8.93 (s, 1H), 8.89-8.79 (m, 1H), 8.78-8.68 (m, 1H), 8.46-8.34 (m, 1H), 8.04-7.93 (m, 1H), 7.60 (s, 1H), 7.32-7.22 (m, 2H), 3.69-3.63 (m, 1H), 3.48-3.39 (m, 2H), 3.25-3.17 (m, 2H), 2.66-2.58 (m, 1H), 2.38 (s, 3H), 2.37-2.32 (m, 1H).

Example 16

Compounds of Formula (I) Using the General Methods Illustrated in Scheme 16

Example 16.1

N-(methylsulfonyl)-5-(3-methyl-5-{[4-(trifluoromethyl)pyrimidin-2-yl]amino}phenyl)pyridine-2-carboxamide

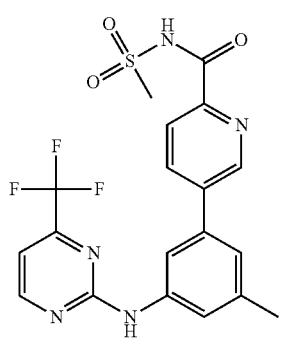

16.1

Dichloromethane (670 μL), EDC (38 mg, 0.20 mmol), methylsulfonamide (25 mg, 0.27 mmol) and DMAP (1.6 mg, 0.013 mmol) were added to 5-(3-methyl-5-{[4-(trifluoromethyl)pyrimidin-2-yl]amino}phenyl)pyridine-2-carboxylic acid (50 mg, 0.13) and the reaction was allowed to stir for 16 hours at room temperature. DMF (500 μL) was added to the reaction and stirred overnight at room temperature. The reaction was then diluted with aqueous saturated ammonium chloride and extracted with dichloromethane. The organic layer was washed with water, dried over sodium sulfate, filtered and concentrated under reduced pressure. The residue was purified by reverse phase HPLC (10-100% acetonitrile/water with 0.1% TFA) to afford N-(methylsulfonyl)-5-(3-methyl-5-{[4-(trifluoromethyl)pyrimidin-2-yl]amino}phenyl)pyridine-2-carboxamide as a TFA salt. MS ESI calc'd for C$_{19}$H$_{17}$F$_3$N$_5$O$_3$S [M+H]$^+$ 452. found 452. $^1$H NMR (500 MHz, DMSO-d$_6$) δ 10.45-10.28 (m, 1H), 9.05-8.91 (m, 1H), 8.92-8.78 (m, 1H), 8.39-8.25 (m, 1H), 8.25-8.12 (m, 1H), 8.12-8.02 (m, 1H), 7.71-7.57 (m, 1H), 7.44-7.21 (m, 1H), 3.39 (s, 3H), 2.40 (s, 3H).

The following example in Table 16 was prepared in an analogous manner to that described in Example 16.1 and general scheme 16.

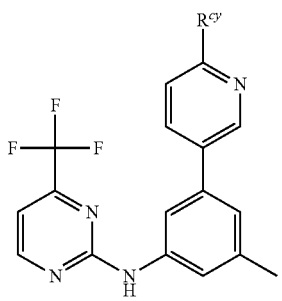

| Ex. | R^cy | Name | [M + H]+ Calc'd | [M + H]+ Obsv'd | Form(s) |
|---|---|---|---|---|---|
| 16.2 | (O=S(=O)(NH2)-NH-C(=O)-) | 5-(3-methyl-5-{[4-(trifluoromethyl)pyrimidin-2-yl]amino}phenyl)-N-sulfamoyl-pyridine-2-carboxamide | 453 | 453 | TFA Salt |

Example 16.3

3-{[5-(3-Methyl-5-{[4-(trifluoromethyl)pyrimidin-2-yl]amino}phenyl)pyridin-2-yl]carbonyl}-1,3-oxazolidin-2-one

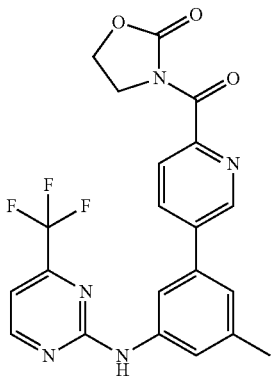

DMF (800 µL), 1,3-oxazolidin-2-one (28 mg, 0.32 mmol), triethylamine (67 µL, 0.48 mmol) and (benzotriazol-1-yloxy) tripyrrolidinophosphonium hexafluorophosphate (100 mg, 0.19 mmol) were added to 5-(3-methyl-5-{[4-(trifluoromethyl)pyrimidin-2-yl]amino}phenyl)pyridine-2-carboxylic acid (60 mg, 0.16 mmol) and the reaction was stirred for 60 hours at room temperature. The reaction mixture was then diluted with water and extracted with dichloromethane. The organic layer was dried over sodium sulfate, filtered and concentrated under reduced pressure. The residue was purified by reverse phase HPLC (10-80% acetonitrile/water with 0.1% TFA) and then chromatography on silica gel (10-100% acetone gradient in hexanes) to afford 3-{[5-(3-methyl-5-{[4-(trifluoromethyl)pyrimidin-2-yl]amino}phenyl)pyridin-2-yl]carbonyl}-1,3-oxazolidin-2-one. MS ESI calc'd for $C_{21}H_{17}F_3N_5O_3$ [M+H]+ 444. found 444. $^1$H NMR (500 MHz, DMSO-$d_6$) δ 10.31 (s, 1H), 8.87-8.77 (m, 2H), 8.13 (dd, J=2.2 Hz, 8.1, 1H), 8.02 (s, 1H), 7.74 (d, J=8.1 Hz, 1H), 7.60 (s, 1H), 7.31-7.21 (m, 2H), 4.49 (t, J=7.8 Hz, 2H), 4.11 (t, J=7.8 Hz, 2H), 2.37 (s, 3H).

Example 16.4

4-{[5-(3-Methyl-5-{[4-(trifluoromethyl)pyrimidin-2-yl]amino}phenyl)pyridin-2-yl]carbonyl}piperazin-2-one

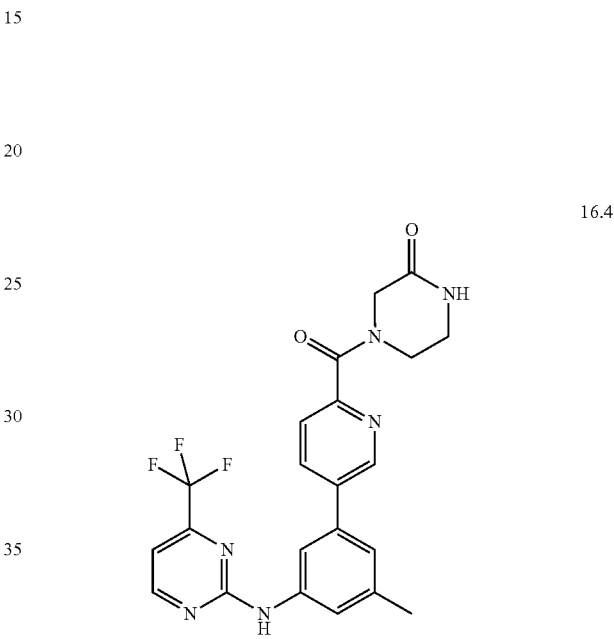

Piperazin-2-one (80.0 mg, 0.801 mmol), silica-bound carbodiimide (1.08 mmol/g load, 989 mg, 1.07 mmol), and HOBT (123 mg, 0.801 mmol) were added to a solution of 5-(3-methyl-5-{[4-(trifluoromethyl)pyrimidin-2-yl]amino}phenyl)pyridine-2-carboxylic acid (200 mg, 0.534 mmol) in DMF (5.30 mL) and the reaction mixture was stirred at room temperature overnight. Macroporous-carbonate (3.17 mmol/g load, 1.01 g, 3.21 mmol) was added to the reaction mixture and stirred overnight at room temperature. The reaction mixture was filtered, washed with DMF and was concentrated under reduced pressure. The residue was triturated with dichloromethane and was isolated by filtration (cold ether wash) to yield 4-{[5-(3-methyl-5-{[4-(trifluoromethyl)pyrimidin-2-yl]amino}phenyl)pyridin-2-yl]carbonyl}piperazin-2-one. MS APCI calc'd for $C_{22}H_{20}F_3N_6O_2$ [M+H]+ 457. found 457. $^1$H NMR (500 MHz, DMSO-d6) δ 10.30 (s, 1H), 8.84 (d, J=5.5 Hz, 2H), 8.14 (s, 2H), 8.00 (s, 1H), 7.76 (t, 1H), 7.60 (s, 1H), 7.32-7.13 (m, 2H), 4.16 (d, J=12.2 Hz, 2H), 3.92-3.77 (m, 1H), 3.72 (s, 1H), 2.37 (s, 3H).

The following examples were prepared in an analogous manner to that described in general scheme 16 using commercially available or known amines.

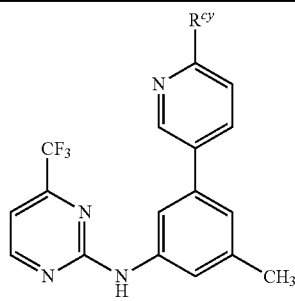

| Ex. | R$^{cy}$ | Name | [M + H]$^+$ Calc'd | [M + H]$^+$ Obsv'd | Form(s) |
|---|---|---|---|---|---|
| 16.5 | (2-hydroxyethylamide) | N-(2-hydroxyethyl)-5-(3-methyl-5-{[4-(trifluoromethyl)pyrimidin-2-yl]amino}phenyl)pyridine-2-carboxamide | 418 | 418 | Formate Salt |
| 16.6 | (N-(2-hydroxyethyl)-N-methyl amide) | N-(2-hydroxyethyl)-N-methyl-5-(3-methyl-5-{[4-(trifluoromethyl)pyrimidin-2-yl]amino}phenyl)pyridine-2-carboxamide | 432 | 432 | Formate Salt |
| 16.7 | (2-hydroxy-1-methylethyl amide, racemic) | N-(2-hydroxy-1-methylethyl)-5-(3-methyl-5-{[4-(trifluoromethyl)pyrimidin-2-yl]amino}phenyl)pyridine-2-carboxamide | 432 | 432 | Formate Salt |
| 16.8 | (1-(hydroxymethyl)cyclopropyl amide) | N-[1-(hydroxymethyl)cyclopropyl]-5-(3-methyl-5-{[4-(trifluoromethyl)pyrimidin-2-yl]amino}phenyl)pyridine-2-carboxamide | 444 | 444 | Formate Salt |
| 16.9 | (1-(hydroxymethyl)propyl amide, racemic) | N-[1-(hydroxymethyl)propyl]-5-(3-methyl-5-{[4-(trifluoromethyl)pyrimidin-2-yl]amino}phenyl)pyridine-2-carboxamide | 446 | 446 | Formate Salt |
| 16.10 | (2-hydroxy-2-methylpropyl amide) | N-(2-hydroxy-2-methylpropyl)-5-(3-methyl-5-{[4-(trifluoromethyl)pyrimidin-2-yl]amino}phenyl)pyridine-2-carboxamide | 446 | 446 | Formate Salt |

-continued

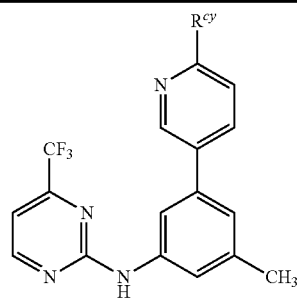

| Ex. | R<sup>cy</sup> | Name | [M + H]⁺ Calc'd | [M + H]⁺ Obsv'd | Form(s) |
|---|---|---|---|---|---|
| 16.11 | (2-hydroxy-1,1-dimethylethyl amide) | N-(2-hydroxy-1,1-dimethylethyl)-5-(3-methyl-5-{[4-(trifluoromethyl)pyrimidin-2-yl]amino}phenyl)pyridine-2-carboxamide | 446 | 446 | Formate Salt |
| 16.12 | (4-methylpiperazin-1-yl carbonyl) | N-(3-methyl-5-{6-[(4-methylpiperazin-1-yl)carbonyl]pyridin-3-yl}phenyl)-4-(trifluoromethyl)pyrimidin-2-amine | 457 | 457 | Formate Salt |
| 16.13 | (bis-hydroxymethyl-methyl amide) | N-[2-hydroxy-1-(hydroxymethyl)-1-methylethyl]-5-(3-methyl-5-{[4-(trifluoromethyl)pyrimidin-2-yl]amino}phenyl)pyridine-2-carboxamide | 462 | 462 | Formate Salt |
| 16.14 | (1-methyl-1H-pyrazol-4-ylmethyl amide) | N-[(1-methyl-1H-pyrazol-4-yl)methyl]-5-(3-methyl-5-{[4-(trifluoromethyl)pyrimidin-2-yl]amino}phenyl)pyridine-2-carboxamide | 468 | 468 | Formate Salt |
| 16.15 | (1-methyl-1H-imidazol-5-ylmethyl amide) | N-[(1-methyl-1H-imidazol-5-yl)methyl]-5-(3-methyl-5-{[4-(trifluoromethyl)pyrimidin-2-yl]amino}phenyl)pyridine-2-carboxamide | 468 | 468 | Formate Salt |
| 16.16 | (1H-imidazol-4-yl ethyl amide) | N-[1-(1H-imidazol-4-yl)ethyl]-5-(3-methyl-5-{[4-(trifluoromethyl)pyrimidin-2-yl]amino}phenyl)pyridine-2-carboxamide | 468 | 468 | Formate Salt |

-continued

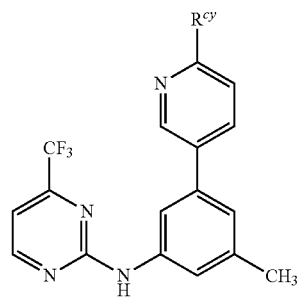

| Ex. | R^cy | Name | [M + H]+ Calc'd | [M + H]+ Obsv'd | Form(s) |
|---|---|---|---|---|---|
| 16.17 | (1-methyl-1H-imidazol-4-yl)methyl-aminocarbonyl group | N-[(1-methyl-1H-imidazol-4-yl)methyl]-5-(3-methyl-5-{[4-(trifluoromethyl)pyrimidin-2-yl]amino}phenyl)pyridine-2-carboxamide | 468 | 468 | Formate Salt |
| 16.18 | 2,6-dioxopiperazin-1-yl carbonyl group | 4-{[5-(3-methyl-5-{[4-(trifluoromethyl)pyrimidin-2-yl]amino}phenyl)pyridin-2-yl]carbonyl}piperazine-2,6-dione | 471 | 471 | Formate Salt |
| 16.19 | 5-oxo-1,4-diazepan-1-yl carbonyl group | 1-{[5-(3-methyl-5-{[4-(trifluoromethyl)pyrimidin-2-yl]amino}phenyl)pyridin-2-yl]carbonyl}-1,4-diazepan-5-one | 471 | 471 | Formate Salt |
| 16.20 | 4-methyl-3-oxopiperazin-1-yl carbonyl group | 1-methyl-4-{[5-(3-methyl-5-{[4-(trifluoromethyl)pyrimidin-2-yl]amino}phenyl)pyridin-2-yl]carbonyl}piperazin-2-one | 471 | 471 | Formate Salt |
| 16.21 | 1-(hydroxymethyl)cyclopentyl-aminocarbonyl group | N-[1-(hydroxymethyl)cyclopentyl]-5-(3-methyl-5-{[4-(trifluoromethyl)pyrimidin-2-yl]amino}phenyl)pyridine-2-carboxamide | 472 | 472 | Formate Salt |

-continued

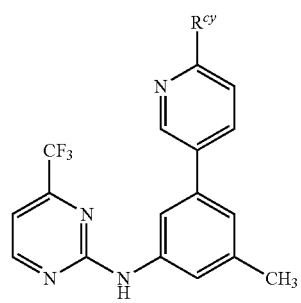

| Ex. | R<sup>cy</sup> | Name | [M + H]<sup>+</sup> Calc'd | [M + H]<sup>+</sup> Obsv'd | Form(s) |
|---|---|---|---|---|---|
| 16.22 | racemic | 5-(3-methyl-5-{[4-(trifluoromethyl)pyrimidin-2-yl]amino}phenyl)-N-(1-pyridin-2-ylethyl)pyridine-2-carboxamide | 479 | 479 | Formate Salt |
| 16.23 | racemic | 1,3-dimethyl-4-{[5-(3-methyl-5-{[4-(trifluoromethyl)pyrimidin-2-yl]amino}phenyl)pyridin-2-yl]carbonyl}piperazin-2-one | 485 | 485 | Formate Salt |
| 16.24 | | N-(3-{6-[(4-acetylpiperazin-1-yl)carbonyl]pyridin-3-yl}-5-methylphenyl)-4-(trifluoromethyl)pyrimidin-2-amine | 485 | 485 | Formate Salt |
| 16.25 | | N-[2-(1,3-dioxolan-2-yl)ethyl]-N-methyl-5-(3-methyl-5-{[4-(trifluoromethyl)pyrimidin-2-yl]amino}phenyl)pyridine-2-carboxamide | 488 | 488 | Formate Salt |
| 16.26 | racemic | 5-(3-methyl-5-{[4-(trifluoromethyl)pyrimidin-2-yl]amino}phenyl)-N-(2-oxopyrrolidin-3-yl)pyridine-2-carboxamide | 457 | 457 | Formate Salt |

-continued

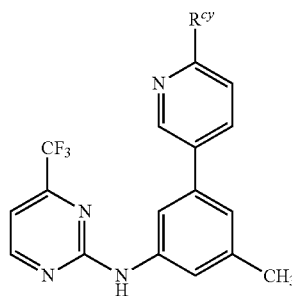

| Ex. | R<sup>cy</sup> | Name | [M + H]⁺ Calc'd | [M + H]⁺ Obsv'd | Form(s) |
|---|---|---|---|---|---|
| 16.27 | (1-methyl-1H-1,2,4-triazol-5-yl)methyl-NHC(O)- | N-[(1-methyl-1H-1,2,4-triazol-5-yl)methyl]-5-(3-methyl-5-{[4-(trifluoromethyl)pyrimidin-2-yl]amino}phenyl)pyridine-2-carboxamide | 469 | 469 | Formate Salt |
| 16.28 | (2-fluoroprop-2-en-1-yl)-NHC(O)- | N-(2-fluoroprop-2-en-1-yl)-5-(3-methyl-5-{[4-(trifluoromethyl)pyrimidin-2-yl]amino}phenyl)pyridine-2-carboxamide | 432 | 432 | Formate Salt |
| 16.29 | pyrimidin-5-yl-NHC(O)- | 5-(3-methyl-5-{[4-(trifluoromethyl)pyrimidin-2-yl]amino}phenyl)-N-pyrimidin-5-ylpyridine-2-carboxamide | 452 | 452 | Formate Salt |
| 16.30 | (5-oxopyrrolidin-2-yl)methyl-NHC(O)- racemic | 5-(3-methyl-5-{[4-(trifluoromethyl)pyrimidin-2-yl]amino}phenyl)-N-[(5-oxopyrrolidin-2-yl)methyl]pyridine-2-carboxamide | 471 | 471 | Formate Salt |
| 16.31 | (1,4-dioxan-2-yl)methyl-NHC(O)- racemic | N-(1,4-dioxan-2-ylmethyl)-5-(3-methyl-5-{[4-(trifluoroethyl)pyrimidin-2-yl]amino}phenyl)pyridine-2-carboxamide | 474 | 474 | Formate Salt |

-continued

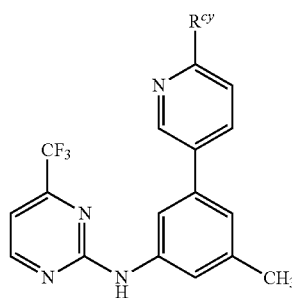

| Ex. | R<sup>cy</sup> | Name | [M + H]⁺ Calc'd | [M + H]⁺ Obsv'd | Form(s) |
|---|---|---|---|---|---|
| 16.32 | | N-{3-[6-(5,6-dihydroimidazo[1,2-a]pyrazin-7(8H)-ylcarbonyl)pyridin-3-yl]-5-methylphenyl}-4-(trifluoromethyl)pyrimidin-2-amine | 480 | 480 | Formate Salt |
| 16.33 | racemic | 5-(3-methyl-5-{[4-(trifluoromethyl)pyrimidin-2-yl]amino}phenyl)-N-(tetrahydrofuran-3-yl)pyridine-2-carboxamide | 444 | 444 | Formate Salt |
| 16.34 | | N-(3-{6-[(3-methoxyazetidin-1-yl)carbonyl]pyridin-3-yl}-5-methylphenyl)-4-(trifluoromethyl)pyrimidin-2-amine | 444 | 444 | Formate Salt |
| 16.35 | racemic | N-(4-chloro-2-hydroxybutyl)-5-(3-methyl-5-{[4-(trifluoromethyl)pyrimidin-2-yl]amino}phenyl)pyridine-2-carboxamide | 480 | 480 | Formate Salt |
| 16.36 | | N-(dicyclopropylmethyl)-N-methyl-5-(3-methyl-5-{[4-(trifluoromethyl)pyrimidin-2-yl]amino}phenyl)pyridine-2-carboxamide | 482 | 482 | Formate Salt |

-continued

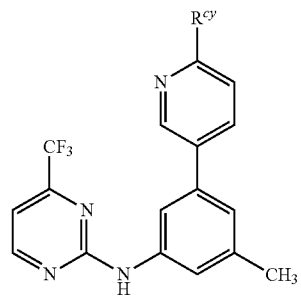

| Ex. | R<sup>cy</sup> | Name | [M + H]⁺ Calc'd | [M + H]⁺ Obsv'd | Form(s) |
|---|---|---|---|---|---|
| 16.37 | (2-hydroxyethyl morpholine carbonyl, racemic) | 2-(4-{[5-(3-methyl-5-{[4-(trifluoromethyl)pyrimidin-2-yl]amino}phenyl)pyridin-2-yl]carbonyl}morpholin-2-yl)ethanol | 488 | 488 | Formate Salt |
| 16.38 | (1,4-dioxan-2-ylmethyl-N-methylamide, racemic) | N-(1,4-dioxan-2-ylmethyl)-N-methyl-5-(3-methyl-5-{[4-(trifluoromethyl)pyrimidin-2-yl]amino}phenyl)pyridine-2-carboxamide | 488 | 488 | Formate Salt |
| 16.39 | (2-(methoxymethyl)morpholine carbonyl, racemic) | N-[3-(6-{[2-(methoxymethyl)morpholin-4-yl]carbonyl}pyridin-3-yl)-5-methylphenyl]-4-(trifluoromethyl)pyrimidin-2-amine | 488 | 488 | Formate Salt |
| 16.40 | ((1R,4R)-2-oxa-5-azabicyclo[2.2.1]heptane carbonyl) | N-(3-methyl-5-{6-[(1R,4R)-2-oxa-5-azabicyclo[2.2.1]hept-5-ylcarbonyl]pyridin-3-yl}phenyl)-4-(trifluoromethyl)pyrimidin-2-amine | 456 | 456 | Formate Salt |
| 16.41 | ((3R,5R)-3-hydroxy-5-methylpyrrolidine carbonyl) | (3R,5R)-5-methyl-1-{[5-(3-methyl-5-{[4-(trifluoromethyl)pyrimidin-2-yl]amino}phenyl)pyridin-2-yl]carbonyl}pyrrolidin-3-ol | 458 | 458 | Formate Salt |

-continued

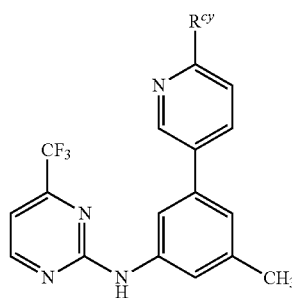

| Ex. | R^cy | Name | [M + H]+ Calc'd | [M + H]+ Obsv'd | Form(s) |
|---|---|---|---|---|---|
| 16.42 | 3-methyl-3-hydroxypyrrolidin-1-yl carbonyl (racemic) | 3-methyl-1-{[5-(3-methyl-5-{[4-(trifluoromethyl)pyrimidin-2-yl]amino}phenyl)pyridin-2-yl]carbonyl}pyrrolidin-3-ol | 458 | 458 | Formate Salt |
| 16.43 | (3S)-3-(hydroxymethyl)pyrrolidin-1-yl carbonyl | [(3S)-1-{[5-(3-methyl-5-{[4-(trifluoromethyl)pyrimidin-2-yl]amino}phenyl)pyridin-2-yl]carbonyl}pyrrolidin-3-yl]methanol | 458 | 458 | Formate Salt |
| 16.44 | 1,7-diazaspiro[4.4]nonan-6-one-1-yl carbonyl (racemic) | 1-{[5-(3-methyl-5-{[4-(trifluoromethyl)pyrimidin-2-yl]amino}phenyl)pyridin-2-yl]carbonyl}-1,7-diazaspiro[4.4]nonan-6-one | 497 | 497 | Formate Salt |
| 16.45 | N-(2-hydroxy-3-methoxypropyl)carboxamide (racemic) | N-(2-hydroxy-3-methoxypropyl)-5-(3-methyl-5-{[4-(trifluoromethyl)pyrimidin-2-yl]amino}phenyl)pyridine-2-carboxamide | 462 | 462 | Formate Salt |
| 16.46 | N-(dicyclopropylmethyl)carboxamide (racemic) | N-(dicyclopropylmethyl)-5-(3-methyl-5-{[4-(trifluoromethyl)pyrimidin-2-yl]amino}phenyl)pyridine-2-carboxamide | 468 | 468 | Formate Salt |

-continued

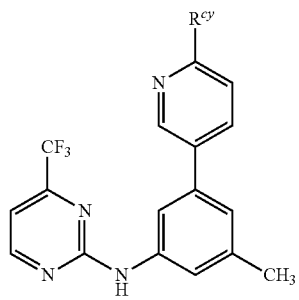

| Ex. | R<sup>cy</sup> | Name | [M + H]<sup>+</sup> Calc'd | [M + H]<sup>+</sup> Obsv'd | Form(s) |
|---|---|---|---|---|---|
| 16.47 | (3-methyl-3-hydroxypiperidine, racemic) | 3-methyl-1-{[5-(3-methyl-5-{[4-(trifluoromethyl)pyrimidin-2-yl]amino}phenyl)pyridin-2-yl]carbonyl}piperidin-3-ol | 472 | 472 | Formate Salt |
| 16.48 | (4-methyl-4-hydroxypiperidine) | 4-methyl-1-{[5-(3-methyl-5-{[4-(trifluoromethyl)pyrimidin-2-yl]amino}phenyl)pyridin-2-yl]carbonyl}piperidin-4-ol | 472 | 472 | Formate Salt |
| 16.49 | (1-oxidothiomorpholine) | N-(3-methyl-5-{6-[(1-oxidothiomorpholin-4-yl)carbonyl]pyridin-3-yl}phenyl)-4-(trifluoromethyl)pyrimidin-2-amine | 476 | 476 | Formate Salt |
| 16.50 | (sulfamoylethyl amide) | 5-(3-methyl-5-{[4-(trifluoromethyl)pyrimidin-2-yl]amino}phenyl)-N-(2-sulfamoylethyl)pyridine-2-carboxamide | 481 | 481 | Formate Salt |
| 16.51 | (triazolone methyl amide) | N-methyl-5-(3-methyl-5-{[4-(trifluoromethyl)pyrimidin-2-yl]amino}phenyl)-N-[(5-oxo-4,5-dihydro-1H-1,2,4-triazol-3-yl)methyl]pyridine-2-carboxamide | 485 | 485 | Formate Salt |
| 16.52 | (1-oxido-1,4-thiazepane) | N-(3-methyl-5-{6-[(1-oxido-1,4-thiazepan-4-yl)carbonyl]pyridin-3-yl}phenyl)-4-(trifluoromethyl)pyrimidin-2-amine | 490 | 490 | Formate Salt |

-continued

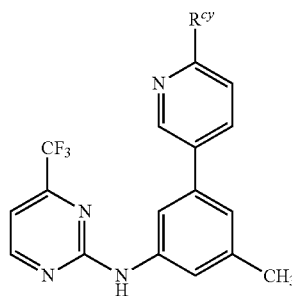

| Ex. | R<sup>cy</sup> | Name | [M + H]⁺ Calc'd | [M + H]⁺ Obsv'd | Form(s) |
|---|---|---|---|---|---|
| 16.53 | (1H-imidazol-2-ylmethyl-carboxamide group) | N-(1H-imidazol-2-ylmethyl)-5-(3-methyl-5-{[4-(trifluoromethyl)pyrimidin-2-yl]amino}phenyl)pyridine-2-carboxamide | 454 | 454 | Formate Salt |
| 16.54 | (1,1-dioxidotetrahydrothiophen-3-yl-carboxamide, racemic) | N-(1,1-dioxidotetrahydrothiophen-3-yl)-5-(3-methyl-5-{[4-(trifluoromethyl)pyrimidin-2-yl]amino}phenyl)pyridine-2-carboxamide | 492 | 492 | Formate Salt |
| 16.55 | (1,1-dioxidothiomorpholin-4-yl-carbonyl) | N-(3-{6-[(1,1-dioxidothiomorpholin-4-yl)carbonyl]pyridin-3-yl}-5-methylphenyl)-4-(trifluoromethyl)pyrimidin-2-amine | 492 | 492 | Formate Salt |
| 16.56 | (2,3-dihydroxypropyl-N-methyl-carboxamide, racemic) | N-(2,3-dihydroxypropyl)-N-methyl-5-(3-methyl-5-{[4-(trifluoromethyl)pyrimidin-2-yl]amino}phenyl)pyridine-2-carboxamide | 462 | 462 | Formate Salt |
| 16.57 | (2-(methylsulfamoyl)ethyl-carboxamide) | N-[2-(methylsulfamoyl)ethyl]-5-(3-methyl-5-{[4-(trifluoromethyl)pyrimidin-2-yl]amino}phenyl)pyridine-2-carboxamide | 495 | 495 | Formate Salt |

-continued

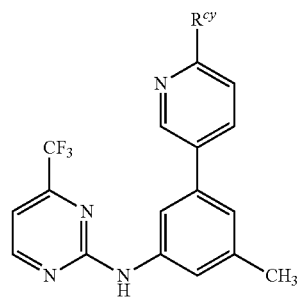

| Ex. | R<sup>cy</sup> | Name | [M + H]<sup>+</sup> Calc'd | [M + H]<sup>+</sup> Obsv'd | Form(s) |
| --- | --- | --- | --- | --- | --- |
| 16.58 | (methylsulfonylethyl-N-methylamide group) | N-methyl-N-[2-(methylsulfonyl)ethyl]-5-(3-methyl-5-{[4-(trifluoromethyl)pyrimidin-2-yl]amino}phenyl)pyridine-2-carboxamide | 494 | 494 | Formate Salt |
| 16.59 | (N-ethyl-N-methylamide group) | N-ethyl-N-methyl-5-(3-methyl-5-{[4-(trifluoromethyl)pyrimidin-2-yl]amino}phenyl)pyridine-2-carboxamide | 416 | 416 | Formate Salt |
| 16.60 | (N,N-bis(2-hydroxyethyl)amide group) | N,N-bis(2-hydroxyethyl)-5-(3-methyl-5-{[4-(trifluoromethyl)pyrimidin-2-yl]amino}phenyl)pyridine-2-carboxamide | 462 | 462 | Formate Salt |
| 16.61 | (N-methyl-N-[2-(methylamino)-2-oxoethyl]amide group) | N-methyl-N-[2-(methylamino)-2-oxoethyl]-5-(3-methyl-5-{[4-(trifluoromethyl)pyrimidin-2-yl]amino}phenyl)pyridine-2-carboxamide | 459 | 459 | Formate Salt |
| 16.62 | (N-(2-amino-2-oxoethyl)-N-methylamide group) | N-(2-amino-2-oxoethyl)-N-methyl-5-(3-methyl-5-{[4-(trifluoromethyl)pyrimidin-2-yl]amino}phenyl)pyridine-2-carboxamide | 445 | 445 | Formate Salt |
| 16.63 | (N-[2-(methylamino)-2-oxoethyl]amide group) | N-[2-(methylamino)-2-oxoethyl]-5-(3-methyl-5-{[4-(trifluoromethyl)pyrimidin-2-yl]amino}phenyl)pyridine-2-carboxamide | 445 | 445 | Formate Salt |

-continued

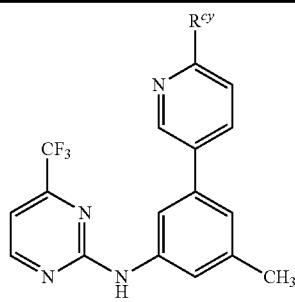

| Ex. | R<sup>cy</sup> | Name | [M + H]<sup>+</sup> Calc'd | [M + H]<sup>+</sup> Obsv'd | Form(s) |
|---|---|---|---|---|---|
| 16.64 | | N-[2-(methylsulfonyl)ethyl]-5-(3-methyl-5-{[4-(trifluoromethyl)pyrimidin-2-yl]amino}phenyl)pyridine-2-carboxamide | 480 | 480 | Formate Salt |
| 16.65 | | N-[3-methyl-5-(6-{[4-(2,2,2-trifluoroethyl)piperazin-1-yl]carbonyl}pyridin-3-yl)phenyl]-4-(trifluoromethyl)pyrimidin-2-amine | 525 | 525 | Formate Salt |
| 16.66 | | N-cyclopropyl-5-(3-methyl-5-{[4-(trifluoromethyl)pyrimidin-2-yl]amino}phenyl)pyridine-3-carboxamide | 414 | 414 | TFA Salt |
| 16.67 | | N,N-dimethyl-2-[5-(3-methyl-5-{[4-(trifluoromethyl)pyrimidin-2-yl]amino}phenyl)pyridin-2-yl]acetamide | 416 | 416 | TFA Salt |
| 16.68 | | 4-{[5-(3-methyl-5-{[4-(trifluoromethyl)pyrimidin-2-yl]amino}phenyl)pyridin-2-yl]carbonyl}piperazin-2-one | 457 | 457 | Free Base, Formate Salt |

Example 17

Compounds of Formula (I) Using the General Methods Illustrated in Scheme 17

Example 17.1

1-{[5-(3-Methyl-5-{[4-(trifluoromethyl)pyrimidin-2-yl]amino}phenyl)pyridin-2-yl]methyl}imidazolidin-2-one 17.1

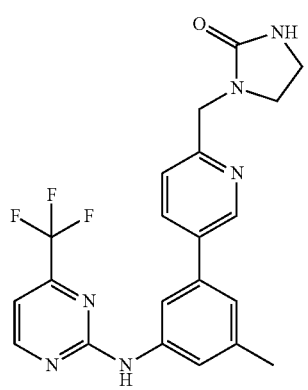

Step 1:

HCl (4 M in dioxanes, 0.844 mL, 3.38 mmol) followed by palladium on carbon (599 mg, 0.281 mmol) were added to a mixture of 5-(3-methyl-5-{[4-(trifluoromethyl)pyrimidin-2-yl]amino}phenyl)pyridine-2-carbonitrile (1.00 g, 2.81 mmol) and ethanol (200 mL). The reaction mixture was purged and flushed with $H_2(g)$ and was stirred under 1 atm of $H_2(g)$ for 3.5 hours at room temperature. The reaction mixture was filtered through CELITE, washed with ethanol and ethyl acetate and concentrated under reduced pressure to afford N-{3-[6-(Aminomethyl)pyridin-3-yl]-5-methylphenyl}-4-(trifluoromethyl)pyrimidin-2-amine hydrochloride as a yellow powder. MS APCI calc'd for $C_{18}H_{17}F_3N_5$ [M+H]$^+$ 360. found 360.

Step 2:

A 2-5 mL microwave vial was charged with N-{3-[6-(aminomethyl)pyridin-3-yl]-5-methylphenyl}-4-(trifluoromethyl)pyrimidin-2-amine hydrochloride (100 mg, 0.278 mmol) and flushed and purged with Ar(g) (3×). Toluene (2.78 mL), followed by of 1-chloro-2-isocyanatoethane (24.2 μL, 0.284 mmol) were added to the reaction mixture and stirred at room temperature until the reaction precipitated out. The solvent was removed in vacuo and 1-(2-chloroethyl)-3-{[5-(3-methyl-5-{[4-(trifluoromethyl)pyrimidin-2-yl]amino}phenyl)pyridin-2-yl]methyl}urea was carried forward without further purification. MS APCI calc'd for $C_{21}H_{21}ClF_3N_6O$ [M+H]$^+$ 465. found 465.

Step 3:

Potassium tert-butoxide (34.3 mg, 0.305 mmol) was added to a solution of 1-(2-chloroethyl)-3-{[5-(3-methyl-5-{[4-(trifluoromethyl)pyrimidin-2-yl]amino}phenyl)pyridin-2-yl]methyl}urea (129 mg, 0.277 mmol) in THF (4.62 mL). The reaction mixture was stirred at room temperature overnight under an argon atmosphere. An additional equivalent of potassium tert-butoxide was added to the reaction. The solvent was removed under reduced pressure and the residue was directly purified by reverse phase HPLC (10-75% acetonitrile in water+0.5% TFA). The isolated fractions were partitioned between 10% IPA/chloroform and saturated aqueous $NaHCO_3$. The organic layer was washed with brine, dried over sodium sulfate, filtered, and concentrated under reduced pressure to give 1-{[5-(3-methyl-5-{[4-(trifluoromethyl)pyrimidin-2-yl]amino}phenyl)pyridin-2-yl]methyl}imidazolidin-2-one. MS APCI calc'd for $C_{21}H_{20}F_3N_6O$ [M+H]$^+$ 429. found 429. $^1$H NMR (500 MHz, DMSO-d6) δ 10.27 (s, 1H), 8.82 (d, J=4.8 Hz, 1H), 8.75 (d, J=2.4 Hz, 1H), 8.05-7.83 (m, 2H), 7.55 (s, 1H), 7.35 (d, J=8.0 Hz, 1H), 7.27 (d, J=4.9 Hz, 1H), 7.18 (s, 1H), 6.47 (s, 1H), 4.36 (s, 2H), 3.38-3.44 (m, 4H), 2.35 (s, 3H).

The following examples were prepared in an analogous manner to that described in general scheme 17 using commercially available isocyanates in step 2.

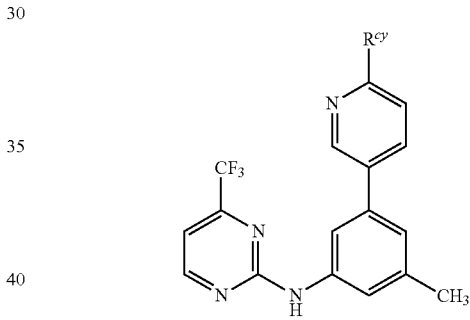

| Ex. | R$^{Cy}$ | Name | [M + H]$^+$ Calc'd | [M + H]$^+$ Obsv'd | Form(s) |
|---|---|---|---|---|---|
| 17.2 | ![O=C(NH2)NH-CH2-] | 1-{[5-(3-methyl-5-{[4-(trifluoromethyl)pyrimidin-2-yl]amino}phenyl)pyridin-2-yl]methyl}urea | 403 | 403 | Free Base |
| 17.3 | ![O=C(NHCH3)NH-CH2-] | 1-methyl-3-{[5-(3-methyl-5-{[4-(trifluoromethyl)pyrimidin-2-yl]amino}phenyl)pyridin-2-yl]methyl}urea | 417 | 417 | Free Base |

Example 18

Compounds of Formula (I) Using the General Methods Illustrated in Scheme 18

Procedure A

Example 18.1

2-Methyl-2-{[5-(3-methyl-5-{[4-(trifluoromethyl)pyrimidin-2-yl]amino}phenyl)pyridin-2-yl]amino}butanenitrile

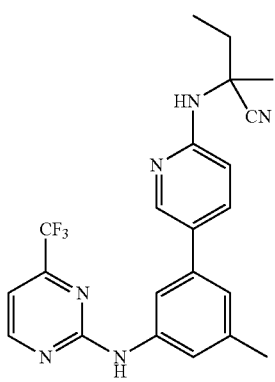

18.1

Step 1:

A mixture of 5-bromopyridin-2-amine (500 mg, 2.89 mmol), butan-2-one (611 µl, 6.82 mmol), and zinc chloride (0.5 M, 1.15 mL, 0.578 mmol) in acetonitrile (1.44 mL) was purged with Ar(g) for ~5 minutes. The reaction was cooled to 0° C. and TMS-CN (775 µl, 5.78 mmol) was added dropwise. The reaction mixture was heated to 85° C. overnight. Upon cooling, the reaction mixture was diluted with water and extracted with dichloromethane (3×). The organic layer was concentrated under reduced pressure and the residue was purified by silica gel chromatography (ethyl acetate/hexanes) to yield 2-[(5-bromopyridin-2-yl)amino]-2-methylbutanenitrile. $^1$H NMR (500 MHz, CDCl$_3$) δ 8.19 (d, J=3.2, 1H), 7.49 (dd, J=2.6, 8.9, 1H), 6.46 (d, J=9.6, 1H), 4.74 (s, 1H), 2.11-1.95 (m, 2H), 1.69 (s, 3H), 1.10-1.06 (m, 3H).

Step 2:

Argon was bubbled through a mixture of 2-[(5-bromopyridin-2-yl)amino]-2-methylbutanenitrile (327 mg, 1.29 mmol), N-[3-methyl-5-(4,4,5,5-tetramethyl-1,3,2-dioxaborolan-2-yl)phenyl]-4-(trifluoromethyl)pyrimidin-2-amine (488 mg, 1.29 mmol), and sodium carbonate (2 M, 1.28 mL, 2.57 mmol) in 2-methyl-THF (6.43 mL) for ~5 minutes. PdCl$_2$(dppf)-dichloromethane adduct (52.5 mg, 0.064 mmol) was added and the reaction was heated to 100° C. overnight. The cooled reaction mixture was diluted with water and extracted dichloromethane (3×). The organic layer was concentrated under reduced pressure and purified by reverse phase chromatography to yield 2-methyl-2-{[5-(3-methyl-5-{[4-(trifluoromethyl)pyrimidin-2-yl]amino}phenyl)pyridin-2-yl]amino}butanenitrile. MS APCI calc'd for C$_{22}$H$_{22}$F$_3$N$_6$ [M+H]$^+$ 427. found 427. $^1$H NMR (500 MHz, CDCl$_3$) δ 8.66 (d, J=5.3, 1H), 8.44 (s, 1H), 7.85-7.68 (m, 1H), 7.31 (t, J=17.9, 2H), 7.14-6.93 (m, 2H), 6.76 (d, J=9.3, 1H), 2.41 (s, 3H), 2.17-2.03 (m, 2H), 1.62 (s, 3H), 0.93 (t, J=7.3, 3H).

The following examples were prepared in an analogous manner to that described in general scheme 18 using commercially available ketones in step 1.

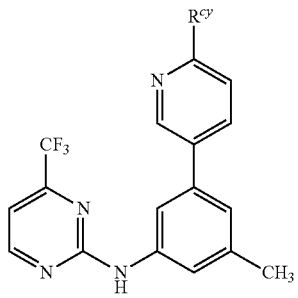

| Ex. | R$^{cy}$ | Name | [M + H]$^+$ Calc'd | [M + H]$^+$ Observed | Form(s) |
|---|---|---|---|---|---|
| 18.2 | CN, NH (gem-dimethyl) | 2-methyl-2-{[5-(3-methyl-5-{[4-(trifluoromethyl)pyrimidin-2-yl]amino}phenyl)pyridin-2-yl]amino}propanenitrile | 413 | 413 | Free Base |
| 18.3 | CN, NH (tert-butyl, methyl) racemic | 2,3,3-trimethyl-2-{[5-(3-methyl-5-{[4-(trifluoromethyl)pyrimidin-2-yl]amino}phenyl)pyridin-2-yl]amino}butanenitrile | 455 | 455 | Free Base |
| 18.4 | CN, NH (ethyl, methyl) racemic | 2-methyl-2-{[5-(3-methyl-5-{[4-(trifluoromethyl)pyrimidin-2-yl]amino}phenyl)pyridin-2-yl]amino}butanenitrile | 427 | 427 | Free Base, TFA Salt |

Procedure B

Example 18.5

4,4,4-Trifluoro-N-[5-(3-methyl-5-{[4-(trifluoromethyl)pyrimidin-2-yl]amino}phenyl)pyridin-2-yl]isovaline

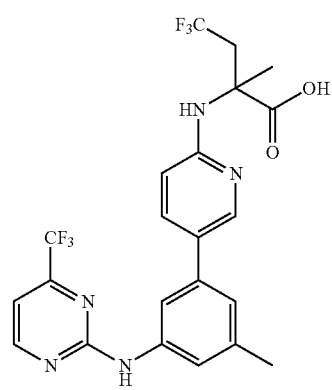

18.5

Sodium hydroxide (5 M, 33.3 µL, 0.167 mmol) was added to a mixture of 4,4,4-trifluoro-2-methyl-2-{[5-(3-methyl-5-{[4-(trifluoromethyl)pyrimidin-2-yl]amino}phenyl)pyridin-2-yl]amino}butanenitrile (40.0 mg, 0.083 mmol) in DMSO (167 µL) and the reaction mixture was stirred at room temperature. Upon the reaction completion (monitored by LCMS) was diluted with DMF and filtered. The residue was directly purified by reverse phase chromatography and then by silica gel chromatography (0-100% ethyl acetate in hexanes) to yield 4,4,4-trifluoro-N-[5-(3-methyl-5-{[4-(trifluoromethyl)pyrimidin-2-yl]amino}phenyl)pyridin-2-yl]isovaline. MS APCI calc'd for $C_{22}H_{20}F_6N_5O_2$ [M+H]$^+$ 500. found 500. $^1$H NMR (500 MHz, CDCl$_3$) δ 8.60 (d, J=5.7 Hz, 1H), 8.07 (s, 1H), 7.95 (d, J=11.2 Hz, 1H), 7.54 (s, 1H), 7.43 (s, 1H), 7.10 (d, J=5.4 Hz, 1H), 6.90 (s, 1H), 6.72 (d, J=9.8 Hz, 1H), 3.04 (s, 1H), 2.59-2.24 (m, 4H), 1.98-1.81 (m, 3H).

The following examples were prepared in an analogous manner to that described in general scheme 18.

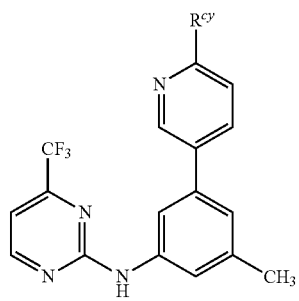

| Ex. | R$^{cy}$ | Name | [M + H]$^+$ Calc'd | [M + H]$^+$ Obsv'd | Form(s) |
|---|---|---|---|---|---|
| 18.6 | ![racemic] racemic | N-[5-(3-methyl-5-{[4-(trifluoromethyl)pyrimidin-2-yl]amino}phenyl)pyridin-2-yl]isovaline | 446 | 446 | TFA Salt |

Procedure C

Example 18.7

N-[3-methyl-5-(6-{[4,4,4-trifluoro-2-(1H-tetrazol-5-yl)butan-2-yl]amino}pyridin-3-yl)phenyl]-4-(trifluoromethyl)pyrimidin-2-amine

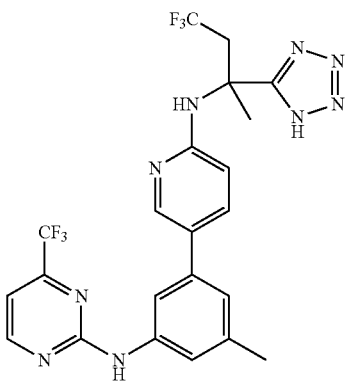

18.7

Ammonium chloride (11.7 mg, 0.219 mmol) and sodium azide (14.2 mg, 0.219 mmol) were added to a solution of 4,4,4-trifluoro-2-methyl-2-{[5-(3-methyl-5-{[4-(trifluoromethyl)pyrimidin-2-yl]amino}phenyl)pyridin-2-yl]amino}butanenitrile (30.0 mg, 0.062 mmol) in DMF (208 µL). Argon was bubbled through a reaction mixture for ~5 minutes and heated to 85° C. for 4 hours. The reaction mixture was cooled to room temperature, diluted with DMF, filtered, and the residue was purified directly by reverse phase HPLC (5-95% acetonitrile in water+0.5% TFA) to yield N-[3-methyl-5-(6-{[4,4,4-trifluoro-2-(1H-tetrazol-5-yl)butan-2-yl]amino}pyridin-3-yl)phenyl]-4-(trifluoromethyl)pyrimidin-2-amine as a bis-TFA salt. MS APCI calc'd for $C_{22}H_{20}F_6N_5O_2$ [M+H]$^+$ 524. found 524. $^1$H NMR (600 MHz, CDCl$_3$) δ 8.63 (d, J=4.9 Hz, 1H), 8.07 (s, 1H), 7.82 (d, J=8.9 Hz, 1H), 7.65 (s, 1H), 7.48 (s, 1H), 7.29 (s, 1H), 7.03 (d, J=4.9 Hz, 1H), 6.85 (s, 1H), 6.50 (d, J=8.9 Hz, 1H), 3.48-3.39 (m, 1H), 3.26-3.18 (m, 1H), 2.35 (s, 3H), 2.07 (s, 3H).

The following example was prepared in an analogous manner to that described in Example 18, Procedure C and general scheme 18.

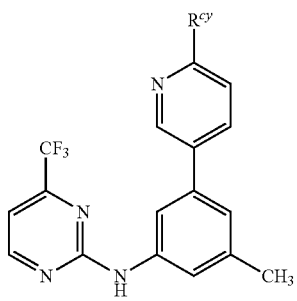

Step 1:

Hydroxylamine hydrochloride (101 mg, 1.46 mmol) and potassium carbonate (201 mg, 1.46 mmol) were added to a mixture of 2-methyl-2-{[5-(3-methyl-5-{[4-(trifluoromethyl)pyrimidin-2-yl]amino}phenyl)pyridin-2-yl]amino}propanenitrile (100 mg, 0.242 mmol) in ethanol (404 µL). The reaction stirred at 85° C. overnight. The reaction mixture was diluted with DMSO, filtered, and purified by reverse phase HPLC (5-95% acetonitrile in water+0.5% TFA) to yield (1Z)—N'-hydroxy-2-methyl-2-{[5-(3-methyl-5-{[4-(trifluoromethyl)pyrimidin-2-yl]amino}phenyl)pyridin-2-yl]amino}propanimidamide as a bis-TFA salt. MS APCI calc'd for $C_{21}H_{23}F_3N_7O$ [M+H]$^+$ 446. found 446.

| Ex. | R$^{cy}$ | Name | [M + H]$^+$ Calc'd | [M + H]$^+$ Observed | Form(s) |
|---|---|---|---|---|---|
| 18.8 | (tetrazole structure) | N-[3-methyl-5-(6-{[1-methyl-1-(1H-tetrazol-5-yl)ethyl]amino}pyridin-3-yl)phenyl]-4-(trifluoromethyl)pyrimidin-2-amine | 456 | 456 | TFA Salt |
| 18.9 | (tetrazole structure) RACEMIC | N-[3-methyl-5-(6-{[1,2,2-trimethyl-1-(1H-tetrazol-5-yl)propyl]amino}pyridin-3-yl)phenyl]-4-(trifluoromethyl)pyrimidin-2-amine | 498 | 498 | TFA Salt |

Procedure D

Example 18.10

3-(2-{[5-(3-Methyl-5-{[4-(trifluoromethyl)pyrimidin-2-yl]amino}phenyl)pyridin-2-yl]amino}propan-2-yl)-1,2,4-oxadiazol-5(4H)-one

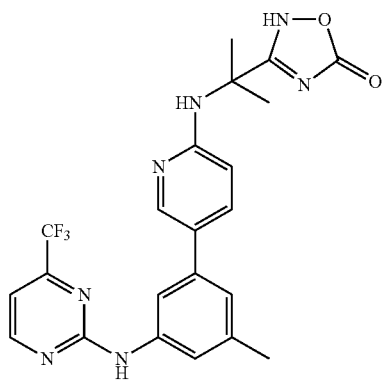

Step 2:

DBU (10.0 µL, 0.066 mmol) was added to a mixture of (1Z)—N'-hydroxy-2-methyl-2-{[5-(3-methyl-5-{[4-(trifluoromethyl)pyrimidin-2-yl]amino}phenyl)pyridin-2-yl]amino}propanimidamide bis-TFA salt (14.0 mg, 0.025 mmol) and CDI (4.26 mg, 0.026 mmol) in dioxane (100 µL). The reaction was stirred at room temperature overnight. The reaction mixture was filtered, diluted with DMF (500 µL), and directly purified by reverse phase HPLC. The isolated material was repurified by silica gel chromatography (0-100% ethyl acetate in hexanes with 1% triethylamine and then 20% methanol in dichloromethane) to yield 3-(2-{[5-(3-methyl-5-{[4-(trifluoromethyl)pyrimidin-2-yl]amino}phenyl)pyridin-2-yl]amino}propan-2-yl)-1,2,4-oxadiazol-5(4H)-one. MS APCI calc'd for $C_{22}H_{21}F_3N_7O_2$ [M+H]$^+$ 472. found 472. $^1$H NMR (500 MHz, CDCl$_3$) δ 8.67 (d, J=5.2 Hz, 1H), 8.34 (s, 1H), 7.79 (d, J=11.5 Hz, 2H), 7.41 (s, 1H), 7.31 (s, 1H), 7.05 (d, J=5.2 Hz, 2H), 6.64 (d, J=9.1 Hz, 1H), 2.43 (s, 3H), 1.80 (s, 6H).

The following example was prepared in an analogous manner to that described in Example 18, Procedure D and general scheme 18.

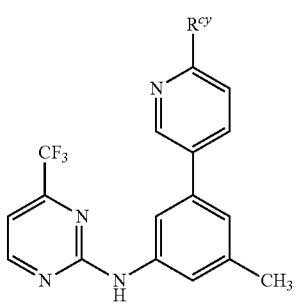

| Ex. | R<sup>cy</sup> | Name | [M + H]+ Calc'd | [M + H]+ Obsv'd | Form(s) |
|---|---|---|---|---|---|
| 18.11 | 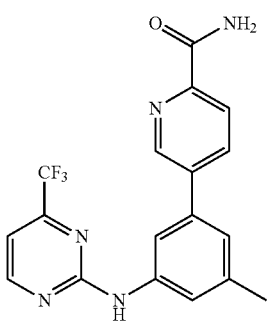 | 3-[5-(3-methyl-5-{[4-(trifluoromethyl)pyrimidin-2-yl]amino}phenyl)pyridin-2-yl]-1,2,4-oxadiazol-5(4H)-one | 415 | 415 | Free Base |

Procedure E

Example 18.12

5-(3-Methyl-5-{[4-(trifluoromethyl)pyrimidin-2-yl]amino}phenyl)pyridine-2-carboxamide

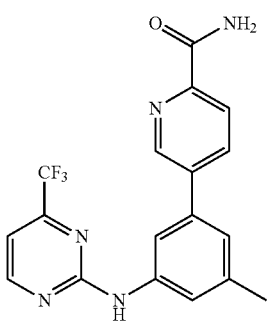

A mixture of with 5-(3-methyl-5-{[4-(trifluoromethyl)pyrimidin-2-yl]amino}phenyl)pyridine-2-carbonitrile (50.0 mg, 0.141 mmol) in DMSO (281 µL) was slowly added to a solution of hydrogen peroxide (10.0 µL, 0.326 mmol) and sodium hydroxide (5 M, 56.3 µL, 0.281 mmol). The reaction was stirred at room temperature overnight. The reaction mixture was filtered, diluted with DMF, and directly purified by reverse phase HPLC (5-95% acetonitrile in water+0.5% TFA) to yield 5-(3-methyl-5-{[4-(trifluoromethyl)pyrimidin-2-yl]amino}phenyl)pyridine-2-carboxamide. MS APCI calc'd for $C_{18}H_{15}F_3N_5O$ [M+H]+ 374. found 374. $^1$H NMR (500 MHz, CDCl$_3$) δ 8.85 (s, 1H), 8.65 (d, J=5.6 Hz, 1H), 8.27 (d, J=8.6 Hz, 1H), 8.09 (d, J=8.5, 1H), 7.98 (s, 1H), 7.39 (s, 1H), 7.19 (s, 1H), 7.09 (d, J=5.5 Hz, 1H), 2.47 (s, 3H).

Example 19

Compounds of Formula (I) Using the General Methods Illustrated in Scheme 19

Example 19.1

1-{Dicyclopropyl[5-(3-methyl-5-{[4-(trifluoromethyl)pyrimidin-2-yl]amino}phenyl)pyridin-2-yl]methyl}urea

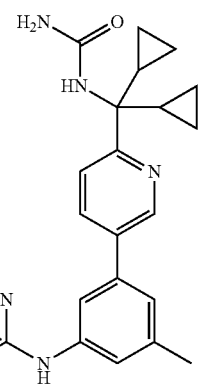

Step 1:

A mixture of tert-butylsulfinamine (6.00 g, 49.5 mmol), dioxane (100 mL), dicyclopropyl ketone (5.94 mL, 52.0 mmol), and titanium ethoxide (20.8 mL, 99.0 mmol) was purged and flushed with Ar(g) and then heated to 105° C. for 24 hours. The reaction was further heated to 123° C. for 24 hours. Upon cooling to room temperature and the reaction mixture was poured into brine (100 mL) and the mixture was vigorously stirred. The reaction mixture was filtered through CELITE, washed 1×100 mL, 1×200 mL, 1×100 mL with ethyl acetate. The layers were separated and the aqueous was re-extracted with 100 mL ethyl acetate. The combined organics were dried over sodium sulfate, filtered, and concentrated under reduced pressure. The residue was purified by chromatography (25-75% ethyl acetate in hexanes) to yield (R)—N-(dicyclopropylmethylidene)-2-methylpropane-2-sulfinamide as a light brown solid. MS APCI calc'd for $C_{11}H_{20}NOS$ [M+H]+ 214. found 214.

Step 2:

Isopropylmagnesium chloride (2 M in THF, 1.843 mL, 3.69 mmol) was added dropwise over 5 minutes to a cooled solution of 5-bromo-2-iodopyridine (0.999 g, 3.52 mmol) in THF (7.00 mL) under Ar(g) at 0° C. and then the reaction mixture was stirred for 1 hour. A solution of (R)—N-(dicyclopropylmethylidene)-2-methylpropane-2-sulfinamide (0.715 g, 3.35 mmol) in THF (3.00 mL) was added via syringe over 4 min at 0° C. to the reaction mixture. The reaction mixture was stirred at 0° C. for 1 hour and was warmed to room temperature. Saturated aqueous NH$_4$Cl (15.0 mL) was added to the reaction and extracted with ethyl acetate (30 mL). The organic layer was washed with saturated aqueous NaHCO$_3$, brine, dried over sodium sulfate, filtered, and concentrated under reduced pressure. The residue was purified by silica gel chromatography (0.5-3% methanol in dichlo-

337 romethane) to yield (R)—N-[(5-bromopyridin-2-yl)(dicyclopropyl)methyl]-2-methylpropane-2-sulfinamide as a yellow oil. MS APCI calc'd for $C_{16}H_{24}BrN_2OS$ [M+H]$^+$ 371 and 373. found 371 and 373.

Step 3:

N-[3-methyl-5-(4,4,5,5-tetramethyl-1,3,2-dioxaborolan-2-yl)phenyl]-4-(trifluoromethyl)pyrimidin-2-amine (300 mg, 0.791 mmol), PdCl$_2$(dppf)-dichloromethane adduct (32.3 mg, 0.040 mmol), and sodium carbonate (2 M, 0.791 mL, 1.58 mmol) were added to a solution of (R)—N-[(5-bromopyridin-2-yl)(dicyclopropyl)methyl]-2-methylpropane-2-sulfinamide (344 mg, 0.926 mmol) in 2-methyl-THF (2.60 mL) and flushed and purged with Ar(g). The reaction mixture was irradiated in a microwave reactor for 5 minutes at 170° C. Upon cooling, the reaction mixture was diluting with saturated aqueous NaHCO$_3$ (10.0 mL) and extracted with ethyl acetate (20.0 mL). The organic layer was washed with brine, dried over sodium sulfate, filtered, concentrated under reduced pressure. The residue was purified by silica gel chromatography (0.5-3% methanol in dichloromethane) to yield (R)—N-{dicyclopropyl[5-(3-methyl-5-{[4-(trifluoromethyl)pyrimidin-2-yl]amino}phenyl)pyridin-2-yl]methyl}-2-methylpropane-2-sulfinamide. MS APCI calc'd for $C_{28}H_{33}F_3N_5OS$ [M+H]$^+$ 544. found 544.

Step 4:

Methanol (5.00 mL) and HCl (4 M in dioxanes, 0.584 mL, 2.34 mmol) were added to (R)—N-{dicyclopropyl[5-(3-methyl-5-{[4-(trifluoromethyl)pyrimidin-2-yl]amino}phenyl)pyridin-2-yl]methyl}-2-methylpropane-2-sulfinamide (317.5 mg, 0.584 mmol) and the reaction mixture was stirred for 25 minutes at room temperature. An additional 150 uL of 4 M HCl in dioxane was added to the reaction mixture, stirred for 45 minutes, diluted with saturated aqueous NaHCO$_3$ (20.0 mL) and extracted with ethyl acetate (30.0 mL). The organic layer was washed with brine, dried over sodium sulfate, filtered, and was concentrated under reduced pressure to yield N-(3-{6-[amino(dicyclopropyl)methyl]pyridin-3-yl}-5-methylphenyl)-4-(trifluoromethyl)pyrimidin-2-amine. MS APCI calc'd for $C_{24}H_{25}F_3N_5$ [M+H]$^+$ 440. found 440.

Step 5:

Potassium cyanate (71.1 mg, 0.876 mmol) was added to a mixture of N-(3-{6-[amino(dicyclopropyl)methyl]pyridin-3-yl}-5-methylphenyl)-4-(trifluoromethyl)pyrimidin-2-amine (257 mg, 0.584 mmol), THF (4.00 mL), acetic acid (0.050 ml, 0.876 mmol), and water (2.00 mL) and the reaction mixture was stirred overnight at room temperature. The reaction mixture was diluted with saturated aqueous NaHCO$_3$ (20.0 mL) and extracted with ethyl acetate (50.0 mL). The organic layer was washed with brine, dried over sodium sulfate, filtered, and concentrated under reduced pressure. The residue was purified by silica gel column chromatography (0-20% methanol in ethyl acetate) and the isolated material was then triturated with ethyl acetate (4.00 mL) and methanol (0.50 mL) to yield 1-{dicyclopropyl[5-(3-methyl-5-{[4-(trifluoromethyl)pyrimidin-2-yl]amino}phenyl)pyridin-2-yl]methyl}urea.
MS APCI calc'd for $C_{25}H_{26}F_3N_6O$ [M+H]$^+$ 483. found 483.
$^1$H NMR (500 MHz, CD$_3$OD) δ11.08 (s, 1H), 9.65 (d, J=5.3 Hz, 1H), 9.49 (d, 1H), 8.74 (s, 1H), 8.68 (d, J=11.2 Hz, 1H), 8.47-8.19 (m, 2H), 8.08 (d, J=5.2 Hz, 1H), 7.98 (s, 1H), 6.87 (s, 1H), 6.24 (s, 2H), 3.16 (s, 4H), 2.26 (s, 2H), 1.26 (d, J=25.7 Hz, 3H), 1.10 (d, J=6.0 Hz, 4H).

Example 20

Compounds of Formula (I) Using the General Methods Illustrated in Scheme

Procedure A

Example 20.1

4-(1,1-Difluoroethyl)-N-[3-methyl-5-(pyridin-3-yl)phenyl]pyrimidin-2-amine

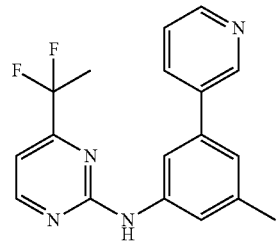

20.1

Step 1:

In 2 L flask outfitted with condenser and stir bar was added 1-bromo-3-methyl-5-nitrobenzene (50.0 g, 231 mmol), ethanol (967 mL), and saturated aqueous NH$_4$Cl (141 mL). The system was evacuated and flushed with N$_2$(g) and then iron (38.8 g, 694 mmol) was added before heating the reaction to reflux for 2 days. The reaction was cooled to room temperature and CELITE (15 g) was added to the flask. This was then filtered through CELITE, washing the cake with ethanol (500 mL) and ethyl acetate (500 mL). The filtrate was concentrated and the solvent was removed. The residue was diluted with ethyl acetate (500 mL) and water (500 mL). After cutting the layers, the organic was washed with saturated aqueous NaHCO$_3$ (400 mL) and then brine (400 mL), before drying over sodium sulfate and concentrating. MTBE (~500 mL) was added to the resultant residue and HCl in dioxane (4 M, 57.9 mL, 231 mmol) was added dropwise at RT over 30 min. The resultant precipitate was collected by filtration. This creme colored solid was placed in a beaker and was dissolved in ethyl acetate and partitioned with saturated aqueous NaHCO$_3$ and then 10% NH$_4$OH (aq). The organic was cut and dried over sodium sulfate before concentrating to dryness. 3-Bromo-5-methylaniline was isolated as a brown oil. MS APCI calc'd for $C_7H_9BrN$ [M+H]$^+$ 186. found 186/188.

Step 2:

To 3-bromo-5-methylaniline (10.0 g, 53.7 mmol) a 250 mL flask was added dioxane (179 mL), bis(pinacolato)diboron (15.0 g, 59.1 mmol), and potassium acetate (8.44 g, 86 mmol). The system was purged and flushed with Ar(g) (3×) before adding Pd(PCy$_3$)$_2$ (0.897 g, 1.34 mmol). The system was purged and flushed with Ar(g) (3×) before sealing the system and heating to 80° C. overnight. The reaction was cooled to room temperature and filtered through CELITE (washed with chloroform) and diluted with water. The organic was extracted, dried over sodium sulfate, and was concentrated to dryness before purification by column chromatography (10-50% ethyl acetate in hexanes) to yield 3-methyl-5-(4,4,5,5-tetramethyl-1,3,2-dioxaborolan-2-yl)aniline. MS APCI calc'd for $C_{13}H_{21}BNO_2$ [M+H]$^+$ 234. found 234.

Step 3:

To 3-methyl-5-(4,4,5,5-tetramethyl-1,3,2-dioxaborolan-2-yl)aniline (0.693 g, 2.97 mmol) was added sodium carbonate (2 M, 2.97 mL, 5.95 mmol), and dioxanes (14.9 mL). The system was purged and flushed with Ar(g) (3×) before adding PdCl$_2$(dppf)-dichloromethane adduct (0.121 g, 0.149 mmol). The system was purged and flushed with Ar(g) (3×) before sealing the system and heating to 80° C. overnight. The reaction was cooled to room temperature and was filtered through CELITE (washed with dichloromethane) and diluted with water. The organic was extracted, dried over sodium sulfate, and was concentrated to dryness before purification by column chromatography (10-40% acetone in hexanes) to yield 3-methyl-5-(pyridin-3-yl)aniline (0.463 g, 2.51 mmol, 85%). MS APCI calc'd for $C_{12}H_{13}N_2$ [M+H]$^+$ 185. found 185.

Step 4:

To 2,4-dichloropyrimidine (1.10 g, 7.38 mmol) in a scintillation vial was added toluene (73.8 mL). The system was purged and flushed with Ar(g) (3×) before adding PdCl$_2$(dppf)-dichloromethane adduct (0.301 g, 0.369 mmol) and commercially available tributyl(1-ethoxyethenyl)stannane (3.74 mL, 11.1 mmol). The system was purged and flushed with Ar(g) (3×) before sealing the system and heating to 80° C. The reaction was complete after 1.5 hours and was cooled to room temperature before being filtered through CELITE (washed with dichloromethane) and diluted with water. The organic was extracted, dried over sodium sulfate, and was concentrated to dryness before purification by column chromatography (5-20% ethyl acetate in hexanes, linear gradient) to yield the ethyl enol ether. The material was subject to hydrolysis with 2 M HCl in MeOH at 50° C. After 2 hours, the reaction was cooled to room temperature and was diluted with saturated aqueous NaHCO$_3$ and dichloromethane. The organic was dried over sodium sulfate and was concentrated to dryness before purification by column chromatography (10-50% acetone in hexanes) to yield 1-(2-chloropyrimidin-4-yl)ethanone as a clear oil. $^1$H NMR (500 MHz, CDCl$_3$) δ 8.86 (d, J=4.9 Hz, 1H), 7.84 (d, J=4.9 Hz, 1H), 2.72 (s, 3H).

Step 5:

To 3-methyl-5-(pyridin-3-yl)aniline (107 mg, 0.578 mmol) in a scintillation vial was added dioxane (2.41 mL), cesium carbonate (314 mg, 0.964 mmol), and 1-(2-chloropyrimidin-4-yl)ethanone (83.0 mg, 0.530 mmol). The system was purged and flushed with Ar(g) (3×) before adding Xantphos (41.8 mg, 0.072 mmol) and Pd(OAc)$_2$ (11.9 mg, 0.053 mmol). The system was purged and flushed Ar(g) (3×) before sealing the system and heating to 100° C. for 2 days. The reaction was cooled to room temperature and was filtered through CELITE (washed with chloroform) and diluted with water. The organic was extracted, dried over sodium sulfate, and was concentrated to dryness before purification by column chromatography (10-40% acetone in hexanes) to 1-(2-{[3-methyl-5-(pyridin-3-yl)phenyl]amino}pyrimidin-4-yl)ethanone. MS APCI calc'd for $C_{18}H_{17}N_4O$ [M+H]$^+$ 305. found 305.

Step 6:

To 1-(2-{[3-methyl-5-(pyridin-3-yl)phenyl]amino}pyrimidin-4-yl)ethanone (100 mg, 0.164 mmol) was added dichloromethane (548 μL), ethanol (0.959 μL, 0.016 mmol) and deoxofluor (91.0 μL, 0.493 mmol). The reaction was stirred at room temperature overnight. The reaction was diluted with water and dichloromethane. The organic was dried over sodium sulfate and concentrated to dryness before purification by column chromatography (10-45% acetone in hexanes) to afford 4-(1,1-difluoroethyl)-N-[3-methyl-5-(pyridin-3-yl)phenyl]pyrimidin-2-amine. MS APCI calc'd for $C_{18}H_{17}F_2N_4$ [M+H]$^+$ 327. found 327. $^1$H NMR (500 MHz, DMSO-d$_6$) δ 10.02 (s, 1H), 8.82 (s, 1H), 8.69 (d, J=4.9 Hz, 1H), 8.55 (d, J=3.6 Hz, 1H), 7.98 (d, J=13.4 Hz, 2H), 7.59 (s, 1H), 7.48 (dd, J=4.7 Hz, 7.8 Hz, 1H), 7.16 (s, 1H), 7.07 (d, J=4.9 Hz, 1H), 2.35 (s, 3H), 2.03-1.90 (m, 3H).

Procedure B

Example 20.2

N-[3-methyl-5-(pyridin-3-yl)phenyl]-4-(piperidin-4-yloxy)pyrimidin-2-amine

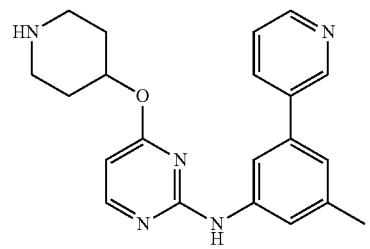

20.2

Step 1:

tert-Butyl 4-hydroxypiperidine-1-carboxylate (500 mg, 2.48 mmol) was added to a suspension of sodium hydride (60%, 149 mg, 3.73 mmol) in THF (8.28 mL) and the mixture was stirred for 30 minutes at room temperature. 2,4-Dichloropyrimidine (333 mg, 2.24 mmol) was added to the reaction mixture at 0° C. and warmed to room temperature over 3 days. The mixture was diluted with ethyl acetate (20.0 mL), and then washed with water:brine 1:1 (3×40 mL). The organic extracts were dried (Na$_2$SO$_4$) and concentrated in vacuo. The residue was purified by silica gel chromatography (10-60% ethyl acetate in hexanes) to yield tert-butyl 4-[(2-chloropyrimidin-4-yl)oxy]piperidine-1-carboxylate. MS APCI calc'd for $C_{14}H_{21}ClN_3O_3$ [M+H]$^+$ 314. found 314.

Step 2, Part A:

3-Methyl-5-(pyridin-3-yl)aniline (50.7 mg, 0.275 mmol) was added a solution of tert-Butyl 4-[(2-chloropyrimidin-4-yl)oxy]piperidine-1-carboxylate (72.0 mg, 0.229 mmol) in dioxane (486 μL). The reaction mixture was flushed and purged with Ar(g) followed by the addition of Pd(OAc)$_2$ (5.15 mg, 0.023 mmol) and Xantphos (19.9 mg, 0.034 mmol). The reaction was heated to 75° C. overnight and then cooled to room temperature. The reaction mixture was diluted with water and extracted with dichloromethane. The organic was dried over sodium sulfate and was concentrated under reduced pressure. The residue was purified by silica gel column chromatography (10% MeOH in DCM:hexanes, 10:90 to 50:50) to yield tert-butyl 4-[(2-{[3-methyl-5-(pyridin-3-yl)phenyl]amino}pyrimidin-4-yl)oxy]piperidine-1-carboxylate.

Step 2, Part B:

TFA deprotection: 1:1 Dichloromethane:TFA (1.00 mL) solution was added to the isolated tert-butyl 4-[(2-{[3-methyl-5-(pyridin-3-yl)phenyl]amino}pyrimidin-4-yl)oxy]piperidine-1-carboxylate at room temperature and stirred for 2 hours. The reaction was concentrated under reduced pressure and the residue was purified by reverse phase chromatography (5-50% acetonitrile in water+0.05% TFA) to yield N-[3-methyl-5-(pyridin-3-yl)phenyl]-4-(piperidin-4-yloxy)pyrimidin-2-amine as a TFA salt. MS APCI calc'd for C$_{21}$H$_{24}$N$_5$O [M+H]$^+$ 362. found 362. $^1$H NMR (500 MHz, DMSO-d$_6$) δ 9.67 (s, 1H), 8.91 (s, 1H), 8.65 (d, J=3.7 Hz, 1H), 8.47 (s, 2H), 8.25 (d, J=5.7 Hz, 1H), 8.19 (d, J=8.0 Hz, 1H), 7.87 (s, 1H), 7.71-7.61 (m, 1H), 7.59 (s, 1H), 7.17 (s, 1H), 6.31 (d, J=5.7 Hz, 1H), 5.24 (s, 1H), 3.19 (s, 2H), 2.97 (s, 2H), 2.36 (s, 2H), 2.09 (s, 3H), 1.90 (s, 2H).

The following example was prepared in an analogous manner to that described in Example 20 and in general scheme 20.

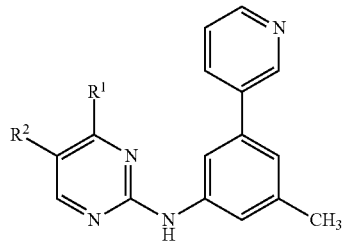

| Ex. | R$^1$ | R$^2$ | Name | [M + H]$^+$ Calc'd | [M + H]$^+$ Obsv'd | Form(s) |
|---|---|---|---|---|---|---|
| 20.3 | —CF$_3$ | —Cl | 5-chloro-N—(3-methyl-5-pyridin-3-ylphenyl)-4-(trifluoromethyl)pyrimidin-2-amine | 365 | 365 | Free Base |

Example 21

Compounds of Formula (I) Using the General Methods Illustrated in Scheme 21

Example 21.1

N-{[5-(3-methyl-5-{[4-(trifluoromethyl)pyrimidin-2-yl]amino}phenyl)pyridin-2-yl]sulfonyl}glycine

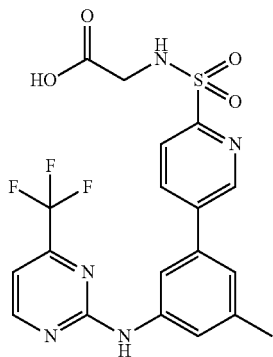

Step 1:

Triethylamine (543 µL, 3.90 mmol) followed by ethyl glycinate (161 mg, 1.56 mmol) were added to a solution of 5-bromopyridine-2-sulfonyl chloride (200 mg, 0.780 mmol) in dichloromethane (2.6 mL) was added. The reaction mixture was stirred at room temperature and was monitored by LCMS. Upon completion, the reaction was diluted with saturated aqueous NH$_4$Cl and the organic layer was dried over sodium sulfate and was concentrated under reduced pressure. The residue was purified by silica gel column chromatography (10% MeOH in DCM:hexanes) to yield ethyl N-[(5-bromopyridin-2-yl)sulfonyl]glycinate. MS APCI calc'd for C$_9$H$_{12}$BrN$_2$O$_4$S [M+H]$^+$ 323 and 325. found 323 and 325.

Step 2:

Ethyl N-[(5-bromopyridin-2-yl)sulfonyl]glycinate (94.0 mg, 0.290 mmol), sodium carbonate (2 M, 264 µL, 0.527 mmol), and dioxane (879 µL) were added to N-[3-methyl-5-(4,4,5,5-tetramethyl-1,3,2-dioxaborolan-2-yl)phenyl]-4-(trifluoromethyl)pyrimidin-2-amine (100 mg, 0.264 mmol). The reaction mixture was purged and flushed with Ar(g) (3×) and then PdCl$_2$(dppf)-dichloromethane adduct (10.8 mg, 0.013 mmol) was added. The system was purged and flushed with Ar(g) (3×) and heated to 85° C. The ethyl ester product was not observed by LCMS, instead, the acid product was observed. The reaction was cooled to room temperature and was concentrated under reduced pressure. The residue was diluted with 1:1 methanol:DMSO and was filtered through a plug of CELITE and florosil and directly purified by reverse phase chromatography (10-95% MeCN in water+0.5% TFA) to yield N-{[5-(3-methyl-5-{[4-(trifluoromethyl)pyrimidin-2-yl]amino}phenyl)pyridin-2-yl]sulfonyl}glycine as the TFA salt. MS APCI calc'd for C$_{19}$H$_{17}$F$_3$N$_5$O$_4$S [M+H]$^+$ 468. found 468. $^1$H NMR (500 MHz, DMSO-d$_6$) δ 10.33 (s, 1H), 8.88 (d, J=45.6 Hz, 2H), 8.37-8.16 (m, 1H), 8.16-7.74 (m, 2H), 7.63 (s, 1H), 7.28 (s, 2H), 3.51 (s, 2H), 2.37 (s, 3H).

The following examples were prepared in an analogous manner to that described in general scheme 21 using commercially available or known amines in step 1.

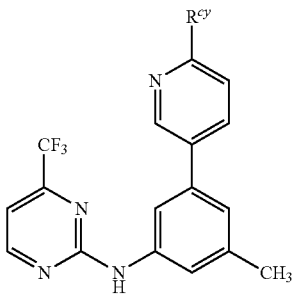

| Ex. | R<sup>ey</sup> | Name | [M + H]<sup>+</sup> Calc'd | [M + H]<sup>+</sup> Obsv'd | Form(s) |
|---|---|---|---|---|---|
| 21.2 | | N-cyclopropyl-5-(3-methyl-5-{[4-(trifluoromethyl)pyrimidin-2-yl]amino}phenyl)pyridine-2-sulfonamide | 450 | 450 | Free Base |
| 21.3 | racemic | 5-(3-methyl-5-{[4-(trifluoromethyl)pyrimidin-2-yl]amino}phenyl)-N-(2-oxopyrrolidin-3-yl)pyridine-2-sulfonamide | 493 | 493 | Free Base |
| 21.4 | | 5-(3-methyl-5-{[4-(trifluoromethyl)pyrimidin-2-yl]amino}phenyl)pyridine-2-sulfonamide | 410 | 410 | TFA Salt |

Example 22

Compounds of Formula (I) Using the General Methods Illustrated in Scheme 22

Example 22.1

Ethyl-3-[5-(3-methyl-5-{[4-(trifluoromethyl)pyrimidin-2-yl]amino}phenyl)pyridin-2-yl]prop-2-enoate

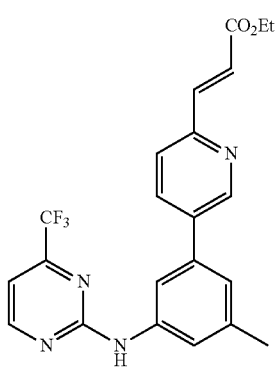

22.1

Step 1:
Ethyl-3-(5-bromopyridin-2-yl)prop-2-enoate

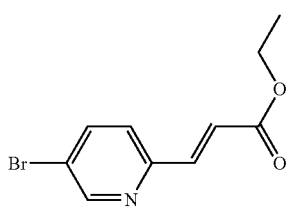

5-Bromopyridine-2-carbaldehyde (502 mg, 2.70 mmol) was added to a solution of ethyl (triphenyl-$\lambda^5$-phosphanylidene)acetate (1570 mg, 4.51 mmol) in DMF (5.00 mL) and the reaction mixture was stirred at room temperature for 40 minutes. The mixture was poured into ice-water, and extracted with ethyl acetate. The organic layer was washed with brine, dried and concentrated under reduced pressure. A mixture of hexane:ethyl acetate (2:1) was added to the crude residue and the insoluble materials were filtered off. The filtrate was concentrated under reduced pressure and purified by silica gel chromatography (4% ethyl acetate in hexanes) to afford ethyl-3-(5-bromopyridin-2-yl)prop-2-enoate MS APCI calc'd for $C_{10}H_{11}BrNO_2$ [M+H]<sup>+</sup> 256 and 258. found 256 and 258.

Step 2:
A mixture of N-[3-methyl-5-(4,4,5,5-tetramethyl-1,3,2-dioxaborolan-2-yl)phenyl]-4-(trifluoromethyl)pyrimidin-2-amine (222 mg, 0.585 mmol), ethyl-3-(5-bromopyridin-2-yl)prop-2-enoate (101 mg, 0.393 mmol), PdCl<sub>2</sub>(dppf) (62.9 mg, 0.086 mmol), sodium carbonate (2 M, 0.40 mL, 0.800 mmol), and dioxane (2.00 mL) was purged and flushed with Ar(g) (3×) and irradiated in a microwave reactor for 10 minutes at 100° C. The reaction mixture was further irradiated with microwave at 150° C. for another 10 minutes. The mixture was filtered, concentrated under reduced pressure and the residue was purified by silica gel chromatography (20% ethyl acetate in hexanes) to afford ethyl-3-[5-(3-methyl-5-{[4-(trifluoromethyl)pyrimidin-2-yl]amino}phenyl)pyridin-2-yl]prop-2-enoate. $C_{22}H_{20}F_3N_4O_2$ [M+H]<sup>+</sup> 429. found 429. <sup>1</sup>H NMR (500 MHz, CDCl<sub>3</sub>) δ 8.89 (d, J=2.1 Hz, 1H), 8.64 (d, J=4.9 Hz, 1H), 7.93-7.85 (m, 2H), 7.73 (d, J=15.7 Hz, 1H), 7.64 (s, 1H), 7.48 (d, J=8.1 Hz, 1H), 7.36 (s, 1H), 7.13 (s, 1H), 7.03 (d, J=4.9 Hz, 1H), 6.94 (d, J=1 Hz, 1H), 4.28 (q, J=7.1 Hz, 2H), 2.42 (s, 3H), 1.34 (t, J=7.1 Hz, 3H).

Example 22.2

3-[5-(3-Methyl-5-{[4-(trifluoromethyl)pyrimidin-2-yl]amino}phenyl)pyridin-2-yl]prop-2-enoic acid

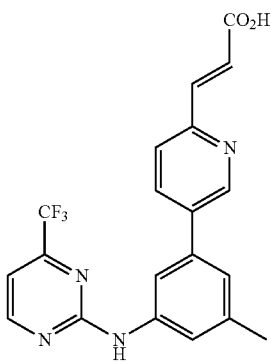

22.2

A mixture of ethyl-3-[5-(3-methyl-5-{[4-(trifluoromethyl)pyrimidin-2-yl]amino}phenyl)pyridin-2-yl]prop-2-enoate (28.0 mg, 0.065 mmol), sodium hydroxide (0.350 mL, 0.350 mmol), THF (0.50 mL) and methanol (0.50 mL) was heated at 50° C. for 2 hours. The reaction was cooled to room temperature and was directly purified by reverse phase HPLC afforded the product as a TFA salt. After basic extraction, 3-[5-(3-methyl-5-{[4-(trifluoromethyl)pyrimidin-2-yl]amino}phenyl)pyridin-2-yl]prop-2-enoic acid was isolated as free base. $C_{20}H_{16}F_3N_4O_2$ [M+H]$^+$ 401. found 401. $^1$H NMR (500 MHz, DMSO-d$_6$) δ 10.27 (s, 1H), 8.98-8.68 (m, 2H), 8.15-7.84 (m, 2H), 7.73-7.59 (m, 1H), 7.59-7.45 (m, 1H), 7.27 (d, J=5.0 Hz, 1H), 7.23 (s, 1H), 6.74 (d, 1H), 2.36 (s, 3H).

Example 22.3

2,2-Dimethyl-3-[5-(3-methyl-5-{[4-(trifluoromethyl)pyrimidin-2-yl]amino}phenyl)pyridin-2-yl]propanic acid

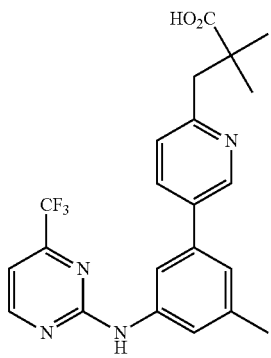

22.3

Step 1:
Pd/C (10.0 mg, 9.40 mol) was added to a solution of ethyl-3-[5-(3-methyl-5-{[4-(trifluoromethyl)pyrimidin-2-yl]amino}phenyl)pyridin-2-yl]prop-2-enoate (96.0 mg, 0.224 mmol) in MeOH (2.00 mL) and THF (1.00 mL). One drop of TFA was added to the reaction mixture and was purged and flushed with argon (3x). The reaction mixture was stirred for 4 hours at room temperature under an atmosphere of hydrogen. The mixture was filtered through CELITE and concentrated under reduced pressure. The residue was purified by silica gel chromatography (3:7 ethyl acetate in hexanes) to afford ethyl 3-[5-(3-methyl-5-{[4-(trifluoromethyl)pyrimidin-2-yl]amino}phenyl)pyridin-2-yl]propanoate. $C_{22}H_{22}F_3N_4O_2$ [M+H]431. found 431.

Step 2:
To a solution of ethyl 3-[5-(3-methyl-5-{[4-(trifluoromethyl)pyrimidin-2-yl]amino}phenyl)pyridin-2-yl]propanoate (59.0 mg, 0.137 mmol) in THF (1.00 mL) at −78° C. was added LDA (2 M, 0.240 mL, 0.480 mmol). The resulting mixture was stirred at −78° C. for 40 minutes, followed by addition of methyliodide (25.0 µL, 0.400 mmol). After 1.5 hours, an additional LDA (2 M, 0.240 mL, 0.480 mmol) was added and the solution was aged for 1 hour and another portion of methyliodide (25.0 µL, 0.400 mmol) was added. Then the mixture was stirred for another 1 hour. The mixture was quenched with saturated aqueous NH$_4$Cl and was extracted with ethyl acetate. The organic phase was concentrated and purified on silica gel (3:7 ethyl acetate:hexanes) to afford ethyl 2,2-dimethyl-3-[5-(3-methyl-5-{[4-(trifluoromethyl)pyrimidin-2-yl]amino}phenyl)pyridin-2-yl]propanoate. $C_{24}H_{26}F_3N_4O_2$ [M+H]459. found 459.

Step 3:
1 M NaOH (0.230 mL, 0.230 mmol) and MeOH (0.400 mL) were added to a solution of ethyl 2,2-dimethyl-3-[5-(3-methyl-5-{[4-(trifluoromethyl)pyrimidin-2-yl]amino}phenyl)pyridin-2-yl]propanoate (20.7 mg, 0.045 mmol) in THF (0.50 mL) and the reaction mixture was heated to 50° C. for 2 hours. The reaction was cooled to room temperature, concentrated under reduced pressure and the residue was directly purified by reverse phase HPLC to afford 2,2-dimethyl-3-[5-(3-methyl-5-{[4-(trifluoromethyl)pyrimidin-2-yl]amino}phenyl)pyridin-2-yl]propanic acid as a TFA salt. $C_{22}H_{22}F_3N_4O_2$ [M+H]$^+$ 431. found 431. $^1$H NMR (500 MHz, DMSO-d$_6$) δ 10.28 (s, 1H), 8.83 (d, J=4.9 Hz, 1H), 8.79 (s, 1H), 8.17-8.04 (m, 1H), 7.95 (s, 1H), 7.57 (s, 1H), 7.44 (d, 1H), 7.27 (d, J=4.9 Hz, 1H), 7.22 (s, 1H), 3.05 (s, 2H), 2.36 (s, 3H), 1.14 (s, 6H).

Example 23

Compounds of Formula (I) Using the General Methods Illustrated in Scheme 23

Example 23.1

3-Hydroxy-2,2-dimethyl-3-[5-(3-methyl-5-{[4-(trifluoromethyl)pyrimidin-2-yl]amino}phenyl)pyridin-2-yl]propanoic acid

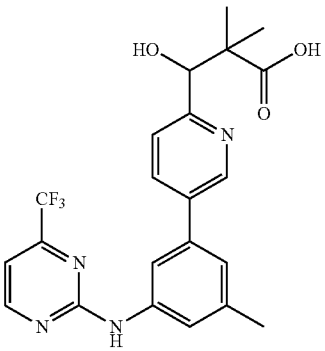

23.1

Step 1:

A mixture of 5-bromopyridine-2-carbaldehyde (500 mg, 2.69 mmol), N-[3-methyl-5-(4,4,5,5-tetramethyl-1,3,2-dioxaborolan-2-yl)phenyl]-4-(trifluoromethyl)pyrimidin-2-amine (1.23 g, 3.24 mmol), PdCl$_2$(dppf) (216 mg, 0.295 mmol), sodium carbonate (2 M, 2.70 mL, 5.40 mmol), and dioxane (10.0 mL) was evacuated and purged with Ar(g) (3×), and then irradiated under microwave at 100° C. for 10 minutes. The mixture was filtered, diluted with ethyl acetate and washed with water. The organic layer was concentrated under reduced pressure and the residue was purified by silica gel chromatography (25% ethyl acetate in hexanes) to afford 5-(3-methyl-5-{[4-(trifluoromethyl)pyrimidin-2-yl]amino}phenyl)pyridine-2-carbaldehyde. C$_{18}$H$_{14}$F$_3$N$_4$O [M+H]$^+$ 359. found 359.

Step 2:

5-(3-Methyl-5-{[4-(trifluoromethyl)pyrimidin-2-yl]amino}phenyl)pyridine-2-carbaldehyde (201 mg, 0.561 mmol) and methyl trimethylsilyl dimethylketene acetal (0.170 mL, 0.839 mmol) were added to a stirred solution of 1-methylimidazole (5.00 mg, 0.061 mmol) and anhydrous lithium chloride (5.00 mg, 0.118 mmol) in DMF (2.50 mL) at room temperature. The reaction mixture was stirred overnight, quenched with aqueous 1N HCl and extracted with ethyl acetate. The organic layer was washed with saturated aqueous NaHCO$_3$ and brine, dried over sodium sulfate and concentrated under reduced pressure. The residue was purified by silica gel chromatography (2:3 ethyl acetate:hexanes) to afford 5-(3-methyl-5-{[4-(trifluoromethyl)pyrimidin-2-yl]amino}phenyl)pyridine-2-carbaldehyde. MS APCI C$_{23}$H$_{24}$F$_3$N$_4$O$_3$ [M+H]$^+$ 461. found 461. $^1$H NMR (500 MHz, DMSO-d$_6$) δ 10.26 (s, 1H), 8.83 (d, J=5.3 Hz, 1H), 8.69 (d, J=3.0 Hz, 1H), 8.03-7.93 (m, 2H), 7.57-7.47 (m, 2H), 7.27 (d, J=5.0 Hz, 1H), 7.20 (s, 1H), 5.77 (s, 1H), 4.88 (s, 1H), 3.60 (s, 3H), 2.35 (s, 3H), 1.11 (s, 3H), 0.94 (s, 3H).

Step 3:

Sodium hydroxide (1 M, 0.65 mL) and methanol (0.800 mL) were added to a solution of 5-(3-methyl-5-{[4-(trifluoromethyl)pyrimidin-2-yl]amino}phenyl)pyridine-2-carbaldehyde (60.0 mg, 0.130 mmol) in THF (1.00 mL) and the mixture was stirred at room temperature for 2 hours. The mixture was directly purified on reverse phase HPLC to afford 3-hydroxy-2,2-dimethyl-3-[5-(3-methyl-5-{[4-(trifluoromethyl)pyrimidin-2-yl]amino}phenyl)pyridin-2-yl]propanoic acid as a TFA salt. MS APCI C$_{22}$H$_{22}$F$_3$N$_4$O$_3$ [M+H]447. found 447. $^1$H NMR (500 MHz, DMSO-d$_6$) δ 10.29 (s, 1H), 8.83 (d, J=5.2 Hz, 1H), 8.75 (d, J=2.6 Hz, 1H), 8.21 (d, J=7.5 Hz, 1H), 7.97 (s, 1H), 7.69 (d, J=8.0 Hz, 1H), 7.58 (s, 1H), 7.27 (d, J=5.1 Hz, 1H), 7.24 (s, 1H), 5.01 (s, 1H), 2.36 (s, 3H), 1.05 (s, 3H), 0.99 (s, 3H).

Example 24

Compounds of Formula (I) Using the General Methods Illustrated in Scheme 24

Example 24.1

Ethyl 2,2-difluoro-3-hydroxy-3-[5-(3-methyl-5-{[4-(trifluoromethyl)pyrimidin-2-yl]amino}phenyl)pyridin-2-yl]propanoate

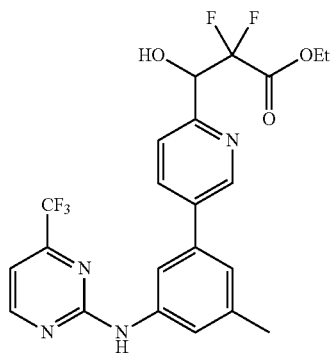

24.1

A flask fitted with a stirring bar was charged with zinc (64.9 mg, 0.992 mmol) and anhydrous THF (5.00 mL) under a nitrogen atmosphere. Then, a solution of 5-(3-methyl-5-{[4-(trifluoromethyl)pyrimidin-2-yl]amino}phenyl)pyridine-2-carbaldehyde (250 mg, 0.698 mmol) in THF (5.00 mL) was added to the flask and the mixture was brought to reflux. Ethyl bromodifluoroacetate (135 μL, 1.048 mmol) was slowly added via syringe to the reaction mixture and refluxed for 1 hour. The reaction mixture was cooled to room temperature, quenched by the addition of saturated aqueous sodium thiosulfate (3.00 mL) and extracted with ethyl acetate. The organic layer was washed with brine, dried over sodium sulfate, filtered and concentrated under reduced pressure. The residue was purified by silica gel chromatography (3:7 ethyl acetate:hexanes) to afford ethyl 2,2-difluoro-3-hydroxy-3-[5-(3-methyl-5-{[4-(trifluoromethyl)pyrimidin-2-yl]amino}phenyl)pyridin-2-yl]propanoate. MS APCI C$_{22}$H$_{20}$F$_5$N$_4$O$_3$ [M+H]$^+$ 483. found 483. $^1$H NMR (500 MHz, CDCl$_3$) δ 8.84 (d, J=1.7 Hz, 1H), 8.66 (d, J=4.8 Hz, 1H), 7.98 (dd, J=2.2 Hz, 8.1 Hz, 1H), 7.89 (s, 1H), 7.52 (d, J=9.1 Hz, 2H), 7.38 (s, 1H), 7.14 (s, 1H), 7.06 (d, J=4.9 Hz, 1H), 5.26 (dd, J=4.9 Hz, 17.5 Hz, 1H), 4.47-4.29 (m, 2H), 2.45 (s, 3H), 1.36 (t, J=7.1 Hz, 3H).

Example 24.2

2,2-Difluoro-3-hydroxy-3-[5-(3-methyl-5-{[4-(trifluoromethyl)pyrimidin-2-yl]amino}phenyl)pyridin-2-yl]propanoic acid

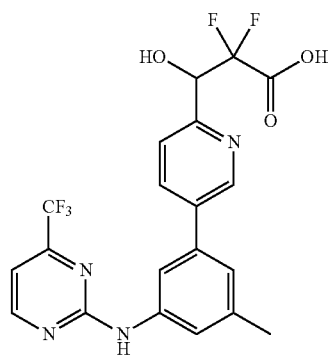

Sodium hydroxide (1 M, 0.190 mL, 0.190 mmol) and methanol (0.300 mL) were added to a solution of ethyl 2,2-difluoro-3-hydroxy-3-[5-(3-methyl-5-{[4-(trifluoromethyl)pyrimidin-2-yl]amino}phenyl)pyridin-2-yl]propanoate (17.8 mg, 0.037 mmol) in THF (0.500 mL). The mixture was stirred at 40° C. for 2 hours and then cooled to room temperature and the crude reaction mixture was directly purified by reverse phase HPLC to afford 2,2-difluoro-3-hydroxy-3-[5-(3-methyl-5-{[4-(trifluoromethyl)pyrimidin-2-yl]amino}phenyl)pyridin-2-yl]propanoic acid. MS APCI $C_{20}H_{16}F_5N_4O_3$ [M+H]455. found 455.0. $^1$H NMR (500 MHz, DMSO-$d_6$)) δ10.28 (s, 1H), 8.83 (d, J=5.3 Hz, 1H), 8.74 (d, J=2.2 Hz, 1H), 8.08 (d, J=11.1 Hz, 1H), 7.96 (s, 1H), 7.66 (d, J=8.7 Hz, 1H), 7.58 (s, 1H), 7.27 (d, J=5.2 Hz, 1H), 7.21 (s, 1H), 5.17 (t, J=12.7 Hz, 1H), 2.36 (s, 3H).

Examples 24.3 and 24.4

2,2-Difluoro-3-[5-(3-methyl-5-{[4-(trifluoromethyl)pyrimidin-2-yl]amino}phenyl)pyridin-2-yl]propanoic acid (24.3) and (2E)-2-Fluoro-3-[5-(3-methyl-5-{[4-(trifluoromethyl)pyrimidin-2-yl]amino}phenyl)pyridin-2-yl]prop-2-enoic acid (24.4)

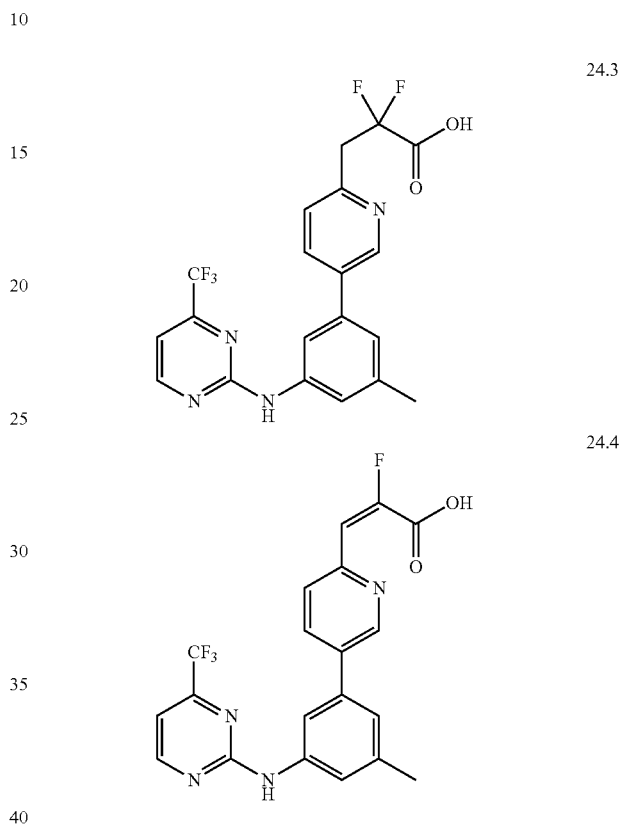

Step 1:

A solution of ethyl 2,2-difluoro-3-hydroxy-3-[5-(3-methyl-5-{[4-(trifluoromethyl)pyrimidin-2-yl]amino}phenyl)pyridin-2-yl]propanoate (86.9 mg, 0.180 mmol), anhydrous DMF (1.00 mL), DBU (0.170 mL, 1.13 mmol) and CS$_2$ (0.110 mL, 1.83 mmol) was stirred at room temperature for 1 hour under Ar(g). Methyliodide (0.110 mL, 1.76 mmol) was added to the reaction mixture and t stirred for 45 minutes at room temperature. The mixture was diluted with water and extracted with ethyl acetate. The organic layer was concentrated under reduced pressure and the residue was purified by silica gel chromatography (20% ethyl acetate in hexanes) to afford ethyl 2,2-difluoro-3-{[(methylsulfanyl)carbonothioyl]oxy}-3-[5-(3-methyl-5-{[4-(trifluoromethyl)pyrimidin-2-yl]amino}phenyl)pyridin-2-yl]propanoate. MS APCI $C_{24}H_{22}F_5N_4O_3S_2$ [M+H]$^+$ 573. found 573.

Step 2:

A mixture of ethyl 2,2-difluoro-3-{[(methylsulfanyl)carbonothioyl]oxy}-3-[5-(3-methyl-5-{[4-(trifluoromethyl)pyrimidin-2-yl]amino}phenyl)pyridin-2-yl]propanoate (68.5 mg, 0.120 mmol), anhydrous dioxane (5.00 mL), diphenylphosphine oxide (25.6 mg, 0.127 mmol) and di-tert-butyl peroxide (10.0 μL, 0.054 mmol) was heated to reflux for 6 hours under Ar(g). The reaction mixture was concentrate under reduced pressure and the residue was purified by reverse phase HPLC to afford ethyl 2,2-difluoro-3-[5-(3-methyl-5-{[4-(trifluoromethyl)pyrimidin-2-yl]amino}phenyl)pyridin-2-yl]propanoate. MS APCI $C_{22}H_{20}F_5N_4O_2$ [M+H]$^+$ 467. found 467.

Step 3:

Sodium hydroxide (1 M, 0.400 mL, 0.400 mmol) was added to a solution of ethyl 2,2-difluoro-3-[5-(3-methyl-5-{[4-(trifluoromethyl)pyrimidin-2-yl]amino}phenyl)pyridin-2-yl]propanoate (23.0 mg, 0.049 mmol) in THF (0.500 mL) and methanol (0.300 mL). The mixture was heated at 50° C. for 1.5 hours. The reaction mixture was concentrated under reduced pressure and the residue was directly purified by reverse phase chromatography to afford:

2,2-Difluoro-3-[5-(3-methyl-5-{[4-(trifluoromethyl)pyrimidin-2-yl]amino}phenyl)pyridin-2-yl]propanoic acid. MS APCI $C_{20}H_{16}F_5N_4O_2$ [M+H]$^+$ 439. found 439. $^1$H NMR (500 MHz, DMSO-$d_6$) δ 10.28 (s, 1H), 8.83 (d, J=4.5 Hz, 1H), 8.74 (s, 1H), 8.00 (d, J=7.0 Hz, 1H), 7.95 (s, 1H), 7.57 (s, 1H), 7.47 (d, J=7.5 Hz, 1H), 7.27 (d, J=4.0 Hz, 1H), 7.20 (s, 1H), 3.67 (t, J=16.2 Hz, 2H), 2.36 (s, 3H); and (2E)-2-Fluoro-3-[5-(3-methyl-5-{[4-(trifluoromethyl)pyrimidin-2-yl]amino}phenyl)pyridin-2-yl]prop-2-enoic acid. MS APCI $C_{20}H_{15}F_4N_4O_2$ [M+H]419. found 419. $^1$H NMR (500 MHz, DMSO-$d_6$) δ 10.30 (s, 1H), 8.93 (d, J=3.2 Hz, 1H), 8.83 (d, J=5.2 Hz, 1H), 8.19-8.08 (m, 1H), 8.02 (s, 1H), 7.91 (d, J=9.0 Hz, 1H), 7.58 (s, 1H), 7.37-7.16 (m, 2H), 7.03 (d, J=35.3 Hz, 1H), 2.37 (s, 3H).

Example 25

Compounds of Formula (I) Using the General Methods Illustrated in Scheme 25

Example 25.1

Methyl {4-[5-(3-methyl-5-{[4-(trifluoromethyl)pyrimidin-2-yl]amino}phenyl)pyridin-2-yl]-1H-1,2,3-triazol-1-yl}acetate

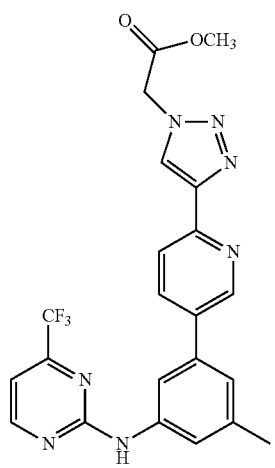

Step 1:

Dimethyl (1-diazo-2-oxopropyl)phosphonate (0.200 mL, 1.15 mmol) was added to a solution of 5-(3-methyl-5-{[4-(trifluoromethyl)pyrimidin-2-yl]amino}phenyl)pyridine-2-carbaldehyde (201 mg, 0.560 mmol) and potassium carbonate (155 mg, 1.12 mmol) in dry methanol (8.00 mL). The mixture was stirred at room temperature for 2 hours. The mixture was diluted with water and extracted with ethyl acetate. The organic layer was concentrated under reduced pressure and the residue was directly purified by reverse phase HPLC to yield N-[3-(6-ethynylpyridin-3-yl)-5-methylphenyl]-4-(trifluoromethyl)pyrimidin-2-amine as a TFA salt. MS APCI $C_{19}H_{14}F_3N_4$ [M+H]$^+$ 355. found 355.

Step 2:

A mixture of methyl azidoacetate (160 mg, 0.452 mmol), sodium 2-(1,2-dihydroxyethyl)-4-hydroxy-5-oxo-2,5-dihydrofuran-3-olate (130 mg, 0.656 mmol), copper sulfate (0.100 mL, 0.100 mmol) in ethanol (2.00 mL) and water (0.500 mL) was added to a solution of N-[3-(6-ethynylpyridin-3-yl)-5-methylphenyl]-4-(trifluoromethyl)pyrimidin-2-amine (100 mg, 0.869 mmol) in DMF (0.500 mL). The mixture was stirred at room temperature for 1 hour. The mixture was diluted with water and extracted with ethyl acetate. The organic layer was concentrated under reduced pressure and the residue was purified by silica gel chromatography (50% ethyl acetate in hexanes) to afford methyl {4-[5-(3-methyl-5-{[4-(trifluoromethyl)pyrimidin-2-yl]amino}phenyl)pyridin-2-yl]-1H-1,2,3-triazol-1-yl}acetate. MS APCI $C_{22}H_{19}F_3N_7O_2$ [M+H]$^+$ 470. found 470. $^1$H NMR (500 MHz, DMSO-$d_6$) δ 10.29 (s, 1H), 8.89-8.86 (m, 1H), 8.84 (d, J=5.1 Hz, 1H), 8.66 (s, 2H), 8.05-7.98 (m, 1H), 7.58 (s, 1H), 7.28 (d, J=5.1 Hz, 1H), 7.26 (s, 1H), 5.50 (s, 2H), 3.72 (d, J=14.9 Hz, 3H), 2.37 (s, 3H).

Example 25.2

{4-[5-(3-Methyl-5-{[4-(trifluoromethyl)pyrimidin-2-yl]amino}phenyl)pyridin-2-yl]-1H-1,2,3-triazol-1-yl}acetic acid

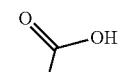
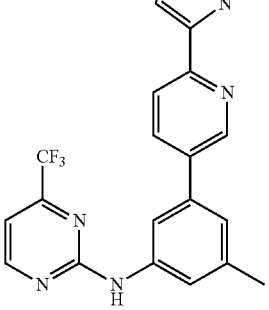

Sodium hydroxide (1 M, 0.55 mL, 0.550 mmol) and methanol (1.5 mL) was added to a solution of methyl {4-[5-(3-methyl-5-{[4-(trifluoromethyl)pyrimidin-2-yl]amino}phenyl)pyridin-2-yl]-1H-1,2,3-triazol-1-yl}acetate (55.0 mg, 0.094 mmol) in THF (1.5 mL). The mixture was stirred at room temperature for 3 hours and then directly purified by reverse phase HPLC to afford {4-[5-(3-methyl-5-{[4-(trifluoromethyl)pyrimidin-2-yl]amino}phenyl)pyridin-2-yl]-1H-1,2,3-triazol-1-yl}acetic acid as a TFA salt. MS APCI $C_{21}H_{17}F_3N_7O_2$ [M+H]456. found 456. $^1$H NMR (500

MHz, DMSO-d$_6$) δ 10.28 (s, 1H), 8.85 (d, J=17.2 Hz, 2H), 8.63 (s, 1H), 8.12 (s, 2H), 8.02 (s, 1H), 7.57 (s, 1H), 7.27 (d, J=13.2 Hz, 2H), 5.36 (s, 2H), 2.37 (s, 3H).

Example 26

Compounds of Formula (I) Using the General Methods Illustrated in Scheme 26

Example 26.1

3-[6-(1-Hydroxyethyl)pyridin-3-yl]-5-{[4-(trifluoromethyl)pyrimidin-2-yl]amino}benzoic acid

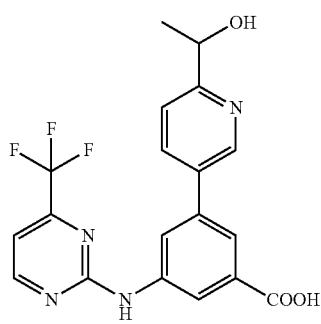

26.1

Step 1:

3-Amino-5-(dihydroxyboranyl)benzoic acid (205 mg, 1.13 mmol) was added to a solution of 2-chloro-4-(trifluoromethyl)pyrimidine (203 mg, 1.11 mmol) in dioxane (3.00 mL). Methanesulfonic acid (70.0 µL, 1.08 mmol) was added to the reaction mixture and heated to reflux at 110° C. overnight. The reaction mixture was cooled to room temperature and the crude mixture was directly purified by reverse HPLC to afford 3-(dihydroxyboranyl)-5-{[4-(trifluoromethyl)pyrimidin-2-yl]amino}benzoic acid. MS APCI C$_{12}$H$_{10}$BF$_3$N$_3$O$_4$ [M+H]328. found 328.

Step 2:

A mixture of 1-(5-bromopyridin-2-yl)ethanol (40.3 mg, 0.199 mmol), 3-(dihydroxyboranyl)-5-{[4-(trifluoromethyl)pyrimidin-2-yl]amino}benzoic acid (31.8 mg, 0.072 mmol), PdCl$_2$(dppf) (11.9 mg, 0.016 mmol), sodium carbonate (2 M, 0.15 mL, 0.300 mmol) and DMF (2 mL) was flushed and purged with Ar(g) (3×) and irradiated in a microwave reactor for 15 minutes at 120° C. The mixture was filtered and was directly purified by reverse phase HPLC to afford 3-[6-(1-hydroxyethyl)pyridin-3-yl]-5-{[4-(trifluoromethyl)pyrimidin-2-yl]amino}benzoic acid (26.7 mg, 0.052 mmol, 71.4%). MS APCI C$_{19}$H$_{16}$F$_3$N$_4$O$_3$ [M+H]$^+$ 405. found 405. $^1$H NMR (500 MHz, DMSO-d$_6$) δ13.1 (s, 1H), 10.54 (s, 1H), 8.88 (d, J=5.1 Hz, 1H), 8.77 (s, 1H), 8.38 (d, J=7.9 Hz, 2H), 8.15 (d, J=8.0 Hz, 1H), 7.86 (s, 1H), 7.68 (d, J=8.0 Hz, 1H), 7.34 (d, J=5.1 Hz, 1H), 4.82 (q, J=6.0 Hz, 1H), 1.41 (d, J=6.0 Hz, 3H).

Example 27

Compounds of Formula (I) Using the General Methods Illustrated in Scheme 27

The description provided in Example 27 is a prophetic example.

Procedure A

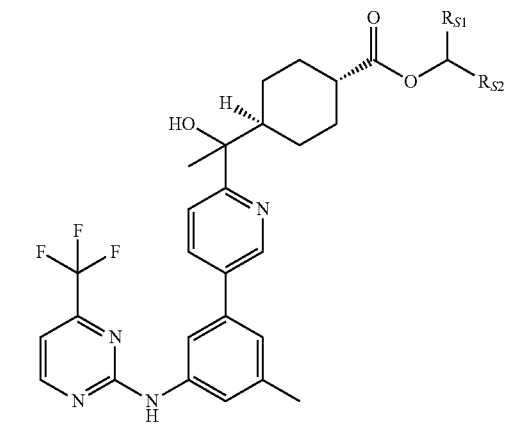

This general procedure describes the procedure for conversion of (A1) to (A) as shown in Scheme 27. To a mixture of (A1) (1 mmol), 1° or 2° alcohol (5 mmol), and triphenylphosphine (resin-bound, 1.6 mmol/g loading, 2 mmol) in tetrahydrofuran is added di-tert butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3×). The filtrate is concentrated under reduced pressure to afford the crude residue as a TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by silica gel chromatography to afford the product residue. The residue is lyophilized from acetonitrile and water to afford a compound of structural subtype (A).

The following compounds could be prepared using procedures which are analogous to those described in Example 27, Procedure A.

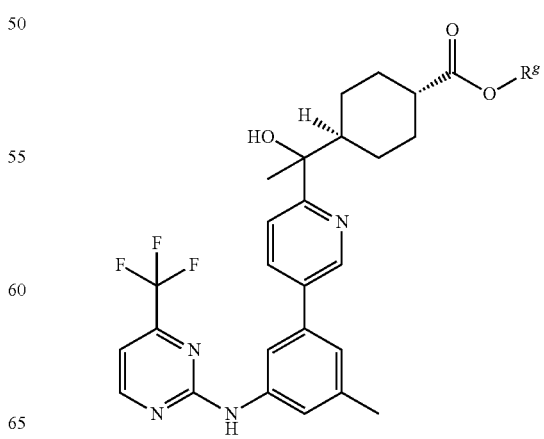

| Ex. | R<sup>g</sup> |
|---|---|
| 27.1 | |
| 27.2 | |
| 27.3 | |
| 27.4 | |
| 27.5 | |
| 27.6 | |
| 27.7 | |
| 27.8 | |
| 27.9 | |
| 27.10 | |
| 27.11 | |
| 27.12 | |
| 27.13 | |
| 27.14 | |

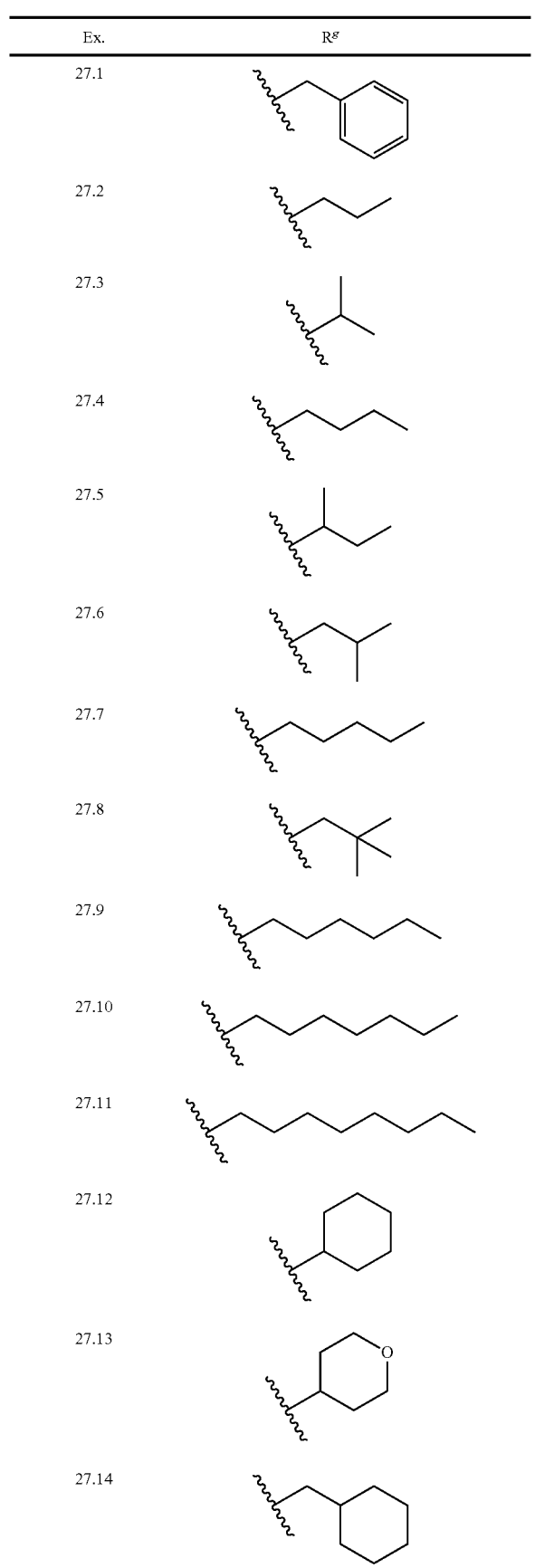

-continued

| Ex. | R<sup>g</sup> |
|---|---|
| 27.15 | |
| 27.16 | |
| 27.17 | |
| 27.18 | |
| 27.19 | |
| 27.20 | |
| 27.21 | |

Procedure B

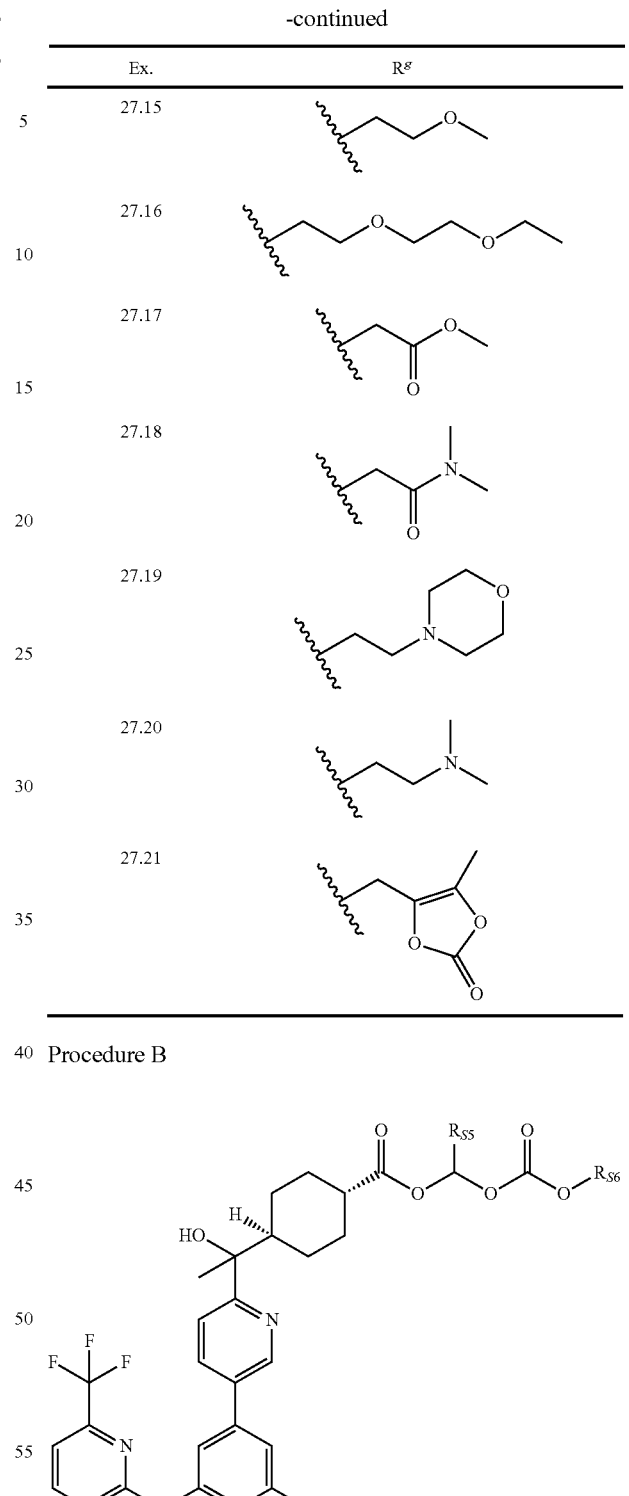

This general procedure describes the procedure for conversion of (A1) to (C) as shown in Scheme 27. A mixture of compound of formula (A1) (1.0 mmol), potassium carbonate (2.0 mmol), and sodium iodide (0.50 mmol) in DMF is stirred at 20° C. After 30 minutes, alkyl halide (C1) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography to afford the product residue. The residue is lyophilized from acetonitrile and water to afford a compound of formula (C).

The following compounds could be prepared according to procedures which were analogous to those described in Example 27, Procedure B.

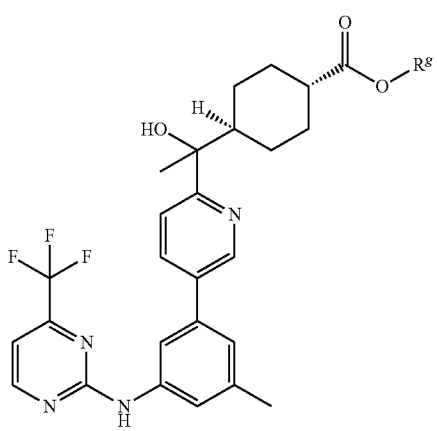

| Ex. | $R^g$ |
|---|---|
| 27.22 | |
| 27.23 | |
| 27.24 | |
| 27.25 | |

Procedure C

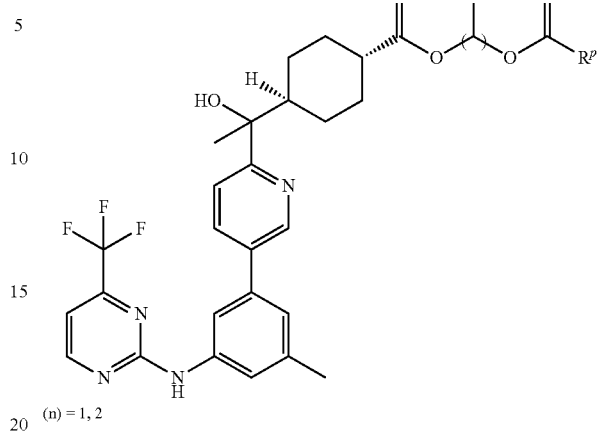

(n) = 1, 2

This general procedure describes the procedure for conversion of (A1) to (B) as shown in Scheme 27. To a solution of (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by silica gel chromatography (ethyl acetate/hexanes, linear gradient) to afford the product residue. The residue is lyophilized from acetonitrile and water to afford (B).

The following compounds could be prepared according to procedures which were analogous to those described in Example 27, Procedure C.

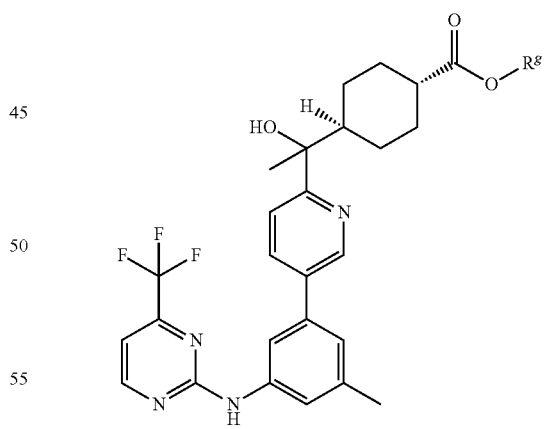

| Ex. | $R^g$ |
|---|---|
| 27.26 |  |

-continued

| Ex. | R$^g$ |
|---|---|
| 27.27 | ![structure](isopropyl acetate ester) |
| 27.28 | ![structure](isopropyl isobutyrate ester) |
| 27.29 | |

Example 28

Compounds of Formula (I) Using the General Methods Illustrated in Scheme 28

The description provided in Example 28 is a prophetic example.

Example 28.1

Methyl trans-4-(1R or 1S)-1-hydroxy-1-[5-(3-methyl-5-{[4-(trifluoromethyl)pyrimidin-2-yl]amino}phenyl)pyridine-2-yl]ethyl)cyclohexanecarboxylate

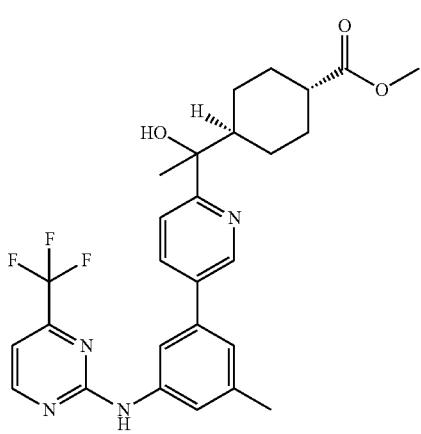

28.1

This general procedure describes the procedure for conversion of (A1) to (D) as shown in Scheme 28. To a suspension of compound of formula (A1) (1.0 mmol) in 1:1 methanol:dichloromethane is added trimethylsilyldiazomethane (2.0 M in diethyl ether, 1.0 mmol) at 0° C. The reaction mixture is stirred at 0° C. until all gas evolution ceases. The reaction mixture is allowed to warm to ambient temperature and quenched by the addition of several drops of acetic acid. The reaction mixture is concentrated under reduced pressure and the residue is purified by silica gel chromatography to afford the product residue. The residue is lyophilized from acetonitrile and water to afford methyl trans-4-(1R or 1S)-1-hydroxy-1-[5-(3-methyl-5-{[4-(trifluoromethyl)pyrimidin-2-yl]amino}phenyl)pyridine-2-yl]ethyl)cyclohexanecarboxylate.

Example 29

The description provided in Example 29 is a prophetic example.

Example 29.1

2-Hydroxyethyl trans-4-(1R or 1S)-1-hydroxy-1-[5-(3-methyl-5-{[4-(trifluoromethyl)pyrimidin-2-yl]amino}phenyl)pyridine-2-yl]ethyl)cyclohexanecarboxylate

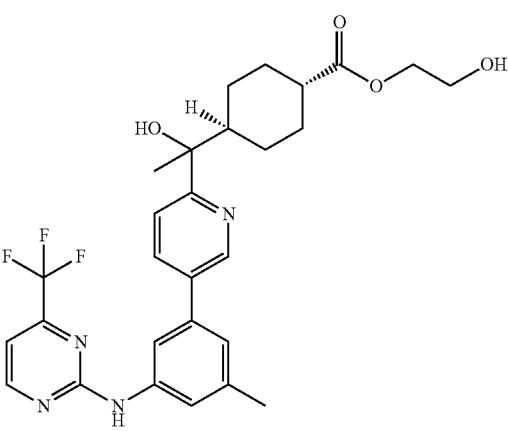

29.1

A mixture of compounds of formula (A1) (1.0 mmol), potassium carbonate (6.0 mmol) and sodium iodide (1.0 mmol) in DMF is stirred for 10 minutes at ambient temperature. To this mixture is added 2-chloroethanol (4.0 mmol) and the reaction mixture is heated at 60° C. for 16 hours. After 16 hours, additional 2-chloroethanol (1.0 mmol) is added and the reaction mixture is heated to 65° C. for an additional 2 hours. The reaction mixture is then diluted with ethyl acetate and washed sequentially with water (3×), aqueous sodium carbonate solution (2×), additional water (3×), and brine (2×). The organic layer is dried over magnesium sulfate, filtered, and concentrated under reduced pressure to afford the crude product residue. The residue was purified by silica gel chromatography in dichloromethane], linear gradient) to afford 2-hydroxyethyl trans-4-(1R or 1S)-1-hydroxy-1-[5-(3-methyl-5-{[4-(trifluoromethyl)pyrimidin-2-yl]amino}phenyl)pyridine-2-yl]ethyl)cyclohexanecarboxylate.

Hydrolysis Assay: Analysis of Hydrolysis of Prodrug to Parent Species

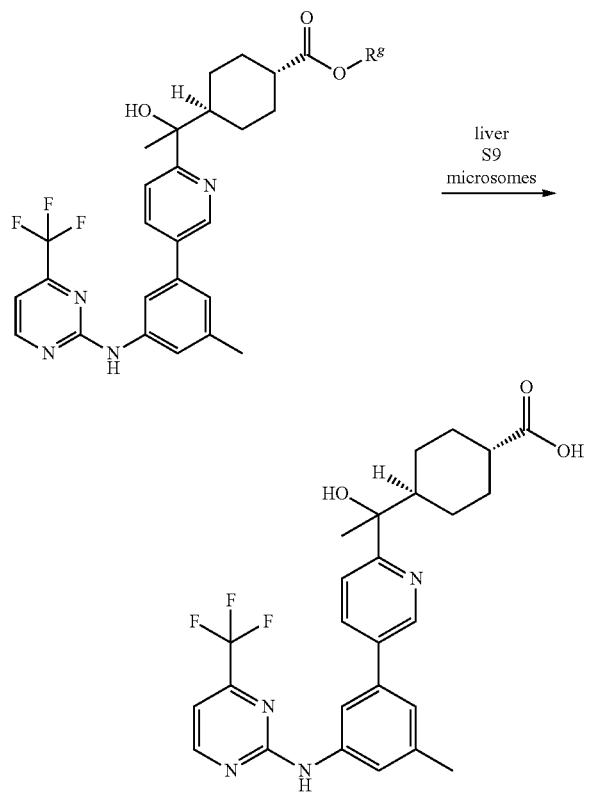

The stability of prodrugs can be investigated in human liver S9 microsomes. Incubations of prodrugs (10 µM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treated with 4 volumes of acetonitrile containing 2% formic acid and an internal standard, and centrifuged. The supernatants are analyzed by LC-MS/MS for prodrug disappearance and appearance of active drug. The half-life of the prodrug is calculated from the percentage of prodrug remaining at different time points calculated from on the peak area ratio relative to t=0. The amount of active drug generated at the different time points is determined using a standard curve.

Biological Assay

Homogeneous Time-Resolved Fluorescence (HTRF) Assay for the Recombinant Human Syk Enzyme A recombinant GST-hSYK fusion protein was used to measure potency of compounds to inhibit human Syk activity. The recombinant human GST-SYK (Carna Biosciences #08-176) (5 µM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on an EnVision (Perkin-Elmer) reader using a time-resolved fluorescence protocol. Table 1 below lists activities for representative compounds of the invention whereby the $IC_{50}$ values are rated "+++" $IC_{50}$ values<100 nM, "++" for $IC_{50}$ values between 100 nM and 1000 nM, and "+" for $IC_{50}$ values between 1000 nM and 10000 nM.

TABLE 1

| Example | rhSYK Activity (nM) |
|---|---|
| 1.1 | ++ |
| 1.2 | +++ |
| 1.3 | +++ |
| 1.4 | ++ |
| 2.1 | +++ |
| 2.2 | +++ |
| 2.3 | + |
| 2.4 | ++ |
| 2.5 | ++ |
| 2.6 | ++ |
| 2.7 | ++ |
| 2.8 | ++ |
| 2.9 | ++ |
| 2.10 | +++ |
| 2.11 | ++ |
| 2.12 | ++ |
| 2.13 | +++ |
| 2.14 | + |
| 2.15 | + |
| 2.16 | ++ |
| 2.17 | ++ |
| 2.18 | ++ |
| 2.19 | ++ |
| 2.20 | +++ |
| 2.21 | +++ |
| 2.22 | +++ |
| 2.23 | +++ |
| 2.24 | +++ |
| 2.25 | ++ |
| 2.26 | ++ |
| 2.27 | ++ |
| 2.28 | + |
| 2.29 | ++ |
| 2.30 | +++ |
| 2.31 | +++ |
| 2.32 | + |
| 2.33 | ++ |
| 2.34 | ++ |
| 2.35 | ++ |
| 2.36 | + |
| 2.37 | ++ |
| 2.38 | ++ |
| 2.39 | ++ |
| 2.40 | +++ |
| 2.41 | ++ |
| 2.42 | ++ |
| 2.43 | ++ |
| 2.44 | +++ |
| 2.45 | +++ |
| 2.46 | +++ |
| 2.47 | +++ |
| 2.48 | +++ |
| 2.49 | +++ |
| 2.50 | +++ |
| 2.51 | ++ |
| 2.52 | +++ |
| 2.53 | ++ |
| 2.54 | ++ |
| 2.55 | +++ |
| 2.56 | +++ |
| 2.57 | +++ |

TABLE 1-continued

| Example | rhSYK Activity (nM) |
|---|---|
| 2.58 | +++ |
| 2.59 | +++ |
| 2.60 | +++ |
| 2.61 | ++ |
| 2.62 | ++ |
| 2.63 | +++ |
| 2.64 | ++ |
| 2.65 | ++ |
| 2.66 | +++ |
| 2.67 | +++ |
| 2.68 | +++ |
| 2.69 | +++ |
| 2.70 | +++ |
| 2.71 | ++ |
| 2.72 | +++ |
| 2.73 | +++ |
| 2.74 | +++ |
| 2.75 | +++ |
| 2.76 | ++ |
| 2.77 | ++ |
| 2.78 | ++ |
| 2.79 | +++ |
| 2.80 | +++ |
| 2.81 | ++ |
| 2.82 | +++ |
| 2.83 | +++ |
| 2.84 | +++ |
| 2.85 | ++ |
| 2.86 | +++ |
| 2.87 | ++ |
| 2.88 | ++ |
| 2.89 | +++ |
| 2.90 | ++ |
| 2.100 | +++ |
| 2.101 | +++ |
| 2.102 | +++ |
| 2.103 | +++ |
| 2.104 | +++ |
| 2.105 | +++ |
| 2.106 | +++ |
| 2.107 | +++ |
| 2.108 | +++ |
| 2.109 | +++ |
| 2.110 | +++ |
| 2.111 | +++ |
| 2.112 | +++ |
| 2.113 | ++ |
| 2.115 | ++ |
| 2.116 | +++ |
| 2.117 | +++ |
| 2.118 | ++ |
| 2.119 | +++ |
| 2.120 | +++ |
| 2.121 | +++ |
| 2.122 | ++ |
| 2.123 | ++ |
| 2.124 | +++ |
| 2.125 | +++ |
| 2.126 | +++ |
| 2.127 | ++ |
| 2.128 | ++ |
| 2.129 | +++ |
| 2.130 | ++ |
| 2.131 | +++ |
| 2.132 | ++ |
| 2.133 | +++ |
| 2.134 | ++ |
| 2.135 | +++ |
| 2.136 | ++ |
| 2.137 | +++ |
| 2.138 | +++ |
| 3.1 | +++ |
| 3.2 | +++ |
| 4.1 | +++ |
| 4.2 | +++ |
| 4.3 | +++ |
| 4.4 | ++ |
| 4.5 | ++ |
| 4.6 | ++ |
| 4.7 | +++ |
| 4.8 | ++ |
| 4.9 | ++ |
| 4.10 | ++ |
| 5.1 | ++ |
| 5.2 | ++ |
| 5.3 | ++ |
| 6.1 | +++ |
| 6.2 | +++ |
| 6.3 | +++ |
| 6.4 | +++ |
| 6.5 | +++ |
| 6.6 | +++ |
| 7.1 | +++ |
| 7.2 | +++ |
| 7.3 | +++ |
| 7.4 | +++ |
| 7.5 | +++ |
| 7.6 | +++ |
| 7.7 | +++ |
| 7.8 | +++ |
| 7.9 | ++ |
| 7.10 | ++ |
| 7.11 | ++ |
| 7.12 | ++ |
| 7.13 | ++ |
| 7.14 | ++ |
| 7.15 | ++ |
| 7.16 | +++ |
| 7.17 | +++ |
| 7.18 | +++ |
| 7.19 | ++ |
| 7.20 | ++ |
| 7.21 | +++ |
| 7.22 | +++ |
| 7.23 | +++ |
| 7.24 | ++ |
| 7.25 | +++ |
| 7.25A | +++ |
| 7.26 | +++ |
| 7.27 | +++ |
| 7.28 | +++ |
| 7.29 | +++ |
| 7.30 | +++ |
| 7.31 | +++ |
| 7.32 | +++ |
| 7.33 | ++ |
| 7.34 | ++ |
| 7.35 | ++ |
| 7.36 | +++ |
| 7.37 | +++ |
| 7.38 | +++ |
| 7.39 | +++ |
| 7.40 | +++ |
| 7.41 | ++ |
| 7.42 | ++ |
| 7.43 | +++ |
| 7.44 | +++ |
| 7.45 | ++ |
| 7.46 | +++ |
| 7.47 | +++ |
| 7.48 | ++ |
| 7.49 | ++ |
| 7.50 | +++ |
| 7.51 | +++ |
| 7.52 | +++ |
| 7.53 | ++ |
| 7.54 | ++ |
| 7.55 | +++ |
| 7.56 | ++ |
| 7.57 | +++ |
| 7.58 | +++ |
| 7.59 | +++ |

TABLE 1-continued

| Example | rhSYK Activity (nM) |
|---|---|
| 7.60 | ++ |
| 7.61 | ++ |
| 7.62 | +++ |
| 7.63 | ++ |
| 7.64 | +++ |
| 7.65 | ++ |
| 7.66 | +++ |
| 7.67 | +++ |
| 7.68 | +++ |
| 7.69 | +++ |
| 7.70 | +++ |
| 7.71 | +++ |
| 7.72 | +++ |
| 7.73 | +++ |
| 7.74 | +++ |
| 7.75 | +++ |
| 7.76 | +++ |
| 7.77 | +++ |
| 7.78 | +++ |
| 7.79 | +++ |
| 7.80 | +++ |
| 7.81 | ++ |
| 7.82 | +++ |
| 7.83 | +++ |
| 7.84 | +++ |
| 7.85 | +++ |
| 7.86 | +++ |
| 7.87 | +++ |
| 7.88 | +++ |
| 7.89 | +++ |
| 7.90 | +++ |
| 7.91 | +++ |
| 7.92 | +++ |
| 7.93 | +++ |
| 7.94 | +++ |
| 7.95 | +++ |
| 7.96 | +++ |
| 7.97 | +++ |
| 7.98 | +++ |
| 7.99 | +++ |
| 7.100 | +++ |
| 7.101 | +++ |
| 7.102 | +++ |
| 7.103 | +++ |
| 7.104 | +++ |
| 7.105 | +++ |
| 7.106 | +++ |
| 7.107 | +++ |
| 7.108 | +++ |
| 7.109 | +++ |
| 7.110 | +++ |
| 7.111 | +++ |
| 7.112 | +++ |
| 7.113 | +++ |
| 7.114 | +++ |
| 7.115 | ++ |
| 7.116 | ++ |
| 7.117 | ++ |
| 7.118 | +++ |
| 7.119 | +++ |
| 7.120 | +++ |
| 7.121 | +++ |
| 7.122 | +++ |
| 7.123 | +++ |
| 7.124 | +++ |
| 7.125 | +++ |
| 7.126 | +++ |
| 7.127 | +++ |
| 7.128 | +++ |
| 7.129 | +++ |
| 7.130 | +++ |
| 7.131 | +++ |
| 7.132 | +++ |
| 7.133 | +++ |
| 7.134 | +++ |
| 7.135 | +++ |
| 7.136 | +++ |
| 7.137 | +++ |
| 7.138 | +++ |
| 7.139 | +++ |
| 7.140 | +++ |
| 7.141 | +++ |
| 7.142 | +++ |
| 7.143 | +++ |
| 7.144 | +++ |
| 7.145 | +++ |
| 7.146 | +++ |
| 7.147 | +++ |
| 7.148 | +++ |
| 7.149 | +++ |
| 7.150 | +++ |
| 7.151 | +++ |
| 7.152 | +++ |
| 7.153 | +++ |
| 7.154 | +++ |
| 7.155 | +++ |
| 7.156 | +++ |
| 7.157 | +++ |
| 7.158 | +++ |
| 7.159 | +++ |
| 7.160 | +++ |
| 7.161 | +++ |
| 8.1 | +++ |
| 8.2 | +++ |
| 8.3 | +++ |
| 8.4 | +++ |
| 9.1 | +++ |
| 9.2 | +++ |
| 9.3 | +++ |
| 9.4 | +++ |
| 9.5 | +++ |
| 9.6 | +++ |
| 9.7 | +++ |
| 9.8 | +++ |
| 9.9 | ++ |
| 9.10 | ++ |
| 9.11 | +++ |
| 9.12 | +++ |
| 9.13 | +++ |
| 9.14 | +++ |
| 9.15 | +++ |
| 9.16 | +++ |
| 9.17 | +++ |
| 9.18 | +++ |
| 9.19 | +++ |
| 9.20 | +++ |
| 9.21 | +++ |
| 9.22 | +++ |
| 9.23 | +++ |
| 9.24 | +++ |
| 9.25 | +++ |
| 9.26 | +++ |
| 9.27 | +++ |
| 9.28 | +++ |
| 9.29 | +++ |
| 9.30 | +++ |
| 9.31 | +++ |
| 9.32 | ++ |
| 9.33 | +++ |
| 9.34 | +++ |
| 9.35 | +++ |
| 9.36 | +++ |
| 9.37 | +++ |
| 9.38 | +++ |
| 9.39 | +++ |
| 9.40 | ++ |
| 9.41 | ++ |
| 9.42 | ++ |
| 9.43 | +++ |
| 9.44 | ++ |
| 9.45 | ++ |
| 9.46 | +++ |

TABLE 1-continued

| Example | rhSYK Activity (nM) |
|---|---|
| 9.47 | + |
| 9.48 | ++ |
| 9.49 | +++ |
| 9.50 | ++ |
| 9.51 | ++ |
| 9.52 | ++ |
| 9.53 | ++ |
| 9.54 | +++ |
| 9.55 | +++ |
| 9.56 | +++ |
| 9.57 | +++ |
| 9.58 | +++ |
| 9.59 | +++ |
| 9.60 | +++ |
| 9.61 | +++ |
| 9.62 | ++ |
| 9.63 | +++ |
| 9.64 | +++ |
| 9.65 | +++ |
| 9.66 | +++ |
| 9.67 | +++ |
| 9.68 | +++ |
| 9.69 | +++ |
| 9.70 | +++ |
| 9.71 | +++ |
| 9.72 | +++ |
| 9.73 | +++ |
| 9.74 | + |
| 9.75 | ++ |
| 9.76 | +++ |
| 9.77 | ++ |
| 9.78 | ++ |
| 9.79 | +++ |
| 9.80 | +++ |
| 9.81 | +++ |
| 9.82 | +++ |
| 9.83 | +++ |
| 10.1 | +++ |
| 10.2 | +++ |
| 10.3 | +++ |
| 10.4 | +++ |
| 11.1 | +++ |
| 12.2 | +++ |
| 12.3 | ++ |
| 12.4 | +++ |
| 12.5 | +++ |
| 12.6 | +++ |
| 12.7 | +++ |
| 12.8 | +++ |
| 12.9 | +++ |
| 13.1 | +++ |
| 13.2 | +++ |
| 13.3 | +++ |
| 13.4 | +++ |
| 13.5 | +++ |
| 14.1 | +++ |
| 15.1 | +++ |
| 15.2 | +++ |
| 15.3 | +++ |
| 15.4 | +++ |
| 15.5 | +++ |
| 15.6 | +++ |
| 15.7 | +++ |
| 15.8 | +++ |
| 15.9 | +++ |
| 15.10 | +++ |
| 15.11 | +++ |
| 15.12 | ++ |
| 15.13 | +++ |
| 15.14 | +++ |
| 15.15 | +++ |
| 15.16 | +++ |
| 15.17 | +++ |
| 15.18 | +++ |
| 15.19 | +++ |
| 15.20 | +++ |
| 15.21 | +++ |
| 15.22 | +++ |
| 15.23 | +++ |
| 15.24 | +++ |
| 15.25 | ++ |
| 15.26 | + |
| 15.27 | +++ |
| 15.28 | ++ |
| 15.29 | +++ |
| 15.30 | +++ |
| 15.31 | ++ |
| 15.32 | +++ |
| 15.33 | ++ |
| 15.34 | ++ |
| 15.35 | ++ |
| 15.36 | ++ |
| 15.37 | +++ |
| 15.38 | ++ |
| 15.39 | ++ |
| 15.40 | ++ |
| 15.41 | +++ |
| 15.42 | +++ |
| 15.43 | +++ |
| 15.44 | +++ |
| 15.45 | +++ |
| 15.46 | +++ |
| 15.47 | +++ |
| 15.48 | +++ |
| 15.49 | +++ |
| 15.50 | +++ |
| 15.51 | +++ |
| 15.52 | +++ |
| 15.53 | +++ |
| 15.54 | +++ |
| 15.55 | +++ |
| 15.56 | +++ |
| 15.57 | ++ |
| 15.58 | ++ |
| 15.59 | +++ |
| 15.60 | ++ |
| 15.61 | ++ |
| 15.62 | ++ |
| 15.63 | ++ |
| 15.64 | ++ |
| 15.65 | ++ |
| 15.66 | +++ |
| 15.67 | +++ |
| 15.68 | ++ |
| 15.69 | ++ |
| 15.70 | ++ |
| 15.71 | +++ |
| 15.72 | +++ |
| 15.73 | +++ |
| 15.74 | +++ |
| 15.75 | ++ |
| 15.76 | +++ |
| 15.77 | ++ |
| 15.78 | ++ |
| 15.79 | + |
| 15.80 | ++ |
| 15.81 | ++ |
| 15.82 | ++ |
| 15.83 | +++ |
| 15.84 | + |
| 15.85 | +++ |
| 15.86 | +++ |
| 15.87 | +++ |
| 15.88 | +++ |
| 15.89 | +++ |
| 15.90 | +++ |
| 16.1 | +++ |
| 16.2 | +++ |
| 16.3 | +++ |
| 16.4 | +++ |
| 16.5 | +++ |
| 16.6 | +++ |

TABLE 1-continued

| Example | rhSYK Activity (nM) |
|---|---|
| 16.7 | +++ |
| 16.8 | ++ |
| 16.9 | ++ |
| 16.10 | ++ |
| 16.11 | ++ |
| 16.12 | ++ |
| 16.13 | +++ |
| 16.14 | ++ |
| 16.15 | ++ |
| 16.16 | ++ |
| 16.17 | ++ |
| 16.18 | +++ |
| 16.19 | +++ |
| 16.20 | +++ |
| 16.21 | ++ |
| 16.22 | ++ |
| 16.23 | ++ |
| 16.24 | +++ |
| 16.25 | ++ |
| 16.26 | +++ |
| 16.27 | ++ |
| 16.28 | ++ |
| 16.29 | ++ |
| 16.30 | +++ |
| 16.31 | ++ |
| 16.32 | +++ |
| 16.33 | ++ |
| 16.34 | ++ |
| 16.35 | ++ |
| 16.36 | ++ |
| 16.37 | +++ |
| 16.38 | ++ |
| 16.39 | +++ |
| 16.40 | +++ |
| 16.41 | +++ |
| 16.42 | +++ |
| 16.43 | +++ |
| 16.44 | +++ |
| 16.45 | +++ |
| 16.46 | ++ |
| 16.47 | +++ |
| 16.48 | +++ |
| 16.49 | +++ |
| 16.50 | +++ |
| 16.51 | +++ |
| 16.52 | +++ |
| 16.53 | ++ |
| 16.54 | +++ |
| 16.55 | +++ |
| 16.56 | +++ |
| 16.57 | +++ |
| 16.58 | +++ |
| 16.59 | +++ |
| 16.60 | +++ |
| 16.61 | +++ |
| 16.62 | +++ |
| 16.63 | ++ |
| 16.64 | ++ |
| 16.65 | ++ |
| 16.66 | +++ |
| 16.67 | +++ |
| 16.68 | +++ |
| 17.1 | +++ |
| 17.2 | +++ |
| 17.3 | +++ |
| 18.1 | +++ |
| 18.2 | +++ |
| 18.3 | ++ |
| 18.4 | ++ |
| 18.5 | +++ |
| 18.6 | +++ |
| 18.7 | +++ |
| 18.8 | +++ |
| 18.9 | +++ |
| 18.10 | +++ |
| 18.11 | +++ |
| 18.12 | +++ |
| 19.1 | +++ |
| 20.1 | +++ |
| 20.2 | +++ |
| 20.3 | ++ |
| 21.1 | +++ |
| 21.2 | ++ |
| 21.3 | +++ |
| 21.4 | +++ |
| 22.1 | ++ |
| 22.2 | +++ |
| 22.3 | +++ |
| 23.1 | +++ |
| 24.1 | +++ |
| 24.2 | +++ |
| 24.3 | +++ |
| 24.4 | +++ |
| 25.1 | ++ |
| 25.2 | +++ |
| 26.1 | ++ |

Representative compounds of the invention have the $IC_{50}$ values specified in parentheses immediately following the compound number in the above-described assay: 1.1 (144 nM), 7.1 (3.9 nM), 7.63 (700 nM), and 9.1 (17.9 nM).

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the Formula (I) or a pharmaceutically acceptable salt thereof,

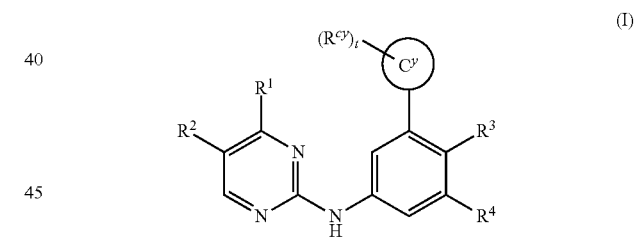

wherein
R$^1$ is selected from the group consisting of $C_1$-$C_3$ fluoroalkyl;
R$^2$ is H;
R$^3$ is H;
R$^4$ is selected from the group consisting of $C_1$-$C_3$ alkyl and —N(H)C(O)R$^{4b}$;
R$^{4b}$ is $C_1$-$C_3$ alkyl;
C$^y$ is

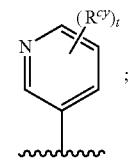

t is 1;

R$^{cy}$ is a group of the formula

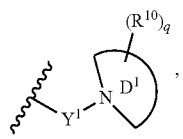

wherein

Y$^1$ is a bond;

D$^1$ is a 4- to 8-membered mono- or bicyclic heterocyclic ring optionally containing one additional heteroatom selected from the group consisting of N and S;

each R$^{10}$ is independently selected from the group consisting of C$_1$-C$_3$ alkyl, hydroxyl, —CO$_2$H, —CH$_2$CO$_2$R$^g$, —C(O)N(H)—(CH$_2$CO$_2$H), or wherein when two R$^{10}$ moieties are geminally substituted on a common ring carbon atom of D$^1$, the two geminally substituted R$^{10}$ moieties together with the carbon atom on which they are attached form —C(O)—;

R$^g$ is H or C$_1$-C$_3$ alkyl; and q is 1.

2. A compound of the Formula (I) or a pharmaceutically acceptable salt thereof,

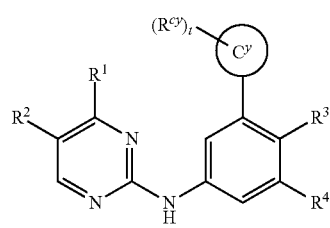

wherein

R$^1$ is selected from the group consisting of C$_1$-C$_3$ alkyl, C$_1$-C$_3$ fluoroalkyl, C$_1$-C$_3$ alkoxy, and cyclopropyl;

R$^2$ is H or halo;

R$^3$ is H;

R$^4$ is selected from the group consisting of H, C$_1$-C$_3$ alkyl, and halo;

C$^y$ is a 6-membered heteroaryl selected from the group consisting of:

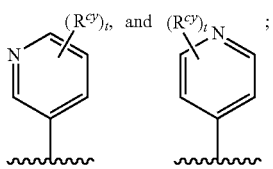

t is 1;

R$^{cy}$ is a group of the formula

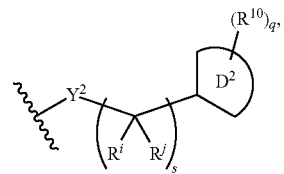

wherein

Y$^2$ is a bond or —N(H)—;

s is 0, 1 or 2;

R$^i$ is H, methyl, hydroxyl, or —CO$_2$H;

R$^j$ is H or methyl;

D$^2$ is selected from the group consisting of:
(i) cyclohexyl;
(ii) a 5- to 6-membered heterocyclyl containing one to two N atoms;
(iii) a 5-membered heteroaryl containing two to three N atoms; and
(iv) phenyl;

each R$^{10}$ is independently selected from the group consisting of C$_1$-C$_3$ alkyl, hydroxyl, —CO$_2$R$^g$, —C(O)NH$_2$, —C(O)CH$_2$CN, and —C(O)CH$_2$OH;

R$^g$ is H or C$_1$-C$_3$ alkyl; and q is 0, 1, 2, 3, or 4.

3. A compound of the Formula (I) or a pharmaceutically acceptable salt thereof

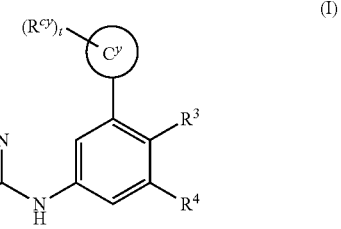

wherein

R$^1$ is selected from the group consisting of C$_1$-C$_3$ fluoroalkyl and cyclopropyl;

R$^2$ is H or halo;

R$^3$ is H;

R$^4$ is selected from the group consisting of H, C$_1$-C$_3$ alkyl, and —N(H)C(O)R$^{4b}$;

R$^{4b}$ is C$_1$-C$_3$ alkyl;

C$^y$ is a 6-membered heteroaryl selected from the group consisting of:

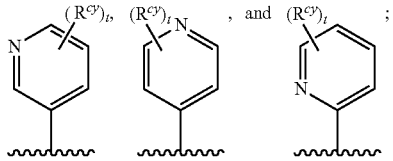

t is 1;

R$^{cy}$ is a group of the formula

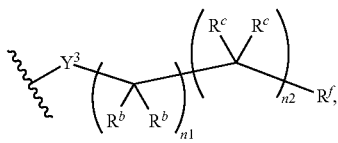

wherein
$Y^3$ is a bond,

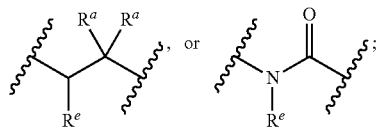

$R^e$ is H, $C_1$-$C_3$ alkyl, or —$(CH_2)_{n3}CN$;
wherein n3 is 2 or 3;
each $R^a$ is independently selected from the group consisting of H, $C_1$-$C_6$ alkyl, hydroxy($C_1$-$C_3$)alkyl, —$(CH_2)_{n4}$—O—($C_1$-$C_3$)alkyl, —$(CH_2)_{n4}C(O)NH_2$, —$(CH_2)_{n4}S$—($C_1$-$C_3$)alkyl, and —$(CH_2)_{n4}S(O)_2$—($C_1$-$C_3$)alkyl;
wherein each n4 is independently 1, 2, or 3;
each $R^b$ is independently selected from the group consisting of H, hydroxyl, $C_1$-$C_6$ alkyl, fluoro, $C_1$-$C_3$ fluoroalkyl, hydroxy($C_1$-$C_3$)alkyl, —$(CH_2)_{n4}$—O—($C_1$-$C_3$)alkyl, —$(CH_2)_{n4}C(O)NH_2$, —$(CH_2)_{n4}S$—($C_1$-$C_3$)alkyl, and —$(CH_2)_{n4}S(O)_2$—($C_1$-$C_3$)alkyl;
each $R^c$ and $R^d$ is independently selected from the group consisting of H or $C_1$-$C_3$ alkyl;
$R^f$ is —$CO_2R^g$, hydroxyl, or —$C(O)N(R^h)_2$;
$R^g$ is H or $C_1$-$C_3$ alkyl;
wherein each $R^h$ is independently H, $C_1$-$C_3$ alkyl, or —$CH_2CO_2H$;
n1 is 0, 1 or 2; and
n2 is 0 or 1.

4. A compound of the Formula (IB) or a pharmaceutically acceptable salt thereof,

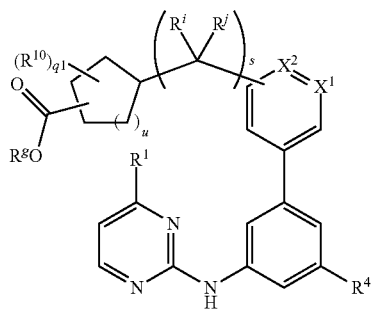

wherein
$R^1$ is selected from the group consisting of $C_1$-$C_3$ alkyl, $C_1$-$C_3$ fluoroalkyl, and $C_3$-$C_6$ cycloalkyl;
$R^4$ is selected from the group consisting of H, $C_1$-$C_3$ alkyl and $C_1$-$C_3$ fluoroalkyl;
one of $X^1$ and $X^2$ is N and the other is C;
$R^i$ is H or hydroxyl;
$R^j$ is H or $C_1$-$C_3$ alkyl;
s is 0, 1, 2, or 3;

$R^{10}$ is $C_1$-$C_3$ alkyl or hydroxyl;
q1 is 0, 1, 2, or 3;
u is 1 or 2; and
$R^g$ is H or $C_1$-$C_3$ alkyl.

5. The compound of claim 4 or a pharmaceutically acceptable salt thereof,
wherein
$R^1$ is selected from the group consisting of methyl, —$CF_3$, and cyclopropyl;
$R^4$ is selected from the group consisting of H, methyl, and —$CF_3$; and
$R^i$ is H or hydroxyl;
$R^j$ is H or methyl;
s is 0 or 1; and
$R^{10}$ is methyl or hydroxyl.

6. The compound of claim 5, or a pharmaceutically acceptable salt thereof,
wherein the group

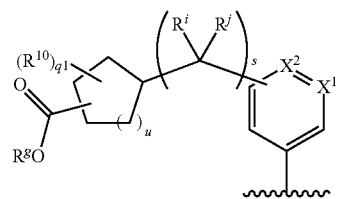

is a group of the formula

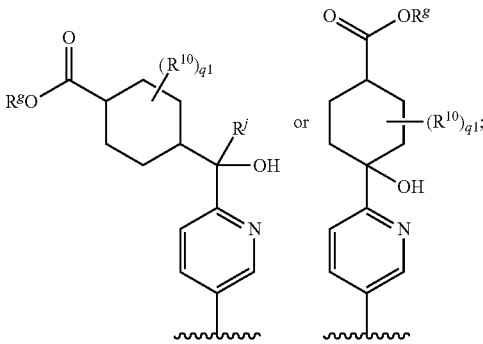

and
q1 is 0, 1, or 2.

7. The compound of claim 1 or a pharmaceutically acceptable salt thereof, wherein $R^g$ is H.

8. A compound or a pharmaceutically acceptable salt thereof, wherein the compound is selected from the group consisting of:
trans-4-[1-hydroxy-1-(5-{3-[(4-methoxypyrimidin-2-yl)amino]-5-methylphenyl}pyridin-2-yl)ethyl]cyclohexanecarboxylic acid;
trans-4-{1-[5-(3-{[4-(difluoromethyl)pyrimidin-2-yl]amino}-5-methylphenyl)pyridin-2-yl]-1-hydroxyethyl}cyclohexanecarboxylic acid;
trans-4-{1-hydroxy-1-[5-(3-methyl-5-{[4-(trifluoromethyl)pyrimidin-2-yl]amino}phenyl)pyridin-2-yl]ethyl}cyclohexanecarboxylic acid;
trans-4-[1-hydroxy-1-(5-{3-methyl-5-[(4-methylpyrimidin-2-yl)amino]phenyl}pyridin-2-yl)ethyl]cyclohexanecarboxylic acid;
2-methyl-N-[5-(3-methyl-5-{[4-(trifluoromethyl)pyrimidin-2-yl]amino}phenyl)pyridin-2-yl]alanine;

trans-4-[1-(5-{3-[(4-cyclopropylpyrimidin-2-yl)amino]-5-methylphenyl}pyridin-2-yl)-1-hydroxyethyl]cyclohexanecarboxylic acid;
cis-4-hydroxy-4-[5-(3-methyl-5-{[4-(trifluoromethyl)pyrimidin-2-yl]amino}phenyl)pyridin-2-yl]cyclohexanecarboxylic acid;
trans-4-hydroxy-2,2-dimethyl-4-[5-(3-methyl-5-{[4-(trifluoromethyl)pyrimidin-2-yl]amino}phenyl)pyridin-2-yl]cyclohexanecarboxylic acid;
1-{[5-(3-methyl-5-{[4-(trifluoromethyl)pyrimidin-2-yl]amino}phenyl)pyridin-2-yl]amino}cyclobutanecarboxylic acid;
3-[5-(3-methyl-5-{[4-(trifluoromethyl)pyrimidin-2-yl]amino}phenyl)pyridin-2-yl]propanoic acid;
1-[5-(3-methyl-5-{[4-(trifluoromethyl)pyrimidin-2-yl]amino}phenyl)pyridin-2-yl]-proline;
N-[5-(3-methyl-5-{[4-(trifluoromethyl)pyrimidin-2-yl]amino}phenyl)pyridin-2-yl]serine;
N-[5-(3-methyl-5-{[4-(trifluoromethyl)pyrimidin-2-yl]amino}phenyl)pyridin-2-yl]-homoserine;
4-{[5-(3-methyl-5-{[4-(trifluoromethyl)pyrimidin-2-yl]amino}phenyl)pyridin-2-yl]amino}piperidine-4-carboxylic acid;
1-[5-(3-methyl-5-{[4-(trifluoromethyl)pyrimidin-2-yl]amino}phenyl)pyridin-2-yl]azetidine-2-carboxylic acid;
O-methyl-N-[5-(3-methyl-5-{[4-(trifluoromethyl)pyrimidin-2-yl]amino}phenyl)pyridin-2-yl]serine;
1-{[5-(3-methyl-5-{[4-(trifluoromethyl)pyrimidin-2-yl]amino}phenyl)pyridin-2-yl]amino}cyclopentanecarboxylic acid;
1-{[5-(3-methyl-5-{[4-(trifluoromethyl)pyrimidin-2-yl]amino}phenyl)pyridin-2-yl]amino}cyclopropanecarboxylic acid;
2-methyl-1-[5-(3-methyl-5-{[4-(trifluoromethyl)pyrimidin-2-yl]amino}phenyl)pyridin-2-yl]-L-proline;
N-[5-(3-methyl-5-{[4-(trifluoromethyl)pyrimidin-2-yl]amino}phenyl)pyridin-2-yl]-alanine;
N-[5-(3-methyl-5-{[4-(trifluoromethyl)pyrimidin-2-yl]amino}phenyl)pyridin-2-yl]glycine;
N-[5-(3-methyl-5-{[4-(trifluoromethyl)pyrimidin-2-yl]amino}phenyl)pyridin-2-yl]-D-alanine;
N-[5-(3-methyl-5-{[4-(trifluoromethyl)pyrimidin-2-yl]amino}phenyl)pyridin-2-yl]-D-valine;
N-[5-(3-methyl-5-{[4-(trifluoromethyl)pyrimidin-2-yl]amino}phenyl)pyridin-2-yl]-L-threonine;
N-2-[5-(3-methyl-5-{[4-(trifluoromethyl)pyrimidin-2-yl]amino}phenyl)pyridin-2-yl]-D-asparagine;
N-2-[5-(3-methyl-5-{[4-(trifluoromethyl)pyrimidin-2-yl]amino}phenyl)pyridin-2-yl]-asparagine;
N-[5-(3-methyl-5-{[4-(trifluoromethyl)pyrimidin-2-yl]amino}phenyl)pyridin-2-yl]-L-methionine;
2-{[5-(3-methyl-5-{[4-(trifluoromethyl)pyrimidin-2-yl]amino}phenyl)pyridin-2-yl]amino}butanoic acid;
N-[5-(3-methyl-5-{[4-(trifluoromethyl)pyrimidin-2-yl]amino}phenyl)pyridin-2-yl]-leucine;
N-[5-(3-methyl-5-{[4-(trifluoromethyl)pyrimidin-2-yl]amino}phenyl)pyridin-2-yl]-L-histidine;
4-[5-(3-methyl-5-{[4-(trifluoromethyl)pyrimidin-2-yl]amino}phenyl)pyridin-3-yl]piperidin-4-ol;
3-hydroxy-3-[5-(3-methyl-5-{[4-(trifluoromethyl)pyrimidin-2-yl]amino}phenyl)pyridin-2-yl]cyclohexanecarboxylic acid;
(2 S)-1-[5-(3-methyl-5-{[4-(trifluoromethyl)pyrimidin-2-yl]amino}phenyl)pyridin-2-yl]azetidine-2-carboxylic acid;
1-[5-(3-methyl-5-{[4-(trifluoromethyl)pyrimidin-2-yl]amino}phenyl)pyridin-2-yl]azetidine-2-carboxylic acid;
1-[5-(3-methyl-5-{[4-(trifluoromethyl)pyrimidin-2-yl]amino}phenyl)pyridin-2-yl]piperidine-2-carboxylic acid;
2,2-dimethyl-3-[5-(3-methyl-5-{[4-(trifluoromethyl)pyrimidin-2-yl]amino}phenyl)pyridin-2-yl]propanoic acid;
trans-4-[(5-{3-methyl-5-[(4-methylpyrimidin-2-yl)amino]phenyl}pyridin-2-yl)amino]cyclohexanecarboxylic acid;
trans-4-[(5-{3-[(4-methoxypyrimidin-2-yl)amino]-5-methylphenyl}pyridin-2-yl)amino]cyclohexanecarboxylic acid;
4-{1-hydroxy-1-[5-(3-methyl-5-{[4-(trifluoromethyl)pyrimidin-2-yl]amino}phenyl)pyridin-2-yl]ethyl}benzoic acid;
3-methyl-N-[5-(3-methyl-5-{[4-(trifluoromethyl)pyrimidin-2-yl]amino}phenyl)pyridin-2-yl]-L-valine;
cis-4-{[5-(3-methyl-5-{[4-(trifluoromethyl)pyrimidin-2-yl]amino}phenyl)pyridin-2-yl]amino}cyclohexanecarboxylic acid;
trans-4-{[5-(3-methyl-5-{[4-(trifluoromethyl)pyrimidin-2-yl]amino}phenyl)pyridin-2-yl]amino}cyclohexanecarboxylic acid;
2-methyl-N-[5-(3-{[4-(trifluoromethyl)pyrimidin-2-yl]amino}phenyl)pyridin-2-yl]alanine;
N-[5-(3-methyl-5-{[4-(trifluoromethyl)pyrimidin-2-yl]amino}phenyl)pyridin-2-yl]-beta-alanine;
N-[5-(3-methyl-5-{[4-(trifluoromethyl)pyrimidin-2-yl]amino}phenyl)pyridin-2-yl]-L-phenylalanine;
3-{[5-(3-methyl-5-{[4-(trifluoromethyl)pyrimidin-2-yl]amino}phenyl)pyridin-2-yl]amino}-3-oxopropanoic acid;
1-{5-[3-(acetylamino)-5-{[4-(trifluoromethyl)pyrimidin-2-yl]amino}phenyl]pyridin-2-yl}azetidine-2-carboxylic acid;
N-{5-[3-(acetylamino)-5-{[4-(trifluoromethyl)pyrimidin-2-yl]amino}phenyl]pyridin-2-yl}-2-methylalanine;
2-methyl-2-{[4-(3-methyl-5-{[4-(trifluoromethyl)pyrimidin-2-yl]amino}phenyl)pyridin-2-yl]amino}propane-1,3-diol;
2-methyl-2-{[4-(3-methyl-5-{[4-(trifluoromethyl)pyrimidin-2-yl]amino}phenyl)pyridin-2-yl]amino}propan-1-ol;
2-{[4-(3-methyl-5-{[4-(trifluoromethyl)pyrimidin-2-yl]amino}phenyl)pyridin-2-yl]amino}propan-1-ol;
5-hydroxy-5-[5-(3-methyl-5-{[4-(trifluoromethyl)pyrimidin-2-yl]amino}phenyl)pyridin-2-yl]azepan-2-one;
N-[5-(3-methyl-5-{[4-(trifluoromethyl)pyrimidin-2-yl]amino}phenyl)pyridin-2-yl]-D-histidine;
4-{[5-(3-methyl-5-{[4-(trifluoromethyl)pyrimidin-2-yl]amino}phenyl)pyridin-2-yl]amino}pyrrolidin-2-one;
3-{[5-(3-methyl-5-{[4-(trifluoromethyl)pyrimidin-2-yl]amino}phenyl)pyridin-2-yl]amino}pyrrolidin-2-one;
4-hydroxy-4-[5-(3-methyl-5-{[4-(trifluoromethyl)pyrimidin-2-yl]amino}phenyl)pyridin-3-yl]piperidine-1-carboxamide;
4-[5-(3-methyl-5-{[4-(trifluoromethyl)pyrimidin-2-yl]amino}phenyl)pyridin-3-yl]piperazin-2-one;
N-(3-[6-(3-oxopiperazin-1-yl)pyridin-3-yl]-5-{[4-(trifluoromethyl)pyrimidin-2-yl]amino}phenyl)acetamide;
N,N-dimethyl-N-2-[5-(3-methyl-5-{[4-(trifluoromethyl)pyrimidin-2-yl]amino}phenyl)pyridin-2-yl]glycinamide;
3-(4-{3-[(4-cyclopropylpyrimidin-2-yl)amino]-5-methylphenyl}pyridin-2-yl)propanoic acid;

trans-4-[(5-{3-[(5-chloro-4-methylpyrimidin-2-yl)amino]-5-methylphenyl}pyridin-2-yl)amino]cyclohexanecarboxylic acid;

N-methyl-N-[5-(3-methyl-5-{[4-(trifluoromethyl)pyrimidin-2-yl]amino}phenyl)pyridin-2-yl]-alanine;

trans-4-[(5-{3-[(5-fluoro-4-methoxypyrimidin-2-yl)amino]-5-methylphenyl}pyridin-2-yl)amino]cyclohexanecarboxylic acid;

1-[5-(3-methyl-5-{[4-(trifluoromethyl)pyrimidin-2-yl]amino}phenyl)pyridin-2-yl]piperidine-3-carboxylic acid;

N-[5-(3-methyl-5-{[4-(trifluoromethyl)pyrimidin-2-yl]amino}phenyl)pyridin-2-yl]-D-leucine;

4-(methylsulfonyl)-2-{[5-(3-methyl-5-{[4-(trifluoromethyl)pyrimidin-2-yl]amino}phenyl)pyridin-2-yl]amino}butanoic acid;

N-(2-cyanoethyl)-N-[5-(3-methyl-5-{[4-(trifluoromethyl)pyrimidin-2-yl]amino}phenyl)pyridin-2-yl]glycine;

1-[5-(3-methyl-5-{[4-(trifluoromethyl)pyrimidin-2-yl]amino}phenyl)pyridin-2-yl-L-prolylglycine;

1-[5-(3-methyl-5-{[4-(trifluoromethyl)pyrimidin-2-yl]amino}phenyl)pyridin-2-yl]-proline;

2,2-difluoro-3-hydroxy-3-[5-(3-methyl-5-{[4-(trifluoromethyl)pyrimidin-2-yl]amino}phenyl)pyridin-2-yl]propanoic acid;

2,2-difluoro-3-[5-(3-methyl-5-{[4-(trifluoromethyl)pyrimidin-2-yl]amino}phenyl)pyridin-2-yl]propanoic acid;

3-hydroxy-2,2-dimethyl-3-[5-(3-methyl-5-{[4-(trifluoromethyl)pyrimidin-2-yl]amino}phenyl)pyridin-2-yl]propanoic acid;

3-hydroxy-3-[5-(3-methyl-5-{[4-(trifluoromethyl)pyrimidin-2-yl]amino}phenyl)pyridin-3-yl]pyrrolidine-1-carboxamide;

{1-[5-(3-methyl-5-{[4-(trifluoromethyl)pyrimidin-2-yl]amino}phenyl)pyridin-2-yl]piperidin-2-yl}acetic acid;

1-[5-(3-methyl-5-{[4-(trifluoromethyl)pyrimidin-2-yl]amino}phenyl)pyridin-2-yl]azetidine-3-carboxylic acid;

3-hydroxy-1-[5-(3-methyl-5-{[4-(trifluoromethyl)pyrimidin-2-yl]amino}phenyl)pyridin-2-yl]-L-proline;

1-[5-(3-methyl-5-{[4-(trifluoromethyl)pyrimidin-2-yl]amino}phenyl)pyridin-2-yl]piperidine-4-carboxylic acid;

3-[5-(3-methyl-5-{[4-(trifluoromethyl)pyrimidin-2-yl]amino}phenyl)pyridin-2-yl]-1,3-thiazolidine-4-carboxylic acid;

N-[5-(3-methyl-5-{[4-(trifluoromethyl)pyrimidin-2-yl]amino}phenyl)pyridin-2-yl]glycylglycine;

{4-[5-(3-methyl-5-{[4-(trifluoromethyl)pyrimidin-2-yl]amino}phenyl)pyridin-2-yl]piperazin-1-yl}acetic acid;

N-[5-(3-{[5-bromo-4-(trifluoromethyl)pyrimidin-2-yl]amino}-5-methylphenyl)pyridin-2-yl]-2-methylalanine;

3-(5-{3-[(4-cyclopropylpyrimidin-2-yl)amino]-5-methylphenyl}pyridin-3-yl)propanoic acid; and 4-({[5-(3-methyl-5-{[4-(trifluoromethyl)pyrimidin-2-yl]amino}phenyl)pyridin-2-yl]amino}methyl)cyclohexanecarboxylic acid.

9. A pharmaceutical composition comprising a therapeutically effective amount of the compound of claim 1 or a pharmaceutically acceptable salt thereof and a pharmaceutically acceptable carrier.

10. A method of treating rheumatoid arthritis comprising administering a therapeutically effective amount of the compound of claim 1 or a pharmaceutically acceptable salt thereof to a patient in need of such treatment.

11. The compound of claim 4 or a pharmaceutically acceptable salt thereof, wherein $R^g$ is H.

12. The compound of claim 6 or a pharmaceutically acceptable salt thereof, wherein $R^g$ is H.

13. The compound of claim 1 or a pharmaceutically acceptable salt thereof, wherein $R^g$ is H.

14. The compound of claim 2 or a pharmaceutically acceptable salt thereof, wherein $R^g$ is H.

15. The compound of claim 3 or a pharmaceutically acceptable salt thereof, wherein $R^g$ is H.

16. A pharmaceutical composition comprising a therapeutically effective amount of the compound of claim 2 or a pharmaceutically acceptable salt thereof and a pharmaceutically acceptable carrier.

17. A pharmaceutical composition comprising a therapeutically effective amount of the compound of claim 3 or a pharmaceutically acceptable salt thereof and a pharmaceutically acceptable carrier.

18. A pharmaceutical composition comprising a therapeutically effective amount of the compound of claim 4 or a pharmaceutically acceptable salt thereof and a pharmaceutically acceptable carrier.

* * * * *